(12) United States Patent  
Marfat

(10) Patent No.: US 6,391,872 B1
(45) Date of Patent: *May 21, 2002

(54) INDAZOLE BIOISOSTERE REPLACEMENT OF CATECHOL IN THERAPEUTICALLY ACTIVE COMPOUNDS

(75) Inventor: Anthony Marfat, Mystic, CT (US)

(73) Assignee: Pfizer Inc, New York, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/381,425
(22) PCT Filed: Oct. 26, 1998
(86) PCT No.: PCT/IB98/01710
§ 371 Date: Sep. 20, 1999
§ 102(e) Date: Sep. 20, 1999
(87) PCT Pub. No.: WO99/23077
PCT Pub. Date: May 14, 1999

Related U.S. Application Data

(60) Provisional application No. 60/064,229, filed on Nov. 4, 1997, provisional application No. 60/064,187, filed on Nov. 4, 1997, provisional application No. 60/064,024, filed on Nov. 4, 1997, provisional application No. 60/064,228, filed on Nov. 4, 1997, and provisional application No. 60/064,198, filed on Nov. 4, 1997.

(51) Int. Cl.[7] .................. A61K 31/4155; A61K 31/416; C07D 231/56
(52) U.S. Cl. ............. 514/218; 514/253.01; 514/254.06; 514/257; 514/403; 540/575; 544/251; 544/363; 544/371; 548/361.1; 548/362.5
(58) Field of Search .................... 548/361.1, 362.5; 544/251, 363, 371; 540/575; 514/218, 253.01, 254.06, 257.403

(56) References Cited

U.S. PATENT DOCUMENTS 5,006,520 A * 4/1991 Oe et al. .................... 514/212
5,593,997 A * 1/1997 Dow et al. .................. 514/258
6,127,398 A * 10/2000 Marfat ........................ 514/403

FOREIGN PATENT DOCUMENTS

EP  338087  * 10/1989
WO  97/42174 * 11/1997

* cited by examiner

Primary Examiner—Richard L. Raymond
(74) Attorney, Agent, or Firm—Peter C. Richardson; Paul H. Ginsburg; Raymond M. Speer

(57) ABSTRACT

Therapeutically active compositions of matter and member species thereof are described which comprise indazole-containing compounds, said compounds and their therapeutic activity resulting directly from an indazole-for-catechol bioisostere replacement of a catechol-containing compound having the same therapeutic activity, where non-catechol substituents are the same or homologous before and after said replacement, and wherein said compositions of matter comprise a compound of Formula ($I^1$) or ($I^2$):

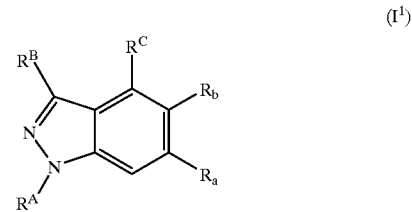

($I^1$)

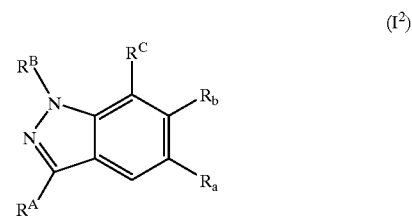

($I^2$)

or a pharmaceutically acceptable salt thereof, wherein in a preferred embodiment $R^C$ is hydrogen; $R^A$ is cyclohexyl; and $R^B$ is ethyl. $R_a$ and $R_b$ are each individually and independently hydrogen or non-catechol substituents of said compounds resulting directly from an indazole-for-catechol bioisostere replacement of said catechol-containing compound having said therapeutic activity, where said non-catechol substituents are the same or homologous before and after said replacement, provided that both of $R_a$ and $R_b$ cannot be hydrogen at the same time. The therapeutic activity involved may comprise cholinesterase inhibitory activity, adrenergic $\alpha_1$-antagonist and $\beta_1$-agonist activity, calcium channel inhibitory activity, antineoplastic activity, and phosphodiesterase type IV inhibitory activity.

3 Claims, No Drawings

INDAZOLE BIOISOSTERE REPLACEMENT OF CATECHOL IN THERAPEUTICALLY ACTIVE COMPOUNDS

REFERENCE TO CO-PENDING AND OTHER RELATED APPLICATIONS

This application is a 371 of PCT/IB98/01710, filed Oct. 26, 1998 and claims benefit of U.S. Provisional Applications Nos. 60/064,229; 60/064,187; 60/064,024; 60/064,228 and 60/064,198, all filed Nov. 4, 1997.

Descriptive reference is made to catechol-containing protein tyrosine kinase receptor antagonists which are useful in treating hyperproliferative diseases in U.S. application Ser. No. 08/653,786 filed May 28, 1996, now U.S. Pat. No. 5,747,498 issued May 5, 1998; International application Ser. No. PCT/IB95/00436 filed Jun. 6, 1995, designating the United States, and published as WO 96/30347 on Oct. 3, 1996; and U.S. application Ser. No. 60/020,491 filed Jun. 24, 1996, now abandoned, filed as International application Ser. No.

PCT/IB97/675 filed Jun. 11, 1997, designating the United States, and published as WO 97/49688 on Dec. 31, 1997; the disclosures of all of which are incorporated herein by reference in their entireties.

Descriptive reference is also made to non-catechol-containing protein tyrosine kinase receptor antagonists useful in treating hyperproliferative diseases in U.S. application Ser. No. 08/682,565 filed Jan, 27, 1995, now U.S. Pat. No. 5,736,534 issued Apr. 7, 1998, corresponding to International application Serial No. PCT/IB95/00061 filed Jan. 27, 1995, and published as WO 95/23141 on Aug. 31, 1995; U.S. application Ser. No. 08/449,381 filed May 23, 1995, now U.S. Pat. No. 5,593,997 issued Jan. 14, 1997; and International application Seri. No. PCT/US95/07881 filed Jun. 7, 1995, designating the United States, and published as WO 96/40142 on Dec. 19, 1996; the disclosures of all of which are incorporated herein by reference in their entireties.

FIELD OF THE INVENTION

The present invention is in the field of compositions of matter, and pharmaceutical compositions and methods of treatment utilizing one or more of said compositions of matter as the active ingredient and the active agent with respect thereto, wherein said composition of matter comprises an indazole moiety as an essential feature of its overall chemical structure. Further, said indazole constitutes a bioisosteric replacement of a catechol moiety or functional derivative thereof in an original composition of matter in which said catechol moiety has been subject to bioisosteric replacement by said indazole moiety. The type and extent of biological activity found in said original composition of matter is retained and even increased and improved in said indazole bioisostere thereof.

BACKGROUND OF THE INVENTION

The term "catechol" as used herein refers to 1,2-benzenediol, sometimes referred to as "pyrocatechol", which may be represented by Formula (1.0):

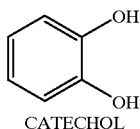

CATECHOL (1.0)

The name is derived from catechin or catechu which in turn refer to a slightly more complex composition derived from Acacia catechu. As a distinct chemical group or moiety, catechol is a key component of number of different molecules having pharmacological activity and consequently, usefulness as therapeutic agents.

The present invention is concerned with the discovery that the indazole nucleus is a moiety which is capable of being a bioisostere replacement for a catechol moiety comprising a functionally essential part of the makeup of compounds which are therapeutically active as a result of their fundamental operation as endogenous ligands, enzyme inhibitors, receptor antagonists, substrate mimics, regulating and signalling entities such as the chemokines, by means of which they carry out essential metabolic functions in the body.

Thus, in accordance with the present invention it has been discovered that the indazole nucleus is a bioisostere replacement for the catechol moiety which is an essential part of many classes and types of compounds, including numerous drugs which have been and will in the future be created and developed for therapeutic treatments as detailed further herein. This bioisostere replacement will be better understood from the following structural representation of the catechol moiety and the indazole moiety which replaces it, which may be represented respectively by Formulas (1.1) and (1.2):

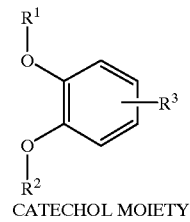

CATECHOL MOIETY (1.1)

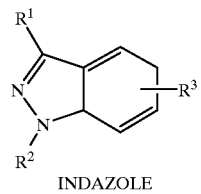

INDAZOLE (1.2)

It will be understood that the substituent "$R^3$" in the above Formulas (1.1) and (1.2) is a generalized illustration, ie., it represents the possibility of more than one substituent as well as substitution at more than one position of the phenyl ring, and further, includes essentially all of the structural elements of all of the catechol-containing compounds for which the indazole-for-catechol bioisostere replacement of the present invention may be carried out.

Consequently, it will be understood that the terms "bioisostere", "bioisosteric replacement", "bioisosterism" and closely related terms as used herein have the same meanings as those generally recognized in the art. Bioisosteres are atoms, ions, or molecules in which the peripheral layers of electrons can be considered identical. The term bioisostere is usually used to mean a portion of an overall molecule, as opposed to the entire molecule itself. Bioisosteric replacement involves using one bioisostere to replace another with the expectation of maintaining or slightly modifying the biological activity of the first bioisostere. The bioisosteres in this case are thus atoms or groups of atoms having similar size, shape and electron density.

Included within the scope of the bioisostere indazole-for-catechol replacements of the present invention are a number of catechol-containing compounds which have a third hydroxy or derivative group, $-OR^X$, on a third carbon of the phenyl ring, usually adjacent to one of the two carbons comprising the catechol moiety. Compounds of this type may be illustrated by Formula (1.3) and exemplified by cinepazet of Formula (6.8):

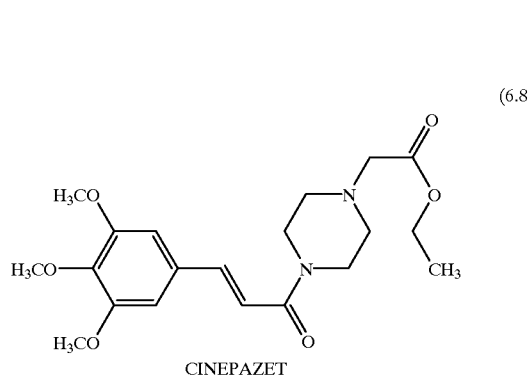

CATECHOL WITH ADDITIONAL
-OR$^x$ SUBSTITUENT
(1.3)

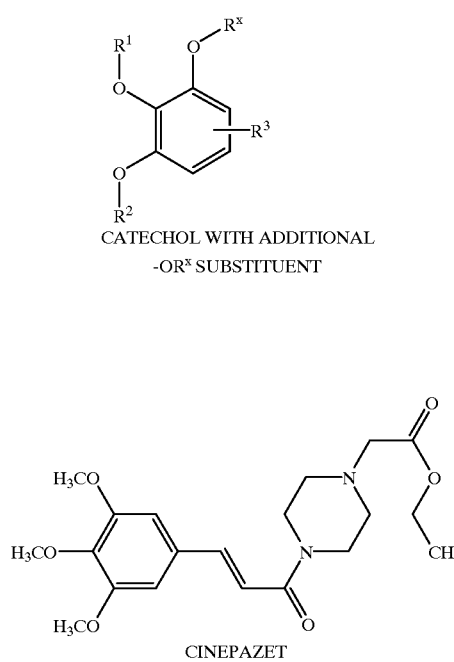

CINEPAZET
(6.8)

In this type of catechol moiety, which is described herein as having an "additional $-OR^X$ substituent", the indazole-for-catechol bioisostere replacement of the present invention may "include" or "exclude" said additional $-OR^X$ substituent.

Where the additional $-OR^X$ substituent is included in the bioisostere replacement, all three of the $-OR$ groups, including said additional substituent $-OR^X$, are replaced by the indazole group, in effect as though the additional $-OR^X$ substituent were not present at all. On the other hand, where said additional $-OR^X$ substituent is excluded from the bioisostere replacement, it will remain as a substituent at the same position of the phenyl ring, but as part of the indazole ring. The case of indazole-for-catechol bioisostere replacement which includes said additional $-OR^X$ substituent may be illustrated by Formulas (1.3) and (1.4):

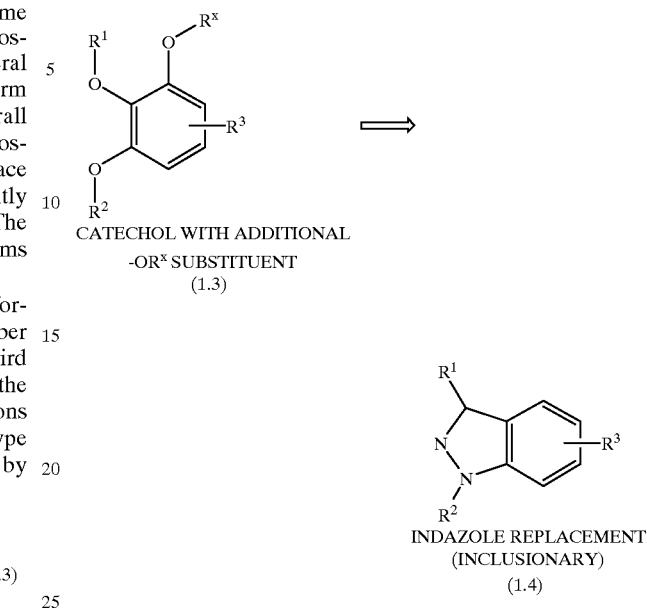

CATECHOL WITH ADDITIONAL
-OR$^x$ SUBSTITUENT
(1.3)

INDAZOLE REPLACEMENT
(INCLUSIONARY)
(1.4)

The case of indazole-for-catechol bioisostere replacement which excludes said additional $-OR^X$ substituent may be illustrated by Formulas (1.3) and (1.5):

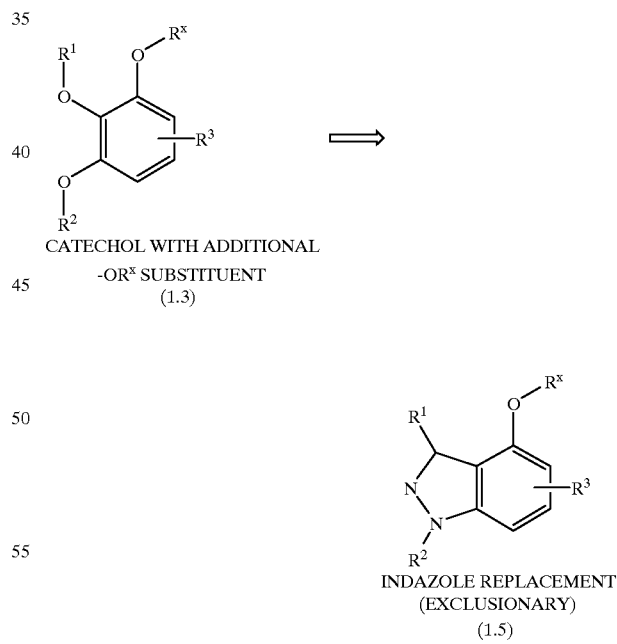

CATECHOL WITH ADDITIONAL
-OR$^x$ SUBSTITUENT
(1.3)

INDAZOLE REPLACEMENT
(EXCLUSIONARY)
(1.5)

Both the inclusionary and exclusionary indazole-for-catechol bioisostere replacements described above may be further illustrated in the case of cinepazet by Formulas (1.6) and (1.7), respectively, as follows:

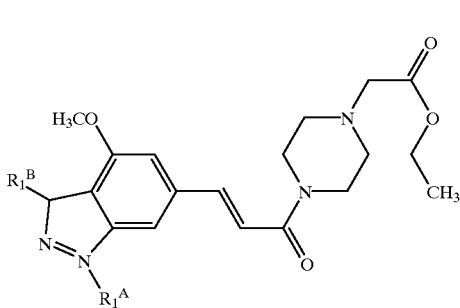

CINEPAZET
BIOISOSTERE (1.6)

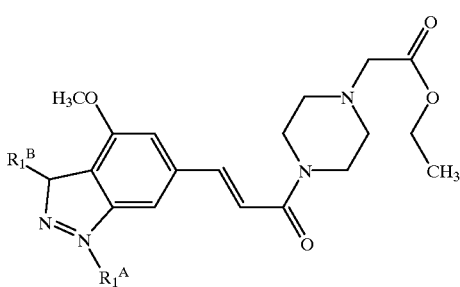

CINEPAZET
BIOISOSTERE
(EXCLUSIONARY)

(1.7)

Bioisosterism has often been viewed as arising from a reasonable expectation that a proposed bioisosteric replacement will result in maintenance of similar biological properties. Such a reasonable expectation may be based on structural similarity alone. This is especially true in those cases where a number of particulars are known regarding the characteristic domains of the receptor, etc. involved, to which the bioisosteres are bound or which works upon said bioisosteres in some manner. In the case of the present invention, however, there is a complete lack of such structural similarity, and the significant number of different therapeutic classes in which this indazole-for-catechol bioisostere replacement may be successfully employed belies any straightforward predictability. These various therapeutic classes will be reviewed briefly before being described in detail further below.

One class of catechol-containing compounds having significant pharmacological and therapeutic activity that is very well-known are the catecholamines. These catecholamines, typically epinephrine, norepinephrine and dopamine, are released by the sympathetic nervous system and by the adrenal medulla and perform an important function in the mammalian body by regulating innumerable aspects of its physiology, especially the myriad responses of said body to multiple stresses which it encounters every day. The chemical structure of norepinephrine is representative and may be illustrated by Formula (2.0):

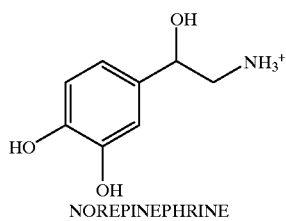

NOREPINEPHRINE (2.0)

Numerous sympathomimetic drugs, which act as agonists and antagonists for the receptors of said catecholamines utilize the catechol component as a key part of their overall chemical structure. The major classes of agonists and antagonists for said receptors of catecholamines, to which the indazole-for-catechol bioisostere replacement of the present invention is applicable, are described in the paragraphs which follow.

Cholinesterase inhibitors, i.e., anticholinesterase agents which have a catechol moiety as a central and characteristic portion of their overall chemical structure, are active in the inhibition of acetylcholinesterase, with the consequent accumulation of endogenous acetylcholine. As a result, such catechol-containing anticholinesterase agents have therapeutic utility in the treatment of glaucoma, the facilitation of gastrointestinal and bladder motility, and in combatting cognitive dysfunction and other aspects of Alzheimer's disease.

Acetylcholinesterase is the enzyme responsible for the breakdown of the neurotransmitter acetylcholine and thus in terminating its action at the junctions of various cholinergic nerve endings with their effector organs or postsynaptic sites. Anticholinesterase agents inhibit acetylcholinesterase and thereby cause acetylcholine to accumulate at cholinergic receptor sites. Their actions are thus cholinomimetic and produce effects equivalent to excessive stimulation of cholinergic receptors throughout the central and peripheral nervous systems. Cholinergic neurons are widely distributed in the body, and many anticholinesterase agents have been discovered to date, several of them being widely used as therapeutic agents.

Adrenergic $\alpha_1$-antagonists and $\beta_1$-agonists interact with certain of the four different catecholamine receptors in mammals, each of which has a distinctive response pattern.

These receptors have been designated the $\alpha_1$-, $\alpha_2$-, $\beta_1$-, and $\beta_2$-adrenergic receptors, and they occur in many different tissues and have various physiological effects. In particular, they play a very significant role in maintaining the activities of the sympathetic nervous system, which is responsible for mediating or regulating innumerable bodily functions. The areas controlled by the sympathetic nervous system are so essential and so diverse that it has long been the focus of medicinal chemists endeavoring to discover drugs which can antagonize, modify or even imitate its activity and thus become useful in the treatment of such important clinical conditions as hypertension, arrhythmias, cardiovascular shock, asthma, anaphylactic reactions, and migraine headaches.

For example, $\alpha_1$-adrenergic receptors may be found in the intestine where they are responsible for decreased motility, in the salivary glands where they regulate potassium and water secretion, in the iris of the eye where they play a role in contraction of the iris, in vascular smooth muscle where they mediate contraction, and in the tissue of the heart where they play a role in providing increased contractile force and in regulating the rhythm of heart muscle contractions.

The $\alpha_2$-adrenergic receptors are located in the stomach where they result in decreased motility, in fat cells where they cause decreased lipolysis, in blood platelets where they are part of the process of aggregation, in pancreatic $\beta$ cells where they have the effect of decreasing secretion, and in vascular smooth muscle where they regulate contraction. There are also tissues in which the particular $\alpha$-adrenergic receptor subtype has not yet been identified. These include the bladder sphincter where they effect contraction, and in arterioles found in the skin and mucosa, where they mediate constriction.

The $\beta_1$-adrenergic receptors occur in heart tissue where they provide increased rate, force and depth of contraction. The $\beta_2$-adrenergic receptors occur in bronchial and lung tissue where they produce muscle relaxation, in liver tissue where they mediate increased glycogenolysis, and in the intestine where they are also responsible for decreased motility.

The mediatory contribution of the $\alpha_1$-, $\alpha_2$-, $\beta_1$-, and $\beta_2$-adrenergic receptors in the body can be modified or eliminated by the use of therapeutic agents which have antagonistic activity. Such antagonists tend to nullify the action of the active agents, e.g., neurotransmitters such as dopamine, by being bound to said receptors without, however, eliciting a biological response. The inhibitory potency of an antagonist is largely a measure of the ability of said antagonist to be bound preferentially and tightly to said receptor so as to competitively displace the natural ligand for said receptor. Accordingly, a compound which has the essential structural features of a catecholamine or catechol that are required for it to be competitively bound to one or more of the $\alpha_1$-, $\alpha_2$-, $\beta_1$-, and $\beta_2$-adrenergic receptors, can function as a pharmaceutical active ingredient. Such an active ingredient would be suitable for the therapeutic treatment of any disease or condition whose treatment or prevention, or the amelioration of whose symptoms would tend to be accomplished by the antagonism, i.e., blockade of any one or more of the receptors for which a catecholamine or catechol type compound is the natural ligand in the body.

In the same manner, the mediatory contribution of the $\alpha_1$-, $\alpha_2$-, $\beta_1$-, and $\beta_2$-adrenergic receptors in the body can be modified or enhanced by the use of therapeutic agents which have agonist activity. Such agonists are structural analogs of catecholamines or catechols which bind productively to a receptor and mimic its biological activity. Thus, an agonist is comparable to an alternative substrate for an enzyme. The binding of the agonist to the receptor is productive in that the metabolic response which is evoked is comparable to that which would result if the natural ligand were bound to said receptor. Accordingly, in the case of agonists a compound which has the essential structural features of a catecholamine or catechol that are required for it not only to be bound to one or more of the $\alpha_1$-, $\alpha_2$-, $\beta_1$-, and $\beta_2$-adrenergic receptors, but also for it to be capable of producing a positive metabolic response, can function as a pharmaceutical active ingredient. Such an active ingredient would be suitable for the therapeutic treatment of any disease or condition whose treatment or prevention, or the amelioration of whose symptoms would tend to be accomplished by agonist activity, i.e., by being bound to any one or more of the receptors for which a catecholamine or catechol type compound is the natural ligand in the body, and further producing a positive metabolic response, usually of the type produced by said natural ligand.

An example of a $\beta_1$-agonist is the active therapeutic agent isoproterenol, which may be represented by Formula (3.0):

(3.0)

Calcium channel antagonists comprise numerous endogenous ligands acting on important calcium channel receptors and thereby carrying out essential metabolic, especially cardiovascular functions in the body. Calcium channel antagonists, particularly those of the verapamil type, have a catechol moiety as a central and characteristic portion of their overall chemical structure, and they are therapeutically useful in the area of antihypertensive treatment, and in the cardiovascular field they are especially useful, often having activity as antianginal and antiarrhythmic agents in addtion to their antihypertensive utility. Calcium channel antagonists are especially useful in the treatment of variant agina, exertional angina, unstable angina, hypertension, myocardial ischemia, arrhythmia, and migraine prophylaxis.

Other calcium channel antagonists and related compounds having a catechol moiety as an essential part of their overall chemical structure, for which the indazole bioisosteres of the present invention possess equivalent or improved biological activity, comprise gallopamil; fantofarone, which possesses calcium transport inhibitory properties, as well as bradycardic, hypotensive and antiadrenergic properties, for which the indazole replacement bioisosteres are useful in the treatment of angina pectoris, hypertension, arrhythmia and cerebral circulatory insufficiency, as well as in the antitumor field, where it is a potentiator of anticancer chemotherapeutic agents; trimetazidine, which is a peripheral vasodilator whose action is exerted both on the peripheral circulation and on the coronary arteries, a mechanism involving the smooth muscle fibers of the vessel walls of the circulatory system and not the autonomous nervous system, for which the indazole replacement bioisosteres are useful in treating various circulatory disorders such as arteritis or coronary insufficiency; lomerizine, for which the indazole replacement bioisosteres are useful as agents for improving cerebrovascular diseases of humans, and in particular are antimigraine agents; and zatebradine, for which the indazole replacement bioisosteres have long-lasting bradycardiac activity and reduce the oxygen requirements of the heart, with only slight side effects such as antimuscarinic activity.

Cerebrovascular diseases, which are beneficially treated with the indazole replacement bioisosteres of the present invention, include intracranial hemorrhages such as intracerebral hemorrhage or subarachnoid hemorrhage, as well as cerebral infarctions such as cerebral thrombosis or cerebral embolus, transient ischemic attack, and hypertensive encephalopathy. A key mechanism in these diseases is infaction of brain parenchymal tissue resulting directly from hemorrhage, thrombus, or an embolus within the brain, which leads in turn to glucose and oxygen insufficiency, depriving the neurons of needed sources of energy. Functional and organic disturbances result in the ischemic area. Consequently, the indazole replacement bioisosteres of the present invention act as therapeutic agents which supply or enhance the supply of glucose and oxygen to the ischemic area by increasing cerebral blood flow, and are, therefore, effective for the treatment and prevention of such cerebrovascular diseases.

Antineoplastic and antiproliferative agents of the present invention include indazole bioisostere replacement compounds based on trimetrexate, which is an antifolate, i.e., an inhibitor of dihydrofolate reductase, and related to methotrexate, which has provided consistent cure of choriocarcinoma. The indazole replacement bioisosteres based on trimetrexate are lipid-soluble folate antagonists which facilitate penetration of the blood-brain barrier. These bioisosteres may also be used in the therapy of psoriasis, a non-neoplastic disease of the skin characterized by abnormally rapid proliferation of epidermal cells, as well as for the beneficial treatment of *Pneumocystis carinii*.

Therapeutic agents of the present invention useful in the treatment of neoplastic diseases also comprise indazole replacement bioisosteres which are protein tyrosine kinase inhibitors. Protein tyrosine kinase inhibitors play a fundamental role in signal transduction pathways, and deregulated protein tyrosine kinase activity has been observed in many proliferative diseases such restenosis in addition to cancer and psoriasis. A number of tumor types have disfunctional growth factor receptor protein tyrosine kinases which result in inappropriate mitogenic signalling; consequently, the indazole replacement bioisosteres are useful for the therapeutic treatment of cancer based on their inhibition of protein tyrosine kinases including particularly epidermal growth factor-receptor protein tyrosine kinase (EGF-R PTK). Especially potent and selective inhibitors of epidermal growth factor-receptor protein tyrosine kinases are indazole replacement bioisosteres which are 4-anilino-quinazolines, e.g., the compound PD-153,035.

Indazole replacement bioisosteres of the present invention also include those wherein the 4-position is occupied by bicyclic aminoheteroaromatic moieties or by heterocyclyl-substituted-6,7-dimethoxy-quinazolines, e.g., those which are the indazole replacement equivalent of the dihydroindolyl compound CP-292,597. Also included are those where the anilino nitrogen is methylated or replaced by oxygen or sulfur; a phenoxyanilino moiety is used; or the analogous phenethylamino moiety is present. Further included are those bioisosteres which are selective EGF-R PTK inhibitors and are quinazoline derivatives which have various substituents in the anilino side chains, e.g., an ethynyl moiety as in the bioisostere equivalent of CP-358,774, or as in bioisosteres which are 4-indolyl compounds.

Modifications of the class of indazole replacement bioisostere comprising 4-anilino quinazoline moieties described above have not been limited to the 4-anilino group alone. Basic amino side chains have been used in the 6-position of the quinazoline ring and various substituents have been added to the 4-anilino moiety in order to improve solubility of the 4-anilino-quinazoline bioisosteres, as in the indazole replacement equivalent of ZD-1839.

Phosphodiesterase 4 (PDE4) inhibitors are another class of catechol-containing compounds having significant pharmacological activity Phosphodiesterase-4 is a cAMP-specific phosphodiesterase which plays an important role in the regulation of inflammatory and immune cell activation. A significant variety of different structural types of compounds active as PDE-4 inhibitors has been reported, and PDE isozymes have been characterized in cardiac muscle, and airway and arterial smooth muscles. Attention has also been focused on a high-affinity allosteric binding site which is abundant in brain PDE4 isozyme, whose differential modulation relative to the cAMP catalytic site has yielded drugs with greater therapeutic utility. Rolipram, which contains catechol as a key part of its overall chemical structure, is representative of this type of PDE4 inhibitor and may be depicted in accordance with Formula (4.0):

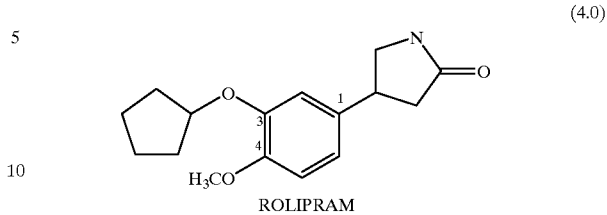

ROLIPRAM

Thus, the present invention as it relates to PDE4 inhibitors includes compounds having therapeutic usefulness based on the activity thereof as phosphodiesterase-4 inhibitors comprising an indazole as one essential component of their overall chemical structure, wherein said indazole constitutes a bioisosteric replacement of a catechol component or functional derivative thereof in a known compound having the same said therapeutic usefulness based on its activity as a phosphodiesterase-4 inhibitor and the same remaining said components of its overall chemical structure. In particular, this therapeutic usefulness includes treating asthma.

The present invention also includes a method of treating asthma using a known compound having a catechol moiety or functional derivative thereof as one essential component of its overall chemical structure, the improvement consisting of using a compound having an indazole moiety as one essential component of its overall chemical structure and having the same remaining said components of its overall chemical structure, wherein said indazole moiety constitutes a bioisosteric replacement for said catechol moiety, and wherein said compound is useful for treating asthma.

The present invention as it relates to PDE4 inhibitors also includes compounds useful in treating or preventing one or members selected from the groups of diseases and conditions consisting essentially of (1) inflammatory diseases and conditions comprising: joint inflammation, rheumatoid arthritis, rheumatoid spondylitis, osteoarthritis, inflammatory bowel disease, ulcerative colitis, chronic glomerulonephritis, dermatitis, and Crohn's disease; (2) respiratory diseases and conditions comprising: asthma, acute respiratory distress syndrome, chronic pulmonary inflammatory disease, bronchitis, chronic obstructive airway disease, and silicosis; (3) infectious diseases and conditions comprising: sepsis, septic shock, endotoxic shock, gram negative sepsis, toxic shock syndrome, fever and myalgias due to bacterial, viral or fungal infection, and influenza; (4) immune diseases and conditions comprising: autoimmune diabetes, systemic lupus erythematosis, graft vs. host reaction, allograft rejections, multiple sclerosis, .psoriasis, and allergic rhinitis; and (5) other diseases and conditions comprising: bone resorption diseases; reperfusion injury; cachexia secondary to infection or malignancy; cachexia secondary to human acquired immune deficiency syndrome (AIDS), human immunodeficiency virus (HIV) infectioin, or AIDS related complex (ARC); keloid formation; scar tissue formation; type 1 diabetes mellitus; and leukemia; wherein said compound comprises an inhibitor of phosphodiesterase isozyme 4 (PDE4).

Especially important among the above-recited diseases and conditions which may be treated using the indazole bioisostere replacement compounds of the present invention are the inflammatory diseases and conditions and the respiratory diseases and conditions. Among the inflammatory diseases and conditions which are especially significant with regard to successful treatment using the compounds of the present invention comprise: joint inflammation, rheumatoid arthritis, osteoarthritis, and inflammatory bowel disease. Among the respiratory diseases and conditions which are especially significant with regard to successful treatment using the compounds of the present invention comprise: asthma, acute respiratory distress syndrome, and bronchitis.

The expression "treating or preventing", as used herein with regard to the administration of the compounds of the present invention for therapeutic purposes in the case of various members selected from the many groups of diseases and conditions specifically recited herein, is intended to denote both the therapeutic objective of said administration as well as the therapeutic results actually achieved by said administration. The extent of therapy accomplished by administration of the compounds of the present invention may range from an amelioration to a significant diminishing of the course of the disease involved, and beyond to active treatment of said disease, including a reversal of the disease process itself which is present. The higher or highest degrees of therapeutic effectiveness result in the prevention of any injury, damage, deterioration, or loss of body tissues or organs and basic body functions subsequent to the early stages of degeneration and decline in said body tissues or organs and basic body functions at the onset of the disease involved.

The expression "the early stages of degeneration and decline in body tissues or organs and basic body functions" is intended to mean the very beginning of the initial pathologic changes in said body tissues or organs and basic body functions which define and are the result of a disease process. Said pathologic changes with respect to tissues and organs include changes in the composition and cohesiveness; form and makeup; rigidity, strength, resilience, elasticity, conformational integrity and stability, density, tensile strength and other measures of physical quality; abundance and extent of its presence throughout the body; viability and regenerative capability on both a micro- and macro-level; and the ability to successfully resist various kinds of external stresses including mechanical force and invasion by microorganisms; of said tissues and organs from that present before the onset of said disease process, which result in a degradation and decline of the beneficial and necessary properties characterizing said tissues and organs.

Pathologic changes with respect to body functions are those which inherently arise from the changes above-described with respect to said tissues and organs, and which also, consequently, result in a degradation and decline in the beneficial and necessary performance which characterizes the normal and proper operation of said body functions. These pathologic changes, both with regard to tissues or organs and with respect to body functions, especially include improper repair of the above-discussed early stages of degeneration and decline.

SUMMARY OF THE INVENTION (I) Bioisostere Replacement Compounds Active As Cholinesterase Inhibitors The present invention relates to the discovery that the indazole nucleus is a bioisostere replacement for the catechol moiety of numerous endogenous ligands acting on important cholinergic receptors and thereby carrying out essential metabolic functions in the body. The present invention relates in particular to indazole-for-catechol bioisostere replacements active as cholinergic antagonists and anticholinesterase agents, comprising a compound of Formulas (5.10) or (5.11):

(I)

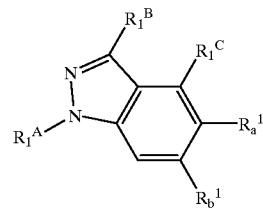

(5.10)

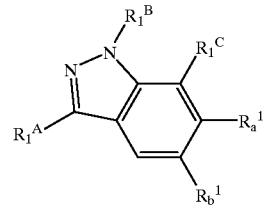

(5.11)

wherein
  $R^C_1$ is a member independently selected from the group consisting essentially of hydrogen; hydroxy; —O—($C_1$–$C_4$)alkyl; and phenyl substituted by 0 to 2 substituents $R^s$ where $R^s$ is a member independently selected from the group consisting essentially of Br, Cl, or F; ($C_1$–$C_4$)alkoxy; and $CF_3$
  $R^A_1$ is a member independently selected from the group consisting essentially of hydrogen; ($C_1$–$C_9$) alkyl; —$(CH_2)_n$($C_3$–$C_{10}$) cycloalkyl wherein n is 0 to 2; —($C_1$–$C_6$) alkyl($C_1$–$C_6$) alkoxy; ($C_2$–$C_6$) alkenyl; —$(CH_2)_n$($C_3$–$C_9$) heterocyclyl wherein n is 0 to 2; and —$(Z')_b(Z'')_c$($C_6$–$C_{10}$) aryl wherein b and c are each independently 0 or 1, Z' is ($C_1$–$C_6$) alkylene or ($C_2$–$C_6$) alkenylene, and Z'' is —O—, —S—, —$SO_2$, or —N($R^9$)—, and wherein said alkyl, alkenyl, alkoxyalkyl, heterocyclyl, and aryl moieties of said $R^A_1$ groups are substituted by 0 to 3 substituents independently selected from halo; hydroxy; ($C_1$–$C_5$) alkyl; ($C_2$–$C_5$) alkenyl; ($C_1$–$C_5$) alkoxy; ($C_3$–$C_6$) cycloalkoxy; trifluoromethyl; nitro; —C(=O)$OR^9$; —C(=O)$NR^9R^{10}$, —$NR^9R^{10}$, and —S(=O)$_2NR^9R^{10}$;
  wherein preferred embodiments, said aryl moiety comprises a membere selected from the group consisting essentially of phenyl; naphthyl; indenyl (from 2,3-dihydro-1H-indene); indanyl; and fluorenyl (from 9-H-fluorene);
  wherein more preferred embodiments said aryl moiety comprises a member independently selected from the group consisting essentially of phenyl and indanyl;
  where in preferred embodiments, said heterocyclyl moiety comprises a member independently selected from the group consisting essentially of acridinyl; benzimidazol; benzodioxolane; 1,3-benzodioxol-5-yl; benzo[b]furanyl; benzo[b]thiophenyl; benzoxazolyl; benzthiazolyl; carbazolyl; cinnolinyl; 2,3-dihydrobenzofuranyl; 1,3-dioxane; 1,3-dioxolane; 1,3-dithiane; 1,3-dithiolane; furanyl; imidazolidinyl; imidazolinyl; imidazolyl; 1H-indazolyl; indolinyl; indolyl; 3H-indolyl; isoindolyl; isoquinolinyl; isothiazolyl; isoxazolyl; morpholinyl; 1,8-naphthyridinyl; oxadiazolyl; 1,3-oxathiolane; oxazolidinyl; oxazolyl; oxiranyl; parathiazinyl; phenazinyl; phenothiazinyl; phenoxazinyl; phthalazinyl; piperazinyl; piperidinyl; pteridinyl; pyranyl; pyrazinyl; pyrazolidinyl; pyrazolyl; pyrazolo[1, 5-c]triazinyl; pyrazolyl; pyridazinyl; pyridyl; pyrimidinyl; pyrimidyl; pyrrolyl; pyrrolidinyl; purinyl; quinazolinyl; quinolinyl; 4H-quinolizinyl; quinoxalinyl; tetrazolidinyl; tetrazolyl; thiadiazolyl; thiazolidinyl; thiazolyl; thienyl; thiomorpholinyl; triazinyl; and triazolyl; and where in more preferred embodiments said heterocyclyl moiety comprises a member independently selected from the group consisting essentially of pyrrolidinyl, piperidinyl, piperazinyl, and morpholinyl;

$R^9$ and $R^{10}$ are independently hydrogen or $(C_1-C_4)$ alkyl substituted by 0 to 3 fluorine atoms;

$R^B_1$ is a member independently selected from the group consisting essentially of hydrogen; $(C_1-C_9)$ alkyl; $(C_2-C_3)$ alkenyl; phenyl; $(C_3-C_7)$ cycloalkyl; and —$(C_1-C_2)$ alkyl$(C_3-C_7)$ cycloalkyl; wherein said alkyl, alkenyl and phenyl $R^B_1$ groups are substituted with 0 to 3 substituents independently selected from the group consisting essentially of methyl; ethyl; trifluoromethyl; and halo; and $R^1_a$ and $R^1_b$ are each individually and independently a member selected from the group consisting essentially of hydrogen and the substituents defined by partial Formulas (5.12); (5.14); (5.16); (5.18); (5.19); (5.21); (5.23); (5.25); (5.26); and (5.28) below, provided that both of $R^1_a$ and $R^1_b$ cannot be hydrogen at the same time;

wherein preferred embodiments comprise compounds where one of $R^1_a$ and $R^1_b$ is independently selected as hydrogen; and wherein said substituents in addition to hydrogen which define each of $R^{1a}$ and $R^{1b}$ comprise a member independently selected from the group consisting essentially of the moieties of partial Formulas (5.12); (5.14); (5.16); (5.18); (5.19); (5.21); (5.23); (5.25); (5.26); and (5.28):

(I-A)

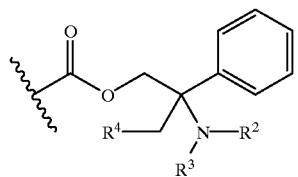

(5.12)

wherein $R^2$, $R^3$, and $R^4$ are independently selected from the group consisting essentially of hydrogen and $(C_1-C_4)$ alkyl substituted by 0 to 3 substituents $R^5$, where the substituent $R^5$ is selected from the group consisting essentially of fluorine, chlorine, methyl, trifluoromethyl hydroxy, and methoxy;

(I-B) $R^1_a$ is $R^6$ and $R^1_b$ is the group of partial Formula (5.14):

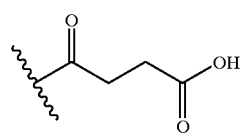

(5.14)

wherein $R^6$ is a member independently selected from the group consisting essentially of $(C_1-C_4)$ alkyl; $(C_1-C_4)$ alkoxy; and hydroxy;

(I-C)

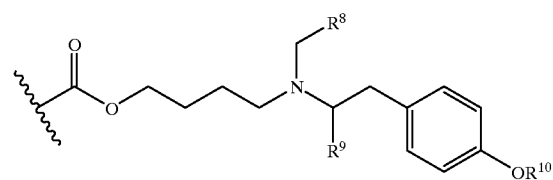

(5.16)

wherein $R^8$, $R^9$ and $R^{10}$ are independently selected from the group consisting essentially of hydrogen and $(C_1-C_4)$ alkyl substituted by 0 to 3 substituents is a member independently selected $R^5$, where the substituent $R^5$ is as defined herein.

(I-D) $R^1_a$ and $R^1_b$ are taken together to form the moiety of partial Formula (5.18):

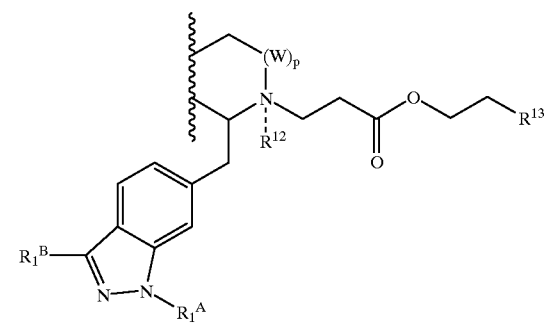

(5.18)

wherein p is 0 or p is 1 and W is —$CH_2$— or —NH—; $R^{12}$ is absent or is $(C_1-C_4)$alkyl; $R_1^A$ and $R_1^B$ are as defined herein; and $R^{13}$ is —$CH_3$ or is the remainder of the moiety of Formula (5.18) whereby a bis compound is formed as represented by partial Formula (5.19):

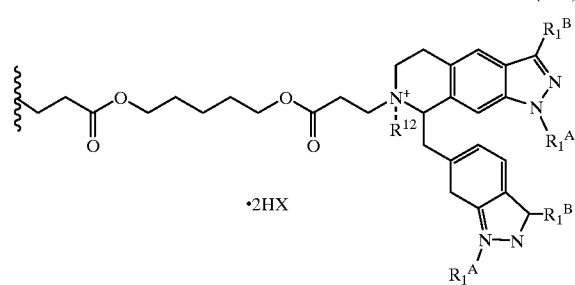

(5.19)

wherein HX is an acid addtion salt, (I-E)

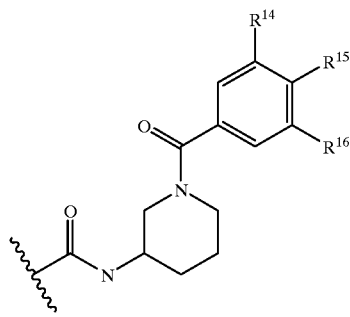

(5.21)

wherein $R^{14}$, $R^{15}$, and $R^{16}$ are each a member independently selected from the group consisting essentially of —$NH_2$; —$NH(C_1-C_4)$ alkyl; and —$N[(C_1-C_4)]alkyl_2$, where the alkyl groups are selected independently of each other, (I-F)

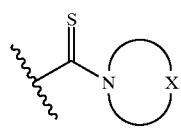

(5.23)

wherein the moiety

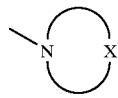

represents the residue of a saturated secondary heterocyclic base having 4, 5, 6, or 7 atoms in the ring, where X is —$CH_2$—, —O—, —S—, or —NH—; and preferably said secondary heterocyclic base is a member selected from the group consisting essentially of pyrrolidine, 1,3-thiazolidine, imidazolidine, 1,2-oxazolidine, 1,3-oxazolidine, piperidine, piperazine, tetrahydro-1,2-oxazine, tetrahydro-1,3-oxazine, tetrahydro-1,4-oxazine, i.e., morpholine, tetrahydro-1,4-thiazine, and perhydroazepine;

(I-G)

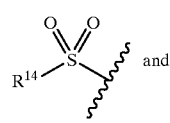

(5.25)

and

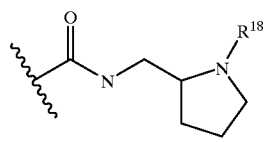

(5.26)

wherein $R^{14}$ is as defined herein; and $R^{18}$ is $(C_1-C_4)$ alkyl or $(C_2-C_4)$ alkenyl where said alkyl and alkenyl groups are substituted by 0 to 3 substituents $R^5$, where the substituent $R^5$ is selected from the group consisting essentially of fluorine, chlorine, methyl, trifluoromethyl hydroxy, and methoxy;

(I-H) $R^1_a$ and $R^1_b$ are taken together to form the moiety:

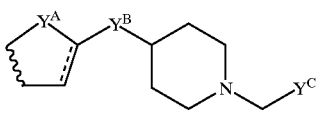

(5.28)

wherein the dashed line represents an optional double bond; $Y^A$ is —C(=O)—; —C(=O)NH—; or —C(=O)N($CH_3$)—; $Y^B$ is a member selected from the group consisting essentially of a direct single bond; a direct double bond; —$CH_2$—; —$CH_2CH_2$—; —$CH_2CH_2CH_2$—; =CH—; =CHCH$_2$—; =CHCH$_2$CH$_2$CH$_2$, =CHCH$_2$CH$_2$CH$_2$CH$_2$—; and =CH—CH=CH—; and $Y^C$ is a member selected from the group consisting essentially of cyclohexyl; phenyl substituted by 0 to 3 $R^{20}$ where $R^{20}$ is a member selected from the group consisting essentially of methyl, methoxy, hydroxy, benzyloxy, and nitro; pyridyl; 1-naphthyl; 2-naphthyl.

(II) Bioisostere Replacement Compounds Active As Adrenergic $\alpha_1$-Antagonists and $\beta_1$-Agonists The subject matter of the present invention relates to all and every indazole-for-catechol bioisostere replacement involving adrenergic receptor agonists and antagonists, and particularly the $\alpha_1$-antagonist and $\beta_1$-agonist classes of adrenergic agents which have a catechol moiety as a central and characteristic portion of their overall chemical structure. The present invention relates to both novel indazole compounds resulting from the indazole-for-catechol bioisostere replacement, as well as to the replacements as a general class or genus of chemical compounds. The present invention further relates to the corresponding therapeutic methods of treatment which utilize said novel indazole compounds as the active therapeutic agent, and to the corresponding pharmaceutical compositions which utilize said novel indazole compounds as the active ingredient therein.

The present invention relates in particular to indazole-for-catechol bioisostere replacements active as adrenergic $\alpha_1$-antagonists and $\beta_1$-agonists, comprising a compound of Formulas (6.22) or (6.23):

(II)

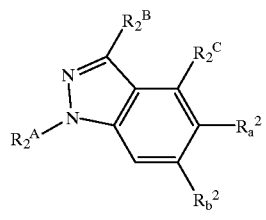

(6.22)

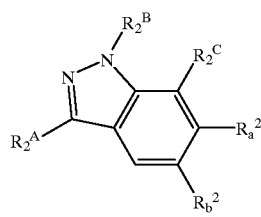

(6.23)

wherein
  $R^C_2$ and $R^A_2$ and $R^B_2$ are defined the same as $R^C_1$ and $R^A_1$ and $R^B_1$ herein under Formulas (5.10) and (5.11), but are selected on an independent basis therefrom; and $R^2_a$ and $R^2_b$ are each individually and independently a member selected from the group consisting essentially of hydrogen and the substituents defined by partial Formulas (6.24), (6.26), (6.41), (6.43), (6.48), and (6.50) below, provided that both of $R^2_a$ and $R^2_b$ cannot be hydrogen at the same time;

wherein preferred embodiments comprise compounds where one of $R^2_a$ and $R^2_b$ is independently selected as hydrogen; and wherein said substituents in addition to hydrogen which define each of $R^2_a$ and $R^2_b$ comprise a member independently selected from the group consisting essentially of the moieties of partial Formulas (6.24), (6.26), (6.41), (6.43), (6.48), and (6.50):

(II-A)

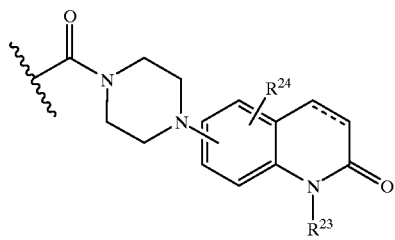

(6.24)

wherein the dashed line represents an optional double bond; $R^{23}$ is a member selected from the group consisting essentially of hydrogen; $(C_1-C_4)$ alkyl, $(C_2-C_4)$ alkenyl, and phenyl$(C_1-C_4)$ alkyl-, where said alkyl, alkenyl, and phenyl or alkyl group attached thereto are substituted by 0 to 3 substituents $R^5$, where the substituent $R^5$ is as defined herein, but independently selected therefrom; and $R^{24}$ is a member selected from the group consisting essentially of hydrogen and $(C_1-C_4)$ alkoxy;

(II-B) $R^2_a$ and $R^2_b$ are taken together to form the moiety of partial Formula (6.26):

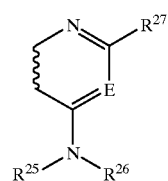

(6.26)

wherein E represents N, resulting in a pyrimidinyl moiety and overall a quinazoline series of compounds; or represents CH, resulting in a pyridyl moiety and overall a quinoline series of compounds; $R^{25}$ and $R^{26}$ are each a member independently selected from the group consisting essentially of hydrogen; $(C_1-C_6)$ alkyl $(C_2-C_6)$ alkenyl; $(C_3-C_8)$ cycloalkyl; hydroxy$(C_1-C_6)$ alkyl; phenyl; benzyl; phenylethyl; and 2-furfuryl; and $R^{27}$ is independently selected from the group consisting essentially of:

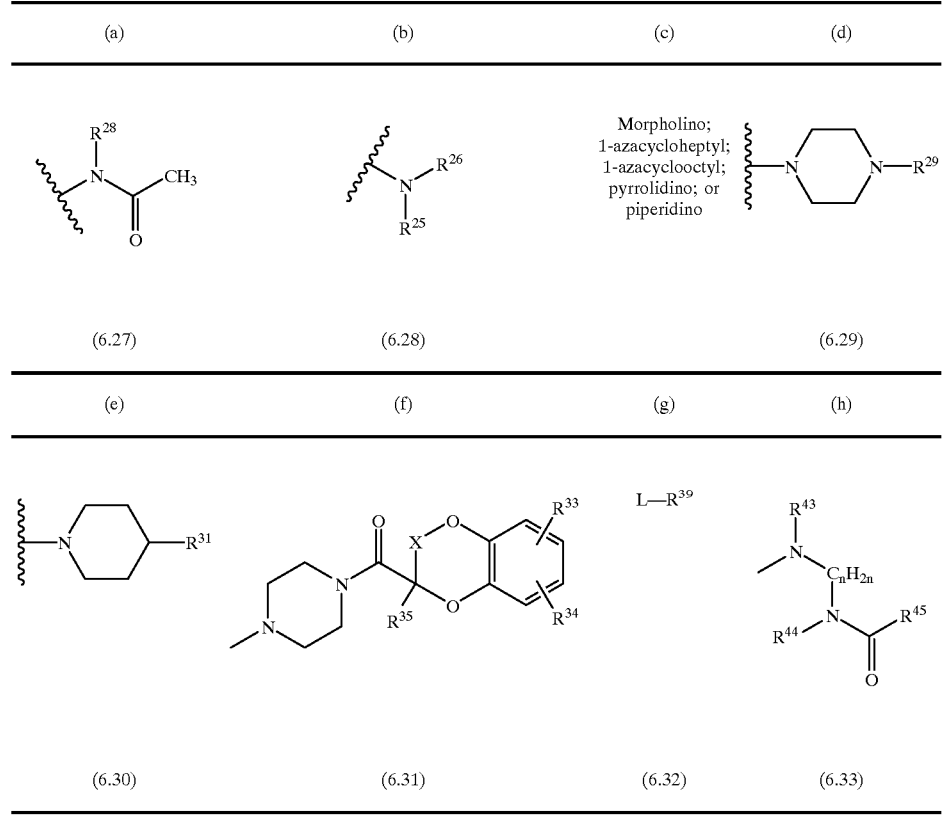

(II-C)

(6.41)

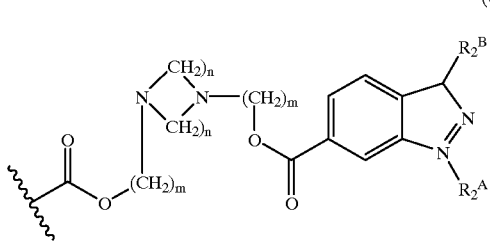

wherein m is an integer independently selected from 2 and 3 in each instance of its occurrence; n is an integer selected from 2, 3, and 4; p is an integer selected from 2 and 3; and n and p together represent a total which is an integer selected from 5, 6, and 7;

(II-D)

(6.43)

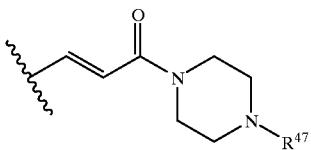

wherein $R^{47}$ is a member independently selected from the group consisting essentially of:
- (a) $(C_1–C_4)$ alkyl optionally substituted by 1 or 2 hydroxyl groups; phenyl$(C_1–C_4)$ alkyl- optionally substituted on the phenyl portion thereof by 1 or 2 hydroxyl groups; and cinnamyl;
- (b) —$CH_2C(=O)NHR^{48}$ where $R^{48}$ is a member independently selected from the group consisting essentially of $(C_1–C_4)$ alkyl; and phenyl optionally substituted by $(C_1–C_4)$ alkoxy, trifluoromethyl, fluoro, bromo, or chloro;
- (c) —$CH_2C(=O)NHR^{49}R^{50}$ where $R^{49}$ and $R^{50}$ are each defined the same as $R^{48}$; but are selected on an independent basis therefrom;
- (d) a radical of partial Formula (6.44):

(6.44)

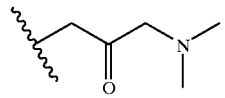

wherein the nitrogen atom forms part of a heterocyclic radical selected from the group consisting essentially of morpholino; hexamethylene-imino; and pyrrolidino; and
- (e) —$CH_2C(=O)OR^{51}$ where $R^{51}$ is hydrogen or $(C_1–C_4)$ alkyl;

(II-E)

(6.48)

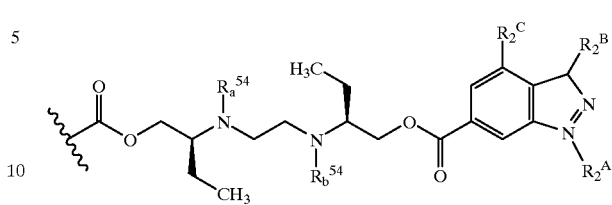

wherein $R^C_2$ is a member independently selected from the group consisting essentially of hydrogen; hydroxy; and —O—$(C_1–C_4)$ alkyl, in accordance with whether an inclusionary or exclusionary bioisostere is intended; and $R^{54}_a$ and $R^{54}_b$ are independently selected from the group consisting essentially of $C_nH_{2n+1}$ where n is an integer selected from 1, 2, 3, and 4; and (II-F)

(6.50)

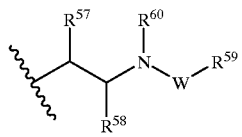

wherein
$R^{57}$ is a member independently selected from the group consisting essentially of hydrogen; $(C_1–C_2)$ alkyl; and hydroxy;
$R^{58}$ is a member independently selected from the group consisting essentially of hydrogen; and $(C_1–C_2)$ alkyl;
W is —$C(R^{64})(R^{65})$—; —$CH(R^{64})CH(R^{65})$—; or —$CH(R^{64})CH(R^{65})CH_2$—, where $R^{64}$ is a member independently selected from the group consisting essentially of hydrogen and methyl; and $R^{65}$ is a member independently selected from the group consisting essentially of hydrogen, methyl, and hydroxy;
$R^{59}$ is a member selected independently from the group consisting essentially of hydrogen; methyl; phenyl; and benzoyl; where said phenyl and benzoyl groups are optionally substituted by a member independently selected from the group consisting essentially of m-hydroxy; p-hydroxy; m- and p-dihydroxy; m-$(C_1–C_2)$ alkyl; $(C_1–C_3)$ alkoxy; fluoro; chloro; cyano; hydroxymethyl; acetyl; and o-allyl; and
$R^{60}$ is a member independently selected from the group consisting essentially of hydrogen; and methyl.

(III) Bioisostere Replacement Compounds Active As Calcium Channel Antagonists

The present invention relates to the discovery that the indazole nucleus is a moiety which is capable of being an bioisostere replacement for the catechol moiety where it is an essential part of numerous endogenous ligands acting on important calcium channel receptors and thereby carrying out essential metabolic, especially cardiovascular functions in the body. Calcium channel antagonists, particularly those of the verapamil, type have such a catechol moiety as a central and characteristic portion of their overall chemical structure, and they are therapeutically useful in the area of antihypertensive treatment, and in the cardiovascular field they are especially useful, often having activity as antianginal and antiarrhythmic agents in addtion to their antihypertensive utility.

In accordance with the present invention the indazole nucleus is a biobioisostere replacement for the catechol moiety which is an essential part of calcium channel antagonists including especially verapamil, which have been and in the future will be created and developed for therapeutic treatments, as detailed further herein. The present invention relates to both novel indazole compounds resulting from the indazole-for-catechol bioisostere replacement in such calcium channel antagonists, as well as to the replacements as a general class or genus of chemical compounds. The present invention further relates to the corresponding therapeutic methods of treatment which utilize said novel indazole compounds as the active therapeutic agent, and to the corresponding pharmaceutical compositions which utilize said novel indazole compounds as the active ingredient therein.

In a preferred embodiment, the present invention relates in particular to indazole-for-catechol bioisostere replacements active as calcium channel antagonists, and in particular to those relating to verapamil and verapamil types of compounds, comprising a compound of Formulas (7.22) or (7.23):

(III)

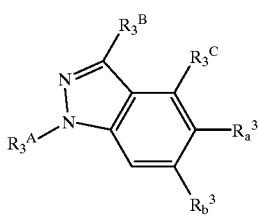
(7.22)

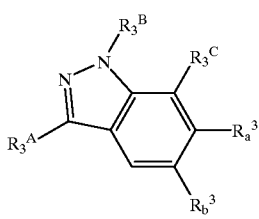
(7.23)

wherein $R^C_3$ and $R^A_3$ and $R^B_3$ are defined the same as $R^C_1$ and $R^A_1$ and $R^B_1$ herein under Formulas (5.10) and (5.11), but are selected on an independent basis therefrom; and $R^3_a$ and $R^3_b$ are each individually and independently a member selected from the group consisting essentially of hydrogen and the substituents defined by partial Formulas (7.25); (7.28); (7.35); and (7.41) below, provided that both of $R^3_a$ and $R^3_b$ cannot be hydrogen at the same time;

wherein preferred embodiments comprise compounds where one of $R^3_a$ and $R^3_b$ is independently selected as hydrogen; and wherein said substituents in addition to hydrogen which define each of $R^3_a$ and $R^3_b$ comprise a member independently selected from the group consisting essentially of the moieties of partial Formulas (7.24); (7.25); (7.28); (7.35); and (7.41):

(III-A)

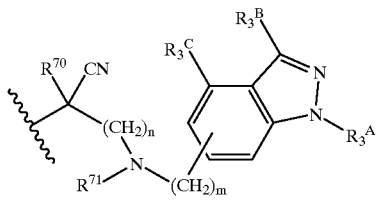
(7.24)

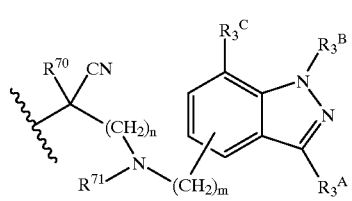
(7.25)

wherein $R^{70}$ is a member independently selected from the group consisting essentially of hydrogen; $(C_1-C_4)$ alkyl; phenyl; benzyl; and cyclohexyl; $R^{71}$ is a member independently selected from the group consisting essentially of $(C_1-C_4)$ alkyl; n is an integer independently selected from 2, 3, and 4; and m is an integer independently selected from 1, 2, and 3;

(III-B)

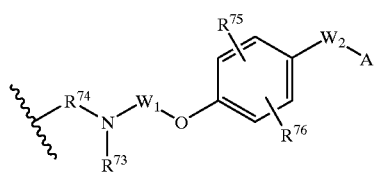
(7.28)

wherein $R^{73}$ is a member independently selected from the group consisting essentially of hydrogen and $(C_1-C_4)$ alkyl; $R^{74}$ is a member independently selected from the group consisting essentially of a single bond and a linear- or branched-alkylene radical $(C_1-C_5)$ alkyl; $W_1$ is a member independently selected from the group consisting essentially of straight- and branched-alkylene radicals $(C_2-C_5)$ alkyl, and 2-hydroxypropylene; $R^{75}$ and $R^{76}$ are members independently selected from the group consisting essentially of hydrogen, methyl, ethyl, chloro, and bromo, $W_2$ is a member independently selected from the group consisting essentially of —S—, —SO—, and —SO$_2$—; and A is a member indpendently selected from the group consisting essentially of (a)

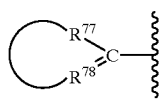
(7.29)

wherein $R^{77}$ and $R^{78}$ are taken together with the carbon atom to which they are attached to form an optionally aromatic mono- or di-cyclic carbocyclic group having from 5 to 10 carbon atoms and optionally substituted in the α-position with respect to the methylene group of partial Formula (7.29) by $R^{84}$ as defined below; an optionally aromatic 5-membered heterocyclic group where the heteroatoms or hetero groups are members independently selected from the group consisting essentially of O, S, N, —N(R$^{79}$)—, O together with N, O together with —N(R$^{79}$)—, S together with N, S together with —N(R$^{79}$)—, N together with N, and N together with —N(R$^{79}$)—, optionally substituted in the ca-position with respect to the methylene group of partial Formula (7.29) by R$^{84}$ as defined below, where R$^{79}$ is hydrogen, (C$_1$–C$_4$) alkyl, or phenyl; or an optionally aromatic 6- to 10-membered mono- or di-cyclic heterocyclic group, where the heteroatoms or heterogroups are members independently selected from the group consisting essentially of O, S, N, —N(R$^{79}$)—, O together with N, O together with —N(R$^{79}$)—, S together with N, S together with —N(R$^{79}$)—, N together with N, and N together with —N(R$^{79}$)—, optionally substituted in the α-position with respect to the methylene group of partial Formula (7.29) by R$^{84}$ as defined below, where R$^{79}$ is hydrogen, (C$_1$–C$_4$) alkyl, or phenyl;

(b)

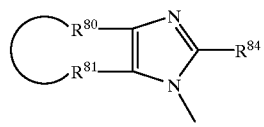

(7.30)

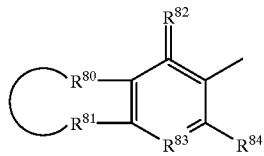

(7.31)

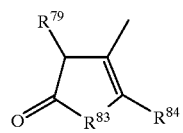

(7.32)

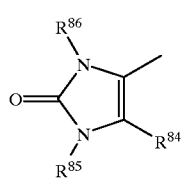

(7.33)

wherein

R$^{80}$ and R$^{81}$ are members independently selected from the group consisting essentially of hydrogen; (C$_1$–C$_4$) alkyl; phenyl; and taken together with the carbon atom to which they are attached represent an optionally aromatic 6-membered carbocyclic ring; R$^{82}$ is O or S; R$^{83}$ is O; S; or —N(R$^{79}$)—; R$^{84}$ is a member independently selected from the group consisting essentially of hydrogen; (C$_1$–C$_4$) alkyl; (C$_3$–C$_7$) cycloalkyl; benzyl; and phenyl optionally substituted with 1 to 3 substituents selected from the group consisting essentially of fluoro, chloro, bromo, (C$_1$–C$_4$) alkyl, (C$_1$–C$_4$) alkoxy, and nitro; and R$^{85}$ and R$^{86}$ are members independently selected from the group consisting essentially of hydrogen; (C$_1$–C$_4$) alkyl; and benzoyl;

(III-C)

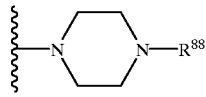

(7.35)

wherein R$^{88}$ is hydrogen or a group of partial Formula (7.36):

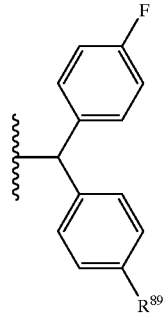

(7.36)

where R$^{89}$ is hydrogen or fluorine;

(III-D)

R$^3_a$ and R$^3_b$ are taken together to form the moiety of partial Formula (7.41):

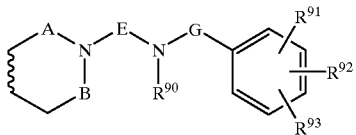

(7.41)

wherein A is —CH$_2$CH$_2$—; —CH=CH—; —NH—C(=O)—; —CH$_2$—C(=O)—; or —C(R$^{94}$)=N— where R$^{94}$ is (C$_1$–C$_3$) alkyl; and B is methylene; carbonyl; or thiocarbonyl; or A is —C(=O)—C(=O)—; —N=CH—; —CH(OH)—C(=O)—; —CH(OH)—CH$_2$—; —C(=NOH)—C(=O)—; or —CH(NHR$^{95}$)—C(=O)—, where R$^{95}$ is hydrogen or (C$_1$–C$_3$) alkyl substituted by phenyl, methoxyphenyl, or dimethoxyphenyl; and B is methylene; E is a member independently selected from the group consisting essentially of n-(C$_2$–C$_4$) alkylene, optionally substituted by (C$_1$–C$_3$) alkyl, 2-hydroxy-n-propylene, 2-hydroxy-n-butylene or 3-hydroxy-n-butylene; G is a member independently selected from the group consisting essentially of n-(C$_1$–C$_5$) alkylene, optionally substituted by (C$_1$–C$_3$) alkyl, where one methylene group of an n-alkylene of 2 to 5 carbon atoms may be replaced by a carbonyl group, with the proviso that B represents a methylene or carbonyl group, or methylene-n-hydroxyalkylene of 1 to 4 carbon atoms, where the methylene group is attached to the nitrogen atom; R$^{90}$ is a member independently selected from the group consisting essentially of hydrogen; (C$_1$–C$_3$) alkyl; phenyl(C$_1$–C$_3$) alkyl; (C$_1$–C$_3$) alkanoyl; (C$_1$–C$_3$) alkoxycarbonyl; and (C$_3$–C$_5$) alkenyl; and R$^{91}$, R$^{92}$, and R$^{93}$ are each a member independently selected from the group consisting essentially of hydrogen; fluorine; chlorine; bromine; hydroxy; cyano; nitro; trifluoromethyl (C$_1$–C$_4$) alkyl; (C$_1$–C$_4$) alkoxy; (C$_1$–C$_3$) alkylamino; di(C$_1$–C$_3$) alkylamino; (C$_1$–C$_3$) alkanoylamino; (C$_1$–C$_3$) alkoxycarbonylamino; bis(C$_1$–C$_3$)

alkoxycarbonylamino; (trifluoromethyl)methylamino; and (trifluoromethyl)ethylamino; and $R^{91}$ and $R^{92}$ taken together with each other are $(C_1-C_2)$ alkylenedixoy.

(IV) Bioisostere Replacement Compounds Active As Antineoplastic Agents

Antineoplastic agents in which bioisosteric replacement of indazole-for-catechol may be carried out in accordance with the present invention are described herein. An example of the catechol-containing antineoplastic agents and their derivatives which have a catechol moiety which may be replaced with the indazole bioisostere moiety while maintaining or improving the biological property of the catechol containing predecessor compound, is trimetrexate. The manner in which such a bioisostere replacement is constructed is illustrated in Formulas (8.0), (8.1), and (8.2):

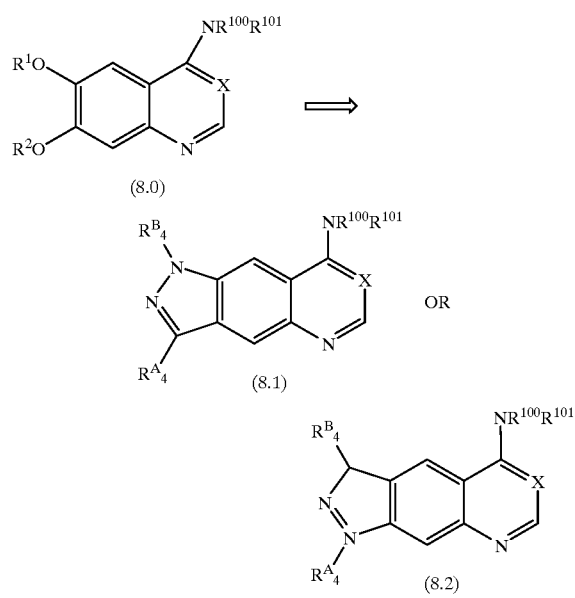

The indazole nucleus is capable of being a bioisostere replacement for the catechol moiety where it is an essential part of numerous endogenous ligands acting on important receptors and signal transduction pathways which are essential to the unwanted proliferation of many types of tissue, including especially neoplasms and psoriasis, a non-neoplastic disease of the skin characterized by abnormally rapid proliferation of epidermal cells. Antineoplastic agents, especially trimetrexate and protein tyrosine kinase inhibitors, particularly those of the 4-anilino-quinazoline type, have such a catechol moiety as a central and characteristic portion of their overall chemical structure, and they are therapeutically useful in the area of antineoplastic treatment, as well as in the treatment of hyperproliferative conditions such as psoriasis.

In accordance with the present invention the indazole nucleus is a biobioisostere replacement for the catechol moiety which is an essential part of antineoplastic and antiproliferative agents, including especially trimetrexate, and 4-anilino-quinazolines such as PD-153,035; CP-292,597; CP-358,774; and ZD-1839, which have been and in the future will be created and developed for therapeutic treatments, as detailed further herein. The present invention relates to both novel indazole compounds resulting from the indazole-for-catechol bioisostere replacement in such antineoplastic and antiproliferative agents, as well as to the replacements as a general class or genus of chemical compounds. The present invention further relates to the corresponding therapeutic methods of treatment which utilize said novel indazole compounds as the active therapeutic agent, and to the corresponding pharmaceutical compositions which utilize said novel indazole compounds as the active ingredient therein.

The present invention relates in particular to indazole-for-catechol bioisostere replacements active as antineoplastic and antiproliferative agents, and in particular to those relating to trimetrexate, and 4-anilino-quinazolines such as PD-153,035; CP-292,597; CP-358,774; and ZD-1839, comprising a compound of Formulas (8.21) or (8.22):

(IV)

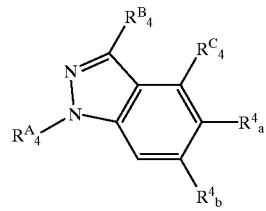

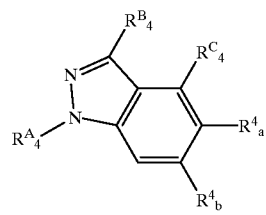

wherein $R^C_4$ and $R^A_4$ and $R^B_4$ are defined the same as $R^C_1$ and $R^A_1$ and $R^B_1$ herein under Formulas (5.10) and (5.11), including preferred embodiments thereof, but are selected on an independent basis therefrom; and $R^4_a$ and $R^4_b$ are each individually and independently a member selected from the group consisting essentially of hydrogen and the substituents defined by partial Formulas (8.23); (8.28); (8.40); and (8.45) below, provided that both of $R^4_a$ and $R^4_b$ cannot be hydrogen at the same time;

wherein preferred embodiments comprise compounds where one of $R^4_a$ and $R^4_b$ is independently selected as hydrogen; and wherein said substituents in addition to hydrogen which define each of $R^4_a$ and $R^4_b$ comprise a member independently selected from the group consisting essentially of the moieties of partial Formulas (8.23); (8.28); (8.40); and (8.45):

(IV-A)

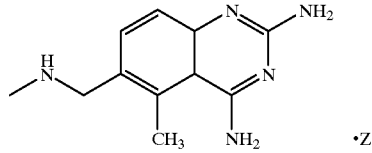

wherein Z is 2-hydroxyethanesulfonic acid or glucuronic acid, as well as pharmaceutically acceptable prodrugs and metabolites thereof;

(IV-B) $R^4_a$ and $R^4_b$ are taken together to form the moiety of partial Formula (8.28):

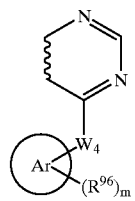

(8.28)

wherein Ar a substituted or unsubstituted mono- or bi-cyclic aryl or heteroaryl ring system of from 5 to 12 atoms where each monocyclic ring may contain 0 to 3 heteroatoms, and each bicyclic ring may contain 0 to 4 heteroatoms selected from N, O, and S, provided said heteroatoms are not vicinal oxygen and/or sulfur atoms; $W_4$ is a member independently selected from the group consisting essentially of a bond; —O—; —S—; —S(=O)—; —S(=O)$_2$—; —OCH$_2$—; —C=C—, —C≡C—; —C(=S)—; —SCH$_2$—; —NH—; —NHCH$_2$—; —NHCH($R^{97}$)—, —N($R^{97}$)— or —N($R^{97}$)CH$_2$— where $R^{97}$ is (C$_1$–C$_4$) alkyl; —CH$_2$—CH$_2$—, and —CH$_2$—CH$_2$—CH$_2$—; m is an integer selected from 0, 1, 2, and 3; and $R^{96}$ is a member independently selected from the group consisting essentially of hydrogen; —(C$_1$–C$_4$) alkyl; —(C$_2$–C$_4$) alkenyl; -phenyl; phenyl(C$_1$–C$_3$) alkyl-; phenyl(C$_2$–C$_3$) alkenyl-; -hydroxy; hydroxy(C$_1$–C$_4$) alkyl-; —(C$_1$–C$_4$) alkoxy; (C$_1$–C$_3$) alkoxy(C$_1$–C$_2$) alkyl-; phenyl (C$_1$–C$_3$) alkoxy-; phenyloxy-; (C$_1$–C$_4$) alkylcarbonyloxy-; phenylcarbonyloxy-; bromo, chloro, or fluoro; (bromo, chloro, or fluoro)(C$_1$–C$_3$) alky-; -nitro; -cyano; -amino; mono- or di-(C$_1$–C$_4$) alkylamino-; (C$_1$–C$_4$) alkylcarbonylamino-; phenylcarbonylamino-; -carboxy; carboxy(C$_1$–C$_3$) alkyl-; (C$_1$–C$_3$) alkoxycarbonyl-; phenyl (C$_1$–C$_3$) alkoxycarbonyl; (C$_1$–C$_3$) alkoxycarbonyl(C$_1$–C$_3$) alkyl-; amino(C$_1$–C$_3$) alkoxy-; amido; mono- and di-(C$_1$–C$_3$) alkylamido; N,N—(C$_1$–C$_3$) cycloalkylamido-; (C$_1$–C$_3$) alkylthio-; (C$_1$–C$_3$) alkylsulfinyl-; -sulfonyl; mono- and di-(C$_1$–C$_3$) alkylsulfonyl-; -sulfamoyl; mono- and di-(C$_1$–C$_3$) alkylsulfamoyl-; (bromo, chloro, or fluoro)phenyl-; benzoyl; and provided that m is 1, azido and $R^{94}_a$-ethynyl, where $R^{94}_a$ is hydrogen or (C$_1$–C$_6$)alkyl substituted by 0 to 2 substituents where said substituent is a member independently selected from the group consisting essentially of hydrogen; amino; hydroxy; $R^{94}_b$—O; $R^{94}_b$—NH; and ($R^{94}_b$)$_2$—N, where $R^{94}_b$ is (C$_1$–C$_4$) alkyl;

(IV-C)

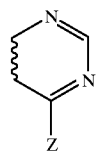

(8.40)

wherein Z is a moiety of partial Formulas (8.41) and (8.42):

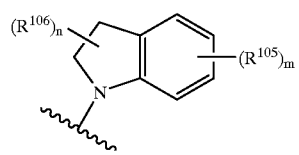

(8.41)

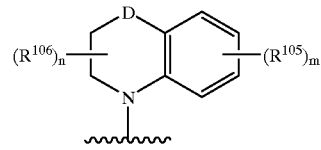

(8.42)

wherein m is an integer selected from 0, 1, 2, 3, and 4; n is an integer selected from 0, 1, and 2; D is saturated carbon; oxy; or thio; $R^{105}$ is a member independently selected, for each occurrence in partial Formulas (8.41) and (8.42), from the group consisting essentially of mono-, di-, or tri-fluoromethyl; bromo, chloro, or fluoro; nitro; hydroxy; amino; azido; isothiocyano; (C$_1$–C$_4$) alkyl; phenyl; thienyl; (C$_1$–C$_4$) alkoxy; benzyloxy; phenoxy; (C$_2$–C$_6$) alkenyl; (C$_2$–C$_6$) alkynyl; (C$_1$–C$_4$) alkylenedioxy; cyano; benzoylamino; trifluoromethylcarbonylamino; (C$_1$–C$_4$) alkanoylamino; (C$_1$–C$_4$) alkanoyl-N-mono- or —N,N-di-(C$_1$–C$_4$) alkylamino; (C$_1$–C$_4$) alkylsulfonylamino; trifluoromethylsulfonylamino; (C$_1$–C$_4$) alkylthio; (C$_1$–C$_4$) alkylsulfinyl; (C$_1$–C$_4$) alkylsulfonyl; pyrrol-1-yl; piperidin-1-yl; and pyrrolidin-1-yl; where said phenyl, benzyloxy, phenoxy and benzoylamino groups are optionally mono-substituted with a member independently selected from the group consising essentially of bromo, chloro, or fluoro; nitro; trifluoromethyl; hydoxy; and (C$_1$–C$_4$) alkyl; and where said (C$_1$–C$_4$) alkylenedioxy is linked at both ends thereof to adjacent carbons of the benzene moiety to which it is attached; $R^{106}$, when it is not attached to a ring carbon which is adjacent to an oxy, thio or —N— ring atom, is a member independently selected, for each occurrence in partial Formulas (8.41) and (8.42), from the group consisting essentially of hydroxy; amino; N-mono- or N,N-di-(C$_1$–C$_4$) alkylamino; sulfo; and (C$_1$–C$_4$) alkoxy; and $R^{106}$, when it is attached to a ring carbon which is adjacent to an oxy, thio or —N— ring atom, is a member independently selected, for each occurrence in partial Formulas (8.41) and (8.42), from the group consisting essentially of carboxy; hydroxy(C$_1$–C$_4$) alkyl; (C$_1$–C$_4$) alkoxy (C$_1$–C$_4$) alkyl; amino(C$_1$–C$_4$) alkyl; mono-N— and di-N,N—(C$_1$–C$_4$) alkylamino(C$_1$–C$_4$) alkyl; morpholino(C$_1$–C$_4$) alkyl; 4-(C$_1$–C$_4$) alkyl-piperazin-1-yl(C$_1$–C$_4$) alkyl; carboxy(C$_1$–C$_4$) alkyl; (C$_1$–C$_4$) alkoxycarbonyl; sulfo(C$_1$–C$_4$) alkyl; and (C$_1$–C$_4$) alkyl;

(IV-D) $R^4_a$ and $R^4_b$ are taken together to form the moiety of partial Formula (8.45):

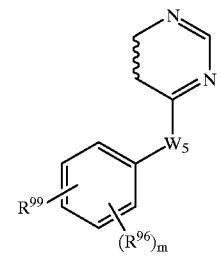

(8.45)

wherein $R^{96}$ and m are as defined under (IV-C) above, but are selected on an independent basis therefrom; $W_5$ is —Y—CH$_2$—; —CH$_2$—Y—; or —Y—; where Y is O, S(O)$_q$ where q is an integer selected from 0, 1, and 2, or NR$^{100}$ where R$^{100}$ is hydrogen or (C$_1$–C$_8$) alkyl; and R$^{99}$ is a group —ZR$^{101}$— where Z is joined to R$^{101}$ through a bridging group (CH$_2$)$_p$ where p is an integer selected from 0, 1 and 2; and Z is a member independently selected from the group consisting essentially of —V—CH$_2$—, —V—CF$_2$—, —CH$_2$—V—, —CF$_2$—V—, and —V—, where V is a hydrocarbyl group containing 0, 1, or 2 carbon atoms; carbonyl; —CH(OH)—; sulfonamide; amide; —O—; —S(O)$_q$—; and —NR$^{102}$ where R$^{102}$ is hydrogen or (C$_1$–C$_4$) alkyl; and R$^{101}$ is optionally substituted (C$_3$–C$_7$) cycloalkyl; or an optionally substituted 5,6,7,8,9, or 10-membered carbocyclic or heterocyclic moiety where said carbocyclic moiety is a member independently selected from the group consisting essentially of phenyl; benzyl; indene; naphthalene; tetralin; decalin; cyclopentyl; cyclohexyl; and cycloheptyl; and said heterocyclic moiety is a member independently selected from the group consisting essentially of furan; dioxolane; thiophene; pyrrole; imidazole; pyrrolidine; pyran; pyridine; pyrimidine; morpholine; piperidine; oxazoline; oxazolidine; thiazole; thiadiazole; benzofuran; indole; isoindole; quinazoline; quinoline; and isoquinoline; or R$^{99}$ is a group —ZR$^{101}$— where Z is —NR$^{102}$, and —NR$^{102}$ and R$^{101}$ together form a 5, 6, 7, 8, 9, or 10-membered heterocyclic moiety as defined under R$^{101}$ above.

(V) Bioisostere Replacement Compounds Active As PDE4 Inhibitors

This particular embodiment of the present invention relates to compounds having therapeutic usefulness based on their activity as phosphodiesterase-4 inhibitors, comprising an indazole-for-catechol bioisosteric replacement wherein said therapeutic usefulness is equivalent to or an improvement over the same activity possessed by the corresponding catechol-containing predecessor compound. In a preferred embodiment of this aspect of the present invention, the indazole-for-catechol bioisostere replacement compounds are therapeutically useful in treating asthma.

The indazole replacement bioisostere compounds of the present invention are useful in treating or preventing one or members selected from the groups of diseases and conditions consisting essentially of (1) inflammatory comprising: joint inflammation, rheumatoid arthritis, rheumatoid spondylitis, osteoarthritis, inflammatory bowel disease, ulcerative colitis, chronic glomerulonephritis, dermatitis, and Crohn's disease; (2) respiratory comprising: acute respiratory distress syndrome, bronchitis, chronic obstructive pulmonary disease (COPD), including asthma, chronic bronchitis and pulmonary emphysema; and silicosis; (3) infectious comprising: sepsis, septic shock, endotoxic shock, gram negative sepsis, toxic shock syndrome, fever and myalgias due to bacterial, viral or fungal infection, and influenza; (4) immune comprising: autoimmune diabetes, systemic lupus erythematosis, graft vs. host reaction, allograft rejections, multiple sclerosis, psoriasis, and allergic rhinitis; and (5) general comprising: bone resorption diseases; reperfusion injury; cachexia secondary to infection or malignancy; cachexia secondary to human acquired immune deficiency syndrome (AIDS), human immunodeficiency virus (HIV) infectioin, or AIDS related complex (ARC); keloid formation; scar tissue formation; type 1 diabetes mellitus; and leukemia; wherein said compounds are inhibitors of phosphodiesterase isozyme 4 (PDE4).

A further embodiment of the present invention relates in particular to indazole-for-catechol bioisostere replacements active as PDE4 inhibitors, especially inhibitors useful in treating asthma and other respiratory and inflammatory diseases and conditions, comprising a compound of Formulas (9.0) and (9.1):

(V)

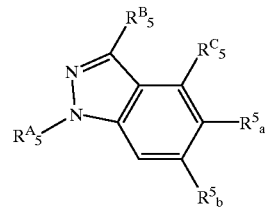

(9.0)

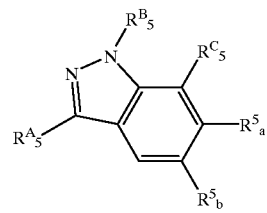

(9.1)

and pharmaceutically acceptable salts thereof, wherein:

R$^C_5$ is a member independently selected from the group consisting essentially of hydrogen; hydroxy; —O—(C$_1$–C$_4$) alkyl —O—(C$_1$–C$_4$) alkyl(C$_1$–C$_2$) alkoxy; and —O—(C$_1$–C$_4$) alkyl-morpholino;

R$^A_5$ is a member independently selected from the group consisting essentially of hydrogen, (C$_1$–C$_9$) alkyl; —(CH$_2$)$_n$(C$_3$–C$_{10}$) cycloalkyl wherein n is an integer selected from 0, 1, and 2; (C$_1$–C$_6$) alkoxy(C$_1$–C$_6$) alkyl; (C$_2$–C$_6$) alkenyl; —(CH$_2$)$_n$(C$_3$–C$_9$) heterocyclyl wherein n is selected from 0, 1, and 2; and —(Z$^1$)$_b$(Z$^2$)$_c$ (C$_6$–C$_{10}$) aryl wherein b and c are integers independently selected from 0 and 1, Z$^1$ is (C$_1$–C$_6$) alkylene or (C$_2$–C$_6$) alkenylene, and Z$^2$ is O, S, SO$_2$, or NR$^{119}$; and further wherein said heterocyclyl is a member independently selected from the group consisting essentially of acridinyl; benzimidazolyl; benzodioxolane; 1,3-benzodioxol-5-yl; benzo[b]furanyl; benzo[b]thiophenyl; benzoxazolyl; benzthiazolyl; carbazolyl; cinnolinyl; 2,3-dihydrobenzofuranyl; 1,3-dioxane; 1,3-dioxolane; 1,3-dithiane; 1,3-dithiolane; furanyl; imidazolidinyl; imidazolinyl; imidazolyl; 1H-indazolyl; indolinyl; indolyl; 3H-indolyl; isoindolyl; isoquinolinyl; isothiazolyl; isoxazolyl; morpholinyl; 1,8-naphthyridinyl; oxadiazolyl; 1,3-oxathiolane; oxazolidinyl; oxazolyl; oxiranyl; parathiazinyl; phenazinyl; phenothiazinyl; phenoxazinyl; phthalazinyl; piperazinyl; piperidinyl; pteridinyl; pyranyl; pyrazinyl; pyrazolidinyl; pyrazolinyl; pyrazolo[1,5-c]triazinyl; pyrazolyi; pyridazinyl; pyridyl; pyrimidinyl; pyrimidyl; pyrrolyl; pyrrolidinyl; purinyl; quinazolinyl; quinolinyl; 4H-quinolizinyl; quinoxalinyl; tetrazolidinyl; tetrazolyl; thiadiazolyl; thiazolidinyl; thiazolyl; thienyl; thiomorpholinyl; triazinyl; and triazolyl; wherein said aryl is a carbocyclic moiety which is a member independently selected from the group consisting essentially of benzyl; cis- and trans-decahydronaphthalenyl; 2,3-1H-dihydroindenyl (indanyl); indenyl; 1-naphthalenyl; 2-naphthalenyl; phenyl; and 1,2,3,4-tetrahydronaphthalenyl; wherein said alkyl, alkenyl, alkoxyalkyl, heterocyclyl, and aryl moieties defining said R$^A_5$ groups are substituted by 0 to 3 substituents where each said substituent comprises a member independently selected from the group consisting essentially of bromo, chloro, or fluoro; hydroxy; $(C_1-C_5)$ alkyl; $(C_2-C_5)$ alkenyl; $(C_1-C_5)$ alkoxy; $(C_3-C_6)$ cycloalkoxy; mono-, di-, and tri-fluoromethyl; nitro; $-C(=O)OR^{119}$, $-C(=O)NR^{119}R^{120}$, $-NR^{119}R^{120}$ and $-S(=O)_2NR^{119}R^{120}$;

$R^B{}_5$ is a member independently selected from the group consisting essentially of hydrogen; $(C_1-C_9)$ alkyl; $(C_2-C_3)$ alkenyl; phenyl; $(C_3-C_7)$ cycloalkyl; and $(C_3-C_7)$ cycloalkyl$(C_1-C_2)$ alkyl; wherein said alkyl, alkenyl and phenyl moieties defining said $R^8{}_5$ groups are substituted by 0 to 3 substituents where each said substituent comprises a member independently selected from the group consisting essentially of methyl; ethyl; mono-, di-, and tri-fluoromethyl; and bromo, chloro, or fluoro;

$R^5{}_a$ and $R^5{}_b$ are independently selected from the group consisting essentially of hydrogen and hereinafter recited substituents, provided that one, but not both of $R^5{}_a$ and $R^5{}_b$ must be independently selected as hydrogen, wherein said substituents comprise moieties of partial Formulas (V-A)—(9.2)-(9.5); (V-B)—(9.6)-(9.14); (V-C)—(9.16)-(9.35); (V-D)—(9.36); and (V-E)—(9.37)-(9.49):

(V-A)

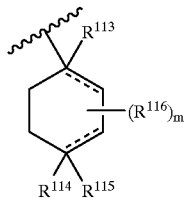
(9.2)

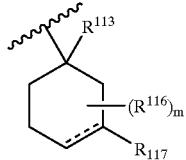
(9.3)

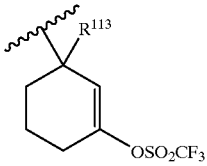
(9.4)

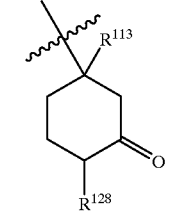
(9.5)

or, said substituents defining $R^5{}_a$ and $R^5{}_b$ comprise:
(V-B)
a member selected from the group consisting essentially of $R^{229}$; $-C(=O)NR^{222}(CHR^{222})_mC(=O)NR^{222}O(CH_2)_q(C_6-C_{10})aryl)$; $-C(=NR^{242})NH(CH_2)_p(C_6-C_{10})$ aryl; $-C(=O)NR^{218}(CHR^{222})_mC(=O)$ $NR^{222}(CH_2)_pOR^{222}$; $-C(=O)NR^{222}(CHR^{222})_mS(C_1-C_4)$ alkyl; $-C[=NOC(=O)R^{235}]R^{236}$; $-CR^{227}R^{228}CHR^{238}NR^{219}SO_2(CH_2)_pA$; $-CR^{227}R^{228}CHR^{238}NR^{219}P(=O)(OR^{222})C(=O)(C_1-C_4)$ alkyl; $-CR^{227}R^{238}CHR^{238}NR^{219}P(=O)[(C_1C_4) alkoxy]_2$, $-Z^3-R^{217}$; and $-(CR^{227}R^{228})_mNR^{219}(C(O))_qR^{220}$ wherein p is an integer selected from 0, 1, and 2; m is an integer selected from 1, 2, 3, 4, 5, and 6; and q is an integer selected from 1 and 2;

or, said substituents defining $R^5{}_a$ and $R^5{}_b$ comprise:
a moiety of partial Formulas (9.6) through (9.14), inclusive:

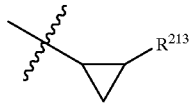
(9.6)

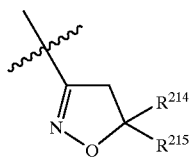
(9.7)

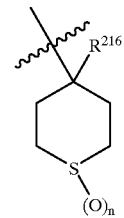
(9.8)

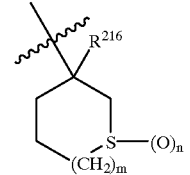
(9.9)

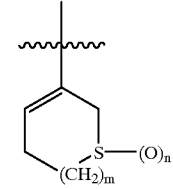
(9.10)

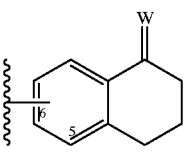
(9.11)

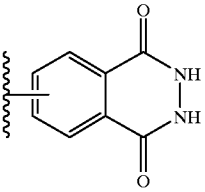
(9.12)

(9.13)
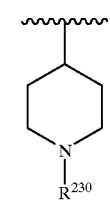

(9.14)
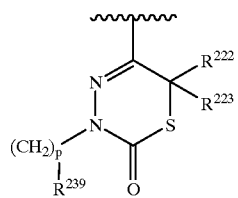

(V-C)
or, said substituents defining $R^5_a$ and $R^5_b$ comprise:
  a member independently selected from the group consisting essentially of 2-oxo-4-pyrrolyl; pyrazolyl; 2-oxo-3,4-dihydro-5-pyrimidyl; 2-oxo-3,4-dihydro-4-pyrimidyl; 2-oxo-tetrahydro-4-pyrimidyl; 2-oxo-tetrahyro-5-pyrimidyl; 2-oxo-4-pyrimidyl; and 2-oxo-5-pyrimidyl; wherein each of said $R^2_a$ and $R^2_b$ groups is substituted by 0, 1, 2, 3, or 4 $R^{236}$ groups;
or, said substituents defining $R^5_a$ and $R^5_b$ comprise:
  a moiety of partial Formulas (9.16) through (9.35), inclusive:

(9.16)
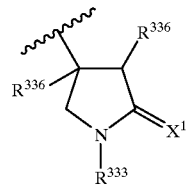

(9.17)
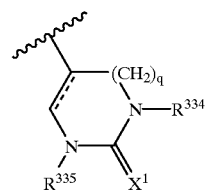

(9.18)
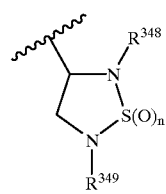

(9.19)
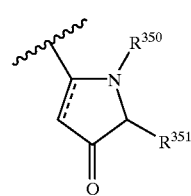

(9.20)
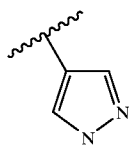

(9.21)
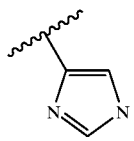

(9.22)
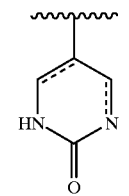

(9.23)
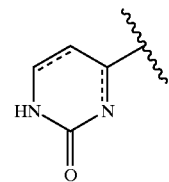

(9.24)
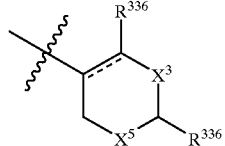

(9.25)
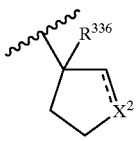

(9.26)
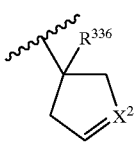

(9.27)
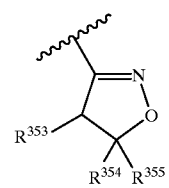

-continued (9.28) 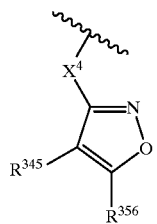

(9.29) 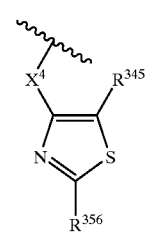

(9.30) 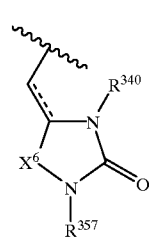

(9.31) 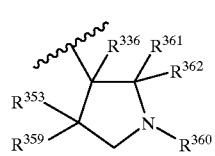

(9.32) 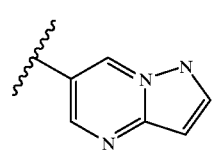

(9.33) 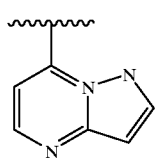

(9.34) 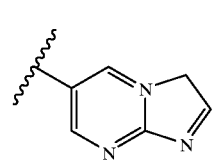

(9.35) 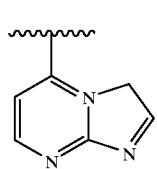

(V-D) or, said substituents defining $R^5_a$ and $R^5_b$ comprise: a moiety of partial Formula (9.36):

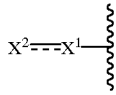

(9.36)

wherein
the broken line indicates a single or double bond;
$X^1$ is —$CR^{472}R^{473}$— where said broken line indicates a single bond; or —$CR^{473}$— where said broken line indicates a double bond;
$X^2$ is —$CR^{475}R^{477}R^{478}$— or —$C(=NOR^{481})R^{482}$— where said broken line indicates a single bond; or —$CR^{477}R^{478}$ where said broken line indicates a double bond;
$R^{472}$ is a member independently selected from the group consisting essentially of H; hydroxy; bromo, chloro, or fluoro; and —$OR^{479}$;
each $R^{473}$ is a member independently selected from the group consisting essentially of cyano; cyanomethyl; benzyloxy; —$R^{475}$; —$CO_2R^{475}$; —$CO_2(CH_2)_n$ $(C_6–C_{10})$ aryl; —$C(Y)NR^{475}R^{476}$; —$C(Y)NR^{475}$ $(CH_2)_n(C_6–C_{10})$ aryl; —$(CH_2)_n(C_6–C_{10})$ aryl; and —$(CH_2)_n$(5- to 10-membered heteroaryl); where n is an integer selected from 0, 1, 2, and 3; each $R^{473}$ group is substituted by 0 to 3 substituents $R^{474}$; and each $R^{473}$ group is substituted by 0 or 1 substituent $R^{480}$;
each $R^{474}$ is a member independently selected from the group consisting essentially of bromo, chloro, or fluoro; cyano; nitro; $(C_1–C_6)$ alkyl; $(C_2–C_6)$ alkenyl; —$OR^{475}$; $(C_3–C_7)$ cycloalkoxy; $NR^{475}R^{476}$; —$NR^{475}OR^{476}$; —$S(O)_mR^{475}$ where m is an integer selected from 0, 1, and 2; —$CO_2R^{475}$, —$C(=O)$ $R^{475}$; —$SO_2NR^{475}R^{476}$; —$C(=O)NR^{475}R^{476}$; —$CR^{475}R^{476}SO_2NR^{475}R^{476}$; —$CR^{475}R^{476}C(=O)$ $NR^{475}R^{476}$; —$NHSO_2R^{475}$; —$NHSO_2NR^{475}R^{476}$; —$NHC(=O)NR^{475}R^{476}$; —$NHC(=O)(C_1–C_6)$ alkyl; and —$NHC(=O)O(C_1–C_6)$ alkyl);
each $R^{475}$ and $R^{476}$ is a member independently selected from the group consisting essentially of H; and $(C_1–C_6)$ alkyl;
$R^{477}$ is a member independently selected from the group consisting essentially of —$R^{473}$; 2-oxo-pyridyl; 3-oxo-pyridyl; 4-oxo-pyridyl; 2-oxo-pyrrolyl; 4-oxo-thiazolyl; 4-oxo-piperidyl; 2-oxo-quinolyl; 4-oxo-quinolyl; 1-oxo-isoquinolyl; 4-oxo-oxazolyl; 5-oxo-pyrazolyl; 5-oxo-isoxazolyl; and 4-oxo-isoxazolyl; where each of said $R^{477}$ groups is substituted by 0 to 3 substituents $R^{474}$;
$R^{478}$ is a member independently selected from the group consisting essentially of —$R^{475}$; cyano; —$(CH_2)_p(C_6–C_{10})$ aryl; and —$(CH_2)_p$(5- to 10-membered heteroaryl); where p is an integer selected from 1, 2, and 3; and where each said $R^{478}$ group is substituted by 0 to 3 substituents $R^{474}$;
$R^{479}$ is a member independently selected from the group consisting essentially of formyl; carbamoyl; thiocarbamyl; $(C_1–C_6)$ alkyl; $(C_2–C_6)$ alkenyl; $(C_1–C_4)$ alkoxy$(C_1–C_4)$ alkyl-; and $(C_1–C_6)$ alkanoyl; where said alkyl moieties of each of said $R^{479}$ groups is substituted by 0 to 3 substituents independently selected from the group consisting essentially of bromo, chloro, or fluoro; hydroxy; and $(C_1–C_4)$ alkoxy;

$R^{480}$ is a member independently selected from the group consisting essentially of cyclobutyl; cyclopentyl; cyclohexyl; 2-cyclobuten-1-yl; 2-cyclopenten-1-yl; 3-cyclopenten-1-yl; 2,4-cyclopentadien-1-yl; 3,5-cyclohexadien-1-yl; pyrrolyl; pyrrolidinyl; dioxolanyl; imidazolyl; oxazolyl; imidazolidinyl; pyrazolyl; pyrazolidinyl; pyranyl; piperidinyl; 1,4-dioxanyl; morpholinyl; 1,4-dithianyl; thiomorpholinyl; piperazinyl; 1,3,5-trithianyl; oxazinyl; isoxazinyl; oxathiazinyl; and oxadiazinyl; where each of said $R^{480}$ groups is substituted by 0 to 2 ($C_1$–$C_2$) alkyl;

$R^{481}$ is a member independently selected from the group consisting essentially of H; ($C_1$–$C_6$) alkyl; ($C_2$–$C_6$) alkenyl; ($C_2$–$C_6$) alkynyl; —C(Y)NR$^{475}$R$^{476}$; —C(Y)NH($C_6$–$C_{10}$) aryl; —C(Y)($C_1$–$C_6$) alkoxy; —C(Y)($C_6$–$C_{10}$) aryloxy; and —C(Y)($C_1$–$C_6$) alkyl);

$R^{482}$ is a member independently selected from the group consisting essentially of phenyl and pyridinyl; where each of said $R^{482}$ groups is substituted by 0 to 3 substituents independently selected from the group consisting essentially of bromo, chloro, or fluoro; ($C_1$–$C_4$) alkyl; hydroxy; ($C_1$–$C_4$) alkoxy; —NR$^{475}$R$^{476}$; and —S(O)$_m$R$^{475}$, where m is an integer selected from 0, 1, and 2; and, Y is O or S; or or, said substituents defining $R^5_a$ and $R^5_b$ comprise:

a moiety of partial Formulas (9.37) through (9.49), inclusive:

(V-E)

(9.37)
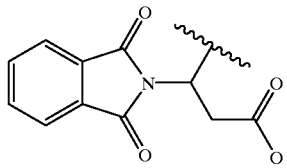

(9.38)
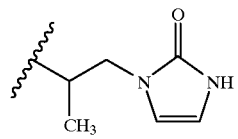

(9.39)
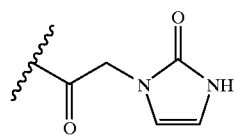

(9.40)
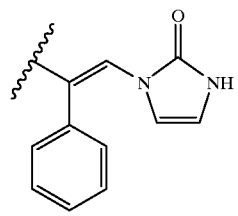

(9.41)
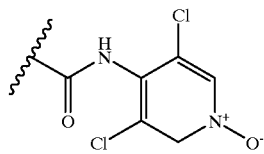

(9.42)
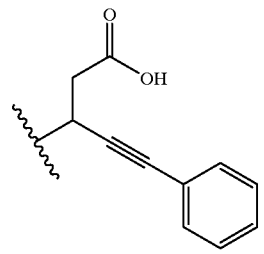

(9.43)
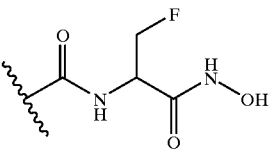

(9.44)
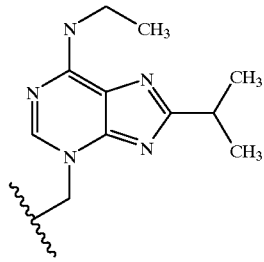

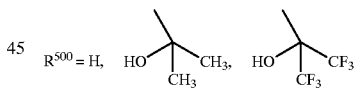

(9.45)
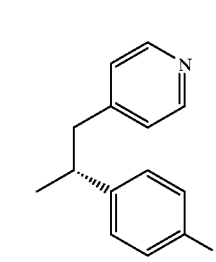

(9.46)
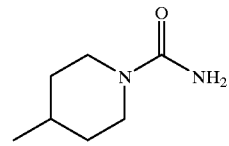

-continued (9.47)

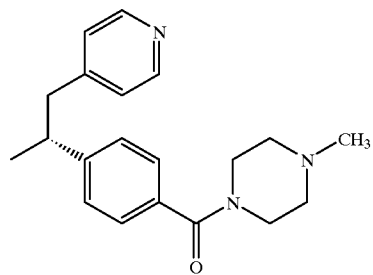

(9.48)

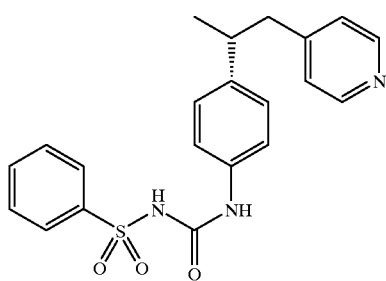

DETAILED DESCRIPTION OF THE INVENTION (I) Bioisostere Replacement Compounds Active As Cholinesterase Inhibitors There are several important therapeutic classes of cholinergic antagonists, especially cholinesterase inhibitor which have a catechol moiety as a central and characteristic portion of their overall chemical structure for which a bioisostere replacement with an indazole moiety may be carried out in accordance with the present invention, wherein the resulting indazole-containing containing compounds have the same or improved biological activity with the same or reduced undesirable side effects, as that exhibited by the catechol-containing compound.

One such important therapeutic class is that of catechol-containing cholinergic muscarinic receptor antagonists which are used as antispasmodic or spasmolytic agents such as trimebutine, trepibutone, mebeverine, and atracurium besylate, which may be represented respectively by Formulas (5.0), (5.1), (5.2), (5.3):

(5.0)

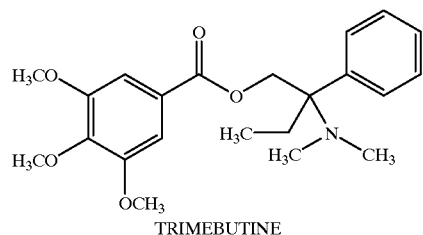

TRIMEBUTINE (5.1)

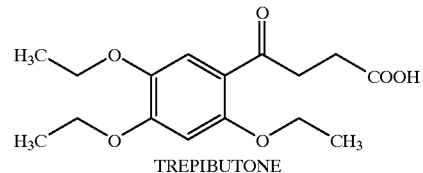

TREPIBUTONE (5.2)

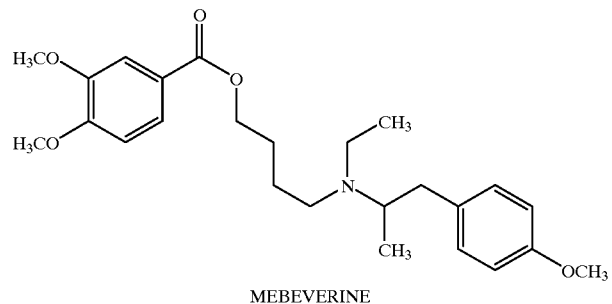

MEBEVERINE

-continued

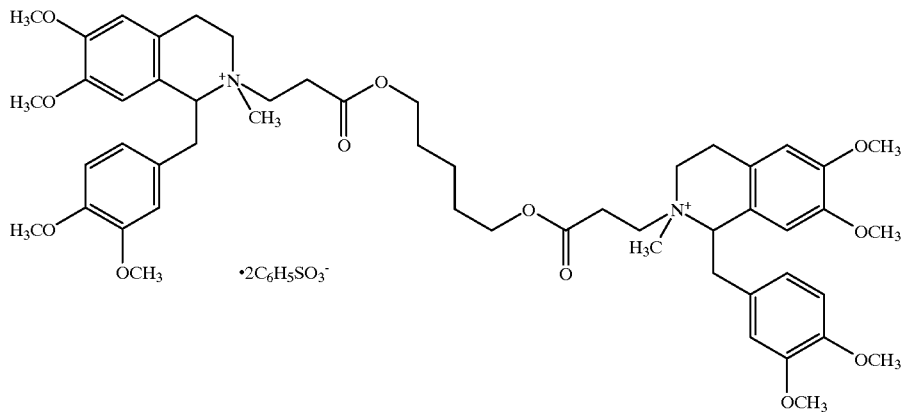

ATRACURIUM BESYLATE

All of these specific agents, and derivatives thereof, have a catechol moiety which may be replaced by an indazole moiety in accordance with the present invention.

These catechol-containing cholinergic muscarinic receptor antagonist are also useful as antiulcerative agents and include, e.g., troxipide and trithiozine, which may be represented by Formulas (5.4) and (5.5):

(5.4)

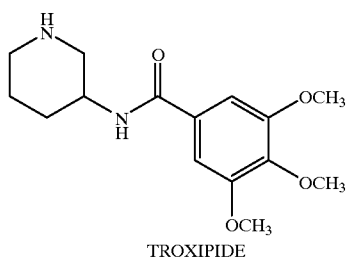

TROXIPIDE (5.5)

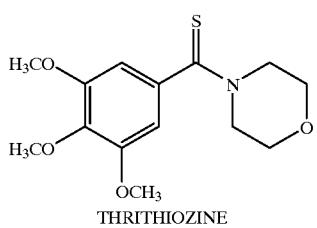

THRITHIOZINE

These agents and derivative thereof, have a catechol moiety which may be replaced with the indazole bioisostere moiety in accordance with the present invention. The catechol-containing cholinergic muscarinic receptor antagonists further include therapeutic agents useful in ophthalmology, e.g., as mydriatic agents, which can be the subject of an indazole bioisostere replacement in accordance with the present invention.

A still further class of catechol-containing cholinergic therapeutic agents suitable for indazole bioisostere replacement comprises dopaminergic receptor antagonists such as veralipride which is useful in the treatment of menopausal disorders. Veralipride may be represented by Formula (5.6):

(5.4)

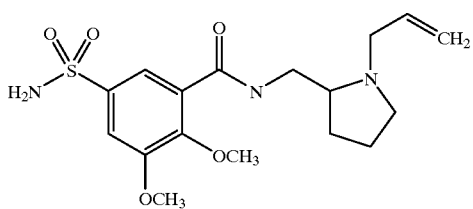

VERALIPRIDE

An important class of catechol-containing acetylcholinesterase inhibitors are those useful in the treatment of Alzheimer's disease, especially cognitive dysfunction associated therewith. A deficiency of structurally intact cholinergic neurons is characteristic of Alzheimer's disease, and therapy is based on enhancing concentrations of cholinergic neurotransmitters in the central nervous system. These catechol-containing anticholinesterase agents are suitable for indazole bioisostere replacement in accordance with the present invention. For example, the agent donepezil which has a catechol-containing structure may be represented by Formula (5.7):

(5.7)

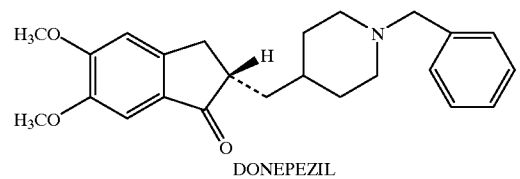

DONEPEZIL

In order to better understand the bioisostere replacement of the catechol moiety with an indazole moiety in accordance with the present invention, the bioisostere of donepezil in which indazole is substituted for catechol, is represented by the compounds of Formulas (5.8) and (5.9):

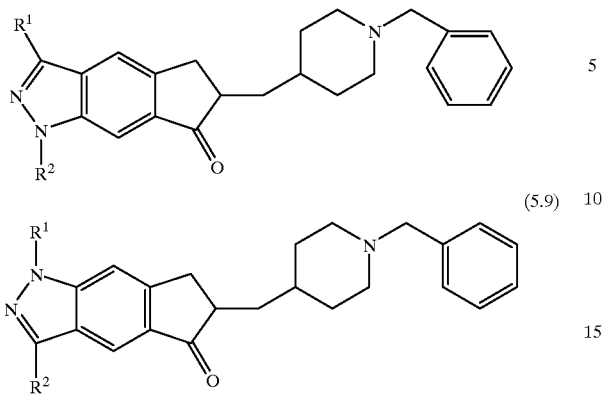

Other catechol-containing anticholinesterase agents of a type similar to donepezil which are also suitable for indazole bioisostere replacement in accordance with the present invention are described in U.S. Pat. No. 4,895,841 which is incorporated herein by reference in its entirety.

The subject matter of the present invention includes within its scope all and every indazole-for-catechol bioisostere replacement relating to cholinergic antagonists and anticholinesterase agents, both as novel indazole compounds in particular and as said replacements in general. Also included within the scope of the present invention are the therapeutic methods of treatment and the pharmaceutical compositions relating thereto in which the active ingredient is an indazole-for-catechol bioisostere replacement compound, and in preferred embodiments of the present invention is as described in more detail further below.

Accordingly, the present invention relates in particular to indazole-for-catechol bioisostere replacements active as cholinergic antagonists and anticholinesterase agents, comprising a compound of Formulas (5.10) or (5.11):

(I)

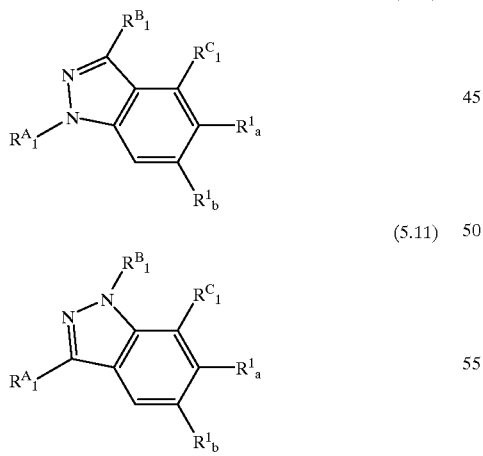

wherein $R^C_1$ is a member independently selected from the group consisting essentially of hydrogen; hydroxy; —O—($C_1$–$C_4$) alkyl; —O—($C_1$–$C_4$) alkyl($C_1$–$C_2$) alkoxy; and —O—($C_1$–$C_4$) alkyl-morpholino;

$R^A_1$ is a member independently selected from the group consisting essentially of hydrogen; ($C_1$–$C_9$) alkyl; —$(CH_2)_n$($C_3$–$C_{10}$) cycloalkyl wherein n is 0 to 2; —($C_1$–$C_6$) alkyl($C_1$–$C_6$) alkoxy; ($C_2$–$C_6$) alkenyl; —$(CH_2)_n$($C_3$–$C_9$) heterocyclyl wherein n is 0 to 2; and —$(Z')_b(Z'')_c$($C_6$–$C_{10}$) aryl wherein b and c are each independently 0 or 1, Z' is ($C_1$–$C_6$) alkylene or ($C_2$–$C_6$) alkenylene, and Z'' is —O—, —S—, —$SO_2$—, or —N($R^9$)—, and wherein said alkyl, alkenyl, alkoxyalkyl, heterocyclyl, and aryl moieties of said $R^A_1$ groups are substituted by 0 to 3 substituents independently selected from halo; hydroxy; ($C_1$–$C_5$) alkyl; ($C_2$–$C_5$) alkenyl; ($C_1$–$C_5$) alkoxy; ($C_3$–$C_6$) cycloalkoxy; trifluoromethyl; nitro; —C(=O)$OR^9$; —C(=O)$NR^9R^{10}$, —$NR^9R^{10}$, and —S(=C)$_2NR^9R^{10}$;

where in preferred embodiments, said aryl moiety comprises a member selected from the group consisting essentially of phenyl; naphthyl; indenyl (from 2,3-dihydro-1H-indene); indanyl; and fluorenyl (from 9-H-fluorene);

where in more preferred embodiments said aryl moiety comprises a member independently selected from the group consisting essentially of phenyl and indanyl;

where in preferred embodiments, said heterocyclyl moiety comprises a member independently selected from the group consisting essentially of acridinyl; benzimidazolyl; benzodioxoiane; 1,3-benzodioxol-5-yl; benzo[b]furanyl; benzo[b]thiophenyl; benzoxazolyl; benzthiazolyl; carbazolyl; cinnolinyl; 2,3-dihydrobenzofuranyl; 1,3-dioxane; 1,3-dioxolane; 1,3-dithiane; 1,3-dithiolane; furanyl; imidazolidinyl; imidazolinyl; imidazolyl; 1H-indazolyl; indolinyl; indolyl; 3H-indolyl; isoindolyl; isoquinolinyl; isothiazolyl; isoxazolyl; morpholinyl; 1,8-naphthyridinyl; oxadiazolyl; 1,3-oxathiolane; oxazolidinyl; oxazolyl; oxiranyl; parathiazinyl; phenazinyl; phenothiazinyl; phenoxazinyl; phthalazinyl; piperazinyl; piperidinyl; pteridinyl; pyranyl; pyrazinyl; pyrazolidinyl; pyrazolinyl; pyrazolo[1,5-c]triazinyl; pyrazolyl; pyridazinyl; pyridyl; pyrimidinyl; pyrimidyl; pyrrolyl; pyrrolidinyl; purinyl; quinazolinyl; quinolinyl; 4H-quinolizinyl; quinoxalinyl; tetrazolidinyl; tetrazolyl; thiadiazolyl; thiazolidinyl; thiazolyl; thienyl; thiomorpholinyl; triazinyl; and triazolyl; and where in more preferred embodiments said heterocyclyl moiety comprises a member independently selected from the group consisting essentially of pyrrolidinyl, piperidinyl, piperazinyl, and morpholinyl;

$R^9$ and $R^{10}$ are independently hydrogen or ($C_1$–$C_4$) alkyl substituted by 0 to 3 fluorine atoms;

$R^B_1$ is a member independently selected from the group consisting essentially of hydrogen; ($C_1$–$C_9$) alkyl; ($C_2$–$C_3$) alkenyl; phenyl; ($C_3$–$C_7$) cycloalkyl; and —($C_1$–$C_2$) alkyl($C_3$–$C_7$) cycloalkyl; wherein said alkyl, alkenyl and phenyl $R^B_1$ groups are substituted with 0 to 3 substituents independently selected from the group consisting essentially of methyl;ethyl; trifluoromethyl; and halo; and $R^1_a$ and $R^1_b$ are each individually and independently a member selected from the group consisting essentially of hydrogen and the substituents defined by partial Formulas (5.12); (5.14); (5.16); (5.18); (5.21); (5.23); (5.25); (5.26); and (5.28) below, provided that both of $R^1_a$ and $R^1_b$ cannot be hydrogen at the same time;

wherein preferred embodiments comprise compounds where one of $R^1_a$ and $R^1_b$ is independently selected as hydrogen;

wherein said substituents in addition to hydrogen which define each of $R^1_a$ and $R^1_b$ comprise a member independently selected from the group consisting essentially of the moieties of partial Formulas (5.12); (5.14); (5.16); (5.18); (5.21); (5.23); (5.25); (5.26); and (5.28):

(I-A)

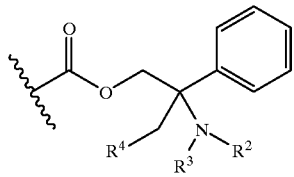
(5.12)

wherein $R^2$, $R^3$, and $R^4$ are independently selected from the group consisting essentially of hydrogen and $(C_1-C_4)$ alkyl substituted by 0 to 3 substituents $R^5$, where the substituent $R^5$ is selected from the group consisting essentially of fluorine, chlorine, methyl, trifluoromethyl hydroxy, and methoxy;

where a preferred embodiment comprises a compound wherein $R^2$, $R^3$, and $R^4$ are methyl and there are 0 substituents $R^5$, represented by Formula (5.13):

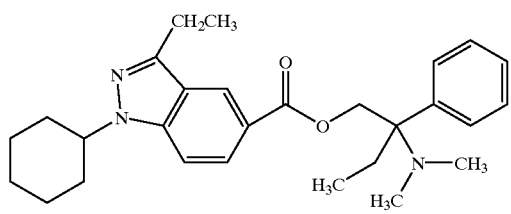
(5.13)

and pharmaceutically acceptable salts, prodrugs, and metabolites thereof;

(I-B) $R^1{}_a$ is $R^6$ and $R^1{}_b$ is the group.

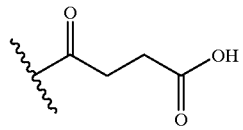
(5.14)

wherein $R^6$ is a member independently selected from the group consisting essentially of $(C_1-C_4)$alkyl; $(C_1-C_4)$ alkoxy; and hydroxy;

where a preferred embodiment comprises a compound where $R^6$ is ethoxy, represented by Formula (5.15):

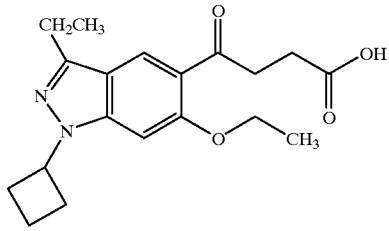
(5.15)

and pharmaceutically acceptable salts, prodrugs, and metabolites thereof; and where further details concerning predecessor catechoL compounds, e.g., trepibutone, of Formula (5.14) are disclosed in Murata et al. U.S. Pat. No. 3,943,169, which is incorporated herein by reference in its entirety;

(I-C)

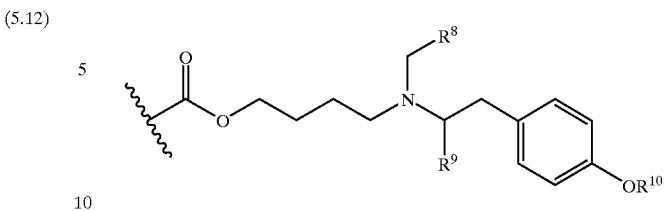
(5.16)

wherein $R^8$, $R^9$ and $R^{10}$ are independently selected from the group consisting essentially of hydrogen and $(C_1-C_4)$ alkyl substituted by 0 to 3 substituents is a member independently selected $R^5$, where the substituent $R^5$ is as defined herein;

where a preferred embodiment comprises a compound where $R^8$ and $R^9$ are methyl and $R^{10}$ is methoxy, represented by Formula (5.17):

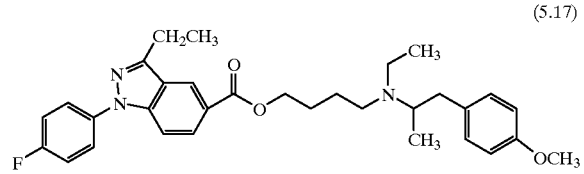
(5.17)

and pharmaceutically acceptable salts, prodrugs, and metabolites thereof; and where further details concerning predecessor catechol compounds, e.g., mebeverine, of Formula (5.16) are disclosed in Kralt et al. U.S. Pat. No. 3,265,577, which is incorporated herein by reference in its entirety;

(I-D) $R^1{}_a$ and $R^1{}_b$ are taken together to form the moiety of partial Formula (5.18):

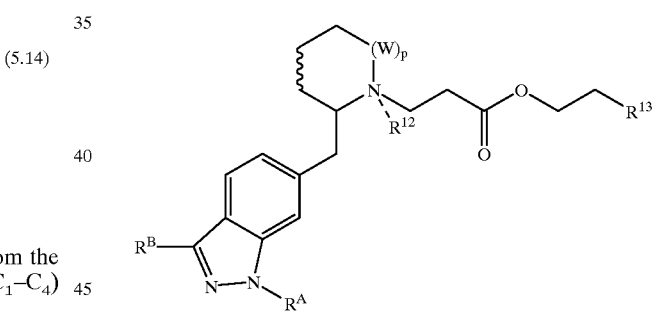
(5.18)

wherein p is 0 or p is 1 and W is —$CH_2$— or —NH—; $R^{12}$ is absent or is $(C_1-C_4)$ alkyl; $R^A$ and $R^B$ are as defined herein; and $R^{13}$ is —$CH_3$ or is the remainder of the moiety of Formula (5.18) whereby a bis compound is formed as represented by Formula (5.19):

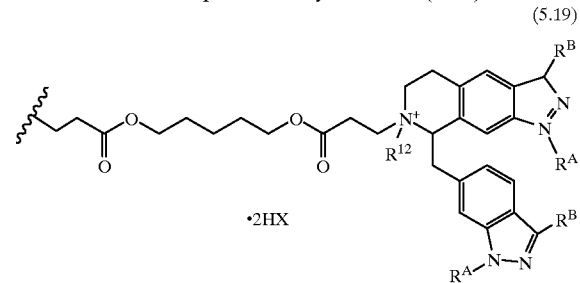
(5.19)

wherein HX is an acid addtion salt, where a preferred embodiment comprises a compound where $R^A$ and $R^B$ are cyclohexyl and ethyl, the acid addtion salt is besylate, and $R^{12}$ is methyl, represented by Formula (5.19):

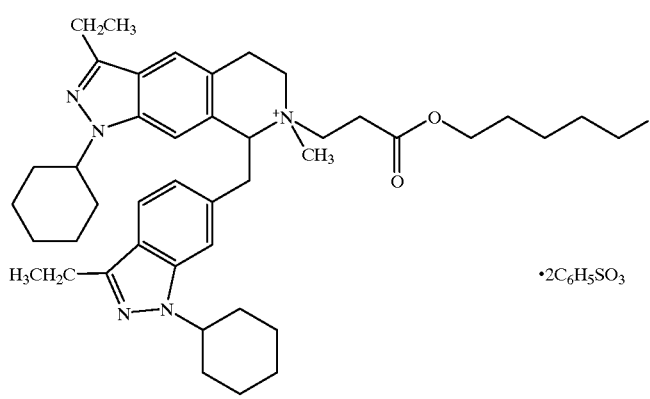

(5.20)

·2C₆H₅SO₃ and pharmaceutically acceptable salts, prodrugs, and metabolites thereof; and where further details concerning predecessor catechol compounds, e.g., atracurium besylate, of Formula (5.19) are disclosed in Hill et al. published International Application WO 92/00965, which is incorporated herein by reference in its entirety;

(I-E)

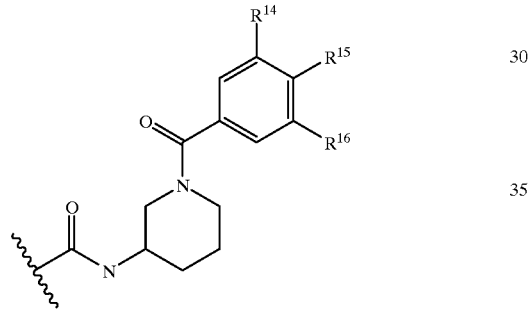

(5.21)

wherein $R^{14}$, $R^{15}$, and $R^{16}$ are each a member independently selected from the group consisting essentially of —NH₂; —NH(C₁-C₄) alkyl; and —N[(C₁-C₄) alkyl]₂, where the alkyl groups are selected independently of each other;

where a preferred embodiment comprises a compound where $R^{14}$, $R^{15}$, and $R^{16}$ are each —NH₂, represented by Formula (5.21):

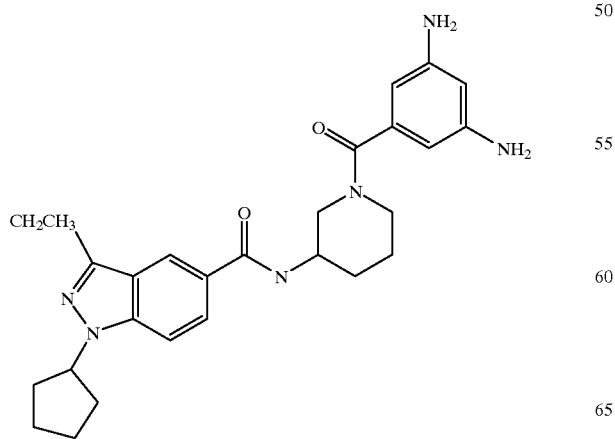

(5.22)

and pharmaceutically acceptable salts, prodrugs, and metabolites thereof; and where further details concerning predecessor catechol compounds, e.g., troxipide, of Formula (5.21) are disclosed in Irikura et al. U.S. Pat. No. 3,647,805, which is incorporated herein by reference in its entirety;

(I-F)

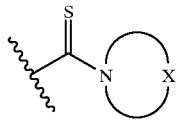

where the moiety

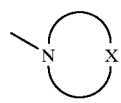

presents the residue of a saturated secondary heterocyclic base having 4, 5, 6, or 7 atoms in the ring, where X is —CH₂—, —O—, —S—, or —NH—; and preferably said secondary heterocyclic base is a member selected from the group consisting essentially of pyrrolidine, 1,3-thiazolidine, imidazolidine, 1,2-oxazolidine, 1,3-oxazolidine, piperidine, piperazine, tetrahydro-1,2-oxazine, tetrahydro-1,3-oxazine, tetrahydro-1,4-oxazine, i.e., morpholine, tetrahydro-1,4-thiazine, and perhydroazepine;

where preferred embodiments of this type include compounds which may be represented by the following Formula (5.24):

| Formula (5.24) | R2 |
|---|---|

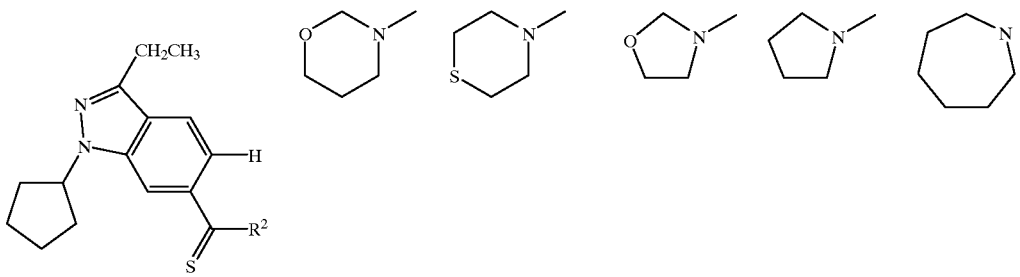

and pharmaceutically acceptable salts, prodrugs, and metabolites thereof; and where further details concerning predecessor catechol compounds, e.g., trithiozine, of Formula (5.23) are disclosed in Pifferi U.S. Pat. No. 3,862,138, which is incorporated herein by reference in its entirety;

(I-G)

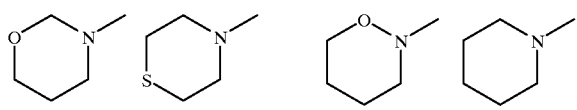 (5.25)

and

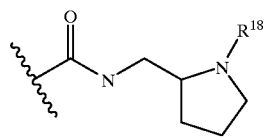 (5.26)

wherein $R^{14}$ is as defined herein; and $R^{18}$ is $(C_1–C_4)$ alkyl or $(C_2–C_4)$ alkenyl where said alkyl and alkenyl groups are substituted by 0 to 3 substituents $R^5$, where the substituent $R^5$ is selected from the group consisting essentially of fluorine, chlorine, methyl, trifluoromethyl hydroxy, and methoxy;

where a preferred embodiment comprises a compound where $R^{14}$ is —NH$_2$, and $R^{18}$ is prop-2-en-1-yl, represented by Formula (5.27):

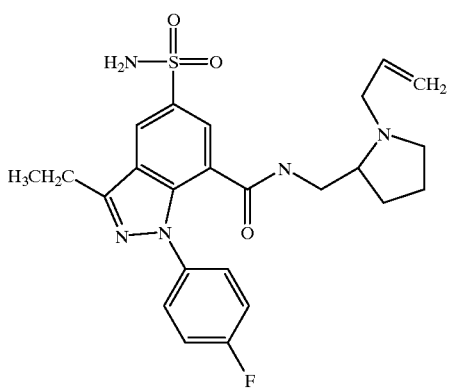 (5.27)

and pharmaceutically acceptable salts, prodrugs, and metabolites thereof, (I-H) $R^1_a$ and $R^1_b$ are taken together to form the moiety:

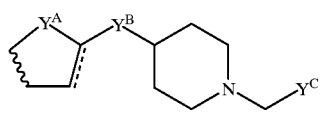 (5.28)

wherein the dashed line represents an optional double bond; $Y^A$ is —C(=O)—; —C(=O)NH—; or —C(=O)N(CH$_3$); $Y^B$ is a member selected from the group consisting essentially of a direct single bond; a direct double bond; —CH$_2$—; —CH$_2$CH$_2$—; —CH$_2$CH$_2$CH$_2$; =CH—; =CHCH$_2$—; =CH CH$_2$CH$_2$CH$_2$—; =CHCH$_2$CH$_2$CH$_2$—; and =CH—CH=CH—; and $Y^C$ is a member selected from the group consisting essentially of cyclohexyl; phenyl substituted by 0 to 3 $R^{20}$ where $R^{20}$ is a member selected from the group consisting essentially of methyl, methoxy, hydroxy, benzyloxy, and nitro; pyridyl; 1-naphthyl; 2-naphthyl;

where a preferred embodiment comprises a compound where $Y^A$ is —C(=O)—; $Y^B$ is =CH—CH=CH—; and $Y^C$ is phenyl; represented by Formula (5.29):

(5.29)

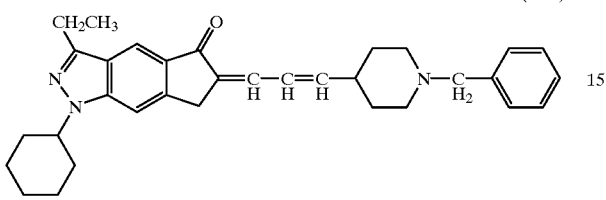

and pharmaceutically acceptable salts, prodrugs, and metabolites thereof, and where further details concerning predecessor catechol compounds of Formula (5.28) are disclosed in Sugimoto et al. U.S. Pat. Nos. 4,895,841 and 5,100,901, which are incorporated herein by reference in their entireties.

(II) Bioisostere Replacement Compounds Active As Adrenergic $\alpha_1$-Antagonists and $\beta_1$-Agonists The gist of the present invention is the discovery that the indazole nucleus is a moiety which is capable of being a bioisostere replacement for the catechol moiety which is an essential part of numerous endogenous ligands acting on important adrenergic receptors and thereby carrying out essential metabolic functions in the body. The indazole nucleus is also a bioisostere replacement for the catechol moiety which is an essential part of numerous drugs which have been and in the future will be created and developed for therapeutic treatments as detailed further herein.

The present invention is especially concerned with the $\alpha_1$-antagonist and $\beta_1$-agonist classes of adrenergic agents which have a catechol moiety as a central and characteristic portion of their overall chemical structure, for which bioisostere replacement with an indazole moiety may be carried out in accordance with the present invention, i.e., while retaining the type of biological activity exhibited by the original catechol-containing compound.

One important therapeutic class of catechol-containing $\alpha_1$-receptor antagonists is that used as antihypertensive agents. Examples of such agents include the following:

vesnarinone, which acts as a cardiostimulant and as a coronary vasodilator:

(6.0)

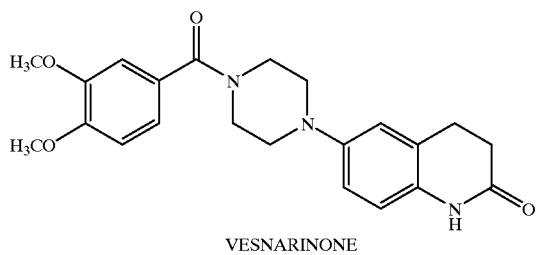

VESNARINONE trimazosin, terazosin, prazosin, doxazosin, alfuzosin, and bunazosin, which are antihypertensive agents:

(6.1)

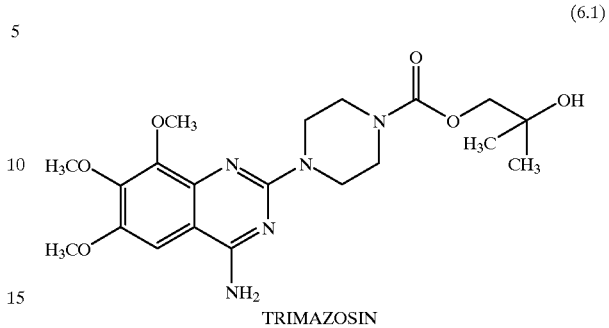

TRIMAZOSIN (6.2)

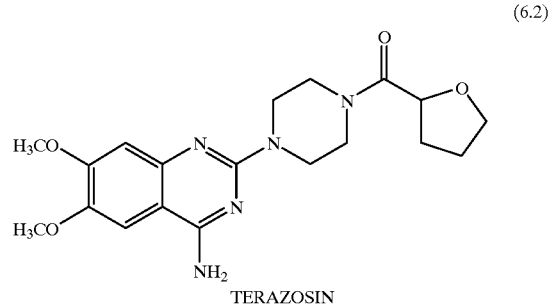

TERAZOSIN (6.3)

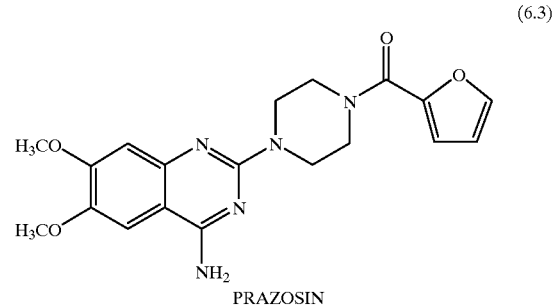

PRAZOSIN (6.4)

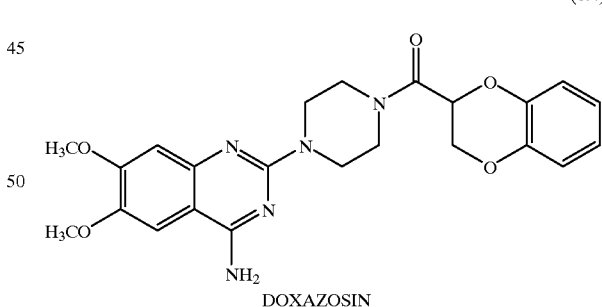

DOXAZOSIN (6.5)

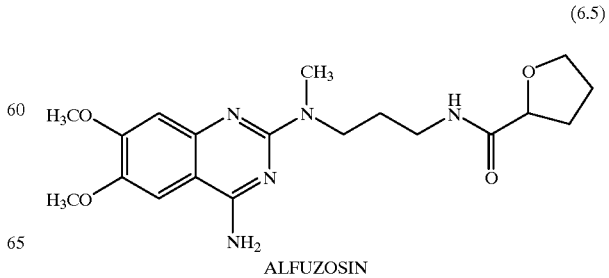

ALFUZOSIN

-continued (6.6)

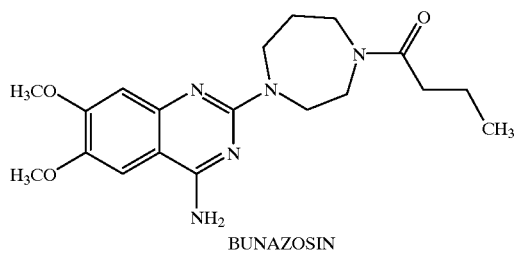

BUNAZOSIN dilazep, which is a coronary vasodilator:

(6.7)

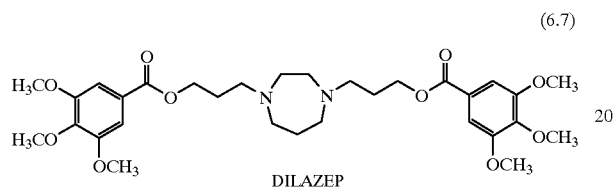

DILAZEP cinepazide, which is a peripheral vasodilator:

(6.8)

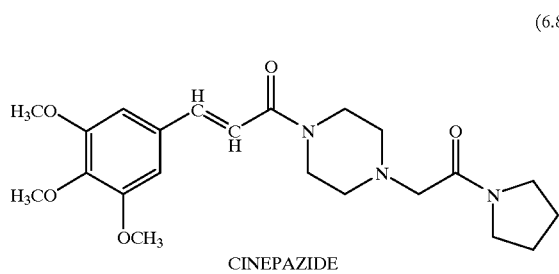

CINEPAZIDE cinepazet, which is an antianginal agent:

(6.9)

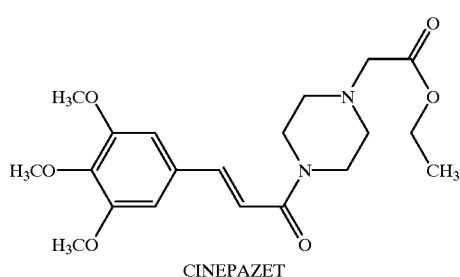

CINEPAZET and butobendine, which is an antiarrhythmic agent which increases cardiac blood flow:

(6.10)

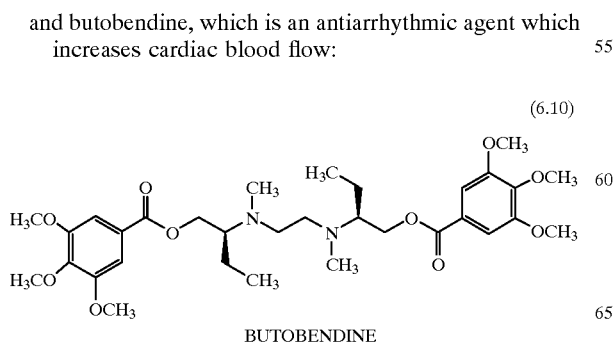

BUTOBENDINE

Another important therapeutic class of catechol-containing $\beta_1$-receptor agonists is that used as agents which favorably affect the contractions of heart muscle. Examples of such agents include ibopamine which is an inotropic agent with dopaminergic and adrenergic agonist activities useful as a cardiotonic:

(6.11)

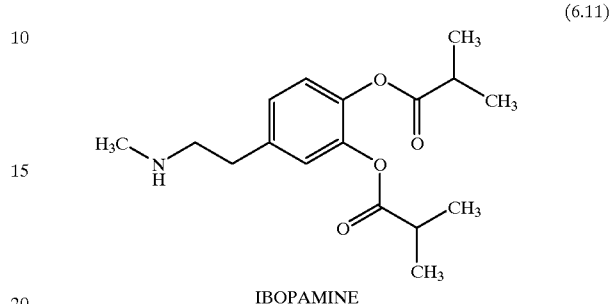

IBOPAMINE denopamine and dobutamine which are selective $\beta_1$-adrenoceptor agonist with positive inotropic activity useful as a cardiotonics:

(6.12)

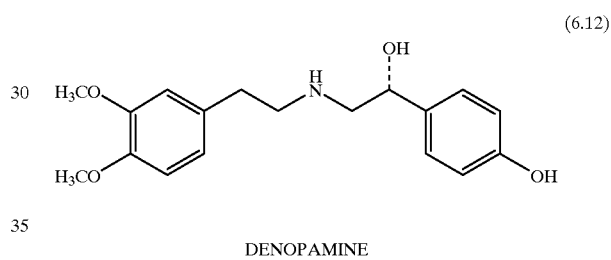

DENOPAMINE (6.13)

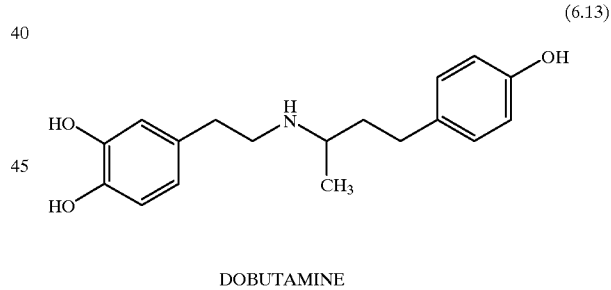

DOBUTAMINE and bevantolol which is a cardioselective $\beta_1$-adrenergic blocker useful as an antianginal, antihypertensive and antiarrhythmic agent:

(6.14)

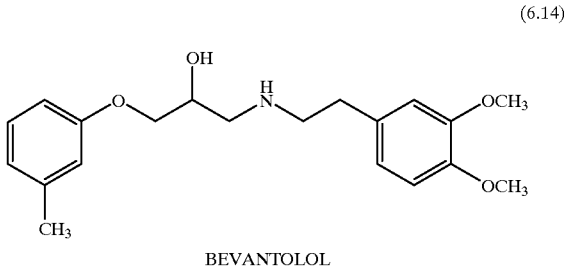

BEVANTOLOL

Other types of catechol-containing adrenergic receptor agonists and antagonists are also suitable for indazole bioisostere replacement in accordance with the present invention. For example, dipivefrin is an adrenergic agent which is ophthalmically active and useful as an antiglaucoma agent:

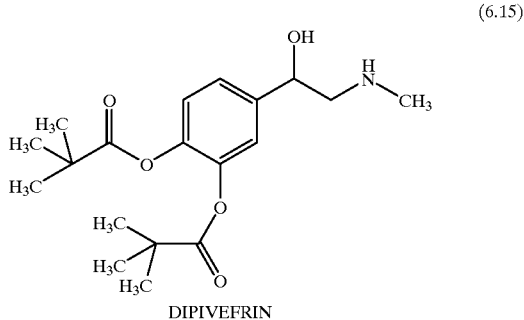

(6.15)

DIPIVEFRIN and bitolterol is a $\beta_2$-adrenergic agonist useful as a bronchodilator:

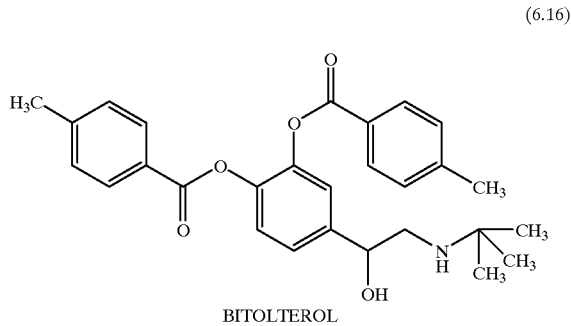

(6.16)

BITOLTEROL

In the basic biosynthesis route for catecholamine production in the body of a mammal, the hydroxylation of tyrosine is regarded as the rate-limiting step. In turn, tyrosine hydroxylase is activated following stimulation of adrenergic nerves or the adrenal medulla. The enzyme is a substrate for cyclic AMP-dependent and $Ca^{2+}$-calmodulain-sensitive protein kinase and protein kinase C. Kinase catalyzed phosphorylation may also be associated with increased hydroxylase activity. This constitutes a mechanism which acts acutely and permits the body to increase catecholamine biosynthesis responsive to nerve stimulation.

The classification and properties of the different types of adrenergic receptors has been described above briefly, but an understanding of these characteristics is essential to an appreciation of the remarkably diverse effects of the catecholamines and related sympathomimetic agents. In turn, this appreciation is imperative if one is to grasp the extensive scope and surprising level of biological activities resulting from the bioisosteric replacement of the catechol moiety in accordance with the present invention.

The responses which follow activation of all of the various types of adrenergic receptors are mediated by G protein effects on the generation of a series of second messengers and on the activity of ion channels. Thus, there are three types of protein interacting in this system, the adrenergic receptor, the G protein, and the effector enzyme, i.e., the ion channel. Although the adrenergic receptors are characterized by heterogeneity of action, they are a closely related family of proteins; and they are also closely related in terms of both structure and functionality to a wide variety of other hormones and neurotransmitters that are coupled to G proteins. Conserved membrane spanning regions of the adrenergic receptors create ligand-binding pockets that are crucially involved in binding.

For example, the individual amino acids of the $\beta_2$-adrenergic receptor which interact with the functional groups of the catecholamine agonist molecule have been identified. Other residues within the transmembrane domains have been found to be particularly involved in antagonist interactions. All of the $\beta$-adrenergic receptors stimulate adenylyl cyclase through interaction with $G_s$ protein, which leads in turn to the accumulation of cyclic AMP, activation of the cyclic AMP-dependent protein kinase, and altered function of numerous cellular proteins as a result of their phosphorylation. Accordingly, it has become accepted in the art that there are multiple points of regulation of the responsiveness of the adrenergic receptors in addition to the receptors themselves, and that these include G proteins, adenylyl cyclase, and cyclic nucleotide phosphodiesterase.

Sympathomimetic drugs exhibit actions which elicit all of the above responses, although the level of response in each case may vary considerably. Many sympathomimetic drugs influence both $\alpha$-receptors and $\beta$-receptors, but usually not equally. In fact, the ratio of such activities constitutes a broad spectrum with predominantly $\alpha$ activity at one end in the case of phenylephrine, to predominantly $\beta$ activity at the other end in the case of isoproterenol. While $\beta$-phenylethylamine is the simplest and therefore parent compound for the sympathomimetic amine drugs discussed herein, the particular class of sympathomimetic drugs with which the present invention is concerned are all ortho-dihydroxybenzenes, i.e., catecholamines.

Some key structure-activity relationships have been established heretofore for the sympathomimetic catecholamines. For example, when the aromatic ring and the amine group are separated by two carbon atoms, the level of sympathomimetic activity is at its highest. Increase in size of the alkyl substituents on the amine group increases $\beta$-receptor activity. For example, the rather low level of $\beta_2$ activity in norepinephrine is increased dramatically by the addition of a methyl group to form epinephrine. Selectivity for $\beta_2$ over $\beta_1$ receptors requires other substitutions. The presence of the ortho-dihydroxy substitutions at positions 3- and 4-, which makes these compounds catechols, is required for maximal $\alpha$ and $\beta$ activity. Studies carried out heretofore on the $\beta$-adrenergic receptor strongly suggest that this optimization of activity results from the formation of hydrogen bonds between the 3- and 4-hydroxy groups of the catechol and corresponding hydroxyl groups on serine residues 204 and 207 which lie in the fifth membrane-spanning region of the receptor protein. These studies also suggest that aspartate 113, which lies in the third membrane-spanning region of the $\beta$-adrenergic receptor, interacts with the amine group of the catecholamine to form an electrostatic bond. It can also be inferred from these spatial relationships that the catecholamine in question binds parallel to the plane of the $\beta$-adrenergic receptor membrane, forming a bridge between the two above-mentioned membrane spans.

Where the hydroxyl groups of the catecholamine are not in the ortho-position but in the meta-position, i.e., at positions 3- and 5-, $\beta_2$-receptor selectivity is conferred on the compound, provided that it has a large amino substituent. Thus, metaproterenol, terbutaline and similar compounds are administered as therapeutic agents to asthma patients, where they relax the bronchial musculature while causing less direct cardiac stimulation than other less selective agents:*

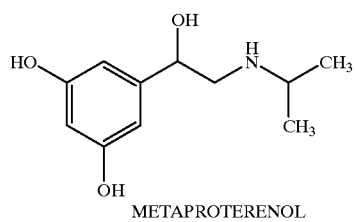

METAPROTERENOL (6.17)

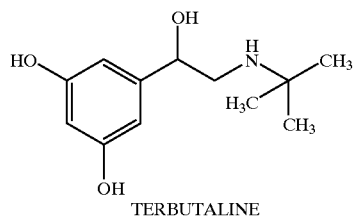

TERBUTALINE (6.18)

In compounds where the hydroxyl groups on the aromatic ring are absent, as well as the β-hydroxyl group of the side chain, the activity of the compounds is limited almost exclusively to causing the release of norepinephrine from adrenergic nerve terminals.

The site of action of a compound, i.e., its tissue compartmentalization, is also important to its therapeutic utilization. For example, the dihydroxy substitution of the catechols makes them less lipophilic, and thus unsubstituted or alkyl-substituted compounds are more able to cross the blood-brain barrier and be active in the central nervous system rather than the sympathetic nervous system. Accordingly, ephedrine, amphetamine, and methamphetamine posses considerable central nervous system activity, while on the other hand, compounds lacking the polar hydroxyl groups lose their direct sympathomimetic activity.

The rate of catabolism, i.e., the duration of action of the catecholamines is also important to their therapeutic use. For example, the catecholamines have a very short duration of action and are rapidly inactivated in the intestinal mucosa and liver by catechol-O-methyltransferase before reaching systemic circulation. They are thus ineffective when administered orally.

The structures of some of the above recited catechol-containing adrenergic agents which are suitable for indazole bioisostere replacement may be illustrated in their indazole form as follows:

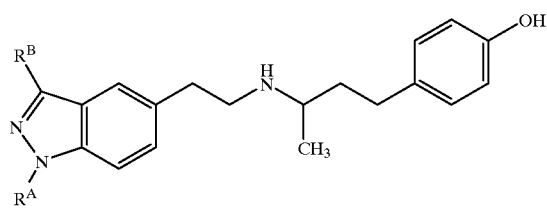

DOBUTAMINE BIOISOSTERE (6.19)

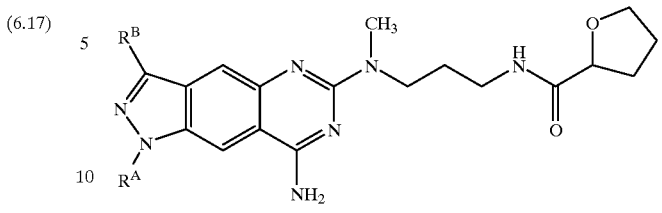

ALFUZOSIN BIOISOSTERE (6.20)

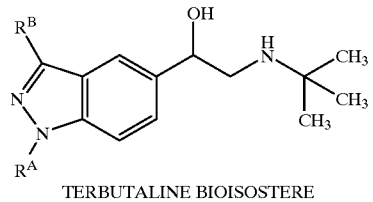

TERBUTALINE BIOISOSTERE (6.21)

The subject matter of the present invention includes within its scope all and every indazole-for-catechol bioisostere replacement relating to $\alpha_1$-antagonist and $\beta_1$-agonist classes of adrenergic agents, both as novel indazole compounds in particular and as said replacements in general. Also included within the scope of the present invention are the therapeutic methods of treatment and the pharmaceutical compositions relating thereto in which the active ingredient is an indazole-for-catechol bioisostere replacement compound, and in preferred embodiments of the present invention is as described in more detail further below.

Accordingly, the present invention relates in particular to indazole-for-catechol bioisostere replacements active as $\alpha_1$-antagonist and $\beta_1$-agonist adrenergic agents, comprising a compound of Formulas (6.22) or (6.23):

(II)

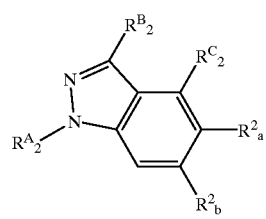

(6.22)

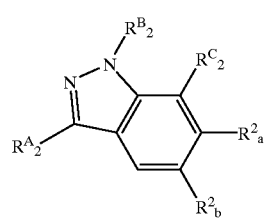

(6.23)

wherein $R^C{}_2$ and $R^A{}_2$ and $R^B{}_2$ are defined the same as $R^C{}_1$ and $R^A{}_1$ and $R^B{}_1$ herein under Formulas (5.10) and (5.11), including preferred embodiments thereof, but are selected on an independent basis therefrom; and $R^2_a$ and $R^2_b$ are each individually and independently a member selected from the group consisting essentially of hydrogen and the substituents defined by partial Formulas (6.24), (6.26), (6.41), (6.43), (6.48), and (6.50) below, provided that both of $R^2_a$ and $R^2_b$ cannot be hydrogen at the same time;

wherein preferred embodiments comprise compounds where one of $R^2_a$ and $R^2_b$ is independently selected as hydrogen;

wherein said substituents in addition to hydrogen which define each of $R^2_a$ and $R^2_b$ comprise a member independently selected from the group consisting essentially of the moieties of partial Formulas (6.24), (6.26), (6.41), (6.43), (6.48), and (6.50):

(II-A)

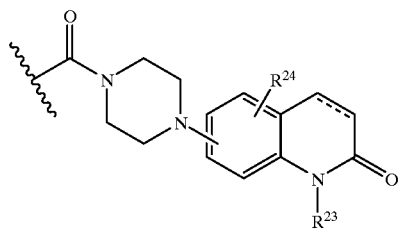

(6.24)

wherein the dashed line represents an optional double bond; $R^{23}$ is a member selected from the group consisting essentially of hydrogen; $(C_1-C_4)$ alkyl, $(C_2-C_4)$ alkenyl, and phenyl$(C_1-C_4)$ alkyl-, where said alkyl, alkenyl, and phenyl or alkyl group attached thereto are substituted by 0 to 3 substituents $R^5$, where the substituent $R^5$ is as defined herein, but independently selected therefrom; and $R^{24}$ is a member selected from the group consisting essentially of hydrogen and $(C_1-C_4)$ alkoxy;

where a preferred embodiment comprises a compound where $R^{23}$ and $R^{24}$ are each hydrogen, e.g., a visnarinone bioisostere, represented by Formula (6.25):

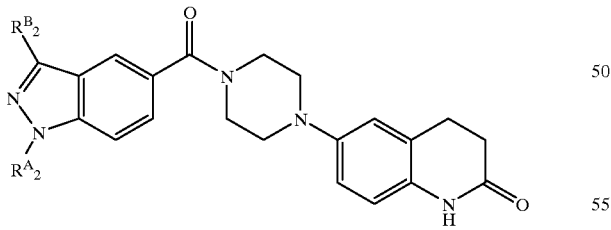

(6.25)

VISNARINONE BIOISOSTERE and pharmaceutically acceptable salts, prodrugs, and metabolites thereof; and where further details concerning predecessor catechol compounds, e.g., vesnarinone, of Formula (6.0) are disclosed in Tominaga et al. U.S. Pat. No. 4,415,572, which is incorporated herein by reference in its entirety;

(II-B) $R^2_a$ and $R^2_b$ are taken together to form the moiety of partial Formula (6.26):

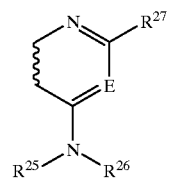

(6.26)

wherein E represents N, resulting in a pyrimidinyl moiety and overall a quinazoline series of compounds; or represents CH, resulting in a pyridyl moiety and overall a quinoline series of compounds; $R^{25}$ and $R^{26}$ are each a member independently selected from the group consisting essentially of hydrogen; $(C_1-C_6)$alkyl; $(C_2-C_6)$ alkenyl; $(C_3-C_8)$cycloalkyl; hydroxy$(C_1-C_6)$alkyl; phenyl; benzyl; phenylethyl; and 2-furfuryl; and $R^{27}$ is independently selected from the group consisting essentially of:

(a) acetylamino of partial Formula (6.27):

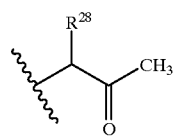

(6.27)

wherein $R^{28}$ is a member selected from the group consisting essentially of hydrogen; acetyl; $(C_1-C_6)$ alkyl; and $(C_2-C_6)$ alkenyl;

(b) amino or substituted amino of partial Formula (6.28):

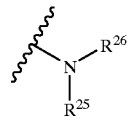

(6.28)

wherein $R^{25}$ and $R^{26}$ are as defined further above;

(c) morpholino; 1-azacycloheptyl; 1-azacyclooctyl; pyrrolidino; or piperidino;

(d) N-substituted piperazino of partial Formula (6.29):

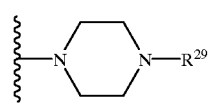

(6.29)

wherein $R^{29}$ is a member selected from the group consisting essentially of hydrogen; $(C_1-C_6)$ alkyl; hydroxy$(C_1-C_6)$ alkyl; allyl; propargyl; 2-methylallyl; phenyl optionally substituted by bromo or chloro; benzyl optionally substituted by bromo or chloro; trifluoromethyl; methoxyphenyl; methylphenyl; carboxylic acid $(C_1-C_6)$ alkyl ester; carboxylic acid $(C_2-C_6)$ alkenyl ester; and —C(=O)—$R^{30}$, where $R^{30}$ is a member independently selected from the group consisting essentially of $(C_1-C_6)$ alkyl; —O—$(C_1-C_6)$ alkyl; hydroxy $(C_1-C_6)$ alkyl—O—; —$(C_2-C_6)$ alkenyl; phenyl optionally substituted by bromo, chloro, methyl, 3,4,5-trimethoxy, or trifluoromethyl; naphthyl; furyl; benzofuryl; thienyl; pyridyl; tetrahydrofuryl; and tetrahydropyran;

(e) piperidino of partial Formula (6.30):

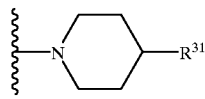
(6.30)

wherein $R^{31}$ is a member independently selected from the group consisting essentially of hydrogen; $(C_1-C_6)$ alkyl; $(C_1-C_4)$ alkoxy; hydroxy; hydroxy $(C_1-C_3)$ alkyl; phenyl; benzyl; and 4-phenyl-4carboxylic acid $(C_1-C_6)$ alkyl ester;

(f) 4-(1,4-benzodioxan-2-carbonyl)-piperazin-1-yl of partial Formula (6.31):

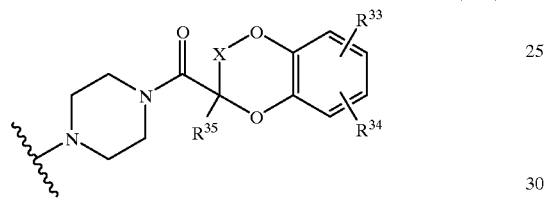
(6.31)

wherein $R^{33}$ and $R^{34}$ are each independently a member selected from the group consisting essentially of hydrogen; $(C_1-C_6)$ alkyl; $(C_1-C_6)$ alkoxy; bromo, chloro and fluoro; —C(=O)$(C_1-C_6)$alkyl; —C(=O)—O—$(C_1-C_6)$ alkyl; —C(=O)NR$^{36}$R$^{37}$ and —S(=O)$_2$ NR$^{36}$R$^{37}$, where $R^{36}$ and $R^{37}$ are each independently hydrogen or $(C_1-C_6)$alkyl; $R^{35}$ is independently hydrogen or $(C_1-C_6)$alkyl; and X is —CHR$^{35}$— or —CH$_2$CH$_2$—, where $R^{35}$ is as defined above, selected on an independent basis;

(g) moiety of partial Formula (6.32):

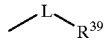
(6.32)

wherein L is absent or represents (i) a heterocyclic group of partial Formula (6.32.1):

(6.32.1)

where N is attached to the 2-position of the guinoline or quinazoline ring; $A^a$ is absent or represents C(=O) or S(=O)$_2$; $Z^a$ represents CH or N; m is an interger selected from 1 and 2, as well as from 0 when $Z^a$ represents CH; and n is an integer selected from 1, 2, and 3; provided that the sum of m and n is an integer selected from 2, 3, 4, and 5; or (ii) a claim of partial Formula (6.32.2):

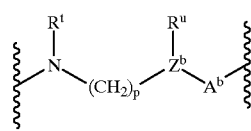
(6.32.2)

where N is attached to the 2-position of the quinoline or quinozline ring; $A^b$ and $Z^b$ have the same definition as $A^a$ and $Z^a$ above; $R^t$ and $R^u$ are each a member independently selected from the group consisting essentially of hydrogen and $(C_1-C_4)$alkyl; and p is an integer selected from 1, 2, and 3, provided that when $Z^b$ is CH, p may also be selected from 0; and $R^{39}$ is a member independently selected from the group consisting essentially of 4-, 5-, and 6-membered heterocyclic rings containing 1 or 2 heteroatoms selected from N, O, and S, said ring optionally being fused to a benzene ring or to a 5- or 6-membered heterocyclic ring containing 1 or 2 heteroatoms selected from N, O, and S, said ring system comprising $R^{39}$ being substituted by 0 to 2 members selected from the group consisting essentially of OH; $(C_1-C_4)$alkyl; $(C_1-C_4)$alkoxy; Br, Cl, or F; S(=O)$_2$NR$'$R$''$; and NHS(=O)$_2(C_1-C_4)$alkyl; and when said ring heteratom is S, it may be substituted by 0 to 2 oxygen atoms; and $R^t$ and $R^u$ are as defined above, but independently selected therefrom; $(C_1-C_6)$alkyl; benzyl optionally substituted by fluroro, bromo, chloro, or methoxy; and where $A^a$ is absent, —C(=O)—R$^{40}$, where $R^{40}$ is a member independently selected from the group consisting essentially of $(C_1-C_6)$alkyl; phenyl optionally substituted by fluoro, bromo, chloro, methoxy, or methanesulfonyl; styryl optionally ring substituted by fluroro, bromo, chloro, methoxy, or 3,4-methylenedioxy; 4-morpholino; and 2-furyl; including particularly wherein $R^{27}$ is a 1,4-diazepan of partial Formula (6.32.3):

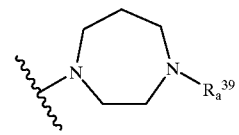
(6.32.3)

where $R_a^{39}$ has the same definition as $R^{39}$ but is independently selected therefrom; provided that —L—R$^{39}$ of partial Formula (6.32) may not be piperidine or piperazine;

(h) alkylenediamine of partial Formula (6.33):

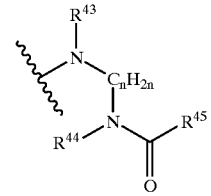
(6.33)

wherein $R^{43}$ and $R^{44}$ are each a member independently selected from the group consisting of hydrogen; $(C_1-C_4)$ alkyl; and benzyl; n is an integer selected from 2, 3, and 4; and $R^{45}$ is $(C_3-C_6)$ cycloalkyl or a radical selected from the group consisting of:

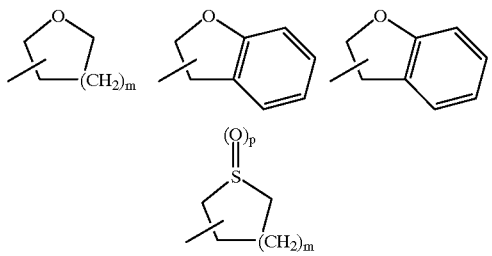

in which m is an integer independently selected from 0, 1 and 2; and p is an integer independently selected from 0, 1 and 2;

where a preferred embodiment comprises a compound where $R^{25}$ and $R^{26}$ are both hydrogen; and $R^{27}$ is (d)-partial Formula (6.29) where $R^{29}$ is —C(=O)—$R^{30}$ and $R^{30}$ is hydroxy$(C_1-C_6)$ alkyl-O—, e.g., a trimazosin bioisostere, represented by Formula (6.34):

(6.34)

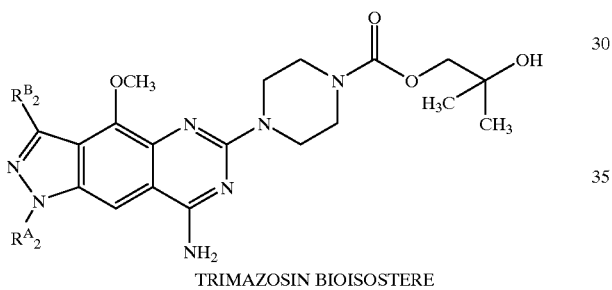

TRIMAZOSIN BIOISOSTERE and pharmaceutically acceptable salts, prodrugs, and metabolites thereof; and where further details concerning predecessor catechol compounds, e.g., trimazosin, of Formula (6.1) are disclosed in Hess U.S. Pat. No. 3,669,968, which is incorporated herein by reference in its entirety;

where further preferred embodiments comprise a compound where $R^{25}$ and $R^{26}$ are both hydrogen; and $R^{27}$ is (d)-partial Formula (6.29) where $R^{29}$ is —C(=O)—$R^{30}$ and $R^{30}$ is tetrahydrofuryl, e.g., a terazosin bioisostere, or tetrahydropyran, represented by Formulas (6.35) and (6.36), respectively:

(6.35)

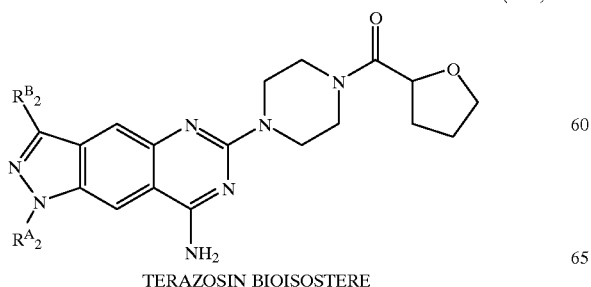

TERAZOSIN BIOISOSTERE (6.36)

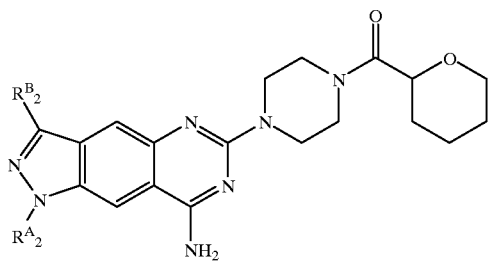

and pharmaceutically acceptable salts, prodrugs, and metabolites thereof; and where further details concerning predecessor catechol compounds, e.g., terazosin, of Formula (6.2) are disclosed in Roteman U.S. Pat. No. 4,251,532, and where further details concerning predecessor catechol compounds of Formula (6.36) are disclosed in Winn et al. U.S. Pat. No. 4,026,894, both of which are incorporated herein by reference in their entireties;

where a still further preferred embodiment comprises a compound where $R^{25}$ and $R^{26}$ are both hydrogen; and $R^{27}$ is (d)-partial Formula (6.29) where $R^{29}$ is —C(=O)—$R^{30}$ and $R^{30}$ is furoyl, e.g., a prazosin bioisostere, represented by Formula (6.37):

(6.37)

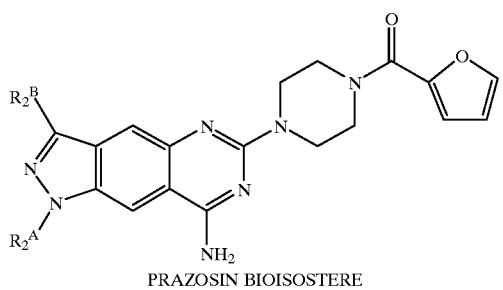

PRAZOSIN BIOISOSTERE and pharmaceutically acceptable salts, prodrugs, and metabolites thereof, and where further details concerning predecessor catechol compounds, e.g., prazosin, of Formula (6.3) are disclosed in Hess U.S. Pat. No. 3,511,836, which is incorporated herein by reference in its entirety;

where a yet still further preferred embodiment comprises a compound where $R^{25}$ and $R^{26}$ are both hydrogen; and $R^{27}$ is (f)-partial Formula (6.31) where $R^{33}$, $R^{34}$, and $R^{35}$ are each hydrogen and X is —$CH_2$—, e.g., a doxazosin bioisostere, represented by Formula (6.38):

(6.38)

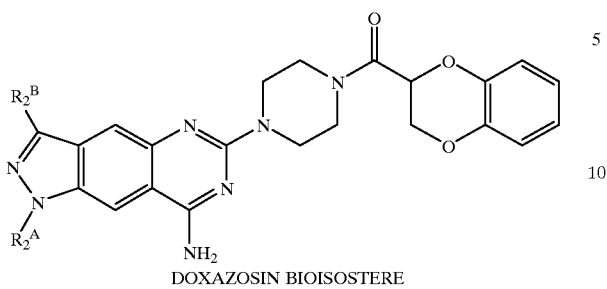

DOXAZOSIN BIOISOSTERE and pharmaceutically acceptable salts, prodrugs, and metabolites thereof; and where further details concerning predecessor catechol compounds, e.g., doxazosin, of Formula (6.4) are disclosed in Campbell U.S. Pat. No. 4,188,390, which is incorporated herein by reference in its entirety;

where an additional preferred embodiment comprises a compound where $R^{25}$ and $R^{26}$ are both hydrogen; and $R^{27}$ is (g)-partial Formula (6.32) where L is absent; n is 2 and m is 3; $Z^a$ is N; $A^a$ is absent; $R^{39}$ is —C(=O)—$R^{40}$ and $R^{40}$ is $(C_1–C_6)$alkyl; a bunazosin bioisostere, represented by Formula (6.39):

(6.39)

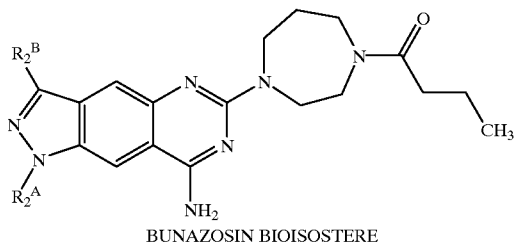

BUNAZOSIN BIOISOSTERE or $R^{40}$ is 4-morpholino, resulting in a bioisostere represented by Formula (6.39.1):

(6.39.1)

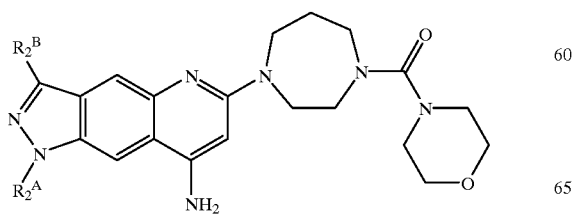

or a bioisostoere represented by Formula (6.39.2):

(6.39.2)

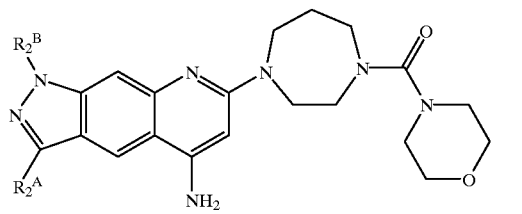

and pharmaceutically acceptable salts, prodrugs, and metabolites thereof; and where further details concerning predecessor catechol compounds, e.g., bunazosin, of Formula (6.6) are disclosed in Takahashi and Sugimoto U.S. Pat. No. 3,920,636, which is incorporated herein by reference in its entirety; and where an another preferred embodiment comprises a compound where $R^{25}$ and $R^{26}$ are both hydrogen; and $R^{27}$ is (h)-partial Formula (6.33) where n is 3; $R^{43}$ is methyl, $R^{44}$ is hydrogen, and $R^{45}$ is a radical:

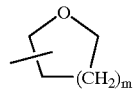

where m is 1, which is an alfuzosin bioisostere, represented by Formula (6.40):

(6.40)

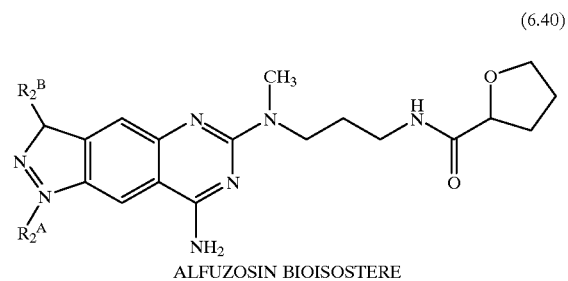

ALFUZOSIN BIOISOSTERE and pharmaceutically acceptable salts, prodrugs, and metabolites thereof; and where further details concerning predecessor catechol compounds, e.g., alfuzosin, of Formula (6.5) are disclosed in Manoury U.S. Pat. No. 4,315,007 which is incorporated herein by reference in its entirety;

(II-C)

(6.41)

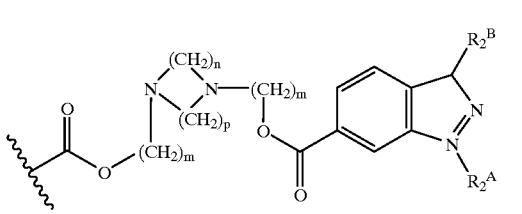

wherein m is an integer independently selected from 2 and 3 in each instance of its occurrence; n is an integer selected from 2, 3, and 4; p is an integer selected from 2 and 3; and n and p together represent a total which is an integer selected from 5, 6, and 7;

where a preferred embodiment comprises a compound where $R^C_2$ is methoxy; where m in both instances is 3; n is 2; and p is 3, e.g., a dilazep bioisostere, represented by Formula (6.42):

(6.42)

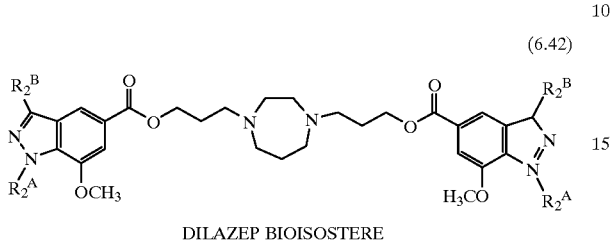

DILAZEP BIOISOSTERE and pharmaceutically acceptable salts, prodrugs, and metabolites thereof; and where further details concerning predecessor catechol compounds, e.g., dilazep, of Formula (6.7) are disclosed in Arnold et al. U.S. Pat. No. 3,532,685, which is incorporated herein by reference in its entirety;

(II-D)

(6.43)

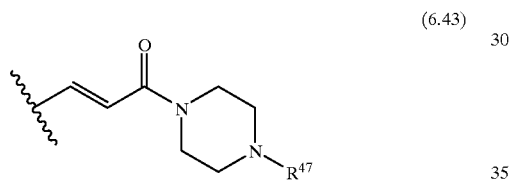

wherein $R^{47}$ is a member independently selected from the group consisting essentially of:
(a) ($C_1$–$C_4$) alkyl optionally substituted by 1 or 2 hydroxyl groups; phenyl($C_1$–$C_4$) alkyl- optionally substituted on the phenyl portion thereof by 1 or 2 hydroxyl groups; and cinnamyl;
(b) —$CH_2C(=O)NHR^{48}$ where $R^{48}$ is a member independently selected from the group consisting essentially of ($C_1$–$C_4$) alkyl; and phenyl optionally substituted by ($C_1$–$C_4$) alkoxy, trifluoromethyl, fluoro, bromo, or chloro;
(c) —$CH_2C(=O)NHR^{49}R^{50}$ where $R^{49}$ and $R^{50}$ are each defined the same as $R^{48}$; but are selected on an independent basis therefrom;
(d) a radical of partial Formula (6.44):

(6.44)

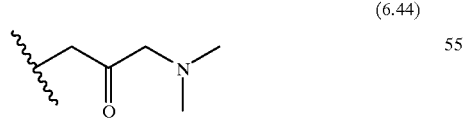

wherein the nitrogen atom forms part of a heterocyclic radical selected from the group consisting essentially of morpholino; hexamethylene-imino; and pyrrolidino; and
(e) —$CH_2C(=O)OR^{51}$ where $R^{51}$ is hydrogen or ($C_1$–$C_4$) alkyl;

where a preferred embodiment comprises a compound where $R^C_2$ is methoxy, giving the exclusionary form of the bioisostere; and where $R^{47}$ is a radical of partial Formula (6.44) in which the nitrogen atom forms the heterocyclic radical pyrrolidino; resulting in cinepazide exclusionary bioisostere, represented by Formula (6.45):

(6.45)

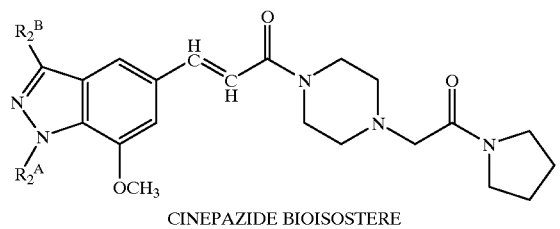

CINEPAZIDE BIOISOSTERE and pharmaceutically acceptable salts, prodrugs, and metabolites thereof; and where further details concerning predecessor catechol compounds, e.g., cinepazide, of Formula (6.8) are disclosed in Fauran et al. U.S. Pat. No. 3,634,411, which is incorporated herein by reference in its entirety; and where another preferred embodiment comprises a compound where $R^C_2$ is hydrogen, giving the inclusionary form of the bioisostere, or is methoxy, giving the exclusionary form of the bioisostere; and where $R^{47}$ is a radical of partial formula (e) in which $R^{51}$ is ethyl; resulting in cinepazet inclusionary and exclusionary bioisosteres, represented by Formula (6.46) and (6.47), respectively:

(6.46)

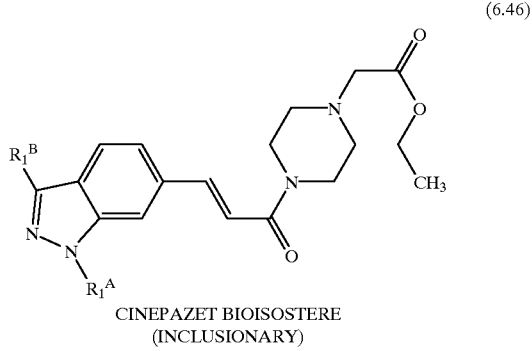

CINEPAZET BIOISOSTERE
(INCLUSIONARY)

(6.47)

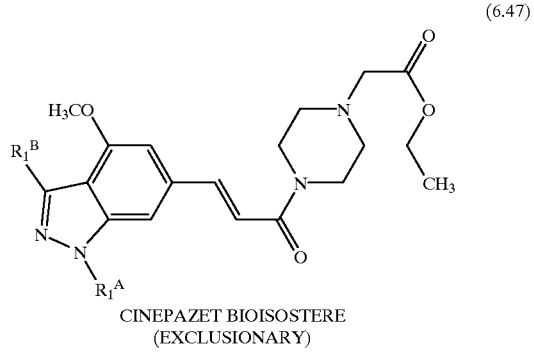

CINEPAZET BIOISOSTERE
(EXCLUSIONARY)

and pharmaceutically acceptable salts, prodrugs, and metabolites thereof; and where further details concerning predecessor catechol compounds, e.g., cinepazet, of Formula (6.9) are disclosed in Fauran et al. U.S. Pat. No. 3,590,034, which is incorporated herein by reference in its entirety;

(II-E)

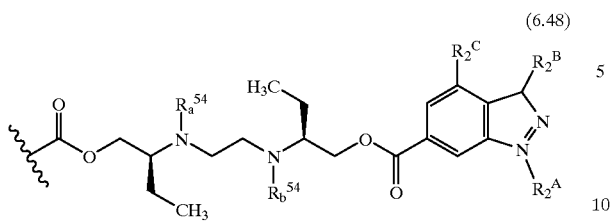

(6.48)

wherein $R^C_2$ is a member independently selected from the group consisting essentially of hydrogen; hydroxy; and —O—$(C_1-C_4)$ alkyl, in accordance with whether an inclusionary or exclusionary bioisostere is intended; and $R^{54}_a$ and $R^{54}_b$ are independently selected from the group consisting essentially of $C_nH_{2n+1}$ where n is an integer selected from 1, 2, 3, and 4;

where a preferred embodiment comprises a compound where $R^C_2$ is methoxy, giving the exclusionary form of the bioisostere; and where n=1 so that both $R^{54}_a$ and $R^{54}_b$ are methyl; resulting in butobendine exclusionary bioisostere; represented by Formula (6.49):

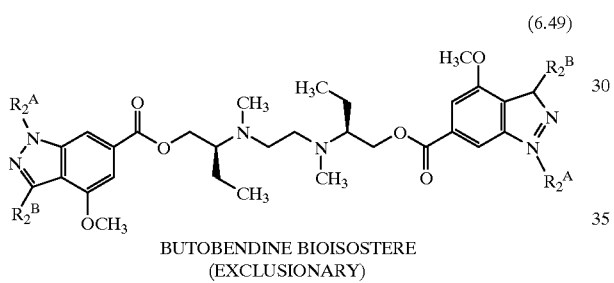

(6.49)

BUTOBENDINE BIOISOSTERE
(EXCLUSIONARY)

and pharmaceutically acceptable salts, prodrugs, and metabolites thereof; and where further details concerning predecessor catechol compounds, e.g., butobendine, of Formula (6.10) are disclosed in Eckstein et al. U.S. Pat. No. 4,021,473, which is incorporated herein by reference in its entirety;

(II-F)

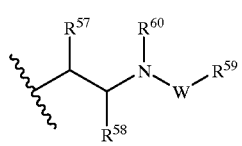

(6.50)

wherein $R^{57}$ is a member independently selected from the group consisting essentially of hydrogen; $(C_1-C_2)$ alkyl; and hydroxy;

$R^{58}$ is a member independently selected from the group consisting essentially of hydrogen; and $(C_1-C_2)$ alkyl;

W is —C($R^{64}$)($R^{65}$)—; —CH($R^{64}$)CH($R^{65}$)—; or —CH($R^{64}$)CH($R^{65}$)CH$_2$—; where $R^{64}$ is a member independently selected from the group consisting essentially of hydrogen and methyl; and $R^{65}$ is a member independently selected from the group consisting essentially of hydrogen, methyl, and hydroxy;

$R^{59}$ is a member selected independently from the group consisting essentially of hydrogen; methyl; phenyl; and benzoyl; where said phenyl and benzoyl groups are optionally substituted by a member independently selected from the group consisting essentially of m-hydroxy; p-hydroxy; m- and p-dihydroxy; m-$(C_1-C_2)$ alkyl; $(C_1-C_3)$ alkoxy; fluoro; chloro; cyano; hydroxymethyl; acetyl; and o-allyl; and $R^{60}$ is a member independently selected from the group consisting essentially of hydrogen; and methyl;

where a preferred embodiment comprises a compound where $R^{57}$, $R^{58}$, and $R^{60}$ are each hydrogen; W is —C($R^{64}$)($R^{65}$)— where $R^{64}$ and $R^{65}$ are both hydrogen; and $R^{59}$ is hydrogen; resulting in an ibopamine bioisostere, represented by Formula (6.51):

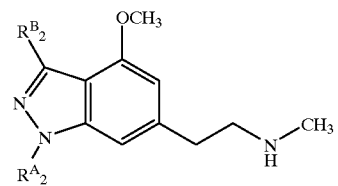

(6.51)

IBOPAMINE BIOISOSTERE and pharmaceutically acceptable salts, prodrugs, and metabolites thereof; and where further details concerning predecessor catechol compounds, e.g., ibopamine, of Formula (6.11) are disclosed in Casagrande and Ferrari U.S. Pat. No. 4,218,470, which is incorporated herein by reference in its entirety;

where another preferred embodiment comprises a compound where $R^{57}$, $R^{58}$, and $R^{60}$ are each hydrogen; W is —CH($R^{64}$)CH($R^{65}$)— where $R^{64}$ is hydrogen and $R^{65}$ is hydroxy; and $R^{59}$ is phenyl substituted by m-hydroxy or p-hydroxy; resulting in a denopamine bioisostere, represented by Formula (6.52):

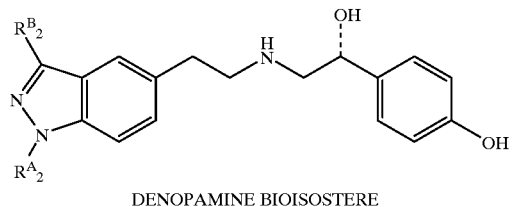

(6.52)

DENOPAMINE BIOISOSTERE and pharmaceutically acceptable salts, prodrugs, and metabolites thereof; and where further details concerning predecessor catechol compounds, e.g., denopamine, of Formula (6.12) are disclosed in Ikezaki et al. U.S. Pat. No. 4,032,575, which is incorporated herein by reference in its entirety;

where yet another preferred embodiment comprises a compound where $R^{57}$, $R^{58}$, and $R^{60}$ are each hydrogen; W is —CH($R^{64}$)CH($R^{65}$)CH$_2$— where $R^{64}$ is methyl and $R^{65}$ is hydrogen; and $R^{59}$ is phenyl substituted by p-hydroxy; resulting in a dobutamine bioisostere, represented by Formula (6.53):

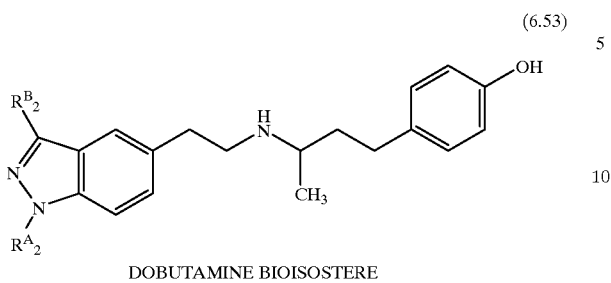

(6.53)

DOBUTAMINE BIOISOSTERE and pharmaceutically acceptable salts, prodrugs, and metabolites thereof; and where further details concerning predecessor catechol compounds, e.g., dobutamine, of Formula (6.13) are disclosed in Tuttle and Mills U.S. Pat. No. 3,987,200, which is incorporated herein by reference in its entirety;

where a still further preferred embodiment comprises a compound where $R^{57}$, $R^{58}$, and $R^{60}$ are each hydrogen; W is —CH($R^{64}$)CH($R^{65}$)CH$_2$— where $R^{64}$ is hydrogen and $R^{65}$ is hydroxy; and $R^{59}$ is benzoyl m-methyl; resulting in a bevantolol bioisostere, represented by Formula (6.54):

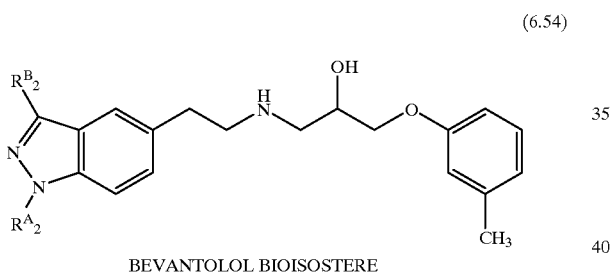

(6.54)

BEVANTOLOL BIOISOSTERE and pharmaceutically acceptable salts, prodrugs, and metabolites thereof, and where further details concerning predecessor catechol compounds, e.g., bevantolol, of Formula (6.14) are disclosed in Holmes and Meyer U.S. Pat. No. 3,857,891, which is incorporated herein by reference in its entirety;

where a yet still further preferred embodiment comprises a compound where $R^{57}$ is hydroxy; $R^{58}$ and $R^{60}$ are each hydrogen; W is —C($R^{64}$)($R^{65}$)— where $R^{64}$ and $R^{65}$ are both hydrogen; and $R^{59}$ is hydrogen; resulting in a dipivefrin bioisostere, represented by Formula (6.55):

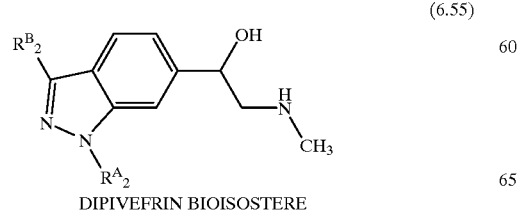

(6.55)

DIPIVEFRIN BIOISOSTERE and pharmaceutically acceptable salts, prodrugs, and metabolites thereof; and where further details concerning predecessor catechol compounds, e.g., dipivefrin, of Formula (6.15) are disclosed in Hussain and Truelove U.S. Pat. No. 3,809,714, which is incorporated herein by reference in its entirety;

where a yet again still further preferred embodiment comprises a compound where $R^{57}$ is hydroxy; $R^{58}$ and $R^{60}$ are each hydrogen; W is —C($R^{64}$)($R^{65}$)— where $R^{64}$ and $R^{65}$ are both methyl; and $R^{59}$ is methyl; resulting in a bitolterol bioisostere, represented by Formula (6.56):

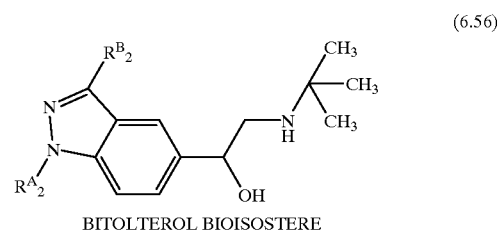

(6.56)

BITOLTEROL BIOISOSTERE and pharmaceutically acceptable salts, prodrugs, and metabolites thereof; and where further details concerning predecessor catechol compounds, e.g., bitolterol, of Formula (6.16) are disclosed in Minatoya et al. U.S. Pat. No. 4,138,581, which is incorporated herein by reference in its entirety;

where a further preferred embodiment comprises a compound where $R^{57}$ is hydroxy; $R^{58}$ and $R^{60}$ are each hydrogen; W is —C($R^{64}$)($R^{65}$)— where $R^{64}$ and $R^{65}$ are both methyl; and $R^{59}$ is hydrogen; resulting in a metaproterenol bioisostere, represented by Formula (6.57):

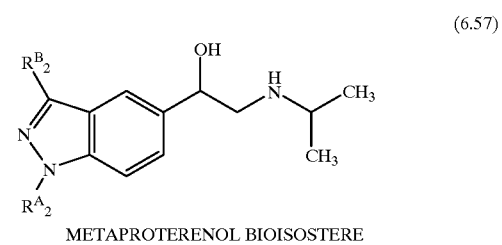

(6.57)

METAPROTERENOL BIOISOSTERE and pharmaceutically acceptable salts, prodrugs, and metabolites thereof; and where further details concerning predecessor catechol compounds, e.g., metaproterenol, of Formula (6.17) are disclosed in Thoma and Zeile U.S. Pat. No. 3,341,594, which is incorporated herein by reference in its entirety;

where a further preferred embodiment comprises a compound where $R^{57}$ is hydroxy; $R^{58}$ and $R^{60}$ are each hydrogen; W is —C($R^{64}$)($R^{65}$)— where $R^{64}$ and $R^{65}$ are both methyl; and $R^{59}$ is methyl; resulting in a terbutaline bioisostere, represented by Formula (6.58):

(6.58)

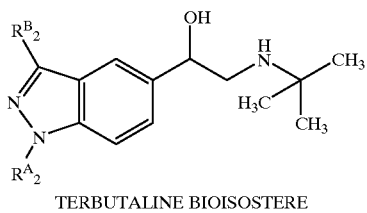

TERBUTALINE BIOISOSTERE and pharmaceutically acceptable salts, prodrugs, and metabolites thereof; and where further details concerning predecessor catechol compounds, e.g., metaproterenol, of Formula (6.18) are disclosed in Wetterlin and Svensson U.S. Pat. No. 3,937,838, which is incorporated herein by reference in its entirety.

(III) Bioisostere Replacement Compounds Active As Calcium Channel Antagonists

There is an important therapeutic class of calcium channel antagonists which includes verapamil, the members of which are characterized by having a catechol moiety as a central and characteristic portion of the overall chemical structure for which a biobioisostere replacement with an indazole moiety may be carried out in accordance with the present invention, i.e., while retaining the type of biological activity exhibited by the original catechol-containing compound. Calcium channel antagonists are useful in the treatment of variant agina, exertional angina, unstable angina, hypertension, myocardial ischemia, arrhythmia, and migraine prophylaxis. The catechol-containing chemical structure of verapamil may be illustrated by Formula (7.0):

(7.0)

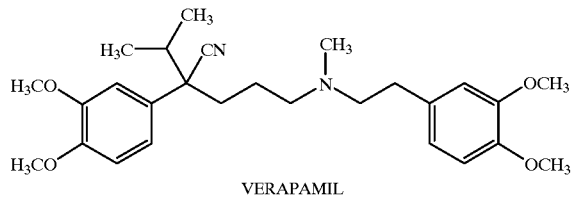

VERAPAMIL

With regard to the catechol moieties of verapamil, it is essentially a dimer in structure, i.e., it comprises two identical, mer, units forming a dipolymer. It is noted that verapamil is not wholly symmetrical in structure, and this is not, totally, a dimer in form. Nevertheless, as already discussed further above, the dimeric nature of the catechol moieties affords two possibilities for different embodiments with respect to the indazole-for-catechol bioisostere replacements of the present invention. These are (1) that both sets of catechol moieties are replaced by indazoles, which is the preferred embodiment; and (2) that only one or the other catechol moiety is replaced by indazole, which is the less preferred embodiment.

Where the chemical structure which exits between the catechol moieities is not symmetrical, as is the case with verapamil, there arises the further posssilbity of two alternative embodiments where only one of the catechol moieties is being replaced by indazole. Accordingly, there are three indazole-for-catechol bioisostere replacement embodiments of verapamil for each isomeric form of the indazole in accordance with the present invention. All together, then, there are a total of six (6) bioisostere replacement embodiments of verapamil, which are represented by Formulas (7.1), (7.2), (7.3), (7.4), (7.5) and (7.6):

(7.1)

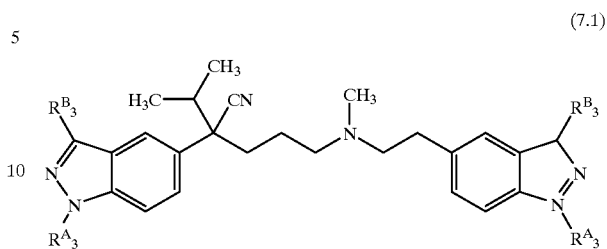

VERAPAMIL BIOISOSTERE;
FIRST INDAZOLE ISOMER;
DOUBLE REPLACEMENT (7.2)

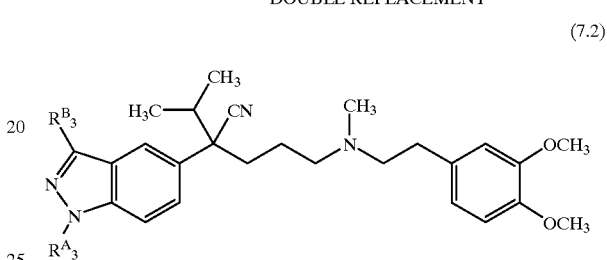

VERAPAMIL BIOISOSTERE;
FIRST INDAZOLE ISOMER;
SINGLE REPLACEMENT - FIRST ISOMER (7.3)

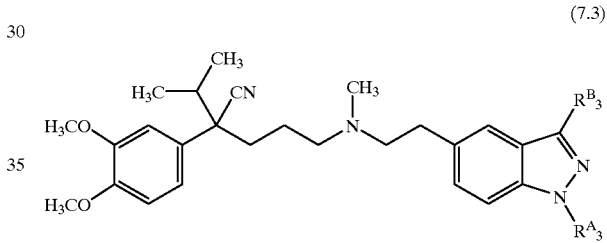

VERAPAMIL BIOISOSTERE;
FIRST INDAZOLE ISOMER;
SINGLE REPLACEMENT - SECOND ISOMER (7.4)

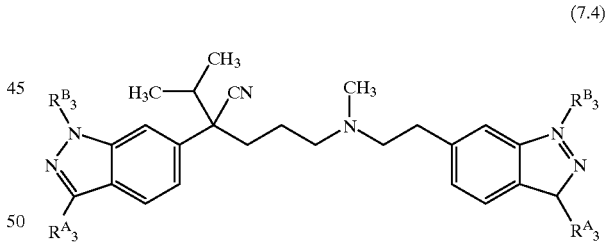

VERAPAMIL BIOISOSTERE;
SECOND INDAZOLE ISOMER;
DOUBLE REPLACEMENT (7.5)

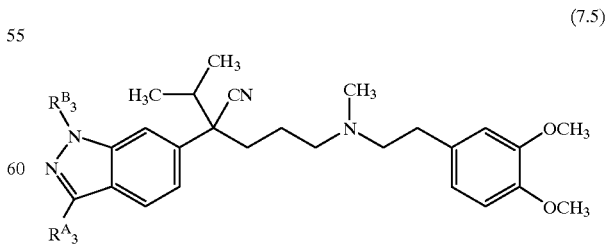

VERAPAMIL BIOISOSTERE;
SECOND INDAZOLE ISOMER;
SINGLE REPLACEMENT
FIRST ISOMER

-continued

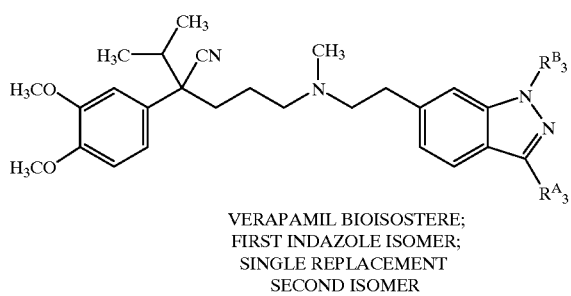

(7.6)

VERAPAMIL BIOISOSTERE;
FIRST INDAZOLE ISOMER;
SINGLE REPLACEMENT
SECOND ISOMER

Another calcium channel antagonist agent of the verapamil type is gallopamil, which may be represented by Formula (7.7):

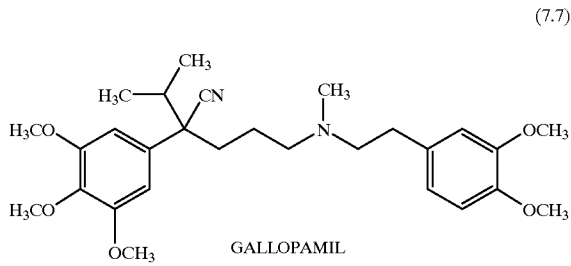

(7.7)

GALLOPAMIL

As already discussed in detail further above, the presence of a third, adjacent methoxy group on one of the phenyl groups of gallopamil affords the possibility of both inclusionary and exclusionary biobioisostere replacement embodiments in accordance with the present invention, which may be represented by Formulas (7.8) and (7.9):

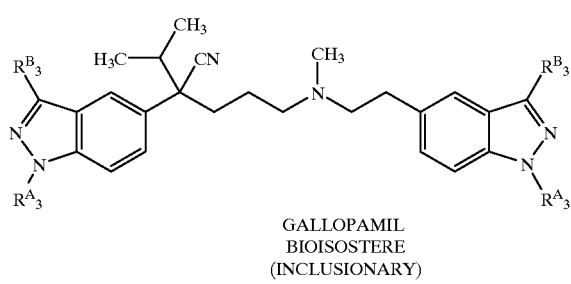

(7.8)

GALLOPAMIL
BIOISOSTERE
(INCLUSIONARY)

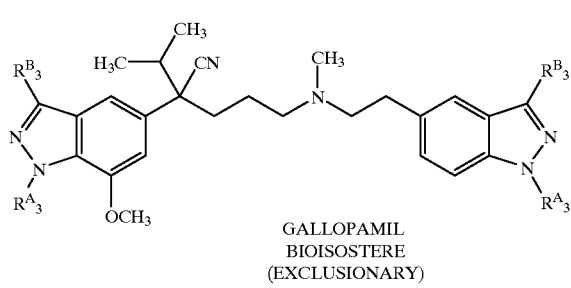

(7.9)

GALLOPAMIL
BIOISOSTERE
(EXCLUSIONARY)

Further embodiments of gallopamil bioisostere replacements of the present invention are possible in view of the isomeric forms discussed further above regarding verapamil. Thus, gallopamil is a dimer in form, but is asymmetrical in structure, as was the case with verapamil. Further, there are two isomeric forms of the indazole replacement. All of these isomeric structures are present in each of the inclusionary and exclusionary embodiments of the indazole-for-catechol bioisostere replacements for gallopamil. Accordingly, there are a total of twelve (12) bioisostere replacement embodiments of gallopamil in accordance with the present invention.

Other verapamil type calcium channel antagonists which are suitable for making indazole-for-catechol replacement bioisosteres in accordance with the present invention comprise fantofarone and closely related aminoalkoxyphenyl derivatives. The indazole bioisosteres of these compounds, as do the indazole bioisosteres of the other verapamil type calcium channel antagonists described herein, possess calcium transport inhibitory properties, as well as bradycardic, hypotensive and antiadrenergic properties. The resulting indazole replacement bioisosteres are, accordingly, useful in the treatment of angina pectoris, hypertension, arrhythmia and cerebral circulatory insufficiency. They are also useful in the antitumor field, where they are potentiators of anticancer chemotherapeutic agents. Fantofarone and its indazole-for-catechol bioisostere replacement may be represented by Formulas (7.10) and (7.11), respectively:

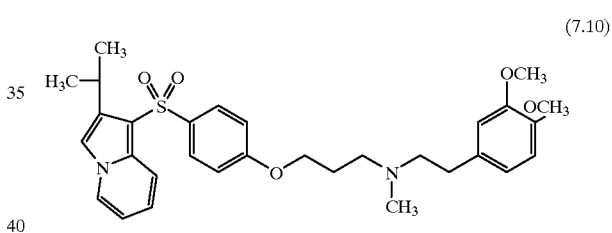

(7.10)

FANTOFARONE

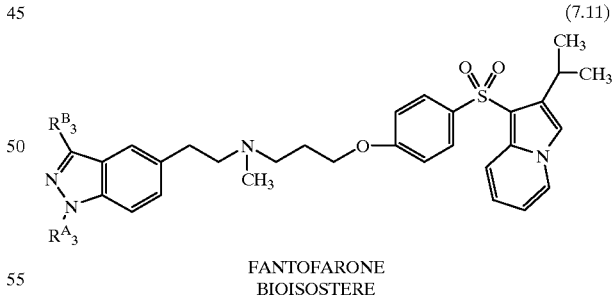

(7.11)

FANTOFARONE
BIOISOSTERE

A further verapamil type of calcium channel antagonist which is suitable for making indazole-for-catechol replacement bioisosteres in accordance with the present invention is trimetazidine and closely related methoxy-benzyl-piperazines. Trimetazidine has a 2,3,4-trimethoxyphenyl structure, and therefore falls within the category of indazole-for-catechol bioisostere replacement embodiments of the present invention which may be inclusionary or exclusionary, as described in detail further above. This may be illustrated in the case of trimetazidine by Formulas (7.12), (7.13), and (7.14):

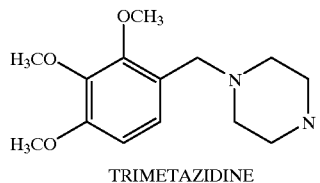

TRIMETAZIDINE (7.12)

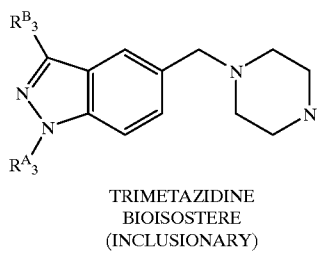

TRIMETAZIDINE
BIOISOSTERE
(INCLUSIONARY) (7.13)

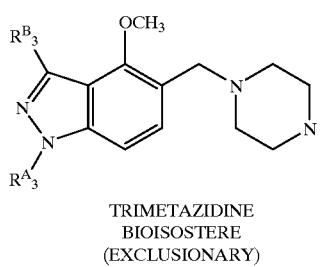

TRIMETAZIDINE
BIOISOSTERE
(EXCLUSIONARY) (7.14)

The indazole-for-catechol bioisostere replacement embodiments of this type possess valuable pharmacological properties as peripheral vasodilators, an action which is exerted both on the peripheral circulation and on the coronary arteries. The mechanism of action involves the smooth muscle fibers of the vessel walls of the circulatory system, and does not involve the autonomous nervous system. Thus, the bioisosteres of the present invention may be used in the treatment of various circulatory disorders such as arteritis or coronary insufficiency.

Further verapamil type calcium channel antagonists which are suitable for making indazole-for-catechol replacement bioisosteres in accordance with the present invention comprise lomerizine and closely related 1-(2,3,4-trimethoxybenzyl-4-[bis(4-fluorophenyl)methyl]piperazine derivatives. The indazole bioisosteres of these compounds are useful as agents for improving cerebrovascular diseases of humans, and in particular are antimigraine agents. Lomerizine and its indazole-for-catechol bioisostere replacements, both inclusionary and exclusionary forms thereof as described above, may be represented by Formulas (7.15), (7.16) and (7.17):

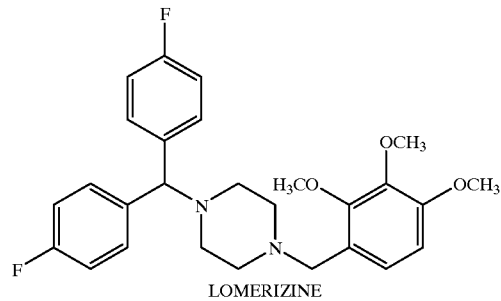

LOMERIZINE (7.15)

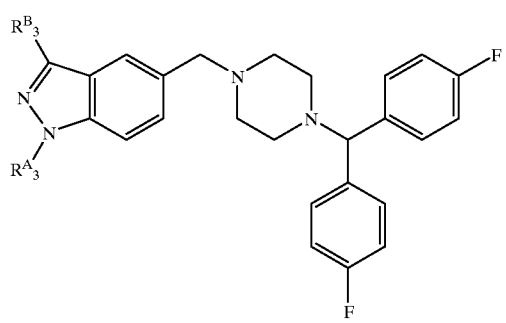

LOMERIZINE
BIOISOSTERE
(INCLUSIONARY) (7.16)

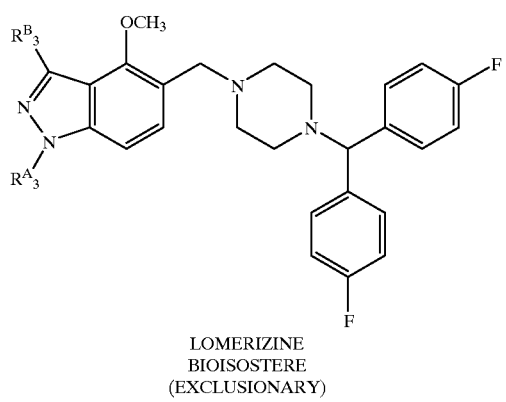

LOMERIZINE
BIOISOSTERE
(EXCLUSIONARY) (7.17)

Cerebrovascular diseases include intracranial hemorrhages such as intracerebral hemorrhage or subarachnoid hemorrhage, as well as cerebral infarctions such as cerebral thrombosis or cerebral embolus, transient ischemic attack, and hypertensive encephalopathy. A key mechanism in these diseases is infaction of brain parenchymal tissue resulting directly from hemorrhage, thrombus, or an embolus within the brain, which leads in turn to glucose and oxygen insufficiency, depriving the neurons of needed sources of energy. Functional and organic disturbances result in the ischemic area; consequently, therapeutic agents which supply or enhance the supply of glucose and oxygen to the ischemic area by increasing cerebral blood flow are effective for the treatment and prevention of such cerebrovascular diseases.

Heretofore, therapeutic agents which have been used clinically for the purpose of treating said cerebrovascular diseases and their subsequent complications, and to prevent relapse, have included such compounds as cinnarizine, bencyclane fumarate, cyclandelate, and cinepazide maleate.

Still further verapamil type calcium channel antagonists which are suitable for making indazole-for-catechol replacement bioisosteres in accordance with the present invention comprise zatebradine and closely related 7,8-dimethoxy-3-benzazepin-2-one derivatives. The indazole bioisosteres of these compounds have long-lasting bradycardiac activity and reduce the oxygen requirements of the heart, with only slight side effects such as antimuscarinic activity. Zatebradine has an asymmetrical dimer structure, as discussed further above, and consequently affords a number of embodiments of the indazole-for-catechol bioisostere replacement compounds of the present invention. These are illustrated in Formulas (7.18), (7.19), (7.20), and (7.21):

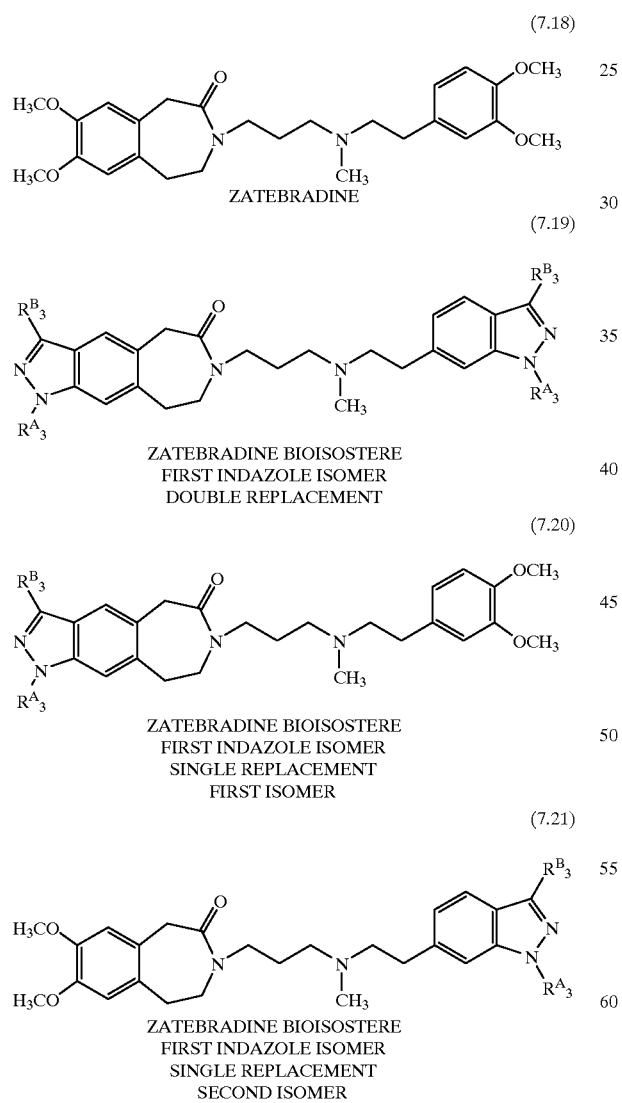

Accordingly, the present invention relates in particular to indazole-for-catechol bioisostere replacements active as calcium channel antagonists, comprising a compound of Formulas (7.22) or (7.23):

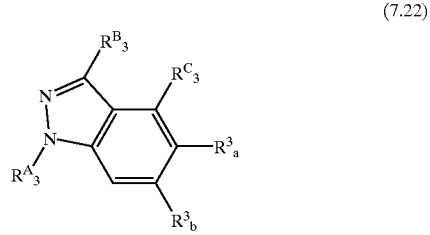

(7.22)

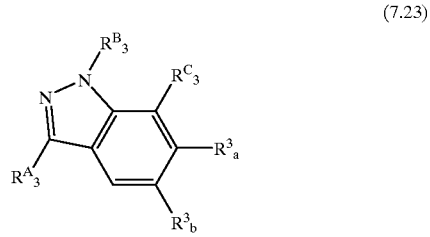

(7.23)

wherein
$R^C_3$ and $R^A_3$ and $R^B_3$ are defined the same as $R^C_1$ and $R^A_1$ and $R^B_1$ herein under Formulas (5.10) and (5.11), including preferred embodiments thereof, but are selected on an independent basis therefrom; and $R^3_a$ and $R^3_b$ are each individually and independently a member selected from the group consisting essentially of hydrogen and the substituents defined by partial Formulas (7.25); (7.28); (7.35); and (7.41) below, provided that both of $R^3_a$ and $R^3_b$ cannot be hydrogen at the same time;

wherein preferred embodiments comprise compounds where one of $R^3_a$ and $R^3_b$ is independently selected as hydrogen;

wherein said substituents in addition to hydrogen which define each of $R^3_a$ and $R^3_b$ comprise a member independently selected from the group consisting essentially of the moieties of partial Formulas (7.25); (7.28); (7.35); and (7.41):

(II-A)

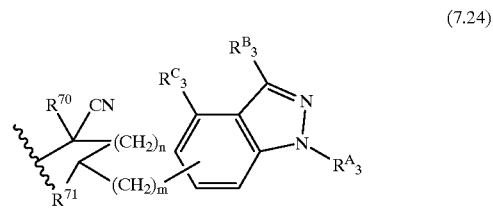

(7.24)

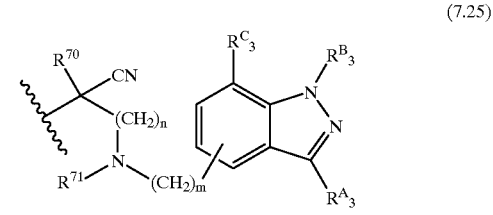

(7.25)

wherein $R^{70}$ is a member independently selected from the group consisting essentially of hydrogen; ($C_1$–$C_4$) alkyl; phenyl; benzyl; and cyclohexyl; $R^{71}$ is a member independently selected from the group consisting essentially of ($C_1$–$C_4$) alkyl; n is an integer independently selected from 2, 3, and 4; and m is an integer independently selected from 1, 2, and 3;

where preferred embodiments comprise compounds where $R^{70}$ is isopropyl; $R^{71}$ is methyl; n is 2; and m is 2, e.g., a verapamil bioisostere, represented by Formula (7.26):

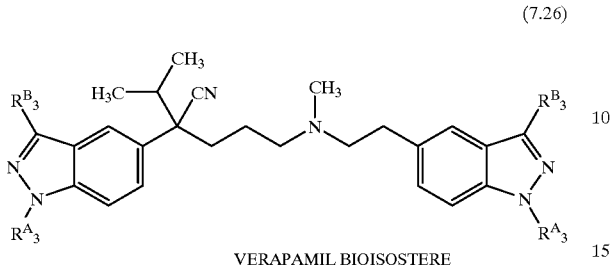

VERAPAMIL BIOISOSTERE (7.26)

and pharmaceutically acceptable salts, prodrugs, and metabolites thereof; and where further details concerning predecessor catechol compounds, e.g., verapamil, of Formula (7.0) are disclosed in Dengel U.S. Pat. No. 3,261,859, which is incorporated herein by reference in its entirety;

where further preferred embodiments comprise compounds where $R^C_3$ is methoxy in Formulas (7.22) and (7.23) but is hydrogen in Formulas (7.24) and (7.25); $R^{70}$ is isopropyl; $R^{71}$ is methyl; n is 2; and m is 2, e.g., a gallopamil bioisostere based on the second indazole isomer as discussed further above, represented by Formula (7.27):

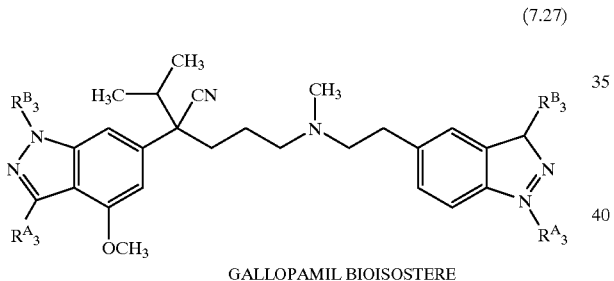

GALLOPAMIL BIOISOSTERE (7.27)

and pharmaceutically acceptable salts, prodrugs, and metabolites thereof; and where further details concerning predecessor catechol compounds, e.g., gallopamil, of Formula (7.7) are also disclosed in said Dengel U.S. Pat. No. 3,261,859, which is incorporated herein by reference in its entirety;

(III-B)

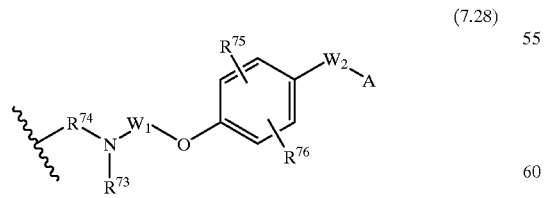

(7.28)

wherein $R^{73}$ is a member independently selected from the group consisting essentially of hydrogen and $(C_1-C_4)$ alkyl; $R^{74}$ is a member independently selected from the group consisting essentially of a single bond and a linear- or branched-alkylene radical $(C_1-C_5)$ alkyl; $W_1$ is a member independently selected from the group consisting essentially of straight- and branched-alkylene radicals $(C_2-C_5)$ alkyl, and 2-hydroxypropylene; $R^{75}$ and $R^{76}$ are members independently selected from the group consisting essentially of hydrogen, methyl, ethyl, chloro, and bromo; $W_2$ is a member independently selected from the group consisting essentially of —S—, —SO—, and —SO$_2$—; and A is a member indpendently selected from the group consisting essentially of (a)

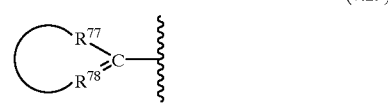

(7.29)

wherein $R^{77}$ and $R^{78}$ are taken together with the carbon atom to which they are attached to form an optionally aromatic mono- or di-cyclic carbocyclic group having from 5 to 10 carbon atoms and optionally substituted in the α-position with respect to the methylene group of partial Formula (7.29) by $R^{84}$ as defined below ; an optionally aromatic 5-membered heterocyclic group where the heteroatoms or heterogroups are members independently selected from the group consisting essentially of O, S, N, —N($R^{79}$)—, O together with N, O together with —N($R^{79}$)—, S together with N, S together with —N($R^{79}$)—, N together with N, and N together with —N($R^{79}$)—, optionally substituted in the α-position with respect to the methylene group of partial Formula (7.29) by $R^{84}$ as defined below, where $R^{79}$ is hydrogen, $(C_1-C_4)$ alkyl, or phenyl; or an optionally aromatic 6- to 10-membered mono- or di-cyclic heterocyclic group, where the heteroatoms or heterogroups are members independently selected from the group consisting essentially of O, S, N, —N($R^{79}$)—, O together with N, O together with —N($R^{79}$)—, S together with N, S together with —N($R^{79}$)—, N together with N, and N together with —N($R^{79}$)—, optionally substituted in the α-position with respect to the methylene group of partial Formula (7.29) by $R^{84}$ as defined below, where $R^{79}$ is hydrogen, $(C_1-C_4)$ alkyl, or phenyl;

(b)

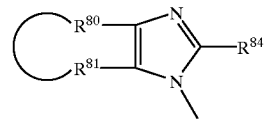

(7.30)

(c)

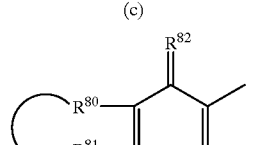

(7.31)

(d)

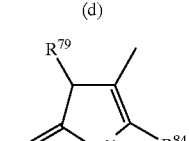

(7.32)

-continued (7.33)

(e)

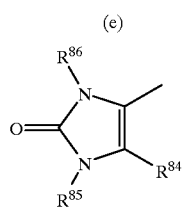

wherein
$R^{80}$ and $R^{81}$ are members independently selected from the group consisting essentially of hydrogen; ($C_1$–$C_4$) alkyl; phenyl; and taken together with the carbon atom to which they are attached represent an optionally aromatic 6-membered carbocyclic ring; $R^{82}$ is O or S; $R^{83}$ is O; S; or —N($R^{79}$)—; $R^{84}$ is a member independently selected from the group consisting essentially of hydrogen; ($C_1$–$C_4$) alkyl; ($C_3$–$C_7$) cycloalkyl; benzyl; and phenyl optionally substituted with 1 to 3 substituents selected from the group consisting essentially of fluoro, chloro, bromo, ($C_1$–$C_4$) alkyl, ($C_1$–$C_4$) alkoxy, and nitro; and $R^{85}$ and $R^{86}$ are members independently selected from the group consisting essentially of hydrogen; ($C_1$–$C_4$) alkyl; and benzoyl;

where in preferred embodiments, the group A is a member independently selected from the group consisting essentially of phenyl, cyclohexenyl, indenyl, naphthyl, dihydronaphthyl, pyridyl, dihydropyridyl, furyl, dihydrofuryl, thienyl, dihydrothienyl, pyrrolyl, dihydropyrrolyl, pyrazolyl, imidazolyl, pyrimidyl, pyrazinyl, pyridazinyl, oxazolyl, isxoazolyl, thiazolyl, benzofuryl, benzothienyl, indolyl, benzimidazolyl, benzoxazolyl, quinolinyl, benzisoxazolyl, cinnolinyl, quinoxalinyl, quinazolinyl, indolizinyl, thienopyridyl, tetrahydrothienopyridyl, pyrrolopyridyl, pyrazolopyridyl, pyrrolopyridazinyl, imidazopyridyl, dihydrofuranonyl, imidazolinonyl, and chromonyl;

where preferred embodiments comprise compounds where $R^{73}$ is $CH^3$—; $R^{74}$ is —$CH_2CH_2$—; $W_1$ is —$CH_2CH_2$—; $R^{75}$ and $R^{76}$ are both hydrogen; $W_2$ is —$SO_2$—; and A is a group of partial Formula (7.29) where $R^{77}$ and $R^{78}$ together are a di-cyclic heterocyclic group, where the heteroatom is N, substituted in the α-position with respect to the methylene group of partial Formula (7.29) by $R^{84}$, where $R^{84}$ is isopropyl, resulting in a fantofarone bioisostere based on the second isomer of indazole as discussed further above, represented by Formula (7.34):

(7.34)

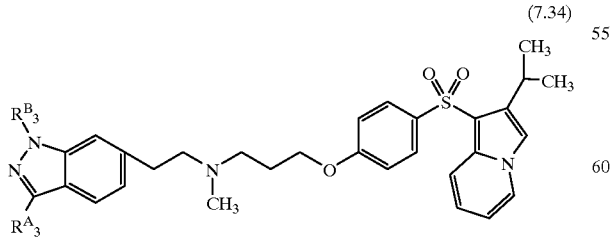

FANTOFARONE
BIOISOSTERE and pharmaceutically acceptable salts, prodrugs, and metabolites thereof; and where further details concerning predecessor catechol compounds, e.g., fantofarone, of Formula (7.10) are disclosed in Gubin et al. U.S. Pat. No. 4,957,925, which is incorporated herein by reference in its entirety;

(III-C)

(7.35)

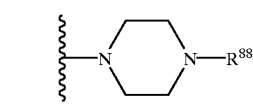

wherein $R^{88}$ is hydrogen or a group of partial Formula (7.36):

(7.36)

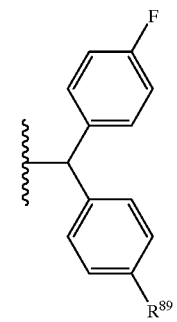

where $R^{89}$ is hydrogen or fluorine;

where preferred embodiments comprise compounds where $R^{88}$ is partial Formula (7.36) where $R^{89}$ is fluorine, a lomerizine bioisostere based on the second isomer of indazole, represented by Formulas (7.37) and (7.38):

(7.37)

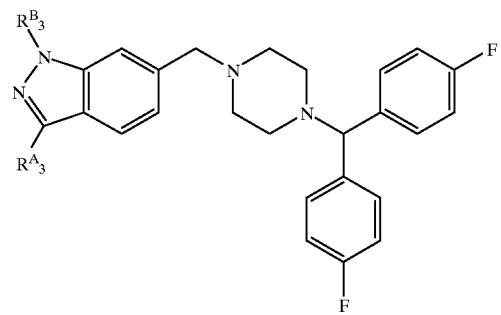

LOMERIZINE
BIOISOSTERE
(INCLUSIONARY)

(7.38)

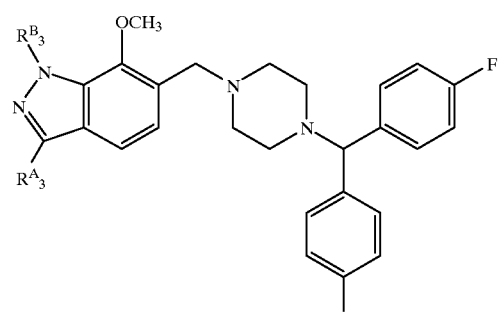

LOMERIZINE
BIOISOSTERE
(EXCLUSIONARY)

and pharmaceutically acceptable salts, prodrugs, and metabolites thereof; and where further details concerning predecessor catechol compounds, e.g., lomerizine, of Formula (7.15) are disclosed in Ohtaka et al. U.S. Pat. No. 4,663,325, which is incorporated herein by reference in its entirety;

where further preferred embodiments comprise compounds where $R^{88}$ is hydrogen, a trimetazidine bioisostere based on the second isomer of indazole, represented by Formulas (7.39) and (7.40):

(7.39)

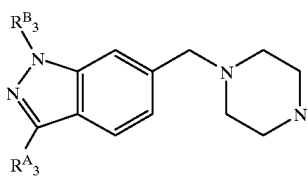

TRIMETAZIDINE
BIOISOSTERE
(INCLUSIONARY)

(7.40)

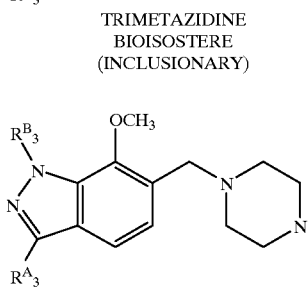

TRIMETAZIDINE
BIOISOSTERE
(EXCLUSIONARY)

and pharmaceutically acceptable salts, prodrugs, and metabolites thereof; and where further details concerning predecessor catechol compounds, e.g., trimetazidine, of Formula (7.12) are disclosed in Servier U.S. Pat. No. 3,262,852, which is incorporated herein by reference in its entirety;

(III-D) $R^3_a$ and $R^3_b$ are taken together to form the moiety of partial Formula (7.41):

(7.41)

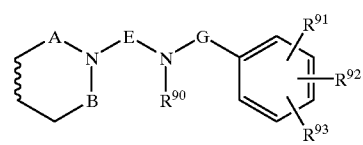

wherein A is —CH$_2$CH$_2$—; —CH=CH—; —NH—C(=O)—; —CH$_2$—C(=O)—; or —C(R$^{94}$)=N— where R$^{94}$ is (C$_1$–C$_3$) alkyl; and B is methylene; carbonyl; or thiocarbonyl; or A is —C(=O)—C(=O)—; —N=CH—; —CH(OH)—C(=O)—; —CH(OH)—CH$_2$—; —C(=NOH)—C(=O)—; or —CH(NHR$^{95}$)—C(=O)—, where R$^{95}$ is hydrogen or (C$_1$–C$_3$) alkyl substituted by phenyl, methoxyphenyl, or dimethoxyphenyl; and B is methylene; E is a member independently selected from the group consisting essentially of n-(C$_2$–C$_4$) alkylene, optionally substituted by (C$_1$–C$_3$) alkyl, 2-hydroxy-n-propylene, 2-hydroxy-n-butylene or 3-hydroxy-n-butylene; G is a member independently selected from the group consisting essentially of n-(C$_1$–C$_5$) alkylene, optionally substituted by (C$_1$–C$_3$) alkyl, where one methylene group of an n-alkylene of 2 to 5 carbon atoms may be replaced by a carbonyl group, with the proviso that B represents a methylene or carbonyl group, or methylene-n-hydroxyalkylene of 1 to 4 carbon atoms, where the methylene group is attached to the nitrogen atom; R$^{90}$ is a member independently selected from the group consisting essentially of hydrogen; (C$_1$–C$_3$) alkyl; phenyl(C$_1$–C$_3$) alkyl; (C$_1$–C$_3$) alkanoyl; (C$_1$–C$_3$) alkoxycarbonyl; and (C$_3$–C$_5$) alkenyl; and R$^{91}$, R$^{92}$, and R$^{93}$ are each a member independently selected from the group consisting essentially of hydrogen; fluorine; chlorine; bromine; hydroxy; cyano; nitro; trifluoromethyl (C$_1$–C$_4$) alkyl; (C$_1$–C$_4$) alkoxy; (C$_1$–C$_3$) alkylamino; di(C$_1$–C$_3$) alkylamino; (C$_1$–C$_3$) alkanoylamino; (C$_1$–C$_3$) alkoxycarbonylamino; bis(C$_1$–C$_3$) alkoxycarbonylamino; (trifluoromethyl)methylamino; and (trifluoromethyl)ethylamino; and R$^{91}$ and R$^{92}$ taken together with each other are (C$_1$–C$_2$) alkylenedixoy;

where preferred embodiments comprise compounds where A is —CH$_2$—C(=O)—; B is methylene; E is n-(C$_3$) alkylene, i.e., n-propylene; R$^{90}$ is methyl; G is n-(C$_2$) alkylene, i.e. ethylene; and one of R$^{91}$, R$^{92}$, and R$^{93}$ is hydrogen, while the other two are both (C$_1$) alkoxy, i.e., methoxy; resulting in zatebradine bioisosteres based on the second isomer of indazole, represented by Formulas (7.42), (7.43), and (7.44):

(7.42)

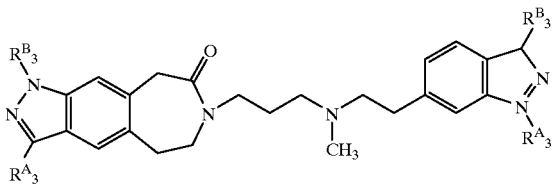

ZATEBRADINE BIOISOSTERE
SECOND INDAZOLE ISOMER
DOUBLE REPLACEMENT (7.43)

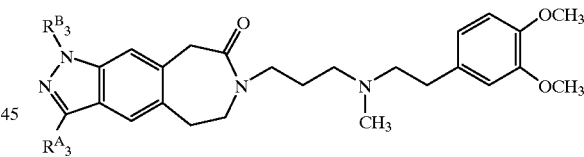

ZATEBRADINE BIOISOSTERE
SECOND INDAZOLE ISOMER
SINGLE REPLACEMENT - FIRST ISOMER (7.44)

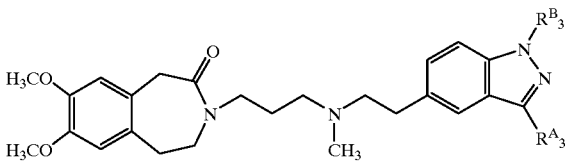

ZATEBRADINE BIOISOSTERE
SECOND INDAZOLE ISOMER
SINGLE REPLACEMENT - SECOND ISOMER and pharmaceutically acceptable salts, prodrugs, and metabolites thereof; and where further details concerning predecessor catechol compounds, e.g., zatebradine, of Formula (7.18) are disclosed in Reiffen et al. U.S. Pat. No. 4,490,369, which is incorporated herein by reference in its entirety.

(IV) Bioisostere Replacement Compounds Active As Antineoplastic Agents

A known antineoplastic agent which has a catechol moiety as part of its essential structure is trimetrexate, which may be represented by Formula (8.3):

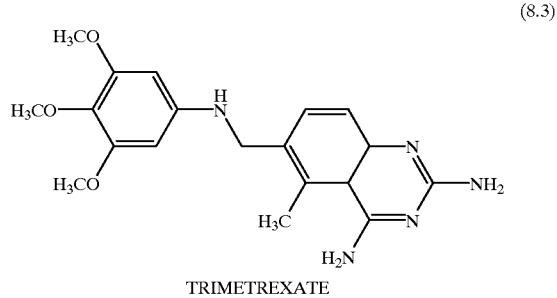

(8.3)

TRIMETREXATE

Trimetrexate is an antifolate, i.e., an inhibitor of dihydrofolate reductase, related to methotrexate, which has provided consistent cure of choriocarcinoma. Trimetrexate is a lipid-soluble folate antagonist which facilitates penetration of the blood-brain barrier. Trimetrexate has also also been used successfully in the therapy of psoriasis, a non-neoplastic disease of the skin characterized by abnormally rapid proliferation of epidermal cells. Trimetrexate has also been beneficial in the treatment of *Pneumocystis carinii*.

Another class of therapeutic agents useful in the treatment of neoplastic diseases is that of the protein tyrosine kinase inhibitors, which play a fundamental role in signal transduction pathways. Deregulated protein tyrosine kinase activity has been observed in many proliferative diseases such restenosis in addition to cancer and psoriasis. A number of tumor types have disfunctional growth factor receptor protein tyrosine kinases which result in inappropriate mitogenic signalling. Consequently, the therapeutic treatment of cancer has been based on agents which exhibit inhibition of protein tyrosine kinases, including particularly epidermal growth factor-receptor protein tyrosine kinase (EGF-R PTK). Among the most potent and selective inhibitors of epidermal growth factor-receptor protein tyrosine kinases are members of the class of 4-anilino-quinazolines. An example of such an inhibitor is the Parke-Davis compound PD-153,035, first described in Ward et al., *Biochem. Pharmacol.* (1994) 48(4) 659–666, and later by Fry et al., *Science* (1994) 265, 1093–1095, which may be represented by Formula (8.4):

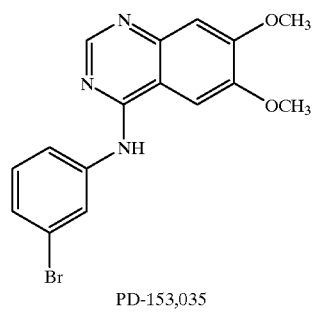

(8.4)

PD-153,035

For acceptable levels of activity, e.g., selective blocking of EGF-R autophosphorylation or c-jun induction, the electron-withdrawing bromine group at the meta-position of the 4-anilino moiety is preferred, as is the presence of small electron-donating substituents at the 6- and 7-positions, e.g., the two methoxy groups which form a catechol moiety. Such compounds are suitable for indazole-for-catechol bioisostere replacement in accordance with the present invention, which may be represented by Formulas (8.5) and (8.6):

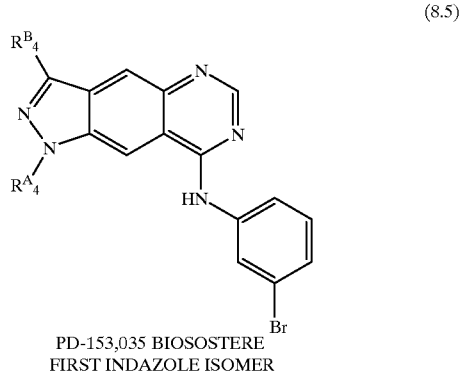

(8.5)

PD-153,035 BIOSOSTERE
FIRST INDAZOLE ISOMER

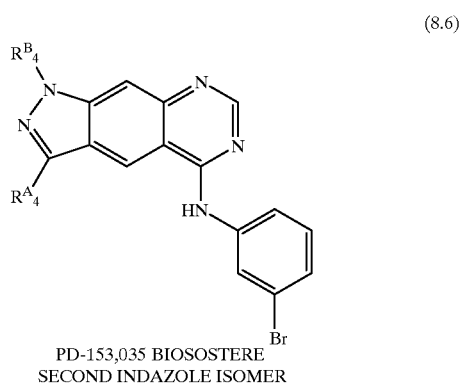

(8.6)

PD-153,035 BIOSOSTERE
SECOND INDAZOLE ISOMER

The 4-position anilino moiety may also be replaced by other substituents which afford the same or enhanced levels of EGF-R PTK inhibition or improved selectivity with respect to other protein tyrosine kinases. The 4-position may be occupied by bicyclic aminoheteroaromatic moieties or by heterocyclyl-substituted-6,7-dimethoxy-quinazolines, e.g., the dihydro-indolyl compound CP-292,597, as represented in Formulas (8.7) and (8.8), respectively:

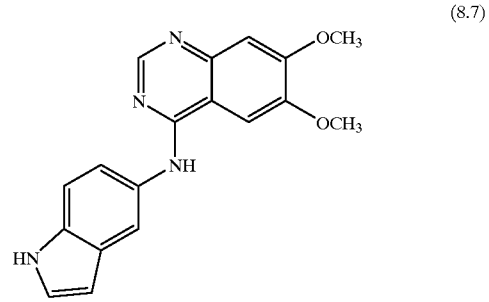

(8.7)

-continued

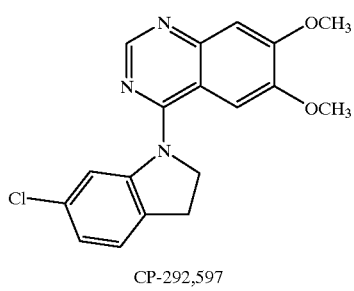
(8.8)

CP-292,597

The resulting compounds are suitable for indazole-for-catechol replacement in accordance with the present invention.

Further, suitable compounds result where the anilino nitrogen is methylated or replaced by oxygen or sulfur; a phenoxyanilino moiety is used; or the analogous phenethylamino moiety is present, as represented by the compounds of Formulas (8.9), (8.10), and (8.11), respectively:

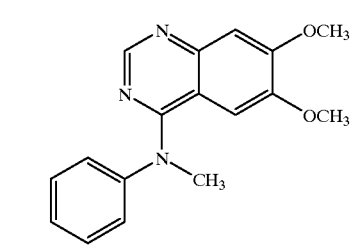
(8.9)

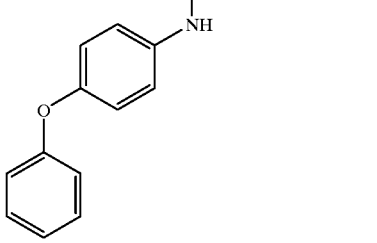
(8.10)

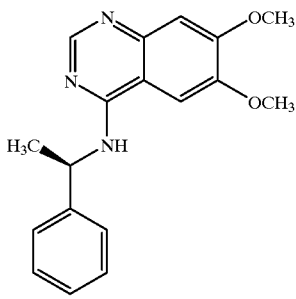
(8.11)

The resulting compounds are suitable for indazole-for-catechol replacement in accordance with the present invention.

Selective EGF-R PTK inhibitors have been obtained with quinazoline derivatives which have various substituents in the anilino side chains, e.g., an ethynyl moiety as in CP-358,774, or with 4-indolyl compounds, as represented by the compounds of Formulas (8.12) and (8.13), respectively:

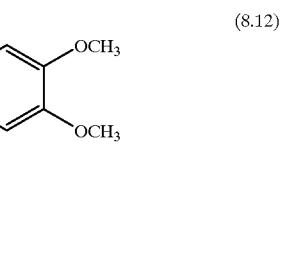
(8.12)

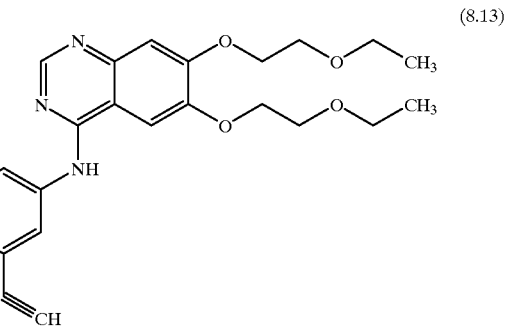
(8.13)

The resulting compounds are suitable for indazole-for-catechol replacement in accordance with the present invention.

The 4-position may be occupied by bicyclic aminoheteroaromatic moieties or by heterocyclyl-substituted-6,7-dimethoxy-quinazolines, e.g., the dihydro-indolyl compound CP-292,597. Modifications of the class of 4-anilino quinazolines described above have not been limited to the 4-anilino group alone. Basic amino side chains have been used in the 6-position of the quinazoline ring and various substituents have been added to the 4-anilino moiety in order to improve solubility of the 4-anilino-quinazolines, as illustrated by ZD-1839, a compound of Formula (8.18):

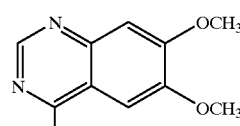
(8.18)

ZD-1839

The resulting compounds are suitable for indazole-for-catechol replacement in accordance with the present invention wherein the basic amino side chain at the 6-position of the predecessor compound is relocated to the corresponding position on the phenyl ring of the indazole group. This principle may be illustrated in the case of the ZD-1839 compounds by Formulas (8.19) and (8.20):

(8.19)

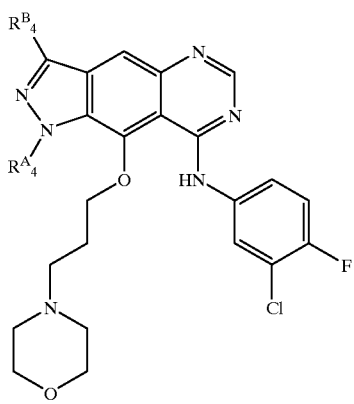

ZD-1839 BIOISOSTERE
FIRST INDAZOLE ISOMER (8.20)

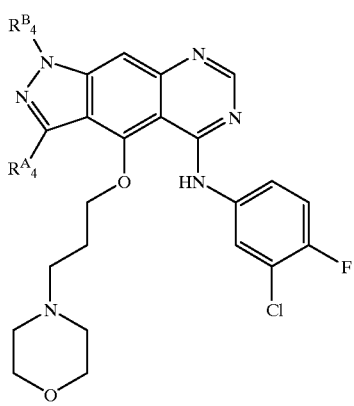

ZD-1839 BIOISOSTERE
SECOND INDAZOLE ISOMER

Accordingly, the present invention relates in particular to indazole-for-catechol bioisostere replacements active as antineoplastic agents, especially inhibitors of protein tyrosine kinases, including particularly epidermal growth factor-receptor protein tyrosine kinase (EGF-R PTK), comprising a compound of Formulas (8.21) or (8.22):

(IV)

(8.21)

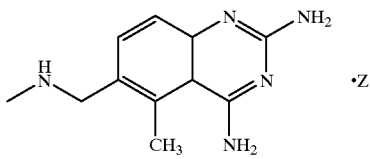

(8.22)

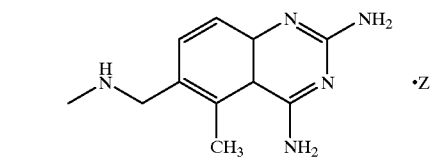

wherein
$R^C_4$ and $R^A_4$ and $R^B_4$ are defined the same as $R^C_1$ and $R^A_1$ and $R^B_1$ herein under Formulas (5.10) and (5.11), including preferred embodiments thereof, but are selected on an independent basis therefrom; and $R^4_a$ and $R^4_b$ are each individually and independently a member selected from the group consisting essentially of hydrogen and the substituents defined by partial Formulas (8.23); (8.28); (8.40); and (8.45) below, provided that both of $R^4_a$ and $R^4_b$ cannot be hydrogen at the same time;

wherein preferred embodiments comprise compounds where one of $R^4_a$ and $R^4_b$ is independently selected as hydrogen;

wherein said substituents in addition to hydrogen which define each of $R^4_a$ and $R^4_b$ comprise a member independently selected from the group consisting essentially of the moieties of partial Formulas (8.23); (8.28); (8.40); and (8.45):

(IV-A)

(8.23)

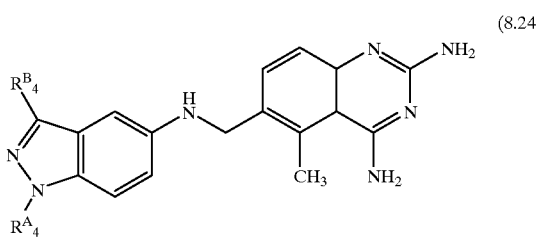

wherein Z is 2-hydroxyethanesulfonic acid or glucuronic acid, as well as pharmaceutically acceptable prodrugs and metabolites thereof; and where further details concerning predecessor catechol compounds, e.g., trimetrexate, of Formula (8.3) are disclosed in Colbry U.S. Pat No. 4,376,858, which is incorporated herein by reference in its entirety;

where embodiments of the present invention comprising trimetrexate bioisosteres may be represented by Formulas (8.24), (8.25), (8.26) and (8.27):

(8.24)

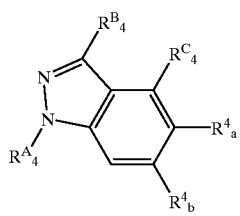

TRIMETREXATE BIOISOSTERE
FIRST INDAZOLE ISOMER
(INCLUSIONARY)

(8.25)

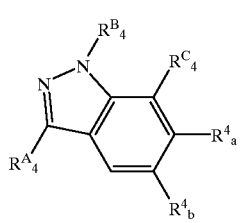

TRIMETREXATE BIOISOSTERE
SECOND INDAZOLE ISOMER
(INCLUSIONARY)

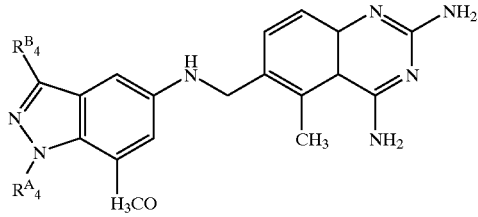

TRIMETREXATE BIOISOSTERE
FIRST INDAZOLE ISOMER
(EXCLUSIONARY)

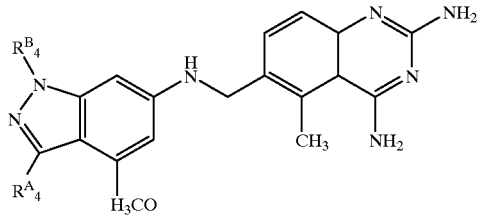

TRIMETREXATE BIOISOSTERE
SECONDARY INDAZOLE ISOMER
(EXCLUSIONARY)

(IV-B) $R^4_a$ and $R^4_b$ are taken together to form the moiety of partial Formula (8.28):

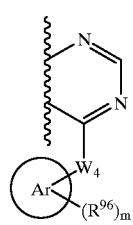

(8.28)

wherein Ar a substituted or unsubstituted mono- or bi-cyclic aryl or heteroaryl ring system of from 5 to 12 atoms where each monocyclic ring may contain 0 to 3 heteroatoms, and each bicyclic ring may contain 0 to 4 heteroatoms selected from N, O, and S, provided said heteroatoms are not vicinal oxygen and/or sulfur atoms; $W_4$ is a member independently selected from the group consisting essentially of a bond; —O—; —S—; —S(=O)—; —S(=O)$_2$—; —OCH$_2$—; —C=C—, —C≡C—; —C(=S)—; —SCH$_2$—; —NH—; —NHCH$_2$—; —NHCH($R^{97}$)—, —N($R^{97}$)— or —N($R^{97}$)CH$_2$— where $R^{97}$ is ($C_1$–$C_4$) alkyl; —CH$_2$—CH$_2$—, and —CH$_2$—CH$_2$—CH$_2$—; m is an integer selected from 0, 1, 2, and 3; and $R^{96}$ is a member independently selected from the group consisting essentially of hydrogen; —($C_1$–$C_4$) alkyl; —($C_2$–$C_4$) alkenyl; -phenyl; phenyl($C_1$–$C_3$) alkyl-; phenyl($C_2$–$C_3$) alkenyl-; -hydroxy; hydroxy($C_1$–$C_4$) alkyl-; —($C_1$–$C_4$) alkoxy; ($C_1$–$C_3$) alkoxy($C_1$–$C_2$) alkyl-; phenyl($C_1$–$C_3$) alkoxy-; phenyloxy-; ($C_1$–$C_4$) alkylcarbonyloxy-; phenylcarbonyloxy-; bromo, chloro, or fluoro; (bromo, chloro, or fluoro)($C_1$–$C_3$) alky-; -nitro; -cyano; -amino; mono- or di-($C_1$–$C_4$) alkylamino-; ($C_1$–$C_4$) alkylcarbonylamino-; phenylcarbonylamino-; -carboxy; carboxy($C_1$–$C_3$) alkyl-; ($C_1$–$C_3$) alkoxycarbonyl-; phenyl($C_1$–$C_3$) alkoxycarbonyl; ($C_1$–$C_3$) alkoxycarbonyl($C_1$–$C_3$) alkyl-; amino($C_1$–$C_3$) alkoxy-; amido; mono- and di-($C_1$–$C_3$) alkylamido; N,N—($C_1$–$C_3$) cycloalkylamido-; ($C_1$–$C_3$) alkylthio-; ($C_1$–$C_3$) alkylsulfinyl-; -sulfonyl; mono- and di-($C_1$–$C_3$) alkylsulfonyl-; -sulfamoyl; mono- and di-($C_1$–$C_3$) alkylsulfamoyl-; (bromo, chloro, or fluoro) phenyl-; benzoyl; and provided that m is 1, azido and $R^{94}_a$-ethynyl, where $R^{94}_a$ is hydrogen or ($C_1$–$C_6$) alkyl substituted by 0 to 2 substituents where said substituent is a member independently selected from the group consisting essentially of hydrogen; amino; hydroxy; $R^{94}_b$—O; $R^{94}_b$—NH; and ($R^{94}_b$)$_2$—N, where $R^{94}_b$ is ($C_1$–$C_4$) alkyl, where preferred embodiments comprise a compound wherein Ar as a monocyclic aryl or heteroaryl ring is a member independently selected from the group consisting essentially of substituted and unsubstituted benzene; pyrrole: thiophene; furan; thiazole; imidazole; pyrazole; 1,2,4-triazole; pyridine; 2(1H)-pyridone; 4(1H)-pyridone; pyrazine; pyrimidine; pyridazine; isothiazole; isoxazole; oxazole; and tetrazole; and wherein Ar as a bicyclic aryl or heteroaryl ring is a member independently selected from the group consisting essentially of substituted and unsubstituted naphthalene; tetralin; naphthyridine; benzofuran; benzothiophene; indole; 2,3-dihydroindole; 1H-indazole; indoline; benzopyrazole; 1,3-benzodioxole; benzoxazole; purine; coumarin; chromone; quinoline; tetrahydroquinoline; isoquinoline; benzimidazole; quinazoline; pyrido[2,3-b]pyrazine; pyrido[3,4-b]pyrazine; pyrido[3,2-c]pyridazine; pyrido[3,4-b]pyridine; 1H-pyrazole[3,4-d]pyrimidine; pteridine; 2(1H)-quinolone; 1(2H)-isoquinolone; 1,4-benzisoxazine; benzothiazole; quinoxaline; quinoline-N-oxide; isoquinoline-N-oxide; quinoxaline-N-oxide; quinazoline-N-oxide; benzoxazine; phthalazine; and cinnoline; and $R^{96}$ is a member independently selected from the group consisting essentially of hydrogen; —($C_1$–$C_4$) alkyl; —($C_2$–$C_4$) alkenyl; hydroxy; —($C_1$–$C_4$) alkoxy; bromo, chloro, or fluoro; (bromo, chloro, or fluoro)($C_1$–$C_3$) alky-; -amino; mono- or di-($C_1$–$C_4$) alkylamino-; ($C_1$–$C_4$) alkylcarbonylamino-; phenylcarbonylamino-; -carboxy; carboxy($C_1$–$C_3$) alkyl-; amido; mono- and di-($C_1$–$C_3$) alkylamido; N,N—($C_1$–$C_3$)cycloalkylamido-; ($C_1$–$C_3$) alkylthio-; ($C_1$–$C_3$) alkylsulfinyl-; mono- and di-($C_1$–$C_3$) alkylsulfonyl-; mono- and di-($C_1$–$C_3$) alkylsulfamoyl-;

where more preferred embodiments comprise a compound wherein Ar is substituted or unsubstituted benzene; pyridine; thiophene; naphthalene; quinoline; indole; 1H-pyrazole[3,4-d]pyrimidine; e.g., a bioisostere represented by Formulas (8.29) and (8.30):

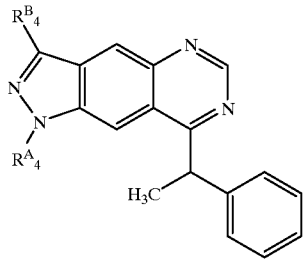

(8.29)

-continued (8.30)

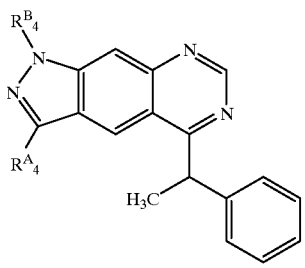

and pharmaceutically acceptable salts, prodrugs, and metabolites thereof; and where further details concerning predecessor catechol compounds, e.g., the compounds of Formula (8.9), are disclosed in Myers et al. International Pat. WO 95/15758, which is incorporated herein by reference in its entirety;

where further preferred embodiments comprise compounds wherein $R^4{}_a$ and $R^4{}_b$ are taken together to form the moiety of partial Formula (8.31):

(8.31)

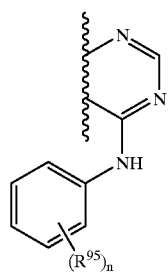

wherein $R^{95}$ is a member independently selected from the group consisting essentially of hydrogen; hydroxy; bromo, chloro or fluoro; trifluoromethyl; amino; nitro; cyano; and ($C_1$–$C_4$) alkyl; and n is an integer selected from 1 and 2; and where especially preferred embodiments comprise a compound where $R^{95}$ is bromo and is meta with respect to the 4-anilino moiety; and n is 1; e.g., a PD-153,035 bioisostere, represented by Formula (8.5) set out further above and repeated here:

(8.5)

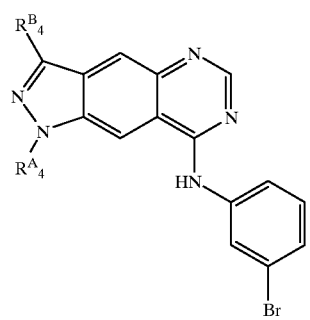

PD-153,035 BIOISOSTERE
FIRST INDAZOLE ISOMER and pharmaceutically acceptable salts, prodrugs, and metabolites thereof; and where further details concerning predecessor catechol compounds, e.g., PD-153,035, of Formula (8.4), are disclosed in Barker et al. European Pat. EP 566,226, which is incorporated herein by reference in its entirety;

where still further preferred embodiments comprise compounds wherein $W_4$ is a bond; Ar is indole; and $R^{96}$ is hydrogen; e.g., a bioisostere of the compounds of Formula (8.12), which may be represented by Formulas (8.32) and (8.33):

(8.32)

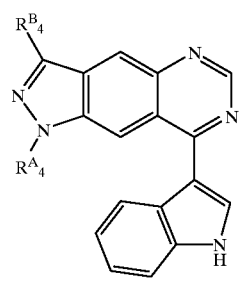

(8.33)

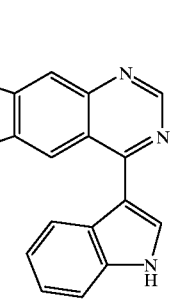

and pharmaceutically acceptable salts, prodrugs, and metabolites thereof;

where further details concerning predecessor catechol compounds, e.g., those of Formula (8.12), are disclosed in Myers et al. International Pat. WO 96/39145, which is incorporated herein by reference in its entirety;

where still yet further preferred embodiments comprise compounds wherein Ar is benzene; $W_4$ is NH; and $R^{96}$ is $R^{94}{}_a$-ethynyl, where $R^{94}{}_a$ is hydrogen, e.g., bioisosteres of the compounds of Formula (8.13), which may be represented by Formulas (8.34) and (8.35):

(8.34)

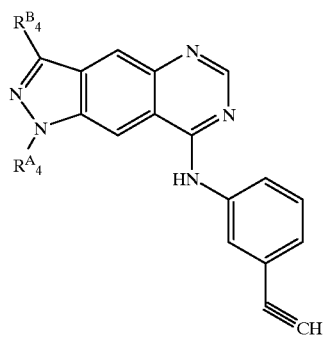

(8.35)

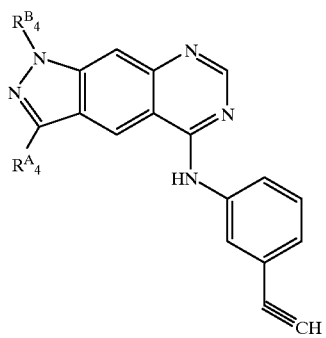

and pharmaceutically acceptable salts, prodrugs, and metabolites thereof;

where further details concerning predecessor catechol compounds, e.g., compounds of Formula (8.13) are disclosed in Schnur and Arnold International Pat. WO 96/30347, which is incorporated herein in its entirety;

where additional preferred embodiments comprise compounds wherein Ar is indole; $W_4$ is NH; and $R^{96}$ is hydrogen, resulting in 4-(5-indolylamino)quinazoline compounds, e.g., bioisosteres of the compounds of Formula (8.7), which may be represented by Formulas (8.36) and (8.37):

(8.36)

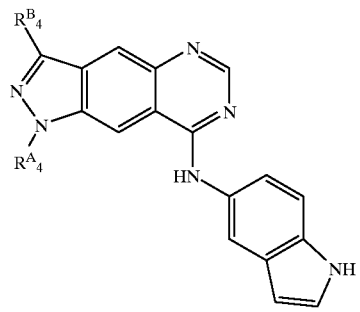

(8.37)

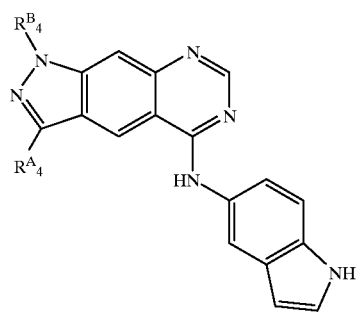

and pharmaceutically acceptable salts, prodrugs, and metabolites thereof;

where further details concerning predecessor catechol compounds, e.g., compounds of Formula (8.7) are disclosed in Barker et al. European Pat. EP 602,851, which is incorporated herein in its entirety;

where further additional preferred embodiments comprise compounds wherein Ar is benzenee; $W_4$ is —NHCH($R^{97}$)— where $R^{97}$ is (R)-methyl; and $R^{96}$ is hydrogen, resulting in (R)-phenylethylamino compounds, e.g., bioisosteres of the compounds of Formula (8.11), which may be represented by Formulas (8.38) and (8.39):

(8.38)

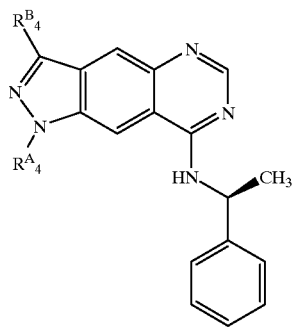

(8.39)

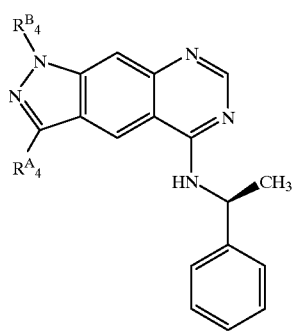

and pharmaceutically acceptable salts, prodrugs, and metabolites thereof;

where further preferred embodiments comprise compounds wherein Ar is benzene; $W_4$ is NH; m is 2; and $R^{96}$ chloro or fluoro; e.g., bioisosteres of the compounds of ZD-1839 of Formula (8.18), which may be represented by Formulas (8.19) and (8.20) set out further above and repeated here:

(8.19)

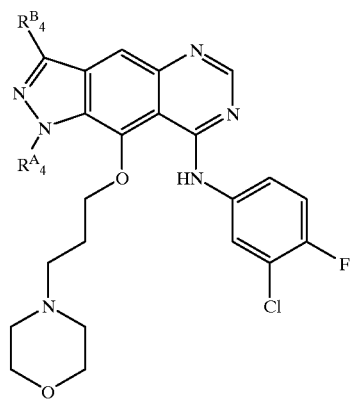

ZD-1839 BIOISOSTERE
FIRST INDAZOLE ISOMER

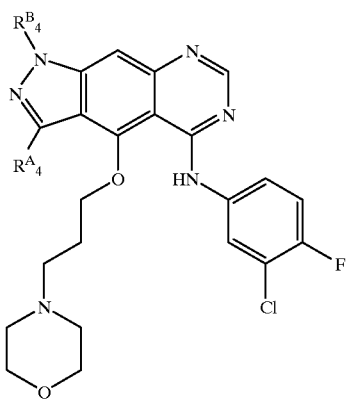

ZD-1839 BIOISOSTERE
SECOND INDAZOLE ISOMER and pharmaceutically acceptable salts, prodrugs, and metabolites thereof;
where further details concerning predecessor catechol compounds, e.g., compounds of ZD-1839 of Formula (8.18) are disclosed in Barker International Pat.'s WO 96/33977; WO 96/33978; WO 96/33979; WO 96/33980; and WO 96/33981; which are incorporated herein in their entireties;

(IV-C)

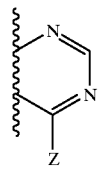

wherein Z is a moiety of partial Formulas (8.41) and (8.42)

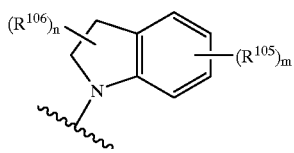

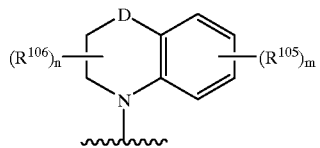

wherein m is an integer selected from 0, 1, 2, 3, and 4; n is an integer selected from 0, 1, and 2; D is saturated carbon; oxy; or thio; $R^{105}$ is a member independently selected, for each occurrence in partial Formulas (8.41) and (8.42), from the group consisting essentially of mono-, di-, or tri-fluoromethyl; bromo, chloro, or fluoro; nitro; hydroxy; amino; azido; isothiocyano; ($C_1$–$C_4$) alkyl; phenyl; thienyl; ($C_1$–$C_4$) alkoxy; benzyloxy; phenoxy; ($C_2$–$C_6$) alkenyl; ($C_2$–$C_6$) alkynyl; ($C_1$–$C_4$) alkylenedioxy; cyano; benzoylamino; trifluoromethylcarbonylamino; ($C_1$–$C_4$) alkanoylamino; ($C_1$–$C_4$) alkanoyl-N-mono- or —N,N-di-($C_1$–$C_4$) alkylamino; ($C_1$–$C_4$) alkylsulfonylamino; trifluoromethylsulfonylamino; ($C_1$–$C_4$) alkylthio; ($C_1$–$C_4$) alkylsulfinyl; ($C_1$–$C_4$) alkylsulfonyl; pyrrol-1-yl; piperidin-1-yl; and pyrrolidin-1-yl; where said phenyl, benzyloxy, phenoxy and benzoylamino groups are optionally mono-substituted with a member independently selected from the group consisting essentially of bromo, chloro, or fluoro; nitro; trifluoromethyl; hydoxy; and ($C_1$–$C_4$) alkyl; and where said ($C_1$–$C_4$) alkylenedioxy is linked at both ends thereof to adjacent carbons of the benzene moiety to which it is attached; $R^{106}$, when it is not attached to a ring carbon which is adjacent to an oxy, thio or —N— ring atom, is a member independently selected, for each occurrence in partial Formulas (8.41) and (8.42), from the group consisting essentially of hydroxy; amino; N-mono- or N,N-di-($C_1$–$C_4$) alkylamino; sulfo; and ($C_1$–$C_4$) alkoxy; and $R^{106}$, when it is attached to a ring carbon which is adjacent to an oxy, thio or —N— ring atom, is a member independently selected, for each occurrence in partial Formulas (8.41) and (8.42), from the group consisting essentially of carboxy; hydroxy ($C_1$–$C_4$) alkyl; ($C_1$–$C_4$) alkoxy($C_1$–$C_4$) alkyl; amino ($C_1$–$C_4$) alkyl; mono-N— and di-N,N—($C_1$–$C_4$) alkylamino($C_1$–$C_4$) alkyl; morpholino($C_1$–$C_4$) alkyl; 4-($C_1$–$C_4$) alkyl-piperazin-1-yl($C_1$–$C_4$) alkyl; carboxy ($C_1$–$C_4$) alkyl; ($C_1$–$C_4$) alkoxycarbonyl; sulfo($C_1$–$C_4$) alkyl; and ($C_1$–$C_4$) alkyl;
where preferred embodiments comprise compounds wherein n is 0; and m is 1 and $R^{105}$ is chloro resulting in quinazoline-(6-chloro-2,3-dihydro-1H-indol-1-yl)-methylamine compounds, e.g., bioisosteres of CP-292,597 of Formula (8.8), which may be represented by Formulas (8.43) and (8.44):

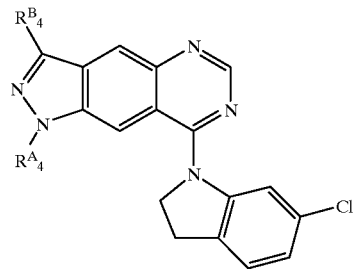

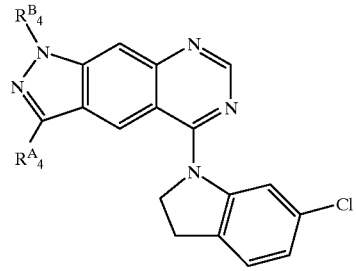

and pharmaceutically acceptable salts, prodrugs, and metabolites thereof;
where further details concerning predecessor catechol compounds, e.g., CP-292,597 compounds of Formula (8.8) are disclosed in Arnold International Pat. WO 95/23141, which is incorporated herein in its entirety;

(IV-D) $R^4_a$ and $R^4_b$ are taken together to form the moiety of partial Formula (8.45);

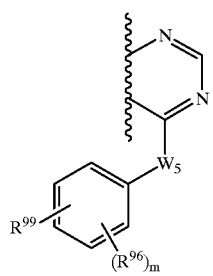

(8.45)

wherein $R^{96}$ and m are as defined under (IV-C) above, but are selected on an independent basis therefrom; $W_5$ is —Y—CH$_2$—; —CH$_2$—Y—, or —Y—; where Y is O, S(O)$_q$ where q is an integer selected from 0, 1, and 2, or NR$^{100}$ where $R^{100}$ is hydrogen or (C$_1$–C$_8$) alkyl; and $R^{99}$ is a group —ZR$^{101}$— where Z is joined to $R^{101}$ through a bridging group (CH$_2$)$_p$ where p is an integer selected from 0, 1 and 2; and Z is a member independently selected from the group consisting essentially of —V—CH$_2$—, —V—CF$_2$—, —CH$_2$—V—, —CF$_2$—V—, and —V—, where V is a hydrocarbyl group containing 0, 1, or 2 carbon atoms; carbonyl; —CH(OH)—; sulfonamide; amide; —O—; —S(O)$_q$—; and —NR$^{102}$ where $R^{102}$ is hydrogen or (C$_1$–C$_4$) alkyl; and $R^{101}$ is optionally substituted (C$_3$–C$_7$) cycloalkyl; or an optionally substituted 5,6,7,8,9, or 10-membered carbocyclic or heterocyclic moiety where said carbocyclic moiety is a member independently selected from the group consisting essentially of phenyl; benzyl; indene; naphthalene; tetralin; decalin; cyclopentyl; cyclohexyl; and cycloheptyl; and said heterocyclic moiety is a member independently selected from the group consisting essentially of furan; dioxolane; thiophene; pyrrole; imidazole; pyrrolidine; pyran; pyridine; pyrimidine; morpholine; piperidine; oxazoline; oxazolidine; thiazole; thiadiazole; benzofuran; indole; isoindole; quinazoline; quinoline; and isoquinoline; or $R^{99}$ is a group —ZR$^{101}$— where Z is —NR$^{102}$, and —NR$^{102}$ and $R^{101}$ together form a 5, 6, 7, 8, 9, or 10-membered heterocyclic moiety as defined under $R^{101}$ above;

where preferred embodiments comprise compounds wherein $R^{99}$ is in the para position with respect to $W_5$; $W_5$ is NR$^{102}$ where $R^{102}$ is hydrogen; and $R^{99}$ is a member selected from the group consisting essentially of benzyl; phenoxy; and benzyloxy; e.g., a bioisostere represented by Formulas (8.46) and (8.47):

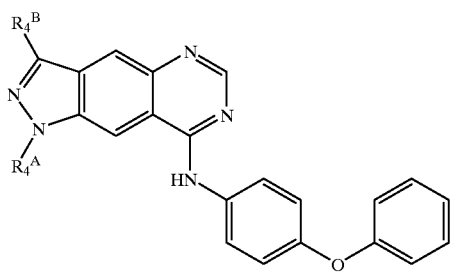

(8.46)

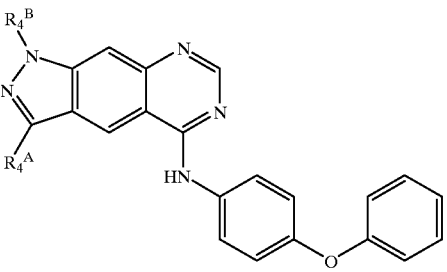

(8.47)

and pharmaceutically acceptable salts, prodrugs, and metabolites thereof, and where further details concerning predecessor catechol compounds, e.g., of Formula (8.10) are disclosed in Hudson et al. International Pat. WO 96/09294, which is incorporated herein by reference in its entirety.

(V) Bioisostere Replacement Compounds Active As PDE4 Inhibitors

Since the recognition that cyclic adenosine phosphate (AMP) is an intracellular second messenger, inhibition of the phosphodiesterases has been a target for modulation and, accordingly, therapeutic intervention in a range of disease processes. More recently, distinct classes of PDE have been recognized, and their selective inhibition has led to improved drug therapy. More particularly, it has been recognized that inhibition of PDE type IV can lead to inhibition of inflammatory mediator release and airway smooth muscle relaxation. Thus, compounds that inhibit PDE type IV, but which have poor activity against other PDE types, inhibit the release of inflammatory mediators and relax airway smooth muscle without causing cardiovascular effects or antiplatelet effects. TNF has also been recognized as being involved in many infectious and auto-immune diseases, and it has been shown that TNF is the prime mediator of the inflammatory response seen in sepsis and septic shock.

This particular embodiment of the present invention relates to compounds having therapeutic usefulness based on their activity as phosphodiesterase-4 inhibitors, comprising an indazole-for-catechol bioisosteric replacement wherein said therapeutic usefulness is equivalent to or an improvement over the same activity possessed by the corresponding catechol-containing predecessor compound. In a preferred embodiment of this aspect of the present invention, the indazole-for-catechol bioisostere replacement compounds are therapeutically useful in treating asthma.

The indazole replacement bioisostere compounds of the present invention are useful in treating or preventing one or members selected from the groups of diseases and conditions consisting essentially of (1) inflammatory comprising: joint inflammation, rheumatoid arthritis, rheumatoid spondylitis, osteoarthtis, inflammatory bowel disease, ulcerative colitis, chronic glomerulonephritis, dermatitis, and Crohn's disease; (2) respiratory comprising: asthma, acute respiratory distress syndrome, chronic pulmonary inflammatory disease, bronchitis, chronic obstructive airway disease, and silicosis; (3) infectious comprising: sepsis, septic shock, endotoxic shock, gram negative sepsis, toxic shock syndrome, fever and myalgias due to bacterial, viral or fungal infection, and influenza; (4) immune comprising: autoimmune diabetes, systemic lupus erythematosis, graft vs. host reaction, allograft rejections, multiple sclerosis, psoriasis, and allergic rhinitis; and (5) general comprising: bone resorption diseases; reperfusion injury; cachexia secondary to infection or malignancy; cachexia secondary to human acquired immune deficiency syndrome (AIDS), human immunodeficiency virus (HIV) infection, or AIDS related complex (ARC); keloid formation; scar tissue formation; type 1 diabetes mellitus; and leukemia; wherein said compounds are inhibitors of phosphodiesterase isozyme 4 (PDE4).

Especially important among the above-recited diseases and conditions which may be treated or prevented using the compounds of the present invention are the inflammatory diseases and conditions and the respiratory diseases and conditions. Among the inflammatory diseases and conditions which are especially significant with regard to successful treatment or prevention using the compounds of the present invention comprise: joint inflammation, rheumatoid arthritis, osteoarthritis, and inflammatory bowel disease. Among the respiratory diseases and conditions which are especially significant with regard to successful treatment or prevention using the compounds of the present invention comprise: asthma, acute respiratory distress syndrome, and bronchitis.

Accordingly, a further embodiment of the present invention relates in particular to indazole-for-catechol bioisostere replacements active as PDE4 inhibitors, especially inhibitors useful in treating asthma and other respiratory and inflammatory diseases and conditions, comprising a compound of Formulas (9.0) and (9.1):

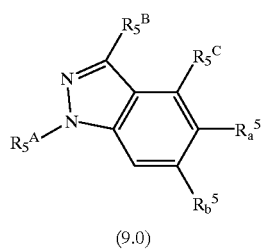

(9.0)

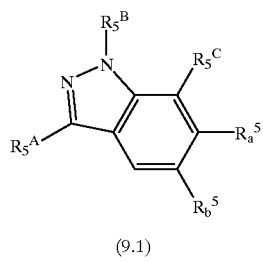

(9.1)

and to pharmaceutically acceptable salts thereof, wherein:
$R^C_5$ is a member independently selected from the group consisting essentially of hydrogen; hydroxy; —O—$(C_1-C_4)$ alkyl; —O—$(C_1-C_4)$ alkyl$(C_1-C_2)$ alkoxy; and —O—$(C_1-C_4)$ alkyl-morpholino;

$R^A_5$ is a member independently selected from the group consisting essentially of hydrogen, $(C_1-C_9)$ alkyl; —$(CH_2)_n(C_3-C_{10})$ cycloalkyl wherein n is an integer selected from 0, 1, and 2; $(C_1-C_6)$ alkoxy$(C_1-C_6)$ alkyl; $(C_2-C_6)$ alkenyl; —$(CH_2)_n(C_3-C_9)$ heterocyclyl wherein n is an integer selected from 0, 1, and 2; and —$(Z^1)_b(Z^2)_c(C_6-C_{10})$ aryl wherein b and c are integers independently selected from 0 and 1, $Z^1$ is $(C_1-C_6)$ alkylene or $(C_2-C_6)$ alkenylene, and $Z^2$ is O, S, $SO_2$, or $NR^{119}$; and further wherein said heterocyclyl is a member independently selected from the group consisting essentially of acridinyl; benzimidazolyl; benzodioxolane; 1,3-benzodioxol-5-yl; benzo[b]furanyl; benzo[b]thiophenyl; benzoxazolyl; benzthiazolyi; carbazolyl; cinnolinyl; 2,3-dihydrobenzofuranyl; 1,3-dioxane; 1,3-dioxolane; 1,3-dithiane; 1,3-dithiolane; furanyl; imidazolidinyl; imidazolinyl; imidazolyl; 1H-indazolyl; indolinyl; indolyl; 3H-indolyl; isoindolyl; isoquinolinyl; isothiazolyl; isoxazolyl; morpholinyl; 1,8-naphthyridinyl; oxadiazolyl; 1,3-oxathiolane; oxazolidinyl; oxazolyl; oxiranyl; parathiazinyl; phenazinyl; phenothiazinyl; phenoxazinyl; phthalazinyl; piperazinyl; piperidinyl; pteridinyl; pyranyl; pyrazinyl; pyrazolidinyl; pyrazolinyl; pyrazolo[1,5-c]triazinyl; pyrazolyl; pyridazinyl; pyridyl; pyrimidinyl; pyrimidyl; pyrrolyl; pyrrolidinyl; purinyl; quinazolinyl; quinolinyl; 4H-quinolizinyl; quinoxalinyl; tetrazolidinyl; tetrazolyl; thiadiazolyl; thiazolidinyl; thiazolyl; thienyl; thiomorpholinyl; triazinyl; and triazolyl; wherein said aryl is a carbocyclic moiety which is a member independently selected from the group consisting essentially of benzyl; cis- and trans-decahydronaphthalenyl; 2,3-1H-dihydroindenyl (indanyl); indenyl; 1-naphthalenyl; 2-naphthalenyl; phenyl; and 1,2,3,4-tetrahydronaphthalenyl; wherein said alkyl, alkenyl, alkoxyalkyl, heterocyclyl, and aryl moieties defining said $R^A_5$ groups are substituted by 0 to 3 substituents where each said substituent comprises a member independently selected from the group consisting essentially of bromo, chloro, or fluoro; hydroxy; $(C_1-C_5)$ alkyl; $(C_2-C_5)$ alkenyl; $(C_1-C_5)$ alkoxy; $(C_3-C_6)$ cycloalkoxy; mono-, di-, and tri-fluoromethyl; nitro; —$C(=O)OR^{119}$, —$C(=O)NR^{119}R^{120}$, —$NR^{119}R^{120}$ and —$S(=O)_2NR^{119}R^{120}$;

$R^B_5$ is a member independently selected from the group consisting essentially of hydrogen; $(C_1-C_9)$ alkyl; $(C_2-C_3)$ alkenyl; phenyl; $(C_3-C_7)$ cycloalkyl; and $(C_3-C_7)$ cycloalkyl$(C_1-C_2)$ alkyl; wherein said alkyl, alkeny) and phenyl moieties defining said $R^B_5$ groups are substituted by 0 to 3 substituents where each said substituent comprises a member independently selected from the group consisting essentially of methyl; ethyl; mono-, di-, and tri-fluoromethyl; and bromo, chloro, or fluoro;

$R^5_a$ and $R^5_b$ are independently selected from the group consisting essentially of hydrogen and hereinafter recited substituents, provided that one, but not both of $R^5_a$ and $R^5_b$ must be independently selected as hydrogen, wherein said substituents comprise moieities of partial Formulas (9.2); (9.3); (9.4); and (9.5):

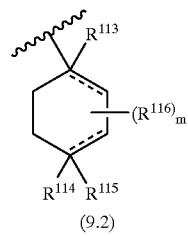

(9.2)

-continued

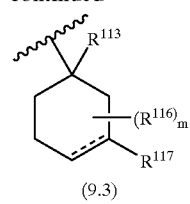

(9.3)

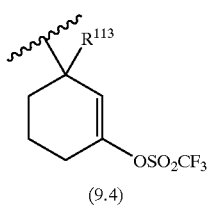

(9.4)

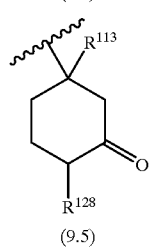

(9.5)

wherein the dashed lines in partial Formulas (9.2) and (9.3) independently and optionally represent a single or double bond, provided that in partial Formula (9.2) both dashed lines cannot both represent double bonds at the same time;

m is an integer selected from 0, 1, 2, 3, and 4, and when 2, may apply to a single carbon atom on the ring;

$R^{113}$ is a member selected from the group consisting essentially of H; bromo, chloro, or fluoro; cyano; $(C_2-C_4)$ alkynyl substituted by 0 or 1 substituent where said substituent is a member selected from the group consisting essentially of phenyl, pyridyl and pyrimidinyl; $(C_1-C_4)$ alkyl substituted by 0 to 6 bromo, chloro, or fluoro; —$CH_2NHC(=O)C(=O)NH_2$; cyclopropyl substituted by 0 or 1 substituent where said substituent is a member selected from the group consisting essentially of $R^{121}$; $R^{127}$; $CH_2OR^{119}$; $NR^{119}R^{120}$; $CH_2NR^{119}R^{120}$; $C(=O)OR^{119}$; $C(=O)NR^{119}R^{120}$; $C\equiv CR_{121}$; C(Z)H; and —$CH=CR^{121}R^{121}$; provided that $R^{113}$ is H in formula (9.2) when the dashed line for the ring carbon atom of $R^{113}$ attachment represents a double bond;

$R^{114}$ is a member selected from the group consisting essentially of H; $R^{116}$; $C(Y)R^{124}$; $C(=O)OR^{124}$; $C(Y)NR^{127}R^{124}$; CN; $C(NR^{127})NR^{127}R^{124}$; $C(NOR^{119})R^{124}$; $C(=O)NR^{119}NR^{119}C(=O)R^{119}$; $C(=O)NR^{119}NR^{127}R^{124}$; $C(NOR^{124})R^{119}$; $C(NR^{119})NR^{127}R^{124}$; $C(NR^{124})NR^{119}R^{120}$; $C(NCN)NR^{127}R^{124}$, $C(NCN)S(C_1-C_4)$ alkyl; $CR^{119}R^{120}OR^{124}$, $CR^{119}R^{120}SR^{124}$, $CR^{119}R^{120}S(O)_nR^{125}$ where n is an integer selected from 0, 1, and 2; $CR^{119}R^{120}NR^{124}R^{127}$; $CR^{119}R^{120}NR^{127}S(=O)_2R_{15}$; $CR^{119}R^{120}NR^{127}C(Y)R^{124}$; $CR^{119}R^{120}NR^{127}C(=O)OR^{125}$; $CR^{119}R^{120}NR^{127}C(Y)NR^{127}R^{124}$; $CR^{119}R^{120}NR^{127}C(NCN)NR^{127}R^{124}$; $CR^{119}R^{120}NR^{127}C(CR^{119}NO_2)S(C_1-C_4)$ alkyl; $CR^{119}R^{120}C(=O)OR^{125}$; $CR^{119}R^{120}C(Y)NR^{127}R^{124}$; $CR^{119}R^{120}C(NR^{127})NR^{127}R^{124}$; $CR^{119}R^{120}CN$; $CR^{119}R^{120}C(NOR^{120})R^{124}$; $CR^{119}R^{120}C(NOR^{124})R^{120}$; $CR^{119}R^{120}NR^{127}C(NR^{127})S(C_1-C_4)$ alkyl; $CR^{119}R^{120}NR^{127}C(NR^{127})NR^{127}R^{124}$; $CR^{119}R^{120}NR^{127}C(=O)C(=O)NR^{127}R^{124}$; $CR^{119}R^{120}NR^{127}C(=O)C(=O)OR^{124}$; tetrazolyl; thiazolyl; imidazolyl; imidazolidinyl; pyrazolyl; thiazolidinyl; oxazolyl; oxazolidinyl; triazolyl; isoxazolyl; oxadiazolyl; thiadiazolyl; $CR^{119}R^{120}$(tetrazolyl); $CR^{119}R^{120}$(thiazolyl); $CR^{119}R^{120}$(imidazolyl); $CR^{119}R^{120}$(imidazolidinyl); $CR^{119}R^{120}$(pyrazolyl); $CR^{119}R^{120}$(thiazolidinyl); $CR^{119}R^{120}$(oxazolyl); $CR^{119}R^{120}$(oxazolidinyl); $CR^{119}R^{120}$(triazolyl); $CR^{119}R^{120}$(isoxazolyl); $CR^{119}R^{120}$(oxadiazolyl); $CR^{119}R^{120}$(thiadiazolyl); $CR^{119}R^{120}$(morpholinyl); $CR^{119}R^{120}$(piperidinyl; $CR^{119}R^{120}$(piperazinyl); and $CR^{119}R^{120}$(pyrrolyl); where the recited heterocyclic groups and moieties for said $R^{114}$ are substituted by 0 to 3 $R^{124}$ substituents;

$R^{115}$ is a member selected from the group consisting essentially of $R^{119}$; $OR^{119}$; —$CH_2OR^{119}$; cyano; $C(=O)R^{119}$; $C(=O)OR^{119}$; $C(=O)NR^{119}R^{120}$; and $NR^{119}R^{120}$; provided that $R^{115}$ is absent when the dashed line in Formula (9.2) represents a double bond;

or $R^{114}$ and $R^{115}$ are taken together to form =O or =$R^{118}$;

or $R^{115}$ is hydrogen and $R^{114}$ is $OR^{124}$; $SR^{124}$; $S(O)_nR^{125}$, where n is an integer selected from 0, 1, and 2; $S(=O)_2NR^{127}R^{124}$; $NR^{127}R^{124}$; $NR^{124}C(=O)R^{119}$; $NR^{127}C(Y)R^{124}$; $NR^{127}C(=O)OR^{125}$; $NR^{127}C(Y)NR^{127}R^{124}$; $NR^{127}S(=O)_2NR^{127}R^{124}$; $NR^{127}C(NCN)NR^{127}R^{124}$; $NR^{127}S(=O)_2R^{125}$; $NR^{127}C(CR^{119}NO_2)NR^{127}R^{124}$; $NR^{127}C(NCN)S(C_1-C_4)$ alkyl; $NR^{127}C(CR^{119}NO_2)S(C_1-C_4)$ alkyl; $NR^{127}C(NR^{127})NR^{127}R^{124}$; $NR^{127}C(=O)C(=O)NR^{127}R^{124}$; and $NR^{127}C(=O)C(=O)OR^{124}$;

$R^{116}$ is a member independently selected from the group consisting essentially of methyl and ethyl substituted by 0 to 5 bromo, chloro, or fluoro, wherein m may be 2 with respect to a single ring carbon atom to which $R^{116}$ is attached;

$R^{117}$ is a member independently selected from the group consisting essentially of $OR^{124}$; $SR^{124}$; $SO_2NR^{127}R^{124}$; $NR^{127}R^{124}$; $NR^{124}C(=O)R^{119}$; $NR^{127}C(Y)R^{124}$; $NR^{127}C(=O)OR^{125}$; $S(O)_nR_{12}$ where n is an integer selected from 0, 1, and 2; $OS(=O)_2R^{122}$; $OR^{122}$; $OC(=O)NR^{123}R^{122}$; $OC(=O)R^{123}$; $OC(=O)OR^{123}$; $O(CR^{122}R^{123})_mOR^{122}$ where m is an integer selected from 0, 1, and 2; $CR^{119}R^{120}OR^{124}$; $CR^{119}R^{120}NR^{127}R^{124}$; $C(Y)R^{124}$; $C(=O)OR^{124}$; $C(Y)NR^{127}R^{124}$; CN; $C(NR^{127})NR^{127}R^{124}$; $C(NOR^{119})R^{124}$; $C(=O)NR^{119}NR^{119}C(=O)R^{119}$; $C(=O)NR^{119}NR^{127}R^{124}$; $C(NOR^{124})R^{119}$; $C(NR^{119})NR^{127}R^{124}$; $C(NR^{124})NR^{119}R^{120}$; $C(NCN)NR^{127}R^{124}$; $C(NCN)S(C_1-C_4)$ alkyl; tetrazolyl; thiazolyl; imidazolyl; imidazolidinyl; pyrazolyl; thiazolidinyl; oxazolyl; oxazolidinyl; triazolyl; isoxazolyl; oxadiazolyl; and thiadiazolyl; where the recited heterocyclic groups are substituted by 0 to 3 substituents where said substituent is $R^{124}$;

$R^{118}$ is a member independently selected from the group consisting essentially of —$NR^{125}$; —$NCR^{119}R^{120}(C_2-C_6)$ alkenyl; —$NOR^{124}$; —$NOR^{129}$; —$NOCR^{119}R^{120}(C_2-C_6)$ alkenyl; —$NNR^{119}R^{124}$; —$NNR^{119}R^{129}$; —NCN; —$NNR^{119}C(Y)NR^{119}R^{124}$; —$C(CN)_2$; —$CR^{124}CN$; —$CR^{124}C(=O)OR^{119}$; —$CR^{124}C(=O)NR^{119}R^{124}$; —$C(CN)NO_2$; —$C(CN)C(=O)O(C_1-C_4)$ alkyl; —$C(CN)OC(=O)O(C_1-C_4)$ alkyl; —$C(CN)(C_1-C_4)$ alkyl; —$C(CN)C(=O)$ NR$^{119}$R$^{124}$; 2-(1,3-dithiane), 2-(1,3-dithiolane), dimethylthio ketal, diethylthio ketal, 2-(1,3-dioxolane), 2-(1,3-dioxane), 2-(1,3-oxathiolane); dimethyl ketal and diethyl ketal;

R$^{119}$ and R$^{120}$ are each a member independently selected from the group consisting essentially of hydrogen and (C$_1$–C$_4$) alkyl substituted by 0 to 3 fluorine atoms;

R$^{121}$ is a member independently selected from the group consisting essentially of fluoro and R$^{120}$;

R$^{122}$ is a member independently selected from the group consisting essentially of (C$_1$–C$_6$) alkyl; (C$_2$–C$_3$) alkenyl; (C$_3$–C$_7$) cycloalkyl; (C$_3$–C$_7$) cycloalkyl(C$_1$–C$_2$) alkyl; (C$_6$–C$_{10}$) aryl; and (C$_3$–C$_9$) heterocyclyl; where said aryl and heterocyclyl are as defined under R$^A{}_5$ above; and where said R$^{122}$ groups are substituted with 0 to 3 substituents independently selected from the group consisting essentially of methyl; ethyl; mono-, di-, and tri-fluoromethyl; and bromo, chloro, or fluoro;

R$^{123}$ is a member independently selected from the group consisting essentially of hydrogen and R$^{122}$;

R$^{124}$ is a member independently selected from the group consisting essentially of hydrogen and R$^{125}$; or when R$^{124}$ and R$^{127}$ appear together as NR$^{127}$R$^{124}$ then R$^{127}$ and R$^{124}$ may be taken together with the nitrogen to which they are attached to form a 5- to 7-membered ring optionally containing one additional heteroatom selected from O, N and S;

R$^{125}$ is a member independently selected from the group consisting essentially of (C$_1$–C$_6$) alkyl and —(CR$^{119}$R$^{120}$)$_n$R$^{126}$, where n is an integer selected from 0, 1, and 2 and R$^{126}$ and said (C$_1$–C$_6$) alkyl are substituted by 0 to 3 substituents where each said substituent is a member independently selected from the group consisting essentially of bromo, chloro, or fluoro; nitro; cyano; NR$^{120}$R$^{127}$; C(=O)R$^{119}$; OR$^{119}$; C(=O)NR$^{120}$R$^{127}$; OC(=O)NR$^{120}$R$^{127}$; NR$^{127}$C(=O)NR$^{127}$R$^{120}$; NR$^{127}$(=O)R$^{120}$; NR$_{17}$C(=O)O (C$_1$–C$_4$) alkyl; C(NR$^{127}$)NR$^{127}$R$^{120}$; C(NCN) NR$^{127}$R$^{120}$; C(NCN)S(C$_1$–C$_4$) alkyl; NR$^{127}$C(NCN)S (C$_1$–C$_4$) alkyl; NR$^{127}$C(NCN)NR$^{127}$R$^{120}$; NR$^{127}$S (=O)$_2$(C$_1$–C$_4$) alkyl; S(O)$_n$(C$_1$–C$_4$) alkyl; where n is an integer selected from 0, 1, and 2; NR$^{127}$C(=O)C (=O)NR$^{127}$R$^{120}$, NR$^{127}$C(=O)C(=O)R$^{127}$; thiazolyl; imidazolyl; oxazolyl; pyrazolyl; triazolyl; tetrazolyl; and (C$_1$–C$_2$) alkyl substituted with 0 to 3 fluorine atoms;

R$^{126}$ is a member independently selected from the group consisting essentially of (C$_3$–C$_7$) cycloalkyl; pyridyl; pyrimidyl; pyrazolyl; imidazolyl; triazolyl; pyrrolyl; piperazinyl; piperidinyl; morpholinyl; furanyl; thienyl; thiazolyl; quinolinyl; naphthyl; and phenyl;

R$^{127}$ is a member independently selected from the group consisting essentially of OR$^{119}$ and R$^{120}$;

R$^{128}$ is a member independently selected from the group consisting essentially of H; C(Y)R$^{124}$; C(=O)OR$^{124}$; C(Y)NR$^{127}$R$^{124}$; CN; C(NR$^{127}$)NR$^{127}$R$^{124}$; C(NOR$^{119}$)R$^{124}$; C(=O)NR$^{119}$NR$^{119}$C(=O)R$^{119}$; C(=O)NR$^{119}$NR$^{127}$R$^{124}$; C(NOR$^{124}$)R$^{119}$; C(NR$^{119}$) NR$^{127}$R$^{124}$; C(NR$^{124}$)NR$^{119}$R$^{120}$; C(NCN)NR$^{127}$R$^{124}$; C(NCN)S(C$_1$–C$_4$) alkyl; CR$^{119}$R$^{120}$OR$^{124}$; CR$^{119}$R$^{120}$SR$^{124}$; CR$^{119}$R$^{120}$S(O)$_n$R$^{125}$, where n is an integer selected from 0, 1, and 2; CR$^{119}$R$^{120}$NR$^{124}$R$^{127}$; CR$^{119}$R$^{120}$NR$^{127}$S(=O)$_2$R$^{125}$; CR$^{119}$R$^{120}$NR$^{127}$C(Y)R$^{124}$; CR$^{119}$R$^{120}$NR$^{127}$C(=O) OR$^{125}$; Cr$^{119}$R$^{120}$NR$^{127}$C(Y)NR$^{127}$R$^{124}$; CR$^{119}$R$^{120}$NR$^{127}$C(NCN)NR$^{127}$R$^{124}$;

CR$^{119}$R$^{120}$NR$^{127}$C(CR$_9$NO$_2$)S(C$_1$–C$_4$) alkyl; tetrazolyl; thiazolyl; imidazolyl; imidazolidinyl; pyrazolyl; thiazolidinyl; oxazolyl; oxazolidinyl; triazolyl; isoxazolyl; oxadiazolyl; thiadiazolyl; wherein said recited heterocyclic groups are substituted by 0 to 3 substituents where each said substituent is independently selected from the group consisting essentially of R$^{124}$;

R$^{129}$ is a member independently selected from the group consisting essentially of —C(=O)R$^{12}$; —C(=O) NR$^{119}$R$^{124}$; —S(=O)$_2$R$_{125}$; and —S(=O) $_2$NR$^{119}$R$^{124}$;

Y is O or S; and,

Z is O; NR$^{127}$; NCN; C(—CN)$_2$; CR$^{119}$CN; CR$^{119}$NO$_2$; CR$^{119}$C(=O)OR$^{119}$; CR$^{119}$C(=O)NR$^{119}$R$^{120}$; C(—CN)C(=O)O(C$_1$–C$_4$) alkyl; and C(=CN)C (=O)NR$^{119}$R$^{120}$;

(V-B)

—OR, said substituents defining R$^5{}_a$ and R$^5{}_b$ comprise:

a member selected from the group consisting essentially of R$^{229}$; —C(=O)NR$^{222}$(CHR$^{222}$)$_m$C(=O)NR$^{222}$O (CH$_2$)$_q$(C$_6$–C$_{10}$) aryl); —C(=NR$^{242}$)NH(CH$_2$)$_p$ (C$_6$–C$_{10}$) aryl; —C(=O)NR$^{218}$(CHR$^{222}$)$_m$C(=O) NR$^{222}$(CH$_2$)$_p$OR$^{222}$; —C(=O)NR$^{222}$(CHR$^{222}$)$_m$S (C$_1$–C$_4$) alkyl; —C[=NOC(=O)R$^{235}$]R$^{236}$; —CR$^{227}$R$^{228}$CHR$^{238}$NR$^{219}$SO$_2$(CH$_2$)$_p$A; —CR$^{227}$R$^{228}$CHR$^{238}$NR$^{219}$P(=O)(OR$^{222}$)C(=O) (C$_1$–C$_4$) alkyl; —CR$^{227}$R$^{238}$CHR$^{238}$NR$^{219}$P(=O) [(C$_1$–C$_4$) alkoxy]$_2$, —Z$^3$—R$^{217}$; and —(CR$^{227}$R$^{228}$) $_m$NR$^{219}$(C(O))$_q$R$^{220}$ wherein p is an integer selected from 0, 1, and 2; m is an integer selected from 1, 2, 3, 4, 5, and 6; and q is an integer selected from 1 and 2;

—OR, said substituents defining R$^5{}_a$ and R$^5{}_b$ comprise a moiety of partial Formulas (9.6) through (9.14), inclusive:

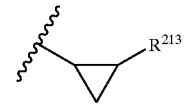

(9.6)

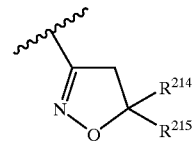

(9.7)

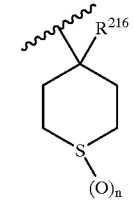

(9.8)

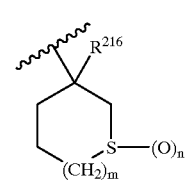

(9.9)

-continued (9.10)
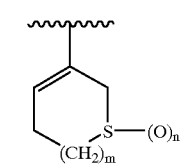

(9.11)
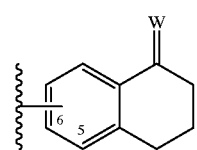

(9.12)
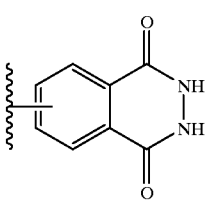

(9.13)
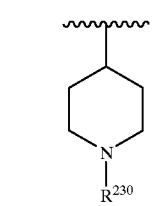

(9.14)
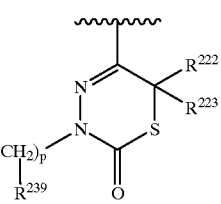

wherein in said partial Formulas (9.6)–(9.14), the structures of partial Formulas (9.11) and (9.12) are attached to the nucleus of Formula (9.0) or (9.1) at carbons 5, 6, or 7 of said partial Formulas (9.6) and (9.7); the dashed line in partial Formulas (9.8) and (9.9) indicates a single bond or double bond, except that $R^{316}$ is absent in formulas (9.8) and (9.9) where said dashed line indicates a double bond; n is an integer selected from 0, 1, and 2; p is an integer selected from 0, 1, 2, 3, 4, 5, and 6; and m is an integer selected from 0, and 1;

$R^{213}$ is a member independently selected from the group consisting essentially of —C(=O)N(CH$_3$)(OCH$_3$) and —(CH$_2$)$_n$OH, where n is an integer selected from 0, 1, 2, 3, and 4;

$R^{214}$ and $R^{215}$ are independently selected from the group consisting essentially of H; ethyl; —CO$_2$H; and —C(=O)NHOH;

$R^{216}$ is a member independently selected from the group consisting essentially of H; hydroxy; (C$_1$–C$_6$) alkyl; (C$_1$–C$_6$) alkoxy; —OC(=O)(C$_1$–C$_6$) alkyl and —OC(=O)(C$_6$–C$_{10}$) aryl;

$R^{217}$ is a member independently selected from the group consisting essentially of (C$_6$–C$_{10}$) aryl and a 5- to 10-membered heterocyclyl, wherein said $R^{217}$ groups are substituted by 0 to 3 substituents independently selected from the group consisting essentially of bromo, chloro, or fluroro; trifluoromethyl; cyano; nitro; —CO$_2$R$^{222}$, (C$_1$–C$_4$) alkoxy; —OC(=O)(C$_1$–C$_4$) alkyl; —NR$_{222}$C(=O)(C$_1$–C$_4$) alkyl; —C(=O)NH$_2$; —C(=O)NHOH; —C(=O)O(C$_1$–C$_4$) alkyl; (C$_1$–C$_4$) alkyl; —S(O)$_n$R$^{222}$ where n is an integer selected from 0, 1, and 2; benzoyl; —NR$^{222}$R$^{223}$, —OR$^{222}$, (C$_1$–C$_6$) alkanoyl; —Y$^1$—(C$_6$–C$_{10}$) aryl; —C(=O)O(C$_6$–C$_{10}$) aryl; —NH(C$_6$–C$_{10}$) aryl; —C(=O)NH(C$_6$–C$_{10}$) aryl; —C(=O)NR$^{222}$O(CH$_2$)$_n$(C$_6$–C$_{10}$) aryl, where n is an integer selected from 1, 2, and 3; and —SO$_2$NH (C$_6$–C$_{10}$) aryl;

$R^{218}$ is a member independently selected from the group consisting essentially of H; (C$_1$–C$_6$) alkyl; and —(CH$_2$)$_n$(C$_6$–C$_{10}$) aryl, where n is an integer selected from 0, 1, 2, 3, and 4;

$R^{219}$ is a member independently selected from the group consisting essentially of H; —OR$^{222}$; —(CH$_2$)$_m$A; and —CH$_2$O(CH$_2$)$_m$A, where m is an integer selected from 0, 1, and 2;

$R^{220}$ is a member independently selected from the group consisting essentially of (C$_1$–C$_4$) alkyl; —OR$^{222}$; —CR$^{222}$R$^{223}$OR$^{222}$; —CR$^{222}$R$^{223}$NR$^{222}$R$^{223}$; —CR$^{222}$(OR$^{223}$)CR$^{222}$R$^{223}$OR$^{222}$; 2,2-dimethyl-1,3-dioxolan-4-yl; —NR$^{222}$C(=O)NR$^{222}$R$^{223}$, —S(CR$^{222}$R$^{223}$)$_n$CH$_n$CH$_3$ where n is an integer selected from 0, 1, 2, 3, 4, and 5; —NR$^{222}$(CH$_2$)$_q$ (pyridyl) where q is an integer selected from 0 and 1; —P(=O)[(C$_1$–C$_4$) alkoxy)]$_2$; —NR$^{222}$R$^{223}$; —NR$^{222}$OR$^{223}$; —NR$^{222}$NR$^{223}$R$^{221}$, —NR$^{222}$CH$_2$R$^{224}$; —OCH$_2$NR$^{222}$C(=O)R$^{224}$; —OCH$_2$C(=O)NR$^{225}$R$^{226}$, —OCHR$^{222}$OC(=O) (C$_1$–C$_4$) alkyl; —OCHR$^{222}$C(=O)(C$_1$–C$_3$) alkoxy; —O(CH$_2$)$_m$R$^{221}$; and —NR$^{222}$(CH$_2$)$_m$R$^{221}$ where m is an integer selected from 0, 1, and 2;

$R^{221}$ is a member independently selected from the group consisting essentially of H and A;

each $R^{222}$ and $R^{223}$ is a member independently selected from the group consisting essentially of H and (C$_1$–C$_4$) alkyl;

$R^{224}$ is a member independently selected from the group consisting essentially of methyl and phenyl;

$R^{225}$ is a member independently selected from the group consisting essentially of H; methyl; ethyl; and —CH$_2$CH$_2$OH;

$R^{226}$ is a member independently selected from the group consisting essentially of H; methyl; ethyl; CH$_2$C(=O) NH$_2$; and —CH$_2$CH$_2$OH;

each $R^{227}$ is a member independently selected from the group consisting essentially of H; hydroxy; cyano; halo; (C$_1$–C$_3$) alkyl; (C$_1$–C$_3$) alkoxy; —NR$^{222}$R$^{223}$; —C(=O)OR$^{222}$; —C(=O)R$^{222}$; —CH=CR$^{222}$R$^{223}$; —C≡CR$^{222}$; —CH$_2$NR$^{222}$R$^{223}$; —CH$_2$OR$^{222}$; —C(=O)NR$^{222}$R$^{223}$; —C(Y$^5$)H; and —CH$_2$NR$_{12}$C (=O)C(=O)NR$^{222}$R$^{223}$; provided that when $R^{227}$ is hydroxy then $R^{228}$ is H or (C$_1$–C$_4$) alkyl;

each $R^{228}$ is a member independently selected from the group consisting essentially of H; fluoro; cyano; and (C$_1$–C$_4$) alkyl; where said methyl is substituted by 0 to 3 substituents each comprising a fluorine atom;

or $R^{227}$ and $R^{228}$ are taken together to form an oxo (=O) moiety;

$R^{229}$ is a member independently selected from the group consisting essentially of phenyl; naphthyl; pyrrolyl; furanyl; thienyl, oxazolyl; pyridinyl; pyrimidinyl;

pyridazinyl; quinolinyl; isoquinolinyl; 5,6,7,8-tetrahydroquinolinyl; and 5,6,7,8-tetrahydroisoquinolinyl, where said $R^{229}$ groups, except said phenyl, are substituted by 0 to 3 substituents $R^{233}$, and wherein said phenyl $R^{229}$ group is substituted by 0 to 3 substituents independently selected from $R^{233}$ and $R^{234}$;

$R^{230}$ is a member independently selected from the group consisting essentially of —C(=O)$R^{231}$; —C(=O)C(=O)$R^{231}$, —C(=O)C($Y^2$)C(=O)$R^{231}$ and a moiety of partial Formula (9.15):

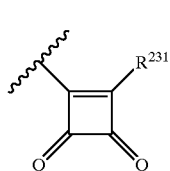

(9.15)

wherein $R^{231}$ is a member independently selected from the group consisting essentially of H; —OR$^{232}$; —NHR$^{232}$; —NHOH; —NHNH$_2$; —(CH$_2$)$_n$Y$^3$(phenyl) and —(CH$_2$)$_n$Y$^3$(pyridyl) where n is an integer selected from 0, 1, 2, 3, and 4;

$R^{232}$ is a member independently selected from the group consisting essentially of H; (C$_1$–C$_8$) alkyl; —(CH$_2$)$_n$Y$^3$(phenyl) and —(CH$_2$)$_n$Y$^3$(pyridyl) where n is an integer selected from 0, 1, 2, 3, and 4;

each $R^{233}$ is a member independently selected from the group consisting essentially of bromo, chloro, or fluoro; (C$_1$–C$_6$) alkyl; (C$_1$–C$_7$) alkoxy; (C$_2$–C$_6$) alkylenedioxy; trifluoromethyl; —NR$^{222}$R$^{223}$; nitro; —C(NR$^{222}$)NR$^{222}$R$^{223}$; —C(=O)NR$^{222}$R$^{223}$C(=O)R$^{222}$; —C(NOR$^{222}$)R$^{223}$; —C(NCN)NR$^{222}$R$^{223}$; —C(NCN)SR$^{222}$; —(CH$_2$)$_m$(CN) where m is an integer selected from 0, 1, 2, and 3; hydroxy; —C(=O)R$^{222}$, —C(=O)NR$^{222}$OR$^{223}$; —C(=O)NR$^{222}$NR$^{222}$R$^{223}$; —OC(=O)NR$^{222}$R$^{223}$; —NR$^{222}$C(=O)R$^{222}$; —C(=O)C(=O)NR$^{222}$R$^{223}$; —CO$_2$R$^{222}$; —SO$_2$R$^{222}$; —SO$_2$NR$^{222}$R$^{223}$; —C(=O)NR$^{222}$R$^{223}$; —NR$^{222}$SO$_2$R$^{223}$; and —NR$^{222}$C(=O)NR$^{222}$R$^{223}$;

each $R^{234}$ is a member independently selected from the group consisting essentially of imidazolyl; pyrazolyl; triazolyl; tetrazolyl; oxazolyl; isoxazolyl; oxadiazolyl; thiadiazolyl; thiazolyl; oxazolidinyl; thiazolidinyl; and imidazolidinyl, where each of said foregoing $R^{234}$ substituents is substituted by 0 to 3 substituents $R^{233}$;

$R^{235}$ is a member independently selected from the group consisting essentially of —NR$^{222}$R$^{223}$; —NH(C$_6$–C$_{10}$) aryl; (C$_1$–C$_6$) alkoxy; and (C$_6$–C$_{10}$) aryloxy;

$R^{236}$ is a member independently selected from the group consisting essentially of H; (C$_1$–C$_6$) alkyl and —(CH$_2$)$_m$Y$^4$(phenyl) where m is an integer selected from 0, 1, 2, 3, and 4 and the phenyl moiety of said —(CH$_2$)$_m$Y$^4$(phenyl)R$^{236}$ group is substituted by 0 to 3 substituents independently selected from the group consisting essentially of bromo, chloro, or fluoro; —OR$^{222}$; (C$_1$–C$_6$) alkanoyloxy; (C$_6$–C$_{10}$) aryloxy; —NR$^{222}$R$^{223}$; —NH(C$_6$–C$_{10}$) aryl; and —NHC(=O)(C$_1$–C$_4$) alkyl;

each $R^{237}$ is a member independently selected from the group consisting essentially of bromo, chloro, or fluoro; —(CH$_2$)$_p$NR$^{222}$C(=O)CH$_3$ where p is an integer selected from 1, 2, 3, 4, and; (C$_1$–C$_4$) alkoxy; nitro;

cyano; —NR$^{222}$R$^{223}$; —CO$_2$R$^{222}$; —OR$^{222}$; —C(Y$^1$)NR$^{222}$R$^{223}$; —NR$^{222}$C(NCN)S(C$_1$–C$_3$) alkyl; —NR$^{222}$C(NCN)NR$^{222}$R$^{223}$; —NR$^{222}$C(=O)NR$^{222}$R$^{223}$; —NR$^{222}$C(=O)C(=O)NR$^{222}$R$^{223}$; —C(=NR$^{222}$)NR$^{222}$R$^{223}$; —S(O)$_m$CH$_3$ where m is an integer selected from 0, 1, and 2; —C(=NR$^{222}$)S(C$_1$–C$_3$) alkyl; —NR$^{222}$SO$_2$(C$_1$–C$_3$) alkyl; —OC(=O)R$^{222}$; —OC(=O)NR$^{222}$R$^{223}$; —NR$^{222}$SO$_2$CF$_3$; —NR$^{222}$C(=O)C(=O)OR$^{222}$; —NR$^{222}$C(=O)R$^{222}$; —NR$^{222}$C(=O)OR$^{222}$; imidazolyl; thiazolyl; oxazolyl; pyrazolyl; triazolyl: and tetrazolyl;

$R^{238}$ is a member independently selected from the group consisting essentially of H; fluoro; cyano; and (C$_1$–C$_2$) alkyl, where said alkyl is substituted by 0 to 3 substituents independently selected from the group consisting essentially of bromo, chloro, or fluoro; —C(=O)NR$^{222}$R$^{223}$; and —C(=O)OR$^{222}$;

$R^{239}$ is a member independently selected from the group consisting essentially of phenyl substituted by 0 to 2 substituents independently selected from —NR$^{222}$R$^{223}$, nitro, halo, —OR$^{222}$, —NHR$^{240}$, —NR$^{240}$R$^{241}$, and —C(=O)OR$^{222}$;

each $R^{240}$ and $R^{241}$ is a member independently selected from the group consisting essentially of (C$_1$–C$_8$) alkyl and (C$_2$–C$_8$) alkenyl;

$R^{242}$ is pyridin-4-yl substituted by 0 to 2 substituents independently selected from the group consisting essentially of bromo, chloro, or fluoro; and (C$_1$–C$_4$) alkyl;

each A is a member independently selected from the group consisting essentially of (C$_1$–C$_6$) alkyl; pyridyl; morpholinyl; piperidinyl; imidazolyl; thienyl; pyrimidyl; thiazolyl; triazolyl; quinolinyl; phenyl; and naphthyl; wherein the foregoing A groups are substituted with 0 to 3 substituents $R^{237}$; or A is —(CH$_2$)$_q$S(C$_1$–C$_4$) alkyl wherein q is an integer selected from 1 and 2;

W is a member independently selected from the group consisting essentially of O; NOH; NNH$_2$; NOC(=O)CH$_3$; and NNHC(=O)CH$_3$;

$Y^1$ is O or S;

$Y^2$ is O, NOH or H$_2$;

$Y^3$ is a bond or —CH=CH—;

$Y^4$ is a bond, O, S, or —NH—;

$Y^5$ is a member independently selected from the group consisting essentially of O; NR$^{222}$; NOR$^{222}$; NCN; C(CN)$_2$; CR$^{222}$NO$_2$; CR$^{222}$C(=O)OR$^{222}$; CR$^{222}$C(=O)NR$^{222}$R$^{223}$; C(CN)NO$_2$; C(CN)C(=O)OR$^{222}$; and C(CN)C(=O)NR$^{222}$R$^{223}$; and $Z^3$ is a member independently selected from the group consisting essentially of —NR$^{222}$—; —(CH$_2$)$_m$—; —CH$_2$C(=O)NH—; —NHCH$_2$C(=O)—; —CH$_2$C(Y$^1$)CH$_2$—; —CH=CH—; —C≡C—, —CH(Y$^1$H)—; —C(Y$^1$)—; —CH$_2$C(Y$^1$); —C(Y$^1$)CH$_2$—; —C(Y$_1$)C(Y$_1$)—; —CH$_2$NR$^{222}$—; —CH$_2$—Y$^1$—; —C(Y$^1$)NR$^{218}$(CHR$^{222}$)$_n$—; —NR$^{218}$C(Y$^1$)(CHR$^{222}$)$_n$—; —NHCH$_2$—; —Y$^1$—CH$_2$—; —SOCH$_2$—; —CH$_2$SO—; —SO$_2$CH$_2$—; —CH$_2$SO$_2$—; —OC(Y$^1$)—; —N=N—; —NHSO$_2$—; —SO$_2$NH—; —C(Y$^1$)C(Y$^1$)NH—; —NHC(=O)O—; —OC(=O)NH—; and —NHC(=O)NH—; wherein for said Z$_3$ moieties n is an integer selected from 0, 1, 2, 3, and 4; and m is an integer selected from 1, 2, and 3;

(V-C)

—OR said substituents defining $R^5_a$ and $R^5_b$ comprise: a member independently selected from the group consisting essentially of 2-oxo-4-pyrrolyl; pyrazolyl; 2-oxo-3,4-dihydro-5-pyrimidyl; 2-oxo-3,4-dihydro-4-pyrimidyl; 2-oxo-tetrahydro-4-pyrimidyl; 2-oxo-tetrahydro-5-pyrimidyl; 2oxo-4-pyrimidyl; and 2-oxo-5-pyrimidyl; wherein each of said $R^2_a$ and $R^2_b$ groups is substituted by 0, 1, 2, 3, or 4 $R^{236}$ groups;
—OR, said substituents defining $R^5_a$ and $R^5_b$ comprise a moiety of partial Formulas (9.16) through (9.35), inclusive:
(9.16)
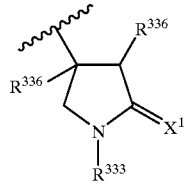
(9.17)
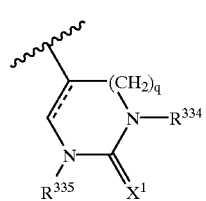
(9.18)
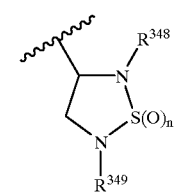
(9.19)
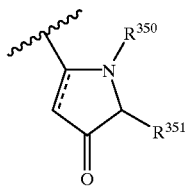
(9.20)
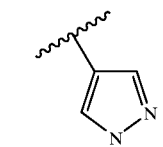
(9.21)
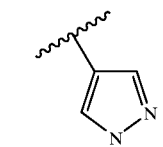
(9.22)
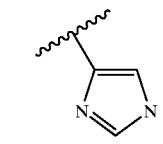
(9.23)
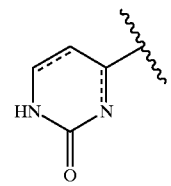
(9.24)
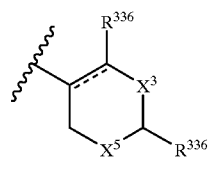
(9.25)
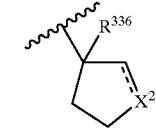
(9.26)
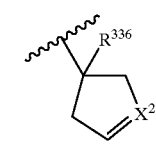
(9.27)
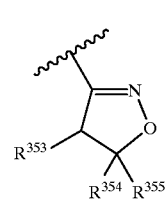
(9.28)
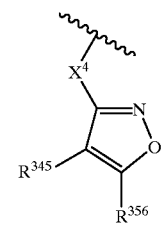
(9.29)
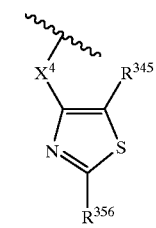
(9.30)
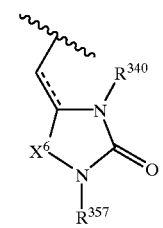

-continued (9.31)
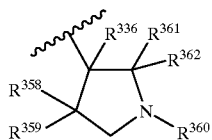

(9.32)
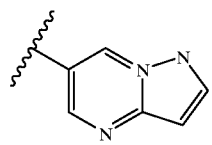

(9.33)
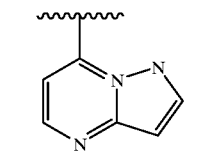

(9.34)
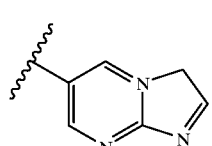

(9.35)
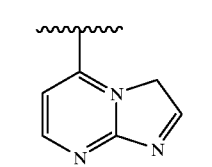

wherein, in said partial Formulas (9.16)–(9.35), q is an integer selected from 0 and 1 in partial Formula (9.17); n is an integer selected from 0, 1, and 2 in partial Formula (9.18); and the dashed lines appearing in formulas (9.17), (9.19), (9.22), (9.23), (9.24), (9.25) and (9.30) represent a double bond or a single bond;

$X^1$ is O or S;

$X^2$, in partial Formula (9.26) and where the dashed line in partial Formula (9.25) represents a double bond, is a member independently selected from the group consisting of $CR^{335}$; $CR^{336}$; $CR^{346}$; and COC($=$O)$NR^{339}R^{342}$; or, where the dashed line in formula (9.25) represents a single bond, $X^2$ is a member independently selected from the group consisting essentially of $CR^{335}R^{339}$; $CR^{336}R^{339}$; and $CR^{346}R^{339}$;

$X^3$ is a member independently selected from the group consisting essentially of $C(=Z^3)$; $C(S)$; and $CR^{336}R^{340}$;

$X^4$ is a member independently selected from the group consisting essentially of $-(CH_2)_m-$ where m is an integer selected from 0, 1, and 2;

$X^5$ is a bond or $-CH_2-$;

$X^6$ is a member independently selected from the group consisting essentially of $-CH_2-$ and $-C(=O)-$;

$R^{333}$ is a member independently selected from the group consisting essentially of H; hydroxy; ($C_1$-$C_4$) alkoxy; $-CHR^{337}(O)_q(CH_2)_m A$ where q is an integer selected from 0 and 1, and m is an integer selected from 0, 1, and 2;

$R^{334}$ is a member independently selected from the group consisting essentially of H; hydroxy; ($C_1$-$C_4$) alkyl; ($C_1$-$C_2$) alkoxy; $-OC(=O)CH_3$; ($C_2$-$C_3$) alkenyl; and phenyl($C_1$-$C_2$) alkyl-;

$R^{335}$ is a member independently selected from the group consisting essentially of H; hydroxy; $-(CH_2)_m A$ where m is an integer selected from 0, 1, and 2; ($C_1$-$C_6$) alkyl; and ($C_2$-$C_3$) alkanoyl; where said alkyl group is substituted by 0 to 3 substituents independently selected from the group consisting essentially of bromo, chloro, or fluoro; nitro; $-NR^{340}R^{341}$; $-CO_2R^{340}$; $-OR^{340}$; $-OC(=O)R^{340}$; $-C(=O)R^{340}$; cyano; $-C(=Y)NR^{340}R^{341}$; $-NR^{340}C(=Y)NR^{340}R^{341}$; $-NR^{340}C(=Y)R^{340}$; $-NR^{340}C(=O)OR^{340}$; $-C(NR^{340})NR^{340}OR^{341}$; $-C(NCN)NR^{340}R^{341}$; $-C(NCN)SR^{340}$; $-NR^{340}SO_2R^{340}$; $-S(O)_m R^{340}$, where m is an integer selected from 0, 1, and 2; $-NR^{340}SO_2CF_3$; $-NR^{340}C(=O)C(=O)NR^{340}R^{341}$; $-NR^{340}C(=O)C(=O)OR^{340}$; imidazolyl; and 1-($NHR^{340}$)-2-imidazolyl;

each $R^{336}$ is a member independently selected from the group consisting essentially of H; bromo, chloro, or fluoro; cyano; $R^{343}$; cyclopropyl substituted by 0 or 1 substituent independently selected from the group consisting essentially of $R^{339}$; $-OR^{340}$; $-CH_2OR^{340}$; $-NR^{340}R^{342}$; $-CH_2NR^{340}R^{342}$; $-C(=O)OR^{340}$; $-C(=O)NR^{340}R^{342}$; $-CH=CR^{339}R^{339}$; $-C\equiv CR^{339}$; and $-C(=Z^3)H$;

$R^{337}$ is a member independently selected from the group consisting essentially of H; $-C(=O)R^{338}$; imidazolyl; pyrazolyl; triazolyl; tetrazolyl; oxazolyl; isoxazolyl; oxadiazolyl; thiadiazolyl; thiazolyl; oxazolidinyl; thiazolidinyl; and imidazolidinyl;

each $R^{338}$ is a member independently selected from the group consisting essentially of $-OR^{340}$; $-NR^{340}R^{342}$; and $-R^{343}$;

each $R^{339}$ is a member independently selected from the group consisting essentially of H; bromo, chloro, or fluoro; and ($C_1$-$C_4$) alkyl substituted by 0 to 3 fluorine atoms;

each $R^{340}$ and $R^{341}$ is a member independently selected from the group consisting essentially of hydrogen and ($C_1$-$C_4$) alkyl;

each $R^{342}$ is a member independently selected from the group consisting essentially of $-OR^{340}$ and $-R^{340}$;

$R^{343}$ is ($C_1$-$C_4$) alkyl;

each $R^{344}$ is a member independently selected from the group consisting essentially of bromo, chloro, or fluoro; nitro; cyano; $-NR^{340}R^{346}$; $-NR^{346}R^{342}$; $-C(=Z^3)R^{338}$; $S(O)_m R^{343}$ where m is an integer selected from 0, 1, and 2; $-OR^{342}$; $-OC(=O)NR^{340}R^{342}$; $-C(NR^{342})NR^{340}R^{342}$; $-C(NR^{340})SR^{343}$; $-OC(=O)CH_3$; $-C(NCN)NR^{340}R^{342}$; $-C(S)NR^{340}R^{342}$; $-NR^{342}C(=O)R^{347}$; $-C(=O)R^{347}$; oxazolyl; imidazolyl; thiazolyl; pyrazolyl; triazolyl; and tetrazolyl;

each $R^{345}$ is a member independently selected from the group consisting essentially of hydrogen and ($C_1$-$C_4$) alkyl substituted by 01 to 3 fluorine atoms;

each $R^{346}$ is a member independently selected from the group consisting essentially of H; $-R^{343}$; $-C(=O)R^{343}$; $-C(=O)C(=O)R^{338}$; $-C(=O)NR^{340}R^{342}$; $-S(O)_m R^{343}$ where m is an inter selected from 0, 1, and 2; $-C(NCN)SR^{343}$; $-C(NCN)R^{343}$; $-C(NR^{342})R^{343}$; $-C(NR^{342})SR^{343}$; and $-C(NCN)NR^{340}R^{342}$;

each $R^{347}$ is a member independently selected from the group consisting essentially of $-R^{343}$; $-C(=O)R^{343}$;

oxazolidinyl; oxazolyl; thiazolyl; pyrazolyl; triazolyl; tetrazolyl; imidazolyl; imidazolidinyl; thiazolidinyl; isoxazolyl; oxadiazolyl; thiadiazolyl; morpholinyl; piperidinyl; piperazinyl; and pyrrolyl; where each of said recited $R^{347}$ heterocyclic groups is substituted by 0 to 2 ($C_1$–$C_2$) alkyl groups;

$R^{348}$ is a member independently selected from the group consisting essentially of H; ($C_1$–$C_5$) alkyl; ($C_2$–$C_5$) alkenyl; benzyl; and phenethyl;

$R^{349}$ is a member independently selected from the group consisting essentially of H; ($C_1$–$C_5$) alkyl; ($C_1$–$C_5$) alkanoyl; and benzoyl;

$R^{350}$ is a member independently selected from the group consisting essentially of H; ($C_1$–$C_4$) alkyl; carboxy; aminocarbonyl; ($C_1$–$C_6$) alkyl substituted by 0 or 1 carboxy, —($CH_2$)$_m$C(=O)($C_1$–$C_6$) alkoxy; or —($CH_2$)$_m$($C_6$–$C_{10}$) aryl; where m is an integer selected from 0, 1, and 2;

$R^{351}$ is a member independently selected from the group consisting essentially of H; ($C_1$–$C_6$) alkyl; —C(=Y)$R^{352}$; —C(=Y)NH35; —C(=O)O$R^{352}$; and —($CH_2$)$_n$$X^7$(pyridyl) where n is an integer selected from 0, 1, 2, 3, 4, and to 5; and $X^7$ is a bond or —CH=CH—; and where said pyridyl moiety is substituted by 0 or 1 bromo, chloro, or fluoro;

$R^{352}$ is a member independently selected from the group consisting essentially of ($C_1$–$C_6$) alkyl ($C_3$–$C_8$) cycloalkyl; —($CH_2$)$_m$($C_6$–$C_{10}$) aryl; and —($CH_2$)$_n$$X^7$ (pyridyl) where n is selected from 0, 1, 2, 3, 4, and 5; and $X^7$ is a bond or —CH=CH—; and where said pyridyl moiety is substituted by 0 or 1 bromo, chloro, or fluoro;

$R^{353}$ is a member independently selected from the group consisting essentially of H; —$R^{345}$; ($C_1$–$C_3$) alkyl substituted by 0 or 1 substituent hydroxy, or ($C_1$–$C_3$) alkyoxy($C_1$–$C_3$) alkyl;

$R^{354}$ is a member independently selected from the group consisting essentially of H; —$R^{345}$; carboxy; ($C_1$–$C_3$) alkyoxy($C_1$–$C_3$) alkyl-; ($C_3$–$C_7$) cycloalkyl; and ($C_1$–$C_5$) alkyl substituted by 0 or 1 —$NR^{340}R^{341}$;

or $R^{353}$ and $R^{354}$ are taken together to form —$CH_2OCH_2OCH_2$—;

$R^{355}$ is a member independently selected from the group consisting essentially of H; hydroxy; ($C_1$–$C_4$) alkyl substituted by 0 or 1 substituent comprising a member independently selected from the group consisting essentially of hydroxy; —C(=O)$R^{340}$; —$NR^{340}R^{341}$; —($CH_2$)$_m$NHC(=O)$R^{340}$; —($CH_2$)$_m$NHC(=O)$R^{343}$; —($CH_2$)$_m$CO$_2R^{340}$; —($CH_2$)$_m$C(=O)$NR^{340}R^{341}$; —($CH_2$)$_m$C(=O)N(OH)$R^{340}$; —($CH_2$)$_m$SO$_2NR^{340}R^{341}$; —($CH_2$)$_m$PO$_3H_2$; —($CH_2$)$_m$SO$_2$NHC(=O)$R^{343}$; and —($CH_2$)$_m$SO$_2$NHC(=O)(phenyl), where m is an integer selected from 0, 1, 2, 3, and 4;

$R^{356}$ is a member independently selected from the group consisting essentially of H; ($C_1$–$C_4$) alkyl; phenyl; —$NR^{340}R^{341}$; and —$NR^{340}$($C_1$–$C_4$) alkanoyl;

$R^{357}$ is a member independently selected from the group consisting essentially of —$R^{340}$; —$CH_2CO_2R^{343}$; and —$CH_2C$(=O)$NR^{340}R^{341}$;

$R^{358}$ is a member independently selected from the group consisting essentially of —C(=O)$R^{340}$; —C(=O)($C_6$–$C_{10}$) aryl; —C(=O)($C_3$–$C_9$) heteroaryl; —$CO_2R^{340}$; —C(=O)$NR^{340}R^{341}$; cyano; nitro; —$CH_2OH$; —$NR^{340}SO_2R^{340}$; —NHSO$_2$($C_6$–$C_{10}$) aryl; —NHCO$_2$($C_1$–$C_4$) alkyl; —$NR^{340}$C(=O)$R^{340}$; and —NHCO$_2$($C_6$–$C_{10}$) aryl;

$R^{359}$ is a member independently selected from the group consisting essentially of —$R^{345}$; cyano; carboxy; formyl; —C(=O)$R^{340}$; and ($C_1$–$C_4$) alkanoyl;

$R^{360}$ is a member independently selected from the group consisting essentially of cyano; —$NR^{340}R^{341}$; —SO$_2$($C_1$–$C_4$) alkyl; —SO$_2$($C_6$–$C_{10}$) aryl; —C(=O)$R^{340}$; —C(=O)($C_6$–$C_{10}$) aryl; —C(=O)($C_3$–$C_9$) heteroaryl; —C(=O)$NR^{340}R^{341}$; and —$CO_2R^{340}$;

$R^{361}$ and $R^{362}$ is each a member independently selected from the group consisting essentially of H; cyano; nitro; —$CO_2R^{340}$; —C(=O)$NR^{340}R^{341}$; —$CH_2OH$; —C(=O)$R^{340}$; —NHCO$_2R^{340}$; and —NHSO$_2R^{340}$;

A is a member independently selected from the group consisting essentially of pyridyl; morpholinyl; piperidinyl, imidazolyl; thienyl; pyrimidyl; thiazolyl; phenyl; and naphthyl; where each of said A groups is substituted by 0 to 2 substituents $R^{344}$ or by 1 substituent $R^{345}$;

$Z^3$ a member independently selected from the group consisting essentially of O; —$NR^{342}$; $NOR^{340}$; N(CN); C(CN)$_2$; $CR^{340}NO_2$; $CR^{340}$C(=O)O$R^{343}$; $CR^{340}$C(=O)$NR^{340}R^{341}$; C(CN)NO$_2$; C(CN)C(=O)O$R^{343}$; and C(CN)C(=O)$NR^{340}R^{341}$; and, Y is O or S;

(V-D)

—OR said substituents defining $R^5_a$ and $R^5_b$ comprise a moiety of partial Formula (9.36):

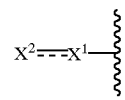

(9.36)

wherein the broken line indicates a single or double bond;

$X^1$ is —$CR^{472}R^{473}$— where said broken line indicates a single bond; or —$CR^{473}$— where said broken line indicates a double bond;

$X^2$ is —$CR^{475}R^{477}R^{478}$— or —C(=$NOR^{481}$)$R^{482}$— where said broken line indicates a single bond; or —$CR^{477}R^{478}$ where said broken line indicates a double bond;

$R^{472}$ is a member independently selected from the group consisting essentially of H; hydroxy; bromo, chloro, or fluoro; and —$OR^{479}$;

each $R^{473}$ is a member independently selected from the group consisting essentially of cyano; cyanomethyl; benzyloxy; —$R^{475}$; —$CO_2R^{475}$; —$CO_2$($CH_2$)$_n$($C_6$–$C_{10}$) aryl; —C(Y)$NR^{475}R^{476}$; —C(Y)$NR^{475}$($CH_2$)$_n$($C_6$–$C_{10}$) aryl; —($CH_2$)$_n$($C_6$–$C_{10}$) aryl; and —($CH_2$)$_n$(5- to 10-membered heteroaryl); where n is an integer selected from 0, 1, 2, and 3; each $R^{473}$ group is substituted by 0 to 3 substituents $R^{474}$; and each $R^{473}$ group is substituted by 0 or 1 substituent $R^{480}$;

each $R^{474}$ is a member independently selected from the group consisting essentially of bromo, chloro, or fluoro; cyano; nitro; ($C_1$–$C_6$) alkyl; ($C_2$–$C_6$) alkenyl; —$OR^{475}$; ($C_3$–$C_7$) cycloalkoxy; —$NR^{475}R^{476}$; —$NR^{475}OR^{476}$; —S(O)$_mR^{475}$ where m is an integer selected from 0, 1, and 2; —$CO_2R^{475}$, —C(=O)$R^{475}$; —$SO_2NR^{475}R^{476}$; —C(=O)$NR^{475}R^{476}$;

—CR$^{475}$R$^{476}$SO$_2$NR$^{475}$R$^{476}$; —CR$^{475}$R$^{476}$C(=O)NR$^{475}$R$^{476}$; —NHSO$_2$R$^{476}$; —NHSO$_2$NR$^{475}$R$^{476}$; —NHC(=O)NR$^{475}$R$^{476}$; —NHC(=O)(C$_1$–C$_6$) alkyl; and —NHC(=O)O(C$_1$–C$_6$) alkyl);

each R$^{475}$ and R$^{476}$ is a member independently selected from the group consisting essentially of H; and (C$_1$–C$_6$) alkyl;

R$^{477}$ is a member independently selected from the group consisting essentially of —R$^{473}$; 2-oxo-pyridyl; 3-oxo-pyridyl; 4-oxo-pyridyl; 2-oxo-pyrrolyl; 4-oxo-thiazolyl; 4-oxo-piperidyl; 2-oxo-quinolyl; 4-oxo-quinolyl; 1-oxo-isoquinolyl; 4-oxo-oxazolyl; 5-oxo-pyrazolyl; 5-oxo-isoxazolyl; and 4-oxo-isoxazolyl; where each of said R$^{477}$ groups is substituted by 0 to 3 substituents R$^{474}$;

R$^{478}$ is a member independently selected from the group consisting essentially of —R$^{475}$; cyano; —(CH$_2$)$_p$(C$_6$–C$_{10}$) aryl; and —(CH$_2$)$_p$(5- to 10-membered heteroaryl); where p is an integer selected from 1, 2, and 3; and where each said R$^{478}$ group is substituted by 0 to 3 substituents R$^{474}$;

R$^{479}$ is a member independently selected from the group consisting essentially of formyl; carbamoyl; thiocarbamyl; (C$_1$–C$_6$) alkyl; (C$_2$–C$_6$) alkenyl; (C$_1$–C$_4$) alkoxy(C$_1$–C$_4$) alkyl-; and (C$_1$–C$_6$) alkanoyl; where said alkyl moieties of each of said R$^{479}$ groups is substituted by 0 to 3 substituents independently selected from the group consisting essentially of bromo, chloro, or fluoro; hydroxy; and (C$_1$–C$_4$) alkoxy;

R$^{480}$ is a member independently selected from the group consisting essentially of cyclobutyl; cyclopentyl; cyclohexyl; 2-cyclobuten-1-yl; 2-cyclopenten-1-yl; 3-cyclopenten-1-yl; 2,4-cyclopentadien-1-yl; 3,5-cyclohexadien-1-yl; pyrrolyl; pyrrolidinyl; dioxolanyl; imidazolyl; oxazolyl; imidazolidinyl; pyrazolyl; pyrazolidinyl; pyranyl; piperidinyl; 1,4-dioxanyl; morpholinyl; 1,4-dithianyl; thiomorpholinyl; piperazinyl; 1,3,5-trithianyl; oxazinyl; isoxazinyl; oxathiazinyl; and oxadiazinyl; where each of said R$^{480}$ groups is substituted by 0 to 2 (C$_1$–C$_2$) alkyl;

R$^{481}$ is a member independently selected from the group consisting essentially of H; (C$_1$–C$_6$) alkyl; (C$_2$–C$_6$) alkenyl; (C$_2$–C$_6$) alkynyl; —C(Y)NR$^{475}$R$^{476}$; —C(Y)NH(C$_6$–C$_{10}$) aryl; —C(Y)(C$_1$–C$_6$) alkoxy; —C(Y)(C$_6$–C$_{10}$) aryloxy; and —C(Y)(C$_1$–C$_6$) alkyl);

R$^{482}$ is a member independently selected from the group consisting essentially of phenyl and pyridinyl; where each of said R$^{482}$ groups is substituted by 0 to 3 substituents independently selected from the group consisting essentially of bromo, chloro, or fluoro; (C$_1$–C$_4$) alkyl; hydroxy; (C$_1$–C$_4$) alkoxy; —NR$^{475}$R$^{476}$; and —S(O)$_m$R$^{475}$, where m is an integer selected from 0, 1, and 2; and, Y is O or S;

(V-E)

—OR, said substituents defining R$^5_a$ and R$^5_b$ comprise a moiety of partial Formulas (9.37) through (9.49), inclusive:

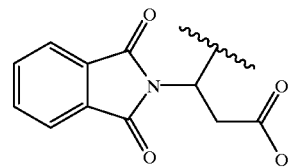
(9.37)

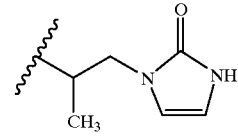
(9.38)

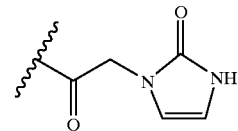
(9.39)

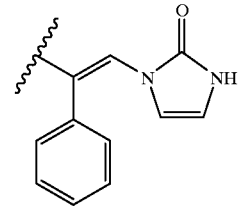
(9.40)

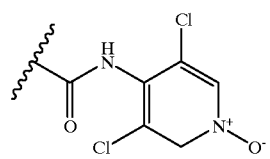
(9.41)

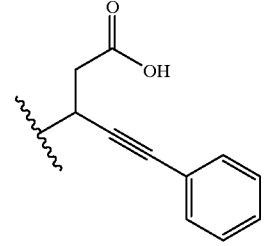
(9.42)

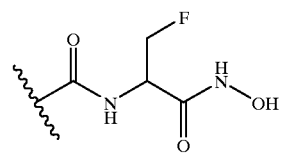
(9.43)

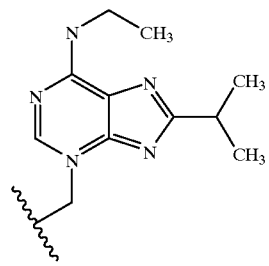
(9.44)

-continued

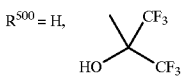

(9.45)

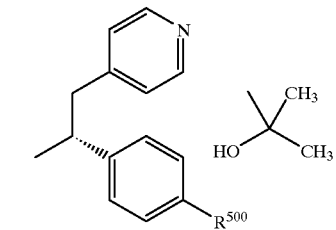

(9.46)

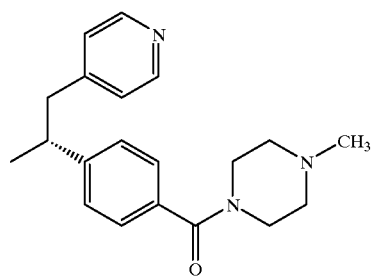

(9.47)

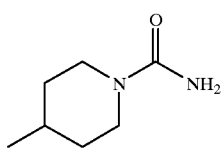

(9.48)

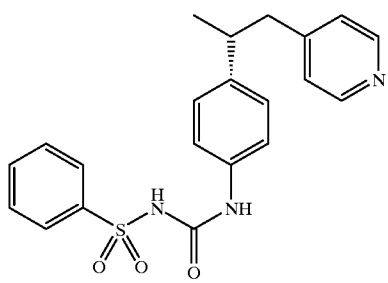

(9.49)

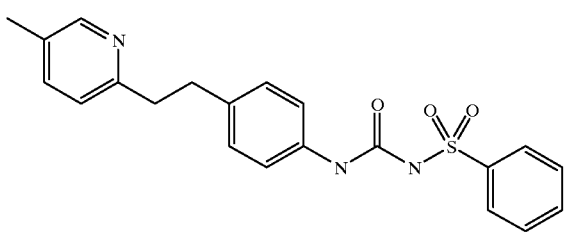

Preferred compounds of Formula (9.0) or (9.1) where $R^5_a$ and $R^5_b$ are as defined under (V-D) above, include those wherein $R^1$ is ethyl and R is cyclopentyl, cyclohexyl, or $(C_6-C_{10})$aryl.

Other preferred compounds of Formula (9.0) or (9.1) include those wherein $R^{473}$ is $—(CH_2)_n(C_6-C_{10})$aryl or $—(CH_2)_n$(5- to 10-membered heteroaryl), where n is an integer selected from 0, 1, 2, and 3; and, more preferably, wherein $R^{473}$ is phenyl or pyridin-4-yl.

Specific embodiments of the compounds of Formula (9.0) or (9.1) where $R^5_a$ and $R^5_b$ are as defined under (V-A) include those wherein R is cyclopentyl or cyclohexyl, $R^1$ is $(C_1-C_2)$ alkyl, preferably ethyl, one of $R^5_a$ and $R^5_b$ is hydrogen and the other is a substituent of Formula (9.2) where the dashed line represents a single bond, m is 0, $R^{113}$ and $R^{114}$ are in a cis relationship to each other, $R^{113}$ is cyano, $R^{115}$ is hydrogen, and $R^{114}$ is carboxy, $—CH_2OH$, or $—CH_2C(=O)NH_2$.

Other specific embodiments of the compounds of Formula (9.0) or (9.1) include those wherein R is phenyl substituted by fluoro, $R^1$ is $(C_1-C_2)$ alkyl, preferably ethyl, one of $R^5_a$ and $R^5_b$ is hydrogen and the other is a substituent of Formula (9.2) where the dashed line represents a single bond, $R^{113}$ is cyano, and $R^{115}$ and $R^{114}$ are both hydrogen.

The term "halo", as used herein, unless otherwise indicated, means fluoro, chloro, bromo or iodo. Preferred halo groups are fluoro, chloro and bromo.

The term "alkyl", as used herein, unless otherwise indicated, means saturated monovalent hydrocarbon radicals which are straight or branched moieties containing from one to six, preferably one to four, carbon atoms.

The term "alkoxy", as used herein, unless otherwise indicated, means O-alkyl groups wherein "alkyl" is defined above.

The term "alkenyl", as used herein, unless otherwise indicated, means unsaturated alkyl groups having one or more double bonds wherein "alkyl" is defined above.

The term "cycloalkyl", as used herein, unless otherwise indicated, means saturated monovalent cyclo hydrocarbon radicals containing from three to seven carbon atoms, preferably five or six carbon atoms, including such specific radicals as cyclobutyl, cyclopentyl and cycloheptyl.

The term "aryl", as used herein, unless otherwise indicated, means an organic radical derived from an aromatic hydrocarbon by removal of one hydrogen, comprising a carbocyclic moiety which is a member independently selected from the group consisting essentially of benzyl; cis- and trans-decahydronaphthalenyl; 2,3-1H-dihydroindenyl (indanyl); indenyl; 1-naphthalenyl; 2-naphthalenyl; phenyl; and 1,2,3,4-tetrahydronaphthalenyl; and preferably means phenyl.

The term "heterocyclyl" or "heterocyclic", as used herein, unless otherwise indicated, means aromatic and non-aromatic heterocyclic groups containing one or more heteroatoms each selected from O, S and N. Included within this meaning are heterocyclic groups which are benzo-fused ring systems and ring systems substituted with an oxo moiety. Included within the scope of this definition are the following specific groups: acridinyl; benzimidazolyl; benzodioxolane; 1,3-benzodioxol-5-yl; benzo[b]furanyl; benzo[b]thiophenyl; benzoxazolyl; benzthiazolyl; carbazolyl; cinnolinyl; 2,3-dihydrobenzofuranyl; 1,3-dioxane; 1,3-dioxolane; 1,3-dithiane; 1,3-dithiolane; furanyl; imidazolidinyl; imidazolinyl; imidazolyl; 1H-indazolyl; indolinyl; indolyl; 3H-indolyl; isoindolyl; isoquinolinyl; isothiazolyl; isoxazolyl; morpholinyl; 1,8-naphthyridinyl; oxadiazolyl; 1,3-oxathiolane; oxazolidinyl; oxazolyl; oxiranyl; parathiazinyl; phenazinyl; phenothiazinyl; phenoxazinyl; phthalazinyl; piperazinyl; piperidinyl; pteridinyl; pyranyl; pyrazinyl; pyrazolidinyl; pyrazolinyl; pyrazolo[1,5-c]triazinyl; pyrazolyl; pyridazinyl; pyridyl; pyrimidinyl; pyrimidyl; pyrrolyl; pyrrolidinyl; purinyl; quinazolinyl; quinolinyl; 4H-quinolizinyl; quinoxalinyl; tetrazolidinyl; tetrazolyl; thiadiazolyl; thiazolidinyl; thiazolyl; thienyl; thiomorpholinyl; triazinyl; and triazolyl.

With reference to the $R^{114}$ substituent of partial Formula (9.2) of Formula (9.0) or (9.1), the $(C_3-C_9)$ heterocyclic group can be attached to the $(C_1-C_6)$ alkyl group by a nitrogen or, preferably, a carbon atom. An example of a $C_3$ heterocyclic group is thiazolyl, and an example of a $C_9$ quinolizinyl; heterocyclic group is quinolinyl. Examples of non-aromatic heterocyclic groups are pyrrolidinyl, piperidino, morpholino, thiomorpholino and piperazinyl. Examples of aromatic heterocyclic groups which are preferred are pyridinyl, imidazolyl, pyrimidinyl, pyrazolyl, triazolyl, pyrazinyl, tetrazolyl, furyl, thienyl, isoxazolyl and thiazolyl. A preferred heterocyclic group having a fused benzene ring is benzimidazolyl.

Where heterocyclic groups are specifically recited or covered as substituents for the compound of Formula (9.0) or (9.1) under (V-A), it is understood that all suitable isomers of such heterocyclic groups are intended. Thus, for example, in the definition of the substituent $R^{114}$, the term "thiazolyl" includes 2-, 4- or 5-thiazolyl; the term "imidazolyl" includes 2-, 4- or 5-imidazolyl; the term "pyrazolyl" includes 3-, 4- or 5-pyrazolyl; the term "oxazolyl" includes 2-, 4- or 5-oxazolyl; the term "isoxazolyl" includes 3-, 4- or 5-isoxazolyl, and so on. Likewise, in the definition of substituent $R^{116}$, the term "pyridyl" includes 2-, 3- or 4-pyridyl.

Certain "aminal" or "acetal"-like chemical structures within the scope of Formula (9.0) or (9.1) may be unstable. Such structures may occur where two heteroatoms are attached to the same carbon atom. For example, where R is $(C_1-C_6)$ alkyl substituted by hydroxy, it is possible that the hydroxy may be attached to the same carbon that is attached to the nitrogen atom from which R extends. It is to be understood that such unstable compounds are not within the scope of the present invention.

Preferred compounds of Formula (9.0) or (9.1) under (V-A) include those wherein $R^5_a$ quinolizinyl; or $R^5_b$ is a group of the partial Formula (9.50) or (9.51):

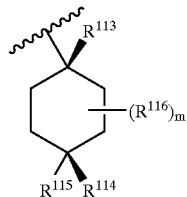

(9.50)

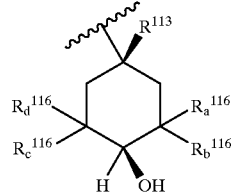

(9.51)

where for partial Formula (9.50) $R^{113}$ and $R^{114}$, especially where $R^{114}$ is —OH, are cis with respect to each other; and for partial Formula (9.51) $R^{116}_a$, $R^{116}_b$, $R^{116}_c$ and $R^{116}_d$ are independently selected from the group consisting essentially of —H; —CH$_3$; —CF$_3$; —CHF$_2$; and —CH$_2$F.

Other preferred compounds of Formula (9.0) or (9.1) under (V-A) include those wherein R is a member independently selected from the group consisting essentially of cyclohexyl, cyclopentyl, cyclobutyl, methylenecyclopropyl, isopropyl, phenyl, and 4-fluoro-phenyl.

Other preferred compounds of Formula (9.0) or (9.1) under (V-A) include those wherein $R^1$ is $(C_1-C_2)$ alkyl substituted by 0 to 3 fluorine atoms, and, more preferably, those wherein $R^1$ is ethyl.

Other preferred compounds of Formula (9.0) or (9.1) under (V-A) include those wherein one of $R^5_a$ and $R^5_b$ is hydrogen and the other is a group of partial Formula (9.2) wherein the dashed line attached to the ring carbon atom to which $R^{113}$ is attached represents a single bond.

Other preferred compounds of Formula (9.0) or (9.1) under (V-A) include those wherein one of $R^5_a$ and $R^5_b$ is hydrogen and the other is a group of partial Formula (9.2) wherein the dashed line attached to the ring carbon atom to which $R^{113}$ is attached represents a single bond and $R^{113}$ is cyano.

Other preferred compounds of Formula (9.0) or (9.1) under (V-A) include those wherein one of $R^5_a$ and $R^5_b$ is hydrogen and the other is a group of partial Formula (9.2) wherein the dashed line attached to the ring carbon atom to which $R^{113}$ is attached represents a single bond, m is 0 and $R^{115}$ is hydrogen.

Other preferred compounds of Formula (9.0) or (9.1) under (V-A) include those wherein one of $R^5_a$ and $R^5_b$ is hydrogen and the other is a group of partial Formula (9.2) wherein the dashed line attached to the ring carbon atom to which $R^{113}$ is attached represents a single bond; m is 0; $R^{115}$ is hydrogen; and $R^{114}$ is a member independently selected from the group consisting essentially of —OH; —CH$_2$OH; —C(CH$_3$)$_2$OH; —C(=O)OH; —C(=O)OCH$_3$; —C(=O)OCH$_2$CH$_3$; and —CH$_2$C(=O)NH$_2$.

Other more preferred compounds of Formula (9.0) or (9.1) under (V-A) include those wherein R is a member independently selected from the group consisting essentially of cyclobutyl, cyclopentyl, cyclohexyl, and 4-fluoro-phenyl; $R^1$ is ethyl; one of $R^5_a$ and $R^5_b$ is hydrogen and the other is a group of partial Formula (9.51) wherein $R^{113}$ is cyano; $R^{115}$ is hydrogen; $R^{114}$ is —OH; $R^{113}$ and $R^{114}$ are cis with respect to each other; and $R^{116}_a$, $R^{116}_b$, $R^{116}_c$ and $R^{116}_d$ are each a member independently selected from the group consisting essentially of —H; and —CH$_3$;

Preferred compounds of Formula (9.0) or (9.1) include those wherein $R^1$ is ethyl.

Other preferred compounds of Formula (9.0) or (9.1) include those wherein R is a member independently selected from the group consisting essentially of cyclohexyl; cyclopentyl; methylenecyclopropyl; isopropyl; phenyl; and 4-fluoro-phenyl.

Specific preferred compounds of Formula (9.0) or (9.1) under (V-A) include:

1-(1-Cyclopentyl-3-ethyl-1H-indazol-6-yl)-4-oxocyclohexanecarbonitrile;

Trans-4-cyano-4-(1-cyclopentyl-3-ethyl-1H-indazol-6-yl) cyclohexanecarboxylic acid methyl ester;

Cis-4-cyano-4-(1-cyclopentyl-3-ethyl-1H-indazol-6-yl) cyclohexanecarboxylic acid methyl ester;

Trans-4-cyano-4-(1-cyclopentyl-3-ethyl-1H-indazol-6-yl) cyclohexanecarboxylic acid;

Cis-4-cyano-4-(1-cyclopentyl-3-ethyl-1H-indazol-6-yl) cyclohexanecarboxylic acid;

1-(1-Cyclohexyl-3-ethyl-1H-indazol-6-yl)-4-oxocyclohexanecarbonitrile;

Cis-4-cyano-4-(1-cyclohexyl-3-ethyl-1H-indazol-6-yl) cyclohexanecarboxylic acid methyl ester;

Trans-4-cyano-4-(1-cyclohexyl-3-ethyl-1H-indazol-6-yl) cyclohexanecarboxylic acid methyl ester;

Cis-4-cyano-4-(1-cyclohexyl-3-ethyl-1H-indazol-6-yl) cyclohexanecarboxylic acid;

Trans-4-cyano-4-(1-cyclohexyl-3-ethyl-1H-indazol-6-yl) cyclohexanecarboxylic acid;

Cis-1-(1-cyclohexyl-3-ethyl-1H-indazole-6-yl)-4-hydroxymethylcyclohexanecarbonitrile;

Cis-4-cyano-4-(1-cyclohexyl-3-ethyl-1H-indazol-6-yl) cyclohexanecarboxylic acid amide;
Trans-4-cyano-4-(1-cyclohexyl-3-ethyl-1H-indazol-6-yl) cyclohexanecarboxylic acid amide;
Cis-1-(1-cyclohexyl-3-ethyl-1H-indazol-6-yl)-4-(1-hydroxy-1-methylethyl)cyclohexanecarbonitrile;
Cis-1-(1-cyclohexyl-3-ethyl-1H-indazol-6-yl)-4-hydroxycyclohexanecarbonitrile;
Cis-1-[3-ethyl-1-(4-fluorophenyl)-1H-indazol-6-yl]-4-hydroxycyclohexanecarbonitrile;
Cis-1-(1-cyclopentyl-3-ethyl-1H-indazol-6-yl)-4-hydroxycyclohexanecarbonitrile;
Cis-1-(1-cyclobutyl-3-ethyl-1H-indazol-6-yl)-4-hydroxycyclohexanecarbonitrile;
Cis-1-(1-cyclopentyl-3-ethyl-1H-indazol-6-yl)-4-hydrox-4-methylcyclohexanecarbonitrile;
Trans-1-(1-cyclopentyl-3-ethyl-1H-indazol-6-yl)-4-hydroxy-4-methylcyclohexanecarbonitrile;
Cis-4-cyano-4-(1-cyclobutyl-3-ethyl-1H-indazol-6-yl) cyclohexanecarboxylic acid;
Trans-4-cyano-4-(1-cyclobutyl-3-ethyl-1H-indazol-6-yl) cyclohexanecarboxylic acid;
6-Bromo-3-ethyl-1-(4-fluorophenyl)-1H-indazole;
4-[3-Ethyl-1-(4-fluorophenyl)-1H-indazol-6-yl]-4-hydroxycyclohexanecarboxylic acid ethyl ester;
4-Cyano-4-[3-ethyl-1-(4-fluorophenyl)-1H-indazol-6-yl] cyclohexanecarboxylic acid ethyl ester;
4-[3-Ethyl-1-(4-fluorophenyl)-1H-indazol-6-yl]cyclohex-3-enecarboxylic acid ethyl ester;
4-Cyano-4-(1-cyclohexyl-3-ethyl-1H-indazol-6-yl)-cyclohexanecarboxylic acid ethyl ester;
Cis-4-Cyano-4-[3-ethyl-1-(4-fluorophenyl)-1H-indazol-6-yl]cyclohexanecarboxylic acid;
4-[3-Ethyl-1-(4-fluorophenyl)-1H-indazol-6-yl]cyclohex-3-enecarboxylic acid; and
4-(1-Cyclohexyl-3-ethyl-1H-indazol-6-yl)-4-hydroxycyclohexanecarboxylic acid.

The phrase "pharmaceutically acceptable salt(s)", as used herein, unless otherwise indicated, includes salts of acidic or basic groups which may be present in the compounds of Formula (9.0) or (9.1). For example, pharmaceutically acceptable salts include sodium, calcium and potassium salts of carboxylic acid groups and hydrochloride salts of amino groups. Other pharmaceutically acceptable salts of amino groups are hydrobromide, sulfate, hydrogen sulfate, phosphate, hydrogen phosphate, dihydrogen phosphate, acetate, succinate, citrate, tartrate, lactate, mandelate, methanesulfonate (mesylate) and p-toluenesulfonate (tosylate) salts.

Certain species of above-desecribed compounds may have asymmetric centers and therefore exist in different enantiomeric forms. All optical isomers and stereoisomers of the compounds of Formula (9.0) or (9.1), and mixtures thereof, are considered to be within the scope of the invention. With respect to the compounds of Formula (9.0) or (9.1), the invention includes the use of a racemate, a single enantiomeric form, a single diastereomeric form, or mixtures thereof. The compounds of Formula (9.0) or (9.1) may also exist as tautomers. This invention relates to the use of all such tautomers and mixtures thereof.

Another embodiment of this aspect of the present invention relates to a pharmaceutical composition for the inhibition of PDE4 or the production of TNF in a mammal comprising a therapeutically effective amount of a therapeutically active composition of matter comprising a compound as above-desecribed, or a pharmaceutically acceptable salt thereof, and a pharmaceutically acceptable carrier therefor.

Another embodiment of the present invention relates to a method for the inhibition of PDE4 or the production of TNF by administering to a patient a therapeutically effective amount of a therapeutically active composition of matter comprising a compound as above-desecribed or a pharmaceutically acceptable salt thereof.

Accordingly, the present invention also relates to method of treating or preventing a disease or condition in a mammal in need of such treatment wherein said disease or condition responds favorably to inhibition of PDE4 or production of TNF and is a member selected from the group consisting essentially of asthma; joint inflammation; rheumatoid arthritis; gouty arthritis; rheumatoid spondylitis; osteoarthritis; sepsis; septic shock; endotoxic shock, gram negative sepsis; toxic shock syndrome; acute respiratory distress syndrome; cerebal malaria; chronic obstructive pulmonary disease (COPD), including asthma, chronic bronchitis and pulmonary emphysema; silicosis; pulmonary sarcoidosis; bone resorption diseases; reperfusion injury; graft vs. host reaction; allograft rejections; fever and myalgias due to bacterial, viral or fungal infection including influenza; cachexia secondary to infection or malignancy; cachexia secondary to human acquired immune deficiency syndrome (AIDS); AIDS; HIV infection; ARC (AIDS related complex); keloid formation; scar tissue formation; Crohn's disease; ulcerative colitis; pyresis; multiple sclerosis; type 1 diabetes mellitus; autoimmune diabetes; systemic lupus erythematosis; bronchitis; psoriasis; Bechet's disease; anaphylactoid purpura nephritis; chronic glomerulonephritis; inflammatory bowel disease; leukemia; allergic rhinitis; and dermatitis, comprising administering to said mammal a therapeutically effective amount of a therapeutically active composition of matter comprising a compound of Formula (IA) or (IB), optionally together with a pharmaceutically acceptable carrier therfor.

The present invention further relates to a pharmaceutical composition for the prevention or treatment of the diseases and conditions enumerated above, especially including asthma, in a mammal, comprising a therapeutically effective amount of a compound according to Formula (9.0) or (9.1), or a pharmaceutically acceptable salt thereof, together with a pharmaceutically acceptable carrier therefor.

This invention further relates to a method of treating or preventing the foregoing specific diseases and conditions by administering to a patient a therapeutically effective amount of a compound of Formula (9.0) or (9.1), or a pharmaceutically acceptable salt thereof. In particular, the present invention includes compounds useful in treating or preventing one or members selected from the groups of diseases and conditions consisting essentially of (1) inflammatory diseases and conditions comprising: joint inflammation, rheumatoid arthritis, rheumatoid spondylitis, osteoarthritis, inflammatory bowel disease, ulcerative colitis, chronic glomerulonephritis, dermatitis, and Crohn's disease; (2) respiratory diseases and conditions comprising: acute respiratory distress syndrome, chronic obstructive pulmonary disease (COPD) including asthma, chronic bronchitis, and pulmonary emphysema, acute bronchitis, and silicosis; (3) infectious diseases and conditions comprising: sepsis, septic shock, endotoxic shock, gram negative sepsis, toxic shock syndrome, fever and myalgias due to bacterial, viral or fungal infection, and influenza; (4) immune diseases and conditions comprising: autoimmune diabetes, systemic lupus erythematosis, graft vs. host reaction, allograft rejections, multiple sclerosis, psoriasis, and allergic rhinitis; and (5) other diseases and conditions comprising: bone resorption diseases; reperfusion injury; cachexia secondary to infection or malignancy; cachexia secondary to human acquired immune deficiency syndrome (AIDS), human immunodeficiency virus (HIV) infection, or AIDS related complex (ARC); keloid formation; scar tissue formation; type 1 diabetes mellitus; and leukemia; wherein said compound comprises an inhibitor of PDE4.

Especially important among the above-recited diseases and conditions which may be treated or prevented using the compounds of the present invention are the inflammatory diseases and conditions and the respiratory diseases and conditions. Among the inflammatory diseases and conditions which are especially significant with regard to successful treatment or prevention using the compounds of the present invention comprise: joint inflammation, rheumatoid arthritis, osteoarthritis, and inflammatory bowel disease. Among the respiratory diseases and conditions which are especially significant with regard to successful treatment or prevention using the compounds of the present invention comprise: asthma, acute respiratory distress syndrome, and bronchitis.

The expression "treating or preventing", as used herein with regard to the administration of the compounds of the present invention for therapeutic purposes in the case of various members selected from the many groups of diseases and conditions specifically recited herein, is intended to denote both the therapeutic objective of said administration as well as the therapeutic results actually achieved by said administration. The extent of therapy accomplished by administration of the compounds of the present invention may range from an amelioration to a significant diminishing of the course of the disease involved, and beyond to active treatment of said disease, including a reversal of the disease process itself which is present. The higher or highest degrees of therapeutic effectiveness result in the prevention of any injury, damage, deterioration, or loss of body tissues or organs and basic body functions subsequent to the early stages of degeneration and decline in said body tissues or organs and basic body functions at the onset of the disease involved.

The expression "the early stages of degeneration and decline in body tissues or organs and basic body functions" is intended to mean the very beginning of the initial pathologic changes in said body tissues or organs and basic body functions which define and are the result of a disease process. Said pathologic changes with respect to tissues and organs include changes in the composition and cohesiveness; form and makeup; rigidity, strength, resilience, elasticity, conformational integrity and stability, density, tensile strength and other measures of physical quality; abundance and extent of its presence throughout the body; viability and regenerative capability on both a micro- and macro-level; and the ability to successfully resist various kinds of external stresses including mechanical force and invasion by microorganisms; of said tissues and organs from that present before the onset of said disease process, which result in a degradation and decline of the beneficial and necessary properties characterizing said tissues and organs.

Pathologic changes with respect to body functions are those which inherently arise from the changes above-described with respect to said tissues and organs, and which also, consequently, result in a degradation and decline in the beneficial and necessary performance which characterizes the normal and proper operation of said body functions. These pathologic changes, both with regard to tissues or organs and with respect to body functions, especially include improper repair of the above-discussed early stages of degeneration and decline.

Synthetic preparation of each and all of the above-described indazole-for-catechol bioisostere replacement compositions of matter does not usually start, of course, with a catechol compound. Direct preparation of an indazole per se using methods well known in the art of preparing organic compounds is usually the most straightforward and efficient method of preparing the bioisostere replacement compounds of the present invention. The technical literature is replete with suitable methods for carrying out such preparations. However, in order to better illustrate the manner in which bioisostere replacement compounds of the present invention may be prepared, there are set out below numerous reaction schemes and working examples for preparing indazole compounds types (II), (III) and (V) as described above, ie., bioisostere replacement compounds which are active as adrenergics, calcium channel blockers, and PDE4 inhibitors. Said reaction schemes are accompanied by an ongoing explanation of each step of the synthesis involved. Working examples in accordance with which these synthesis steps are carried out are also presented further below. Analogous synthesis methods may be carried out in order to prepare other compounds of the present invention, modifying where necessary starting materials and reactants.

Reaction Schemes 1–7 below illustrate the preparation of the compounds of the present invention of type (V):

SCHEME 1

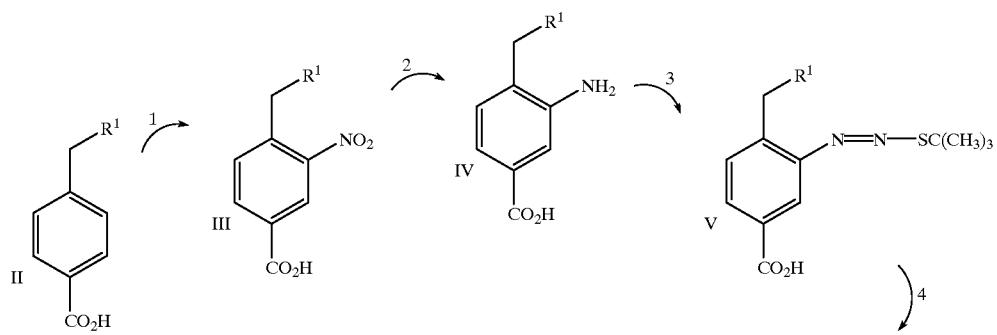

-continued
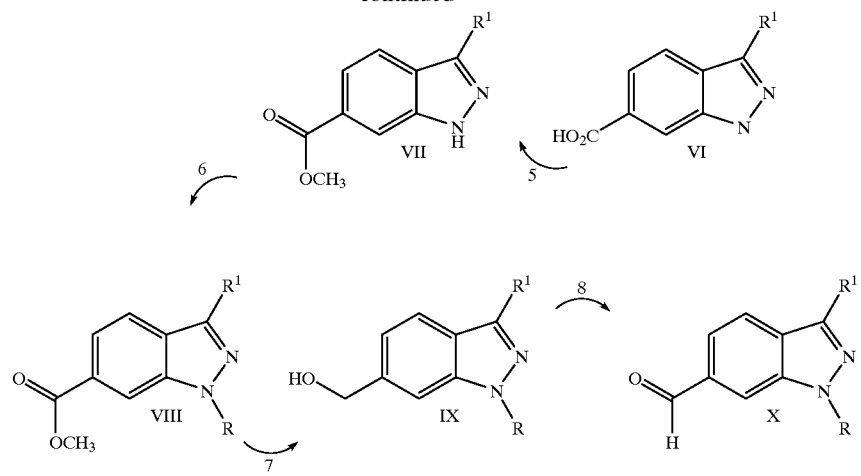
SCHEME 2
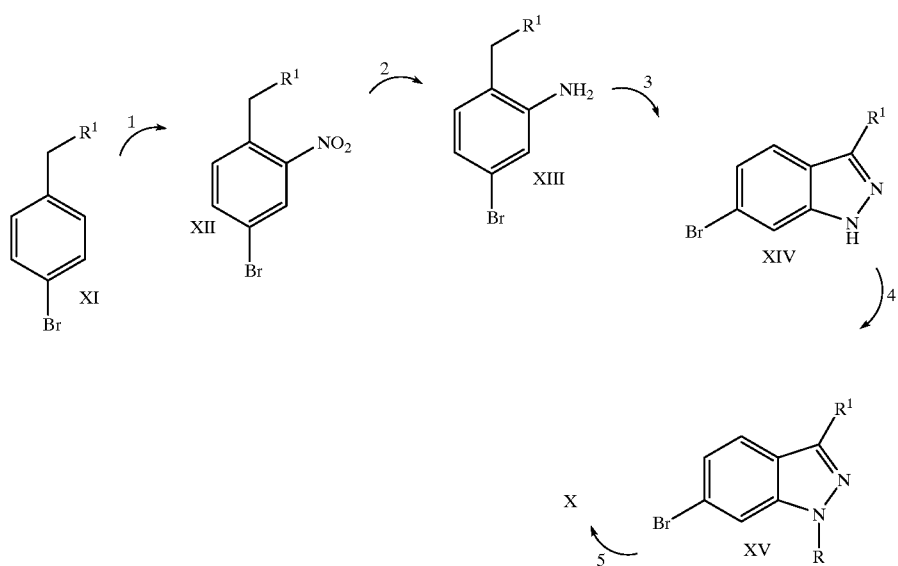
SCHEME 3
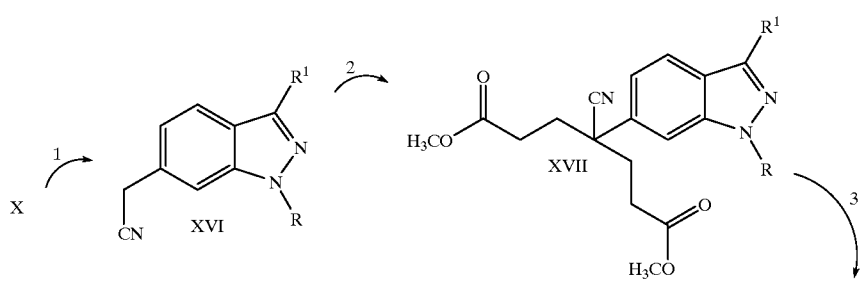

-continued

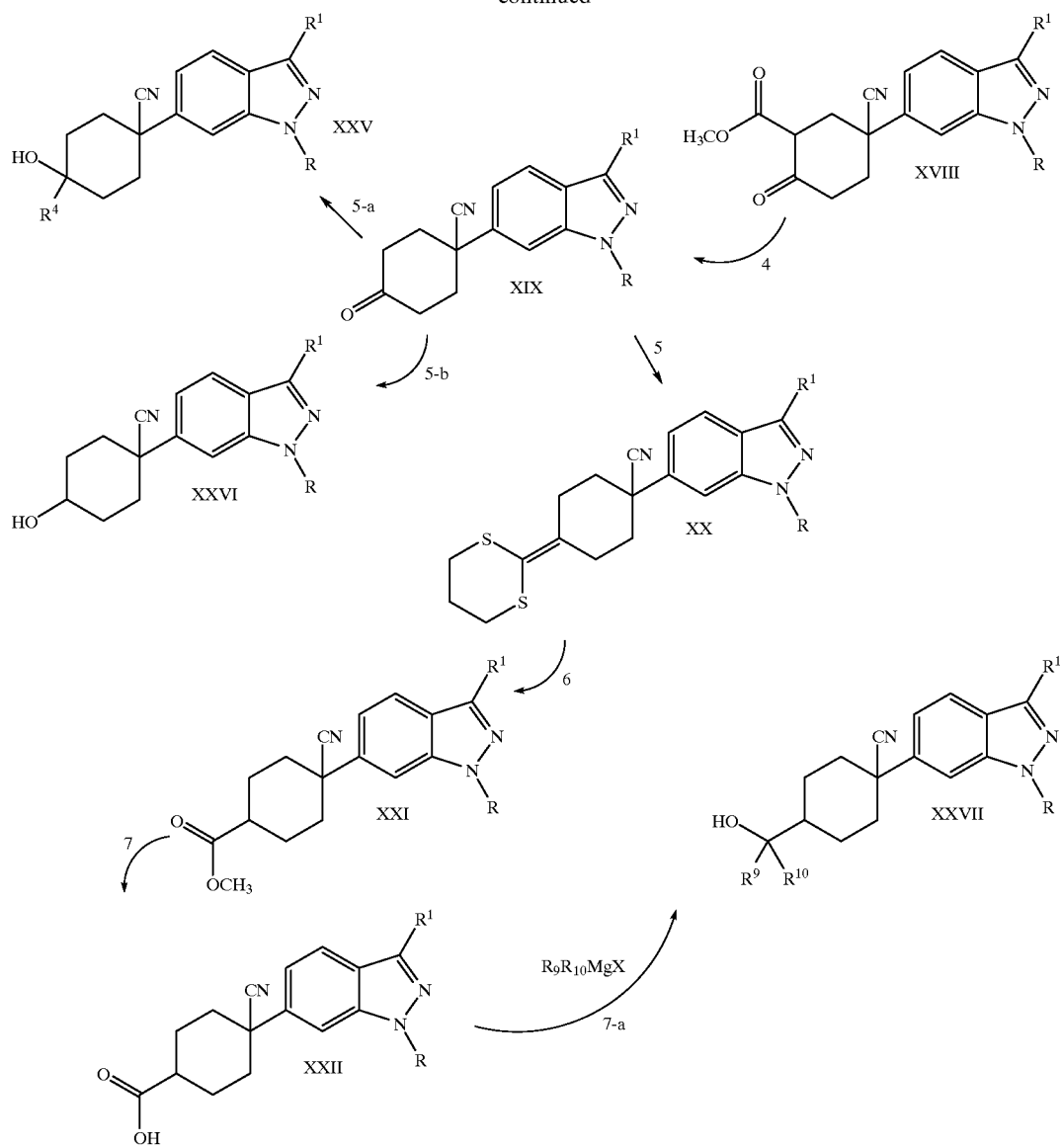

SCHEME 4

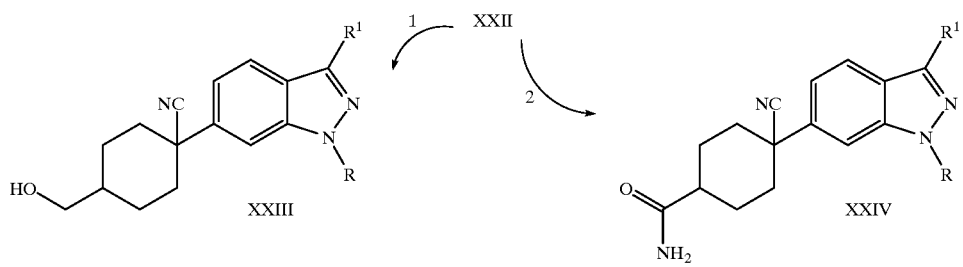

The compounds in the schematic representations above are numbered using Roman numerals in consecutive order, starting with II. These Roman numeral reference numbers are not necessarily related to the Roman numerals used elsewhere in defining the compounds of the present invention. Unless otherwise indicated, R and $R^1$ in the reaction schemes are defined the same as elsewhere herein.

The preparation of indazole bioisostere replacement compounds of the present invention, especially those of Formula (9.0) or (9.1) can be carried out by one skilled in the art according to one or more of the synthetic methods outlined in Schemes 1–4 above and the examples referred to below. In Step 1 of Scheme 1, the carboxylic acid of Formula II, which is available from known commercial sources or can be prepared according to methods known to those skilled in the art, is nitrated under standard conditions of nitration (HON/$H_2SO_4$, 0°C.) and the resulting nitro derivative of Formula III is hydrogenated in Step 2 of Scheme 1 using standard hydrogenation methods ($H_2$—Pd/C under pressure) at ambient temperature (20–25° C.) for several hours (2–10 hours) to provide the compound of Formula IV. In Step 3 of Scheme 1, the amino benzoic acid of Formula IV is reacted with a base such as sodium carbonate under aqueous conditions and gently heated until mostly dissolved. The reaction mixture is chilled to a lower temperature (about 0° C.) and treated with sodium nitrate in water. After about 15 minutes, the reaction mixture is slowly transferred to an appropriate container holding crushed ice and a strong acid such as hydrochloric acid. The reaction mixture is stirred for 10–20 minutes and then added, at ambient temperature, to a solution of excess tert-butyl thiol in an aprotic solvent such as ethanol. The reaction mixture is acidified to a pH of 4–5 through addition of an inorganic base, preferably saturated aqueous $Na_2CO_3$, and the reaction mixture is allowed to stir at ambient temperature for 1–3 hours. Addition of brine to the reaction mixture, followed by filtration, provides the sulfide of Formula V.

In Step 4 of Scheme 1, the sulfide of Formula V is converted to the corresponding indazole carboxylic acid of Formula VI by reacting the sulfide of Formula V with a strong base, preferably potassium teft-butoxide, in dimethyl sulfoxide (DMSO) at ambient temperature. After stirring for several hours (1–4 hours), the reaction mixture is acidified with a strong acid, such as hydrochloric or sulfuric acid, and then extracted using conventional methods. In Step 5 of Scheme 1, the indazole carboxylic acid of Formula VI is converted to the corresponding ester of Formula VII by conventional methods known to those skilled in the art. In Step 6 of Scheme 1, the compound of Formula VII is provided through alkylation of the ester of Formula VII by subjecting the ester to conventional alkylation conditions (strong base/various alkylating agents and, optionally, a copper catalyst such as $CuBr_2$) in a polar aprotic solvent, such as tetrahydrofuran (THF), N-methylpyrrolidinone or dimethylformamide (DMF), at ambient or higher temperature (25–200° C.) for about 6–24 hrs, preferably about 12 hours. In Step 7 of Scheme 1, the compound of Formula VIII is converted to the corresponding alcohol of IX by following conventional methods known to those skilled in the art for reducing esters to alcohols. Preferably, the reduction is effected through use of a metal hydride reducing agent, such as lithium aluminum hydride, in a polar aproptic solvent at a low temperature (about 0° C.). In Step 8 of Scheme 1, the alcohol of Formula IX is oxidized to the corresponding aldehyde of Formula X according to conventional methods known to those skilled in the art. For example, the oxidation can be effected through use of a catalytic amount of tetrapropylammonium perrutenate and excess N-methylmorpholine-N-oxide, as described in *J. Chem. Soc., Chem. Commun.,* 1625 (1987), in an anhydrous solvent, preferably methylene chloride.

Scheme 2 provides an alternative method of preparing the aldehyde of Formula X. In Step 1 of Scheme 2, the compound of Formula XI is nitrated using conventional nitration conditions (nitric and sulfuric acid) to provide the compound of Formula XII. In Step 2 of Scheme 2, the nitro derivative of Formula XII is reduced to the corresponding amine of Formula XIII according to conventional methods known to those skilled in the art. Preferably, the compound of Formula XII is reduced to the amine of Formula XIII using anhydrous stannous chloride in an anhydrous aprotic solvent such as ethanol. In Step 3 of Scheme 2, the amine of Formula XIII is converted to the corresponding indazole of Formula XIV by preparing the corresponding diazonium fluoroforates as described in A. Roe, *Organic Reactions,* Vol. 5, Wiley, New York, 1949, pp. 198–206, followed by phase transfer catalyzed cyclization as described in R. A. Bartsch and I. W. Yang, *J. Het. Chem.* 21, 1063 (1984). In Step 4 of Scheme 2, alkylation of the compound of Formula XIV is performed using standard methods known to those skilled in the art, e.g., strong base, polar aprotic solvent and an alkyl halide, to provide the N-alkylated compound of Formula XV. In Step 5 of Scheme 2, the compound of Formula XV is subjected to metal halogen exchange employing an alkyl lithium, such as n-butyl lithium, in a polar aprotic solvent, such as THF, at low temperature (−50° C. to 100° C., with −78° C. being preferred) followed by quenching with DMF at low temperature and warming to ambient temperature to provide the aldehyde compound of Formula X.

Scheme 3 illustrates the preparation of a compound of Formula XXII which is a compound of Formula (9.0) or (9.1) wherein $R^5_a$ or $R^5_b$ is a ring moiety of Formula (9.2). In Step 1 of Scheme 3, the aldehyde moiety of the compound of Formula X is converted to an appropriate leaving group, such as a halogen, mesylate or another leaving group familiar to those skilled in the art, followed by reacting the resulting compound with sodium cyanate in a polar solvent such as DMF to provide the compound of Formula XVI. In Step 2 of Scheme 3, the compound of Formula XVI is reacted under basic conditions with methyl acrylate or related derivatives depending on the $R^5_a$ or $R^5_b$ group to be added, in an aprotic solvent such as ethylene glycol dimethyl ether (DME) at high temperature, preferably at reflux, to provide the compound of Formula XVII. In Step 3 of Scheme 3, the compound of Formula XVII is converted to the compound of Formula XVIII using a strong base, such as sodium hydride, and a polar aprotic solvent, such as DMF or THF, at elevated temperature, preferably at reflux.

In Step 4 of Scheme 3, the compound of Formula XVIII is decarboxylated using conventional methods, such as using sodium chloride in DMSO at a temperature of about 140° C., to provide the compound of Formula XIX. In Step 5 of Scheme 3, derivatization of the compound of Formula XIX to the corresponding dithian-2-ylidine cyclohexane carbonitrile of Formula XX is done by reaction with 2-lithio-1,3-dithiane. In Step 5-a of Scheme 3, further derivatization of the compound of Formula XIX to the corresponding cyclohexane carbonitrile of Formula XXV which is para-substituted on the cyclohexane group with an hydroxyl moiety and an $R^4$ substituent, e.g., methyl, is carried out by reacting the ketone with a nucleophilic reagent, e.g., an alkyllithium compound or a Grignard reagent in accordance with procedures well known in the art. In Step 5-b of Scheme 3, further derivatization of the compound of Formula XIX to the corresponding cyclohexane carbonitrile of Formula XXVI which is para-substituted on the cyclohexane group with an hydroxyl moiety, is carried out by reducing the ketone with, e.g., lithium aluminum hydride or sodium borohydride in accordance with procedures well known in the art. In Step 6 of Scheme 3, the compound of Formula XX is converted to the corresponding ester of Formula XXI using mercury (II) chloride and perchloric acid in a polar protic solvent such as methanol. In Step 7 of Scheme 3, the compound of Formula XXI is converted through hydrolysis to the corresponding carboxylic acid of Formula XXII using a standard method of hydrolysis, such as using aqueous sodium hydroxide in a polar solvent, or any of numerous existing hydrolysis methods known to those skilled in art as described in T. Green and P. G. M. Wets, *Protecting Groups in Organic Synthesis*, 2nd Edition, John Wiley and Sons, New York (1991). The synthetic steps described for Scheme 3 are analogous to the synthetic methods provided for the preparation of corresponding catechol-containing compounds in PCT published applications WO 93/19751 and WO 93/17949.

Other indazole bioisostere replacement compounds of the present invention, especially those of Formula (9.0) or (9.1) wherein one of $R^5_a$ or $R^5_b$ is selected from moieties (9.2), (9.3), (9.4) and (9.5), can be prepared from one or more of the intermediate compounds described in Schemes 1–3. In particular, the aldehyde of Formula X or the keto compound of Formula XIX can be used to prepare various indazole bioisostere replacement compounds of the present invention, especially those of Formula (9.0) or (9.1). Any of the various $R^5_a$ or $R^5_b$ moieties of formulas (9.2), (9.3), (9.4) or (9.5) can be introduced into one or more of the intermediate compounds referred to above using synthetic methods provided for corresponding non-indazole analogs in PCT published applications WO 93/19748, WO 93/19749, WO 93/09751, WO 93/19720, WO 93/19750, WO 95/03794, WO 95/09623, WO 95/09624, WO 95/09627, WO 95/09836, and WO 95/09837. For example, with reference to Step 1 of Scheme 4, the carboxylic acid of Formula XXII can be converted to the alcohol of Formula XXIII by reduction with various metal hydrides in a polar solvent as described in Example 9, referred to below, and in accordance with synthetic methods provided for corresponding non-indazole analogs in PCT published applications publication numbers WO 93/19747, WO 93/19749 and WO 95/09836. Further, with reference to Step 2 of Scheme 4, the carboxylic acid of Formula XXII can be converted to the corresponding carboxamide of Formula XXIV through conversion to an intermediate acid chloride using conventional synthetic methods, and then reacting the acid chloride with ammonia in an aprotic solvent. Other carboxamide analogs of Formula XXIV can be prepared through reaction of the acid chloride intermediate with various primary or secondary amines according to conventional methods known to those skilled in the art and as described in the PCT published applications referred to above.

Other indazole bioisostere replacement compounds of the present invention, especially those of Formula (9.0) or (9.1) can be prepared from the intermediate compound of Formula XIX in accord with synthetic methods provided for corresponding non-indazole analogs in the PCT published applications referred to above. Compounds of Formula (9.0) or (9.1) wherein $R^5_a$ or $R^5_b$ is a moiety of partial Formula (9.2), and either $R^{114}$ ($R^4$) or R is H, can be prepared from the keto intermediate of Formula XIX by reaction with a base such as lithium diisopropylamine in a polar aprotic solvent, such as THF, and excess N-phenyltrifluoromethylsulfonamide as described in PCT published application WO 93/19749 for corresponding non-indazole analogs. Compounds of Formula (9.0) or (9.1) wherein $R^5_a$ or $R^5_b$ is a moiety of partial Formula (9.2), $R^{114}$ ($R^4$) is hydrogen, and $R^{115}$ ($R^5$) is —CO$_2$CH$_3$ or —CO$_2$H, can be prepared from the keto intermediate of Formula XIX through reaction with triflic anhydride in the presence of a tertiary amine base followed by reaction of the resulting triflate with (triphenylphosphine)palladium and carbon monoxide in the presence of an alcohol or amine to provide the methyl ester compounds of Formula (9.0) or (9.1) wherein $R^{115}$ ($R^5$) is —CO$_2$CH$_3$. The methyl ester compound can be hydrolyzed to obtain the corresponding carboxylic acid compound by employing standard methods for hydrolysis such as sodium or potassium hydroxide in aqueous methanol/tetrahydrofuran. Such synthetic methods are further described in PCT published application WO 93/19749 for corresponding non-indazole analogs.

Other indazole bioisostere replacement compounds of the present invention, especially those of Formula (9.0) or (9.1) can be prepared from the intermediate compound of Formula XIX in accord with synthetic methods described for corresponding non-indazole analogs in the published PCT applications referred to above. Compounds of Formula (9.0) or (9.1) wherein $R^5_a$ or $R^5_b$ is a moiety of partial Formula (9.2), $R^{115}$($R^5$) is hydrogen, and $R^{114}$($R^4$) is hydroxy, can be prepared through reaction of the intermediate of Formula XIX with an appropriate reducing agent such as lithium borohydride, diamyl borane, lithium aluminum tris(tert-butoxide), or sodium borohydride in a suitable non-reacting solvent such as 1,2-dimethoxy ethane, THF or alcohol. Compounds of Formula (9.0) or (9.1) wherein $R^5_a$ or $R^5_b$ is a moiety of Formula (9.2), $R^{115}$ ($R^5$) is hydrogen and $R^{114}$ ($R^4$) is —NH$_2$, —NHCH$_3$, or —N(CH$_3$)$_2$, can be prepared by reacting the intermediate of Formula XIX with an ammonium salt, such as ammonium formate, methylamine hydrochloride or dimethylamine hydrochloride, in the presence of sodium cyanoborohydride in an appropriate solvent such as alcohol.

Alternatively, compounds of Formula (9.0) or (9.1) wherein $R^5_a$ or $R^5_b$ is a moiety of Formula (9.2), $R^{114}$ ($R^4$) is amino, and $R^{115}$ ($R^5$) is hydrogen, can be prepared by reacting the corresponding alcohol of Formula (9.0) or (9.1) where $R^{114}$ ($R^4$)=OH and $R^{115}$ ($R^5$)=H, with a complex of an azadicarboxylate ester in the presence of an imide or phthalimide followed by reaction in an alcoholic solvent such as ethanol. Compounds of Formula (9.0) or (9.1) wherein $R^5_a$ or $R^5_b$ is a moiety of Formula (9.2), $R^{115}$ ($R^5$) is H, and $R^{114}$ ($R^4$) is —SR$^{124}$ can be prepared by reacting the corresponding compound wherein $R^{114}$ ($R^4$) is a leaving group such as mesylate, tosylate, bromine or chlorine, with a metal salt of mercaptan such as NaSR$^{124}$ in an appropriate aprotic solvent. Corresponding compounds of Formula (9.0) or (9.1) wherein $R^{114}$ ($R^4$) is —SH can be prepared by reacting the corresponding alcohol $R^{114}$ ($R^4$)=OH, with a complex of a phosphine, such as triphenyl phosphine, and an azidocarboxylate ester in the presence of thiolacetic acid followed by hydrolysis of the resulting thiolacetate. Furthermore, compounds of this structure wherein $R^{114}$ ($R^4$) is hydroxy can be interconverted using a standard alcohol inversion procedure known to those skilled in the art. The foregoing compounds of Formula (9.0) or (9.1) wherein $R^5_a$ or $R^5_b$ is a moiety of Formula (9.2), $R^{115}$ ($R^5$) is hydrogen, and $R^{114}$ ($R^4$) is hydroxy, —SH or —NH$_2$, can be converted to various other compounds of Formula (9.0) or (9.1) through one or more synthetic methods described in PCT published applications WO 93/19751 and WO 93/19749 for corresponding non-indazole analogs.

Compounds of Formula (9.0) or (9.1) wherein $R^5_a$ or $R^5_b$ is a moiety of Formula (9.2) and the dashed line represents a double bond attached to the ring carbon atom to which substituent $R^{113}$ ($R^3$) is attached, can be prepared from the intermediate of Formula XIX by following one or more synthetic methods provided for the preparation of corresponding non-indazole analogs in PCT published application WO 93/19720. Compounds of Formula (9.0) or (9.1) wherein $R^5_a$ or $R^5_b$ is a moiety of Formula (9.2), and $R^{114}$ ($R^4$) and $R^{115}$ ($R^5$) are taken together to form =O or =$R^{118}$, wherein $R^{118}$ is as defined above, can be prepared from the corresponding ketone intermediate of formula XIX following one or more synthetic methods provided for corresponding non-indazole analogs in PCT published application WO 93/19750. Other compounds of Formula (9.0) or (9.1) wherein $R^5_a$ or $R^5_b$ is a moiety of Formula (9.2) and $R^{114}$ ($R^4$) and $R^{115}$ ($R^5$) are taken together as =$R^{118}$ can be prepared from the intermediate of Formula XIX following one or more synthetic methods provided for the preparation of corresponding non-indazole analogs in PCT published application WO 93/19748.

Compounds of Formula (9.0) or (9.1) wherein $R^5_a$ or $R^5_b$ is a moiety of Formula (9.3) can be prepared from one or more of the intermediates referred to above, such as the bromoindazole intermediate of Formula XV, following one or more synthetic methods provided for the preparation of corresponding non-indazole analogs in PCT published applications WO 95/09627, WO 95/09624, WO 95/09623, WO 95/09836 and WO 95/03794. Compounds of Formula (9.0) or (9.1) wherein $R^5_a$ or $R^5_b$ is a moiety of Formula (9.4) can be prepared from the intermediate of Formula XV following one or more of synthetic methods provided for the preparation of corresponding non-indazole analogs in PCT published applications WO 95/09624 and WO 95/09837. Compounds of Formula (9.0) or (9.1) wherein $R^5_a$ or $R^5_b$ is a moiety of Formula (9.5) can be prepared from the bromoindazole intermediate of Formula XV employing one or more synthetic methods provided for the preparation of the corresponding catechol-containing analogs in PCT published applications WO 95/09627, WO 95/09623 and WO 95/09624.

Particularly preferred indazole bioisostere replacement compounds of the present invention are those represented by Formulas (9.51) and (9.52):

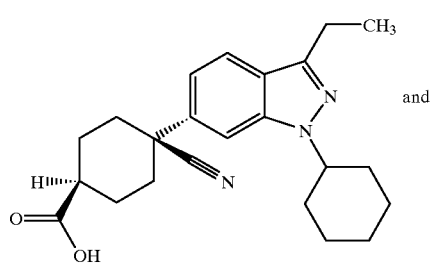
(9.51)

and

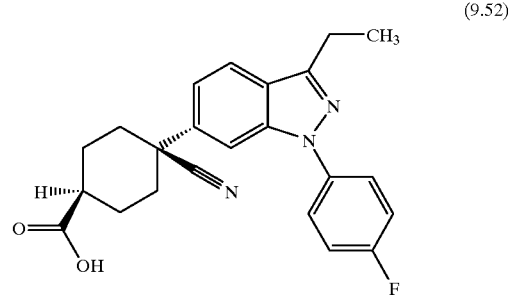
(9.52)

A method for the preparation of the compound of Formula (I-ii) is described in further below-recited Example 23. It is also possible to prepare said compound in accordance with the synthesis method described in above-depicted Scheme 2 and Scheme 3, using as the starting material for said method the compound prepared as described in below-recited Example 20, and represented by Formula (9.53):

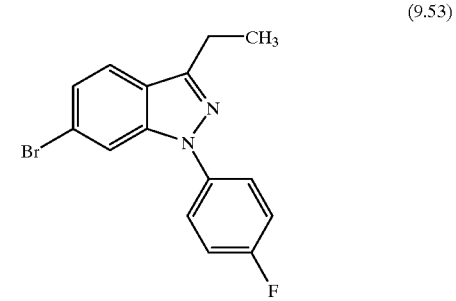
(9.53)

The preferred compound depicted in Formula (9.51) above may be prepared in accordance with the synthesis methods described in above-depicted Scheme 1, Scheme 2, and Scheme 3, and as further detailed in the below-recited Examples. Another, preferred, method of preparing said compound may also be employed, and is represented in the following synthesis Scheme 5, which is a more generalized representation of the above-mentioned preferred method of preparing said above-described preferred compound of the present invention.

SCHEME 5

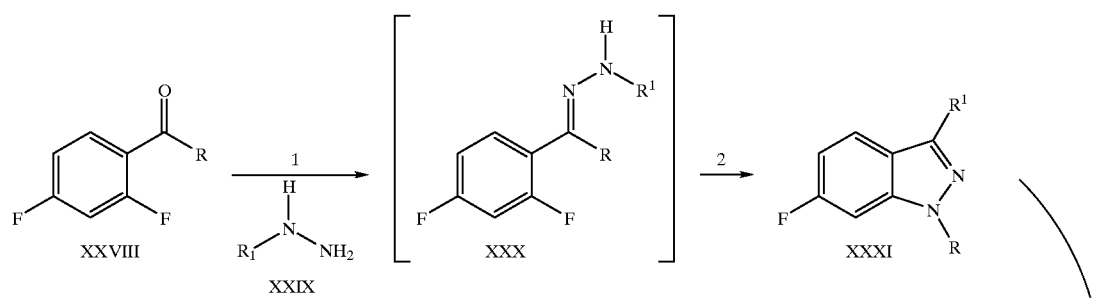

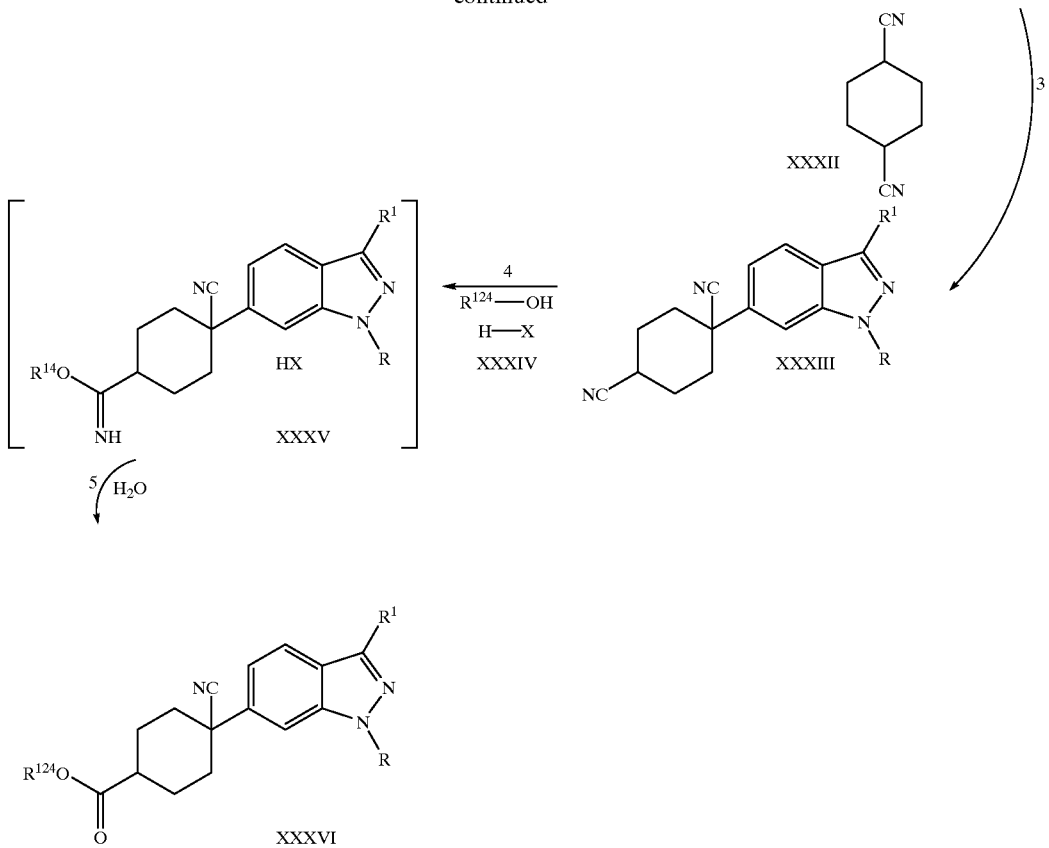

As illustrated, the starting material of Formula XXVIII is reacted with a hydrazine of Formula XXIX and the in sivu product of Formula XXX is heated without separation to yield an indazole of Formula XXXI, which is in turn reacted with dicyanocyclohexane of Formula XXXII to yield the cyano-analog of said above-described preferred compound of Formula XXXIII.

In Step 1 of Scheme 5, the compound of Formula XXVIII is treated with a hydrazine derivative of Formula XXIX and an acid, preferably ammonium acetate, in a solvent such as heptane, tetrahydrofuran, xylenes, toluene, or mesitylene, or a mixture of two or more of the foregoing solvents, preferably toluene, to provide the compound of Formula XXX. In general, the compound of Formula XXX need not be separated or isolated from the reaction mixture.

In Step 2 of Scheme 5, the reaction mixture containing the compound of Formula XXX is heated at a temperature between about 75° C. and about 200° C., preferably between about 90° and 120° C., for a period of about 2 hours to 48 hours, preferably 12 hours, to provide the compound of Formula XXXI.

Alternatively, the process of Step 1 of Scheme 5 may be accomplished using a salt of the hydrazine derivative, such as the hydrochloride, hydrobromide, mesylate, tosylate, or oxalate salt of said compound, preferably the mesylate salt, which is reacted with a base, such as sodium or potassium acetate, in a solvent such as heptane, tetrahydrofuran, xylenes, toluene, or mesitylene, or a mixture of two or more of the foregoing solvents, preferably toluene.

In Step 3 of Scheme 5, the compound of Formula XXXI is treated with the compound of Formula XXXII in the presence of a base such as lithium bis(trimethylsilyl)amide, sodium bis(trimethylsilyl)amide, potassium bis(trimethylsilyl)amide, lithium diisopropylamide, or lithium 2,2,6,6-tetramethylpiperidine, preferably potassium bis(trimethylsilyl)amide, in a solvent such as tetrahydrofuran, toluene, or xylenes, preferably toluene, at a temperature between about 25° C. and about 125° C., preferably about 100° C., for a period 1 hour to 15 hours, preferably 5 hours, to provide compound of Formula XXXIII.

In Step 4 of Scheme 5, the compound of Formula XXXIII is treated with an acid such as hydrochloric acid, hydrobromic acid, sulfuric acid, p-toluenesulfonic acid, methanesulfonic acid, or trifluoromthanesulfonic acid, preferably hydrochloric acid, in a solvent of the Formula XXXIV, i.e., $R^{124}$—OH wherein $R^{124}$ is as defined herein, e.g., ($C_1$–$C_6$) alkyl, such as methanol, ethanol, propanol, isopropanol, preferably ethanol, at a temperature between 0° C. and 50° C., preferably ambient temperature (20–25° C.) for a period of 1 hour to 48 hours, preferably 14 hours, to provide a compound of Formula XXXV. In general, the compound of Formula XXXV need not to be separated or isolated from the reaction mixture.

In step 5 of Scheme 5, the compound of Formula XXXV is treated with water in a solvent such as toluene, ethyl acetate, diIsopropyl ether, methyl tert-butyl ether, or dichloromethane, preferably toluene, at a temperature between about 0° C. and 50° C., preferably ambient temperature (20–25° C.) for a period of 1 hour to 24 hours, preferably 8 hours, to provide a compound of Formula XXXVI.

A particular version of the synthesis of Scheme 5 above carried out with reactants suitable for obtaining the preferred cyclohexanecarboxylic acid compound of the present invention, is illustrated below in Scheme 6:

SCHEME 6

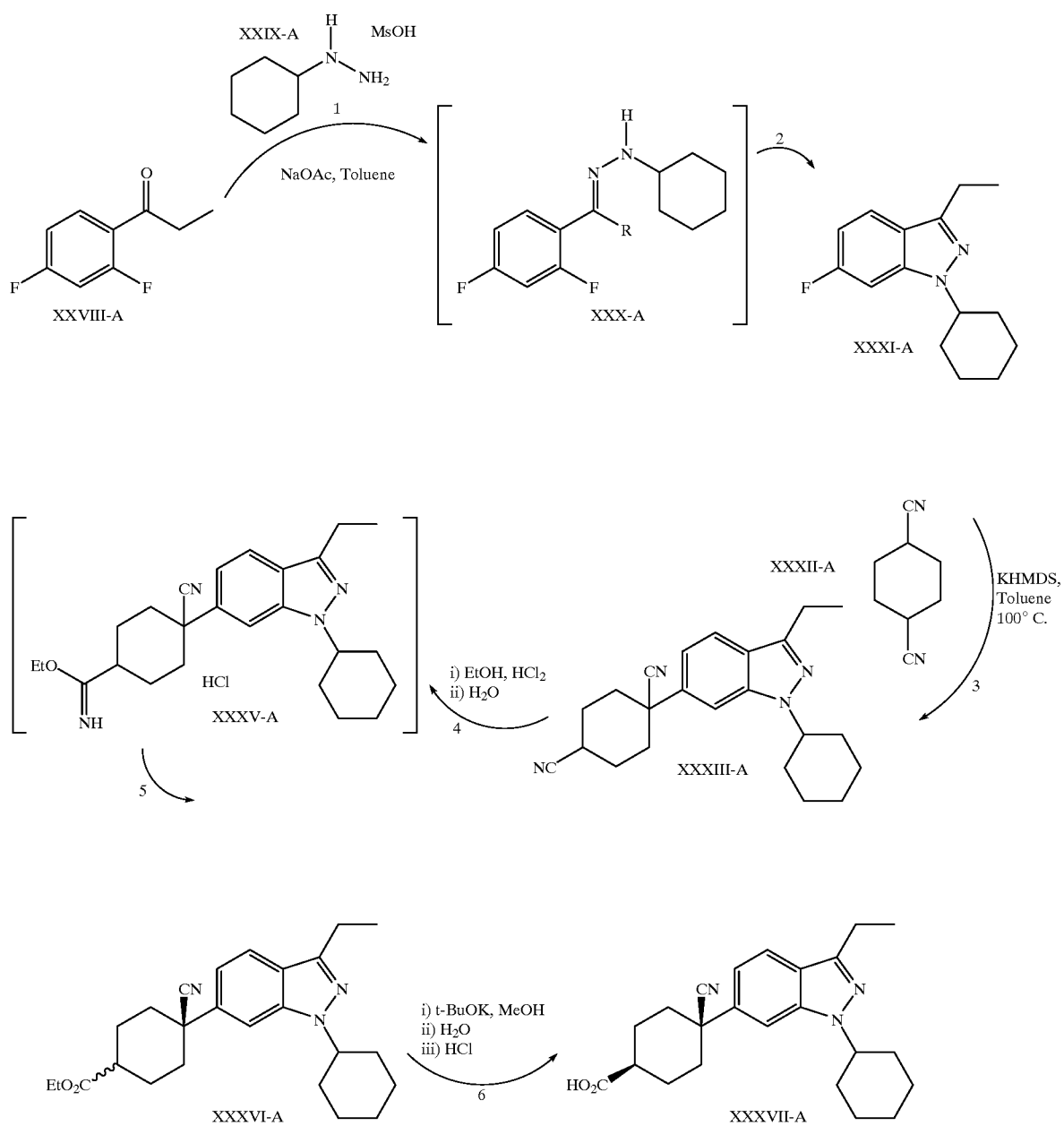

Scheme 7 set out below illustrates a procedure to facilitate the handling and purification of the indazole intermediate of Formula XXXI which is described above in reference to Scheme 5. In Step 1 of Scheme 7, the indazole of Formula XXXI is treated with an acid, such as hydrobromic, hydrochloric, or sulfuric acid, preferably hydrobromic acid, in a solvent such as toluene, xylenes, acetic acid, or ethyl acetate, preferably toluene, at a temperature ranging from 0° C. to ambient temperature (20–25° C.), preferably ambient temperature, to form a salt of the compound of Formula XXXVIII, wherein HX indicates the acid used to prepare the salt and X is the anion of said acid. The salt may be separated and purified according to methods familiar to those skilled in the art. In Step 2 of Scheme 7, the salt is converted back to the free base. In this step, the salt of the compound of Formula XXXVIII is treated with an aqueous base, such as sodium hydroxide, potassium hydroxide, sodium carbonate, sodium bicarbonate, potassium carbonate, or potassium bicarbonate, preferably sodium hydroxide, in a solvent such as hexane, toluene, dichloromethane, diisopropyl ether, methyl tert-butyl ether, or ethyl acetate, preferably toluene, at a temperature ranging from 0° C. to ambient temperature (20–25° C.), preferably ambient temperature, for a period of 5 minutes to 1 hour, preferably 20 minutes, to provide the compound of Formula XXXI.

SCHEME 7

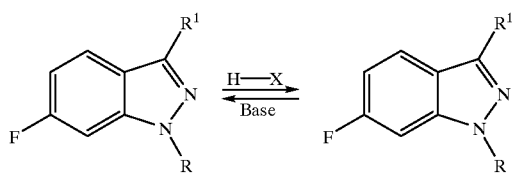

The compounds of the Formulas XXVIII–XXXVIII may have asymmetric carbon atoms and therefore exist in different enantiomeric forms. Diastereomeric mixtures can be separated into their individual diastereomers on the basis of their physical chemical differences by methods known to those skilled in the art, for example, by chromatography or fractional crystallization. Enantiomers may be separated by converting the enantiomeric mixtures into a diastereomeric mixture by reaction with an appropriate optically active compound, e.g., alcohol, separating the diastereomers and converting, e.g., hydrolyzing, the individual diastereomers to the corresponding pure enantiomers. The use of all such isomers, including diastereomer mixtures and pure enantiomers, are considered to be part of the present invention.

Further details concerning the above-identified synthesis methods which are preferred for preparing the above-recited preferred compound of the present invention may be found in copending provisional U.S. Ser. No. 60/064,211, filed Nov. 4, 1997, which is incorporated herein by reference in its entirety.

Reaction Schemes 8 and 9 illustrate the preparation of the compounds of the present invention of type (II), i.e., $\alpha_1$-adrenergic receptor antagonist compounds of type (II):

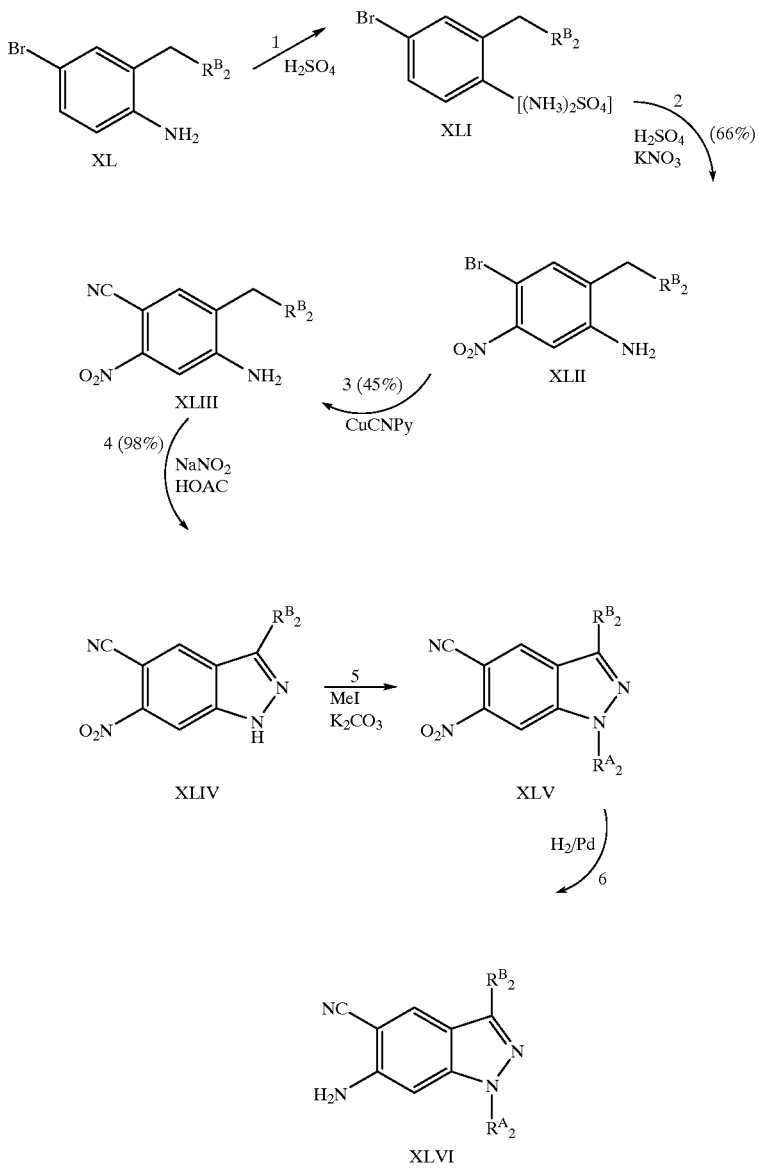

SCHEME 9

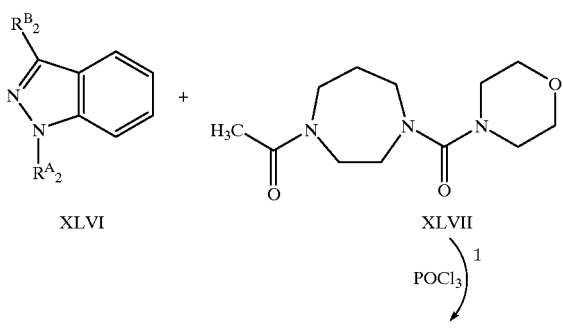

XLVI + XLVII $\downarrow$ POCl$_3$ 1

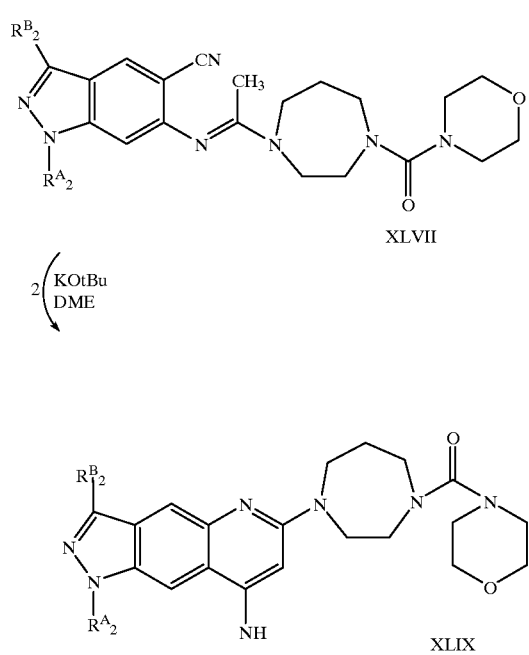

XLVII 2 ( KOtBu / DME )

XLIX

The synthesis depicted in Scheme 8 may be carried out using conventional chemistry such as that described in *J. Org. Chem.*, 44, 4609 (1979). This preparation leads to formation of the key indazole intermediate of Formula XLVI. The key intermediate of Formula XLVI is then reacted with a suitable reactant in order to produce the desired final product. The schematic representation of Scheme 9 shows preparation of a compound of type (II) of the present invention, especially one of the type of Formula (II-B) where $R^2_a$ and $R^2_b$ are taken together to form the moiety of partial Formula (6.26):

(6.26)

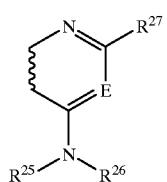

where E is either N, resulting in a pyrimidinyl moiety and overall a quinazoline series of compounds; or is CH, resulting in a pyridyl moiety and overall a quinoline series of compounds.

More especially Scheme 9 demonstrates preparation of a compound of the type of Formula (II-B) where $R^{25}$ and $R^{26}$ are both hydrogen and $R^{27}$ is a moiety of type (g) illustrated by partial Formula (6.32.3), (6.32.3)

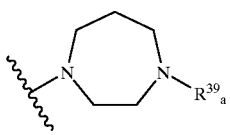

where $R^{39}_a$ is —C(=O)—$R^{40}$ where $R^{40}$ is 4-morpholino. Preparation of the final product of Formula XLIX in Scheme 9 entails use of the reactant of Formula XLVII. The reactant of Formula XLVII is prepared, in turn, using conventional chemistry, such as that referred to in WO 97/23462, which is incorporated herein by reference in its entirety.

Reaction Schemes 10 through 12 illustrate the preparation of the compounds of the present invention type (III), i.e., calcium channel antagonist compounds of Formula (III), especially those that are bioisoteres of verapamil. The known compound verapamil, which may be represented by Formula (7.0):

(7.0)

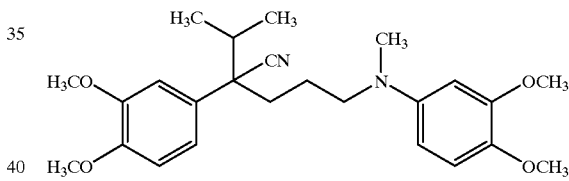

The chemical structure of a total of six (6) verapamil bioisoteres is described further above, and the synthesis of three of these is described in the paragraphs which follow. The six (6) indazole-for-catechol bioisostere replacement embodiments of verapamil described above are based only or first vs. second indazole isomers and single vs. double replacement. A third possibility resulting in isomers occurs where there is both a double replacement and first and second indazole isomers, i.e., the first indazole isomer is on one end of the molecule and the second indazole isomer is at the opposite end of the same molecule. Where the molecule is asymmetrical as in the case of verapamil, two (2) additional bioisotere isomers result, giving an overall total of eight (8) verapamil bioisostere isomers.

The three verapamil bioisostere isomers whose preparation is illustrated herein are species based on the genus of Formula (7.2) and the genus of Formula (7.4), identified as Formula (7.2.1) and Formula (7.4.1), respectively, as well as the species of Formula (7.1.1) representing one of the above-mentioned additional isomers comprising a double replacement involving both first and second indazole isomers, and falling within the scope of the genus of Formula (7.1).

(7.1.1)
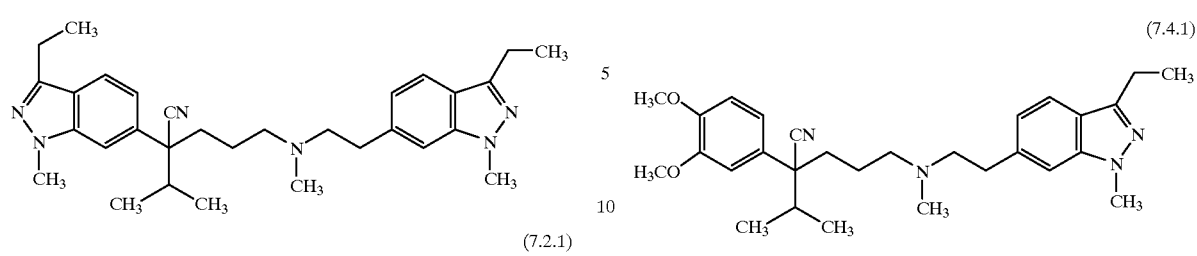
(7.2.1)
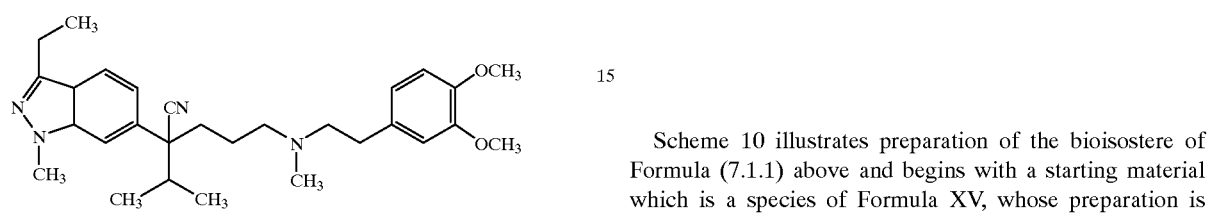
-continued
(7.4.1)
Scheme 10 illustrates preparation of the bioisostere of Formula (7.1.1) above and begins with a starting material which is a species of Formula XV, whose preparation is illustrated in Scheme 2 above and is number L in Scheme 10.
Scheme 10
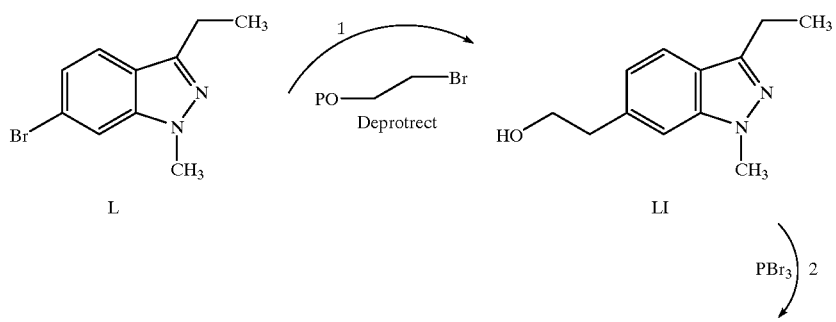
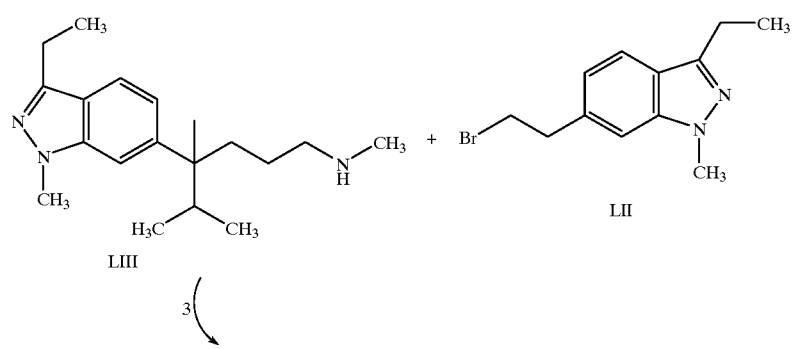
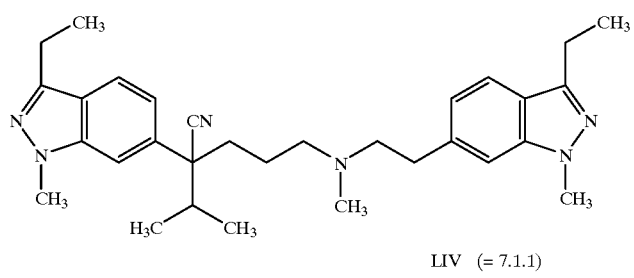

Scheme 11 set out below illustrates preparation of the bioisostere of Formula (7.2.1) above, wherein the starting material is readily available commercially or may be prepared by methods conventional in the art.
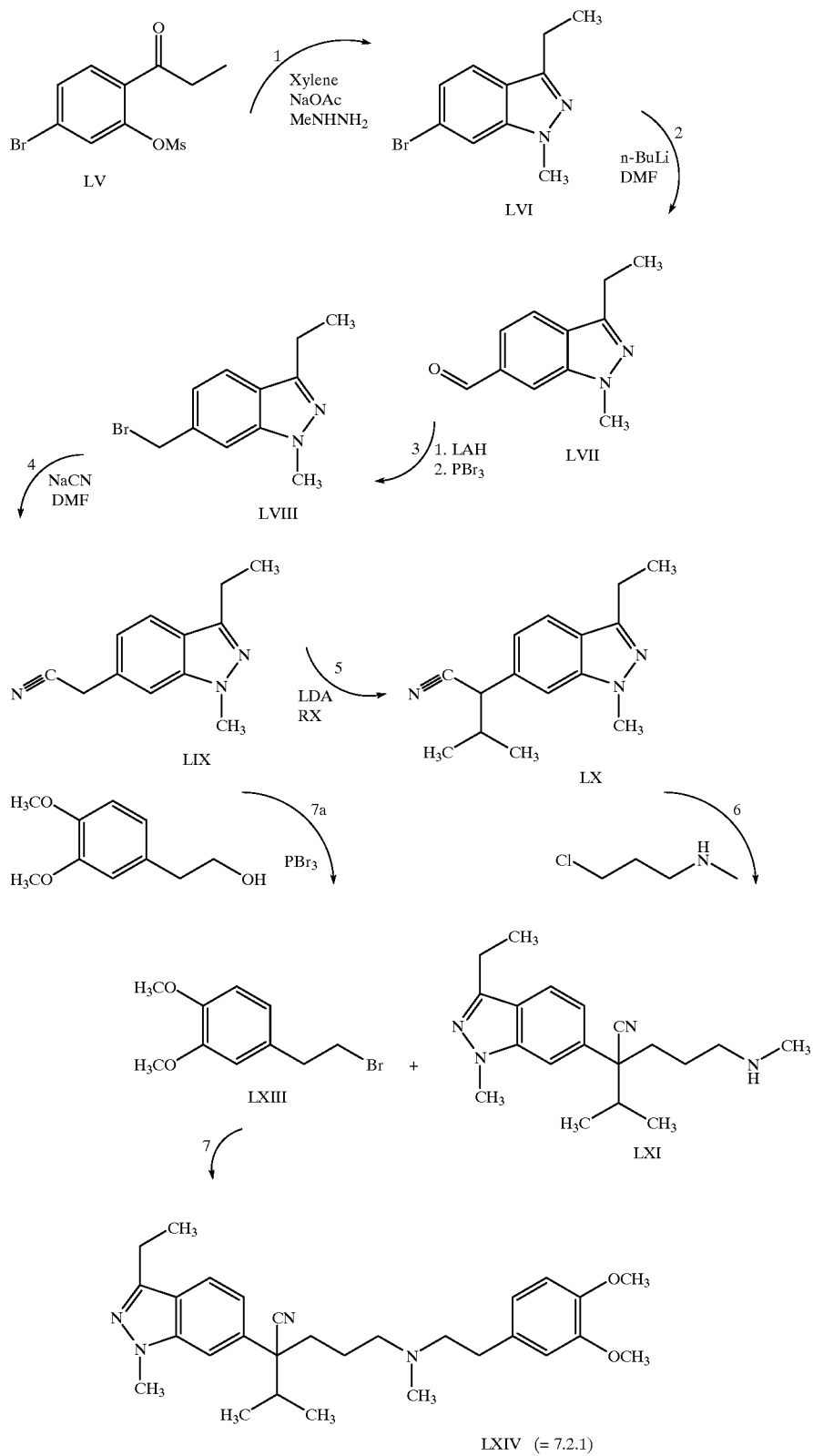
SCHEME 11

Scheme 12 illustrates preparation of the bioisostere of Formula (7.4.1) above and begins with a starting material which is a species of Formula LXX and is readily available commercially or may be prepared by methods well known in the art, Base salts of the indazole bioisostere replacement compounds of the present invention include, but are not limited to ammonium salts; alkali metal salts such as sodium and potassium; alkaline earth metal salts such as calcium and magnesium; salts with organic bases such as

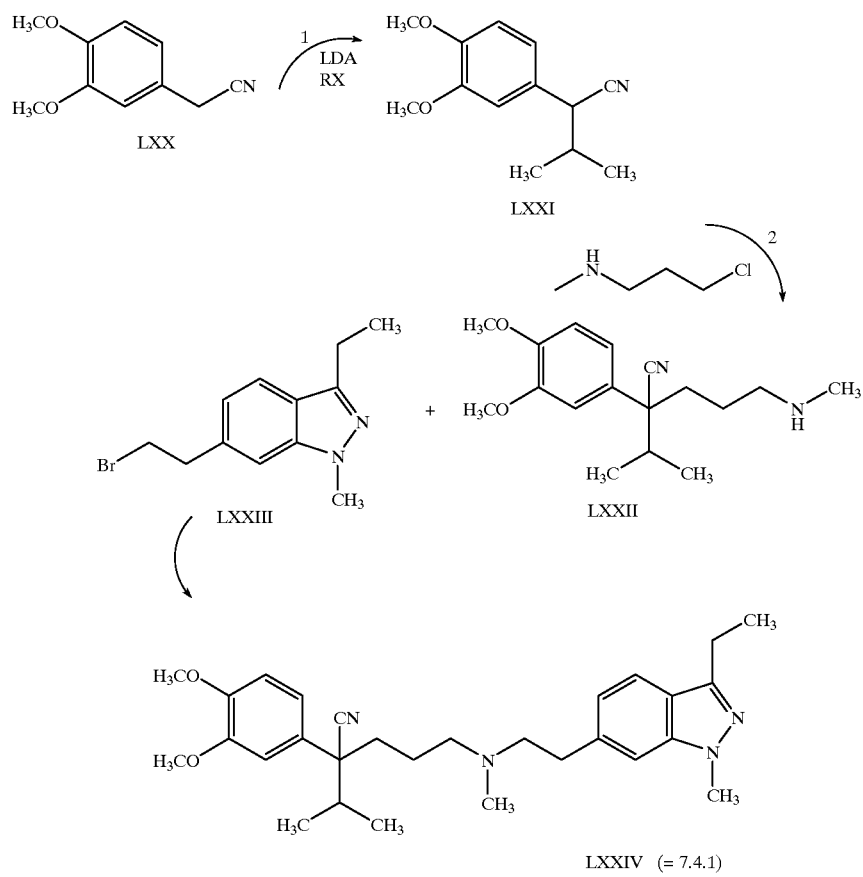

LXXIV (= 7.4.1)

The above-described indazole bioisostere replacement compounds of the present invention may be utilized in the form of acids, esters, or other chemical classes of compounds to which the compounds described belong. It is also within the scope of the present invention to utilize those compounds in the form of pharmaceutically acceptable salts derived from various organic and inorganic acids and bases in accordance with procedures well known in the art. Such well-known pharmaceutically acceptable salts include, but are not limited to acetate, adipate, alginate, aspartate, benzoate, benzenesulfonate, besylate, bisulfate, butyrate, citrate, camphorate, camphorsulfonate, cyclopentanepropionate, digluconate, dodecysulfate, ethanesulfonate, fumarate, glucoheptanoate, gluconate, glycerophosphate, hemisuccinate, hemisulfate, heptanoate, hexanoate, hippurate, hydrochloride, hydrobromide, hydroiodide, 2-hydroxyethanesulfonate, isethionate, lactate, lactobionate, maleate, mandelate, methanesulfonate, 2-naphthalenesulfonate, nicotinate, nitrate, oxalate, oleate, pamoate, pectinate, persulfate, 3-phenylpropionate, phosphonate, picrate, pivalate, propionate, salicylate, sodium phosphate, stearate, succinate, sulfate, sulfosalicylate, tartrate, thiocyanate, thiomalate, tosylate, and undecanoate.

dicyclohexylamine, meglumine, N-methyl-D-glucamine, tris-(hydroxymethyl)-methylamine (tromethamine), and salts with amino acids such as arginine, lysine, etc. Compounds of the present invention which comprise basic nitrogen-containing groups may be quatenized with such agents as ($C_1$–$C_4$) alkyl halides, e.g., methyl, ethyl, isopropyl and tert-butyl chlorides, bromides and iodides; di($C_1$–$C_4$) alkyl sulfate, e.g., dimethyl, diethyl and diamyl sulfates; ($C_{10}$–$C_{18}$) alkyl halides, e.g., decyl, dodecyl, lauryl, myristyl and and stearyl chlorides, bromides and iodides; and aryl-($C_1$–$C_4$) alkyl halides, e.g., benzyl chloride and phenethyl bromide. Such salts permit the preparation of both water-soluble and oil-soluble compounds of the present invention.

Among the above-recited pharmaceutical salts those which are preferred include, but are not limited to acetate, besylate, citrate, fumarate, gluconate, hemisuccinate, hippurate, hydrochloride, hydrobromide, isethionate, mandelate, meglumine, nitrate, oleate, phosphonate, pivalate, sodium phosphate, stearate, sulfate, sulfosalicylate, tartrate, thiomalate, tosylate, and tromethamine.

Multiple salts forms are included within the scope of the present invention where a compound of the present invention contains more than one group capable of forming such pharmaceutically acceptable salts. Examples of typical multiple salt forms include, but are not limited to bitartrate, diacetate, difumarate, dimeglumine, diphosphate, disodium, and trihydrochloride.

The pharmaceutical compositions of the present invention comprise any one or more of the above-described indazole bioisostere replacement compounds of the present invention, or a pharmaceutically acceptable salt thereof as also above-described, together with a pharmaceutically acceptable carrier in accordance with the properties and expected performance of such carriers which are well-known in the pertinent art.

The term "carrier" as used herein includes acceptable diluents, excipient, adjuvants and vehicles. Pharmaceutically acceptable carriers that may be used in the pharmaceutical compositions of this invention include but are not limited to, ion exchange compositions; alumina; aluminum stearate; lecithin; serum proteins, e.g., human serum albumin; phosphates; glycine; sorbic acid; potassium sorbate; partial glyceride mixtures of saturated vegetable fatty acids; water, salts or electrolytes, e.g., prolamine sulfate, disodium hydrogen phosphate, potassium hydrogen phosphate, sodium chloride, and zinc salts; colloidal silica, magnesium trisilicate; polyvinyl pyrrolidone; cellulose-based substances; e.g., sodium carboxymethylcellulose; polyethylene glycol; polyacrylates; waxes; polyethylene-polyoxypropylene-block polymers; and wool fat.

More particularly, the diluents, excipient, adjuvants and vehicles used in the pharmaceutical compositions of the present invention comprise members selected from the groups consisting essentially of the following: acidifying and allalizing agents added to obtain a desired or predetermined pH comprise acidifying agents, e.g., acetic acid, glacial acetic acid, malic acid, and propionic acid, and alkalizing agents, e.g., edetol, potassium carbonate, potassium hydroxide, sodium borate, sodium carbonate, and sodium hydroxide; aerosol propellants required where the pharmaceutical composition is to be delivered as an aerosol under significant pressure, e.g., acceptable halogenated hydrocarbons; nitrogen; or a volatile hydrocarbon such as butane, propane, isobutane or mixtures thereof; antimicrobial agents including antibacterial, antifungal and antiprotozoal agents added where the pharmaceutical composition is topically applied, e.g., antimicrobial agents such as benzyl alcohol, chlorobutanol, phenylethyl alcohol, phenylmercuric acetate, potassium sorbate, and sorbic acid, and antifungal agents such as benzoic acid, butylparaben, ethylparaben, methylparaben, propylparaben, and sodium benzoate; antimicrobial preservatives added to the pharmaceutical compositions in order to protect them against the growth of potentially harmful microorganisms, e.g., alkyl esters of p-hydroxybenzoic acid, propionate salts, phenoxyethanol, methylparaben sodium, propylparaben sodium, sodium dehydroacetate, benzalkonium chloride, benzethonium chloride, and benzyl alcohol; antioxidants added to protect all of the ingredients of the pharmaceutical composition from damage or degradation by oxidizing agents present in the composition itself or the use environment, e.g., anoxomer, ascorbyl palmitate, butylated hydroxyanisole, butylated hydroxytoluene, hypophosphorous acid, potassium metabisulfite, propyl octyl and dodecyl gallate, sodium metabisulfite, sulfur dioxide, and tocopherols; buffering agents used to maintain a desired pH of a composition once established, e.g., calcium acetate, potassium metaphosphate, potassium phosphate monobasic, and tartaric acid; and chelating agents used to help maintain the ionic strength of the pharmaceutical composition and bind to and effectively remove destructive compounds and metals, e.g., edetate dipotassium, edetate disodium, and edetic acid.

Dermatologically active agents are added to the pharmaceutical compositions of the present invention to be applied topically, e.g., wound healing agents such as peptide derivatives, yeast, panthenol, hexylresorcinol, phenol, tetracycline hydrochloride, lamin and kinetin, glucocorticosteroids for treating inflammation, e.g., hydrocortisone, dexamethasone, betamethasone, triamcinolone, fluocinolone and methylprednisolone, retinoids for treating acne, psoriasis, cutaneous aging, and skin cancer, e.g., retinol, tretinoin, isotretinoin, etretinate, acitretin, and arotinoid, immunosuppressive agents for treating inflammation, e.g., dapsone and sulfasalazine; mild antibacterial agents, e.g., resorcinol, salicylic acid, benzoyl peroxide, erythromycin-benzoyl peroxide, erythromycin, clindamycin, and mupirocin, antifungal agents, e.g., griseofulvin, azoles such as miconazole, econazole, itraconazole, fluconazole, and ketoconazole, and allylamines such as naftifine and terfinafine, antiviral agents, e.g., acyclovir, famciclovir, and valacyclovir, antihistamines, e.g., diphenhydramine, terfenadine, astemizole, loratadine, cetirizine, acrivastine, and temelastine, topical anesthetics, e.g., benzocaine, lidocaine, dibucaine, and pramoxine hydrochloride, topical analgesics, e.g., methyl salicylate, camphor, menthol, and resorcinol; topical antiseptics for preventing infection, e.g., benzalkonium chloride and povidone-iodine; vitamins and derivatives thereof such as tocopherol, tocopherol acetate, retinoic acid and retinol.

Further examples of diluents, excipient, adjuvants and vehicles used in the pharmaceutical compositions of the present invention comprise members selected from the groups consisting essentially of the following: dispersing and suspending agents, e.g., poligeenan, povidone, and silicon dioxide; emollients, e.g., hydrocarbon oils and waxes, triglyceride esters, acetylated monoglycerides, methyl and other alkyl esters of $C_{10}$–$C_{20}$ fatty acids, $C_{10}$–$C_{20}$ fatty acids, $C_{10}$–$C_{20}$ fatty alcohols, lanolin and derivatives, polyhydric alcohol esters such as polyethylene glycol (200–600), polyoxyethylene sorbitan fatty acid esters, wax esters, phospholipids, and sterols; emulsifying agents used for preparing oil-in-water emulsions; excipients, e.g., laurocapram and polyethylene glycol monomethyl ether; humectants, e.g., sorbitol, glycerin and hyaluronic acid; ointment bases, e.g., petrolatum, polyethylene glycol, lanolin, and poloxamer; penetration enhancers, e.g., dimethyl isosorbide, diethyl-glycol-monoethylether, 1-dodecylazacycloheptan-2-one, and dimethylsulfoxide (DMSO); preservatives, e.g., benzalkonium chloride, benzethonium chloride, alkyl esters of p-hydroxybenzoic acid, hydantoin derivatives, cetylpyridinium chloride, propylparaben, quaternary ammonium compounds such as potassium benzoate, and thimerosal; sequestering agents comprising cyclodextrins; solvents, e.g., acetone, alcohol, amylene hydrate, butyl alcohol, corn oil, cottonseed oil, ethyl acetate, glycerin, hexylene glycol, isopropyl alcohol, isostearyl alcohol, methyl alcohol, methylene chloride, mineral oil, peanut oil, phosphoric acid, polyethylene glycol, polyoxypropylene 15 stearyl ether, propylene glycol, propylene glycol diacetate, sesame oil, and purified water; stabilizers, e.g., calcium saccharate and thymol; surfactants, e.g., lapyrium chloride; laureth 4, i.e., α-dodecyl-ω-hydroxy-poly(oxy-1,2-ethanediyl) or polyethylene glycol monododecyl ether.

According to this invention, the pharmaceutical compositions may be in the form of a sterile injectable preparation, for example a sterile injectable aqueous or oleaginous suspension. This suspension may be formulated according to techniques known in the art using suitable dispersing or wetting agents and suspending agents. The sterile injectable preparation may also be a sterile injectable solution or suspension in a non-toxic parenterally-acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium. For this purpose, any bland fixed oil may be employed including synthetic mono- or di-glycerides. Fatty acids, such as oleic acid and its glyceride derivatives are useful in the preparation of injectables, as do natural pharmaceutically-acceptable oils, such as olive oil or castor oil, especially in their polyoxyethylated versions. These oil solutions or suspensions may also contain a long-chain alcohol diluent or dispersant, such as Rh, HCIX or similar alcohol.

The pharmaceutical compositions of this invention may be orally administered in any orally acceptable dosage form including, but not limited to, capsules, tablets, aqueous suspensions or solutions. In the case of tablets for oral use, carriers which are commonly used include lactose and corn starch. Lubricating agents, such as magnesium stearate, are also typically added. For oral administration in a capsule form, useful diluents include lactose and dried corn starch. When aqueous suspensions are required for oral use, the active ingredient is combined with emulsifying and suspending agents. If desired, certain sweetening, flavoring or coloring agents may also be added. Alternatively, the pharmaceutical compositions of this invention may be administered in the form of suppositories for rectal administration. These can be prepared by mixing the agent with a suitable non-irritating excipient which is solid at room temperature but liquid at the rectal temperature and therefore will melt in the rectum to release the drug. Such materials include cocoa butter, beeswax and polyethylene glycols.

The pharmaceutical compositions of this invention may also be administered topically, especially when the target of treatment includes areas or organs readily accessible by topical application, including diseases of the eye, the skin, or the lower intestinal tract. Suitable topical formulations are readily prepared for each of these areas or organs.

Topical application for the lower intestinal tract can be effected in a rectal suppository formulation, as described above, or in a suitable enema formulation. Topically active transdermal patches may also be used.

For topical applications, the pharmaceutical compositions may be formulated in a suitable ointment containing the active component suspended or dissolved in one or more carriers. Carriers for topical administration of the compounds of this invention include, but are not limited to, mineral oil, liquid petrolatum, white petrolatum, propylene glycol, polyoxyethylene, polyoxypropylene compound, emulsifying wax and water. Alternatively, the pharmaceutical compositions can be formulated in a suitable lotion or cream containing the active components suspended or dissolved in one or more pharmaceutically acceptable carriers. Suitable carriers include, but are not limited to, mineral oil, sorbitan monostearate, polysorbate, cetyl esters wax, cetearyl alcohol, 2-octyldodecanol, benzyl alcohol and water.

For ophthalmic use, the pharmaceutical compositions may be formulated as micronized suspension in isotonic, pH adjusted sterile saline, or, preferably, as solutions in isotonic, pH adjusted sterile saline, either with our without a preservative such as benzylalkonium chloride. Alternatively, for ophthalmic uses, the pharmaceutical compositions may be formulated in an ointment such as petrolatum.

The pharmaceutical compositions of this invention may also be administered by nasal aerosol or inhalation through the use of a nebulizer, a dry powder inhaler or a metered dose inhaler. Such compositions are prepared according to techniques well-known in the art of pharmaceutical formulation and may be prepared as solutions in saline, employing benzyl alcohol or other suitable preservatives, absorption promoters to enhance bioavailability, hydrofluorocarbons, and/or other conventional solubilizing or dispersing agents.

The amount of active ingredient that may be combined with the carrier materials to produce a single dosage form will vary depending upon the host treated, and the particular mode of administration. It should be understood, however, that a specific dosage and treatment regimen for any particular patient will depend upon a variety of factors, including the activity of the specific compound employed, the age, body weight, general health, sex, diet, time of administration, rate of excretion, drug combination, and the judgment of the treating physician and the severity of the particular disease being treated. The amount of active ingredient may also depend upon the therapeutic or prophylactic agent, if any, with which the ingredient is co-administered.

The dosage and dose rate of the indazole bioisostere replacement compounds of this invention effective for preventing, inhibiting, suppressing or reducing the proximal and consequent or associated pathogenic processes subsequently mediated by the various endogenous ligands, receptors, enzymes, substrates, and regulatory and signal transduction entities herein described, will depend on a variety of factors, such as the nature of the ligand, etc., the size of the patient, the goal of the treatment, the nature of the pathology to be treated, the specific pharmaceutical composition used, and the observations and conclusions of the treating physician.

For example, where the dosage form is oral, e.g., a tablet or capsule, suitable dosage levels of the indazole bioisostere replacement compounds of the present invention will be between about 1.0 $\mu$g and about 10.0 mg/kg body weight per day, preferably between about 5.0 $\mu$g and about 5.0 mg/kg body weight per day, more preferably between about 10.0 $\mu$g and about 1.0 mg/kg of body weight per day, and most preferably between about 20.0 $\mu$g and about 0.5 mg/kg of body weight per day of the active ingredient.

Where the dosage form is topically administered to the bronchia and lungs, e.g., by means of a powder inhaler or nebulizer, suitable dosage levels of the indazole bioisostere replacement compounds of the present invention will be between about 0.1 $\mu$g and about 1.0 mg/kg body weight per day, preferably between about 0.5 $\mu$g and about 0.5 mg/kg body weight per day, more preferably between about 1.0 $\mu$g and about 0.1 mg/kg of body weight per day, and most preferably between about 2.0 $\mu$g and about 0.05 mg/kg of body weight per day of the active ingredient.

Using representative body weights of 10 kg and 100 kg in order to illustrate the range of daily topical dosages which might be used as described above, suitable dosage levels of the indazole bioisostere replacement compounds of the present invention will be between about 1.0–10.0 $\mu$g and 10.0–100.0 mg per day, preferably between about 5.0–50.0 $\mu$g and 5.0–50.0 mg per day, more preferably between about 10.0–100.0 $\mu$g and 1.0–10.0 mg per day, and most perferably between about 20.0–200.0 $\mu$g and about 0.5–5.0 mg per day of the active ingredient comprising an indazole bioisostere replacement compound of the present invention. These ranges of dosage amounts represent total dosage amounts of the active ingredient per day for a given patient. The number of times per day that a dose is administered will depend upon such pharmacological and pharmacokinetic factors as the half-life of the active ingredient, which reflects its rate of catabolism and clearance, as well as the minimal and optimal blood plasma or other body fluid levels of said active ingredient attained in the patient which are required for therapeutic efficacy Numerous other factors must also be considered in deciding upon the number of doses per day and the amount of active ingredient per dose which will be administered. Not the least important of such other factors is the individual respsonse of the patient being treated. Thus, for example, where the active ingredient is used to treat or prevent asthma, and is administered topically via aerosol inhalation into the lungs, from one to four doses consisting of acuations of a dispensing device, i.e., "puffs" of an inhaler, will be administered each day, each dose containing from about 50.0 $\mu$g to about 10.0 mg of active ingredient.

For human use, the active indazole bioisostere replacement compounds of the present invention can be administered alone, but will generally be administered in an admixture with a pharmaceutical diluent or carrier selected with regard to the intended route of administration and standard pharmaceutical practice. Such carriers have already been described in detail. In preferred embodiments, the indazole bioisostere replacement compounds of the present invention may be administered orally in the form of tablets containing such excipients as starch or lactose, or in capsules either alone or in admixture with excipients, or in the form of elixirs or suspensions containing flavoring or coloring agents. They may be injected parenterally; for example, intravenously, intramuscularly or subcutaneously. For parenteral administration, they are best used in the form of a sterile aqueous solution which may contain other substance; for example, enough salts or glucose to make the solution isotonic. Additionally, the active compounds may be administered topically when treating inflammatory conditions of the skin and this may be done by way of creams, jellies, gels, pastes, and ointments, in accordance with standard pharmaceutical practice.

The active indazole bioisostere replacement compounds of the present invention may also be administered to a mammal other than a human. The dosage to be administered to a mammal will depend on the animal species and the disease or disorder being treated. The active compounds may be administered to animals in the form of a capsule, bolus, tablet or liquid drench. The active compounds may also be administered to animals by injection or as an implant. Such formulations are prepared in a conventional manner in accordance with standard veterinary practice. As an alternative the indazole bioisostere replacement compounds of the present invention may be administered with the animal feedstuff and for this purpose a concentrated feed additive or premix may be prepared for mixing with the normal animal feed.

Included within the scope of the present invention are embodiments comprising compositions which contain, in addition to an indazole bioisostere replacement compound of the present invention as active ingredient, additional therapeutic agent active ingredients selected from the group consisting essentially of anti-inflammatory corticosteroids; bronchodilators; antiaasthmatics; non-steroidal anti-inflammatories; immunosuppressants; immunostimulants; antimetabolites; antipsoriatics and antidiabetics. Specific compounds within each of these classes may be selected from those listed under the appropriate headings in *Comprehensive Medicinal Chemistry*, Pergamon Press, Oxford, England, pp. 970–986 (1990); and Goodman and Gilman's *The Pharmacological Basis of Therapeutics*, 9th ed., Hardman, J. G. and Limbird, L. E., eds., McGraw-Hill, 1996, the disclosure of which are incorporated herein by reference in their entireties. Especially preferred active ingredients to be included for use in combination with the compounds of Formula (I) are anti-inflammatory compounds such as theophylline, sulfasalazine and aminosalicylates; immunosuppressants such as cyclosporin, FK-506, and rapamycin; antimetabolites such as cyclophosphamide and methotrexate; and immunomodulators such as the interferons.

The following Examples further illustrate the invention, but they are not intended to be, nor should they be taken as in any way a limitation of the present invention. In the following examples, "DMF" means dimethylformamide, "THF" means tetrahydrofuran, "DMSO" means dimethyl sulfoxide, and "DMAP" means 4-dimethylaminopyridine.

The following examples illustrate preparation of compounds of the present invention of type (II), i.e., bioisostere replacement compounds which are active as adrenergic $\alpha_1$-antagonists, especially those of Formula (6.39.1) and (6.39.2).

EXAMPLE 1

A. 5-Benzyloxy-4-methoxy-2-{1-[4-(morpholinecarbonyl)-1,4-diazepan-1-yl]ethylideneamino}benzonitrile Phosphorous oxychloride (0.81 ml, 0.0086 mol) was added to a solution of 1-acetyl-4-(4-morpholinecarbonyl)-1,4-diazepane (4.02 g, 0.0157 mol) in dichloromethane (25 ml) and the mixture stirred for 30 minutes at room temperature. A solution of 2-amino-5-benzyloxy-4-methoxybenzonitrile (2 g, 0.0078 mol) in dichloromethane (25 ml) was then added and the reaction stirred for 18 hours at 40° C. On cooling, the reaction mixture was poured carefully in to ice/water (100 ml) and extracted with dichloromethane (2×100 ml). The combined organic layers were dried (MgSO$_4$), filtered and evaporated under reduced pressure to give a brown oil. The crude product was purified on silica gel eluting with a solvent gradient of methanol:dichloromethane (2:98 to 10:90 v/v) to give the subtitle compound. $R_f$ 0.67 (0.880 aqueous ammonia:methanol:dichloromethane 1:7:92, v/v). MS m/z 492 (MH)$^+$.

B. 4-Amino-6-benzyloxy-7-methoxy-2-[4-(4-morpholinecarbonyl)-1,4-diazepan-1-yl]quinoline hydrochloride Potassium tert-butoxide (680 mg, 0.0061 mol) was added to a solution of 5-benzyloxy-4-methoxy-2-{1-[4-(morpholinecarbonyl)-1,4-diazepan-1-yl]ethylideneamino}benzonitrile (1.5 g, 0.003 mol) in 1,2-dimethoxyethane (40 ml) and the reaction stirred at 80° C. for 2 hours. On cooling, glacial acetic acid (0.52 ml, 0.0091 mol) was added and the mixture concentrated under reduced pressure. The residue was partitioned between ethyl acetate (50 ml) and 2N aqueous sodium hydroxide solution (50 ml) and the aqueous layer further extracted with ethyl acetate (100 ml). The combined organic extracts were dried (MgSO$_4$), filtered and evaporated under reduced pressure to give a red-brown oil. The crude product was purified on silica gel eluting with a solvent gradient of methanol:dichloromethane. 0.880 aqueous ammonia (2:98:0 to 12:84:2 v/v) followed by crystallisation from ethereal hydrogen chloride, to give the title compound as a solid (600 mg, 37%). $R_f$ 0.22 (0.880 aqueous ammonia:methanol:dichloromethane 1:7:92, v/v). MS m/z 492 (MH)$^+$. $^1$H-NMR (CDCl$_3$): d=2.02 (2H, q), 3.10 (4H, m), 3.30 (2H, m), 3.54 (2H, m), 3.58 (4H, m), 3.64 (2H, t), 3.95 (5H, m), 4.18 (2H, s), 5.18 (2H, s), 5.94 (1H, s), 6.90 (1H, s), 7.02 (1H, s), 7.40 (5H, m). Found: C, 56.71; H, 6.65; N, 11.87; $C_{27}H_{33}N_5O_4$ HCl $H_2O$ 0.4$CH_2Cl_2$ requires C, 56.74, H, 6.40; N, 12.07%.

EXAMPLE 2

Contractile responses of rabbit aorta

Rabbit aorta tissue was cut into rings and suspended in organ baths under a resting tension of 1.5 g in Krebs Ringer bicarbonate of the following composition (mM): NaCl (119), KCl (4.7), $CaCl_2$ (2.5), $KH_2PO_4$ (1.2), $MgSO_4$ (1.2), $NaHCO_3$ (25), glucose (11), and gassed with 95% $O_2$/5% $CO_2$. The solution also contained 1 mM propanol, 0.5 mM idazoxan 10 mM cocaine and 10 mM corticosterone. Tissues were exposed to two sensitising doses of methoxamine (100 mM) and washed over a 1 hour period. Isometric contractions were obtained in response to cumulative additions of methoxamine to obtain control curves in all tissues. A further curve was then generated in the presence or absence of antagonist (incubated for 1 hour). Antagonist affinity estimates ($pK_b$) were determined using a single concentration of competing antagonist, $pK_b=-\log[A]/(DR-1)$ where the dose ratio (DR), relative to corresponding controls, was produced by a single concentration of antagonist [A], assuming competitive antagonism.

The following examples illustrate preparation of compounds of the present invention of type (III), i.e., bioisostere replacement compounds which are active as calcium channel antagonists, especially those of Formula (7.1.1), (7.2.1), and (7.4.1).

EXAMPLE 3

1-(1-Methyl-3-ethyl-indazole)-1-cyano-1-iso-propyl-N-[ethyl-(3,4-dimethyl)-N-methylbutylamine

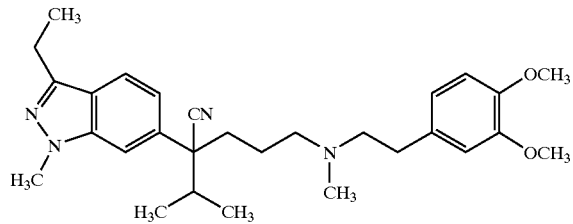

A. 1-Methyl-3-ethyl-6-bromoindazole

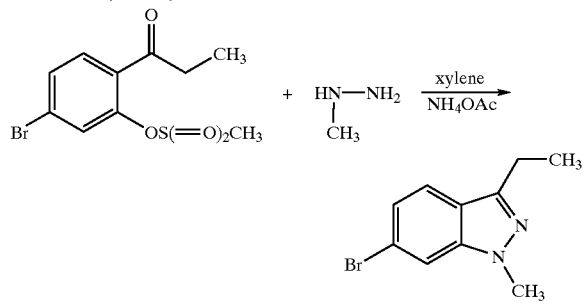

In a first preparation, 1-(1-methylsulfonyl-3-bromo)phenyl-propan-1-one (23.2 g, 76 mmol) was combined with methylhydrazine (8.1 ml, 152 mmol) and ammonium acetate (14.6 g, 190 mmol) in 120 ml of xylene and the reaction mixture was immediately heated to 140° C., removing water with a Dean Stark apparatus. In a second preparation, 1-(1-methylsulfonyl-3-bromo)phenyl-propan-1-one (21 g, 68 mmol) was combined with methylhydrazine (7.2 ml, 136 mmol) and ammonium acetate (13.1 g, 170 mmol) in 110 ml of xylene and the reaction mixture was treated in the same manner as the first preparation. Both resulting reaction mixtures were combined for work-up and the solvent was removed with a roto-evaporator until an oil resulted. The reaction mixture was then worked up with 1N hydrochloric acid and extracted with methylenechloride, then dried over sodium sulfate, and again concentrated on a roto-evaporator. The reaction mixture was purified on a silica column to obtain 35 g of pure product, the NMR spectra of which was consistent with the above-assigned structure.

B. 1-Methyl-3-ethyl-6-methanal-indazole

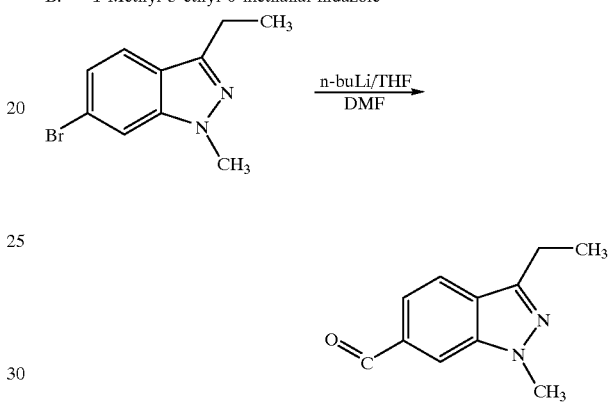

In a first preparation, 1-methyl-3-ethyl-6-bromo-indazole (14 g, 59 mmol) prepared in Step A. was dissolved in 120 ml of dry diethyl ether which was prepared by freshly distilling from Na/benzophenone. The reaction mixture was cooled to −78° C. under nitrogen and then 2.5M n-butyl-lithium (26 ml, 65 mmol) in hexane was added dropwise while maintaining the temperature of the reaction mixture. The reaction mixture was stirred for 1 hour at −78° C. after which dimethylfuran (DMF, 7 ml, 89 mmol) was added and the reaction mixture was stirred again for 1 hour at −78° C. The reaction mixture was then left overnight and allowed to warm to room temperature. In a second preparation, 1-methyl-3-ethyl-6-bromoindazole (11 g, 46 mmol) was dissolved in 100 ml of dry diethyl ether and 2.5M n-butyl-lithium (21 ml, 56 mmol) in hexane and DMF (5.3 ml, 69 mmol) were added, with the reaction mixture being treated in the same manner as the above-described first preparation. Both resulting reaction mixtures were combined and then worked up with 1N hydrochloric acid and extracted with ethyl acetate, then dried over sodium sulfate. The reaction mixture was thereafter concentrated on a roto-evaporator, and then was purified by silica gel column chromatography eluted with 1:3 ethyl acetate/petroleum ether, to obtain 11 g of pure product, the NMR spectra of which was consistent with the above-assigned structure.

C. 1-Methyl-3-ethyl-6-bromomethyl-indazole

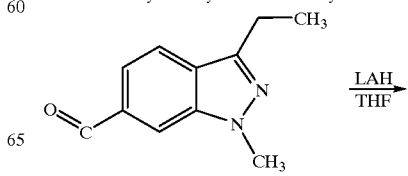

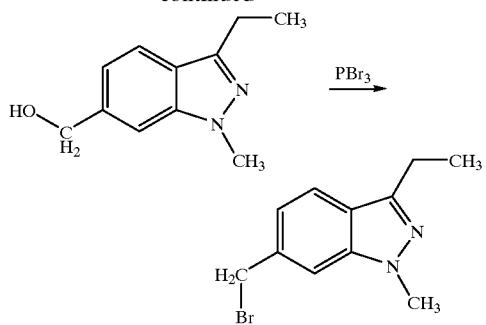

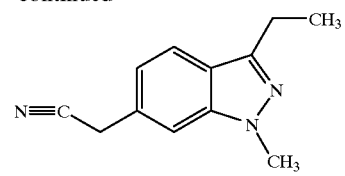

To a solution of 1-methyl-3-ethyl-6-methanal-indazole (10 g, 53 mmol) prepared as above-described in Step B., in 80 ml of tetrahydrofuran (THF) was added dropwise lithium aluminum hydride (LAH, 50 ml, 50 mmol), while the temperature of the reaction mixture was allowed to slowly rise to reflux. The reaction mixture was stirred at reflux for 1 hour and thin-layer chromatography (TLC) was used to determine completion of the reaction. The reaction mixture was then worked up by adding ethyl acetate dropwise thereto followed by concentration on a roto-evaporator. The resulting residue was partitioned between aqueous sodium sulfate and ethyl acetate. The organic phase was separated, dried over sodium sulfat, filtered, concentrated and then dried under vacuum to yield 6 g of the corresponding alcohol. Phosphorus tribromide (PBr$_3$, 8.5 ml, 90 mmol) was added to the alcohol and the reaction mixture was heated to 75° C. and stirred at that temperature for 15 minutes. The reaction mixture turned to an orange color, indicating completion of the reaction, which was confirmed by thin-layer chromatography (TLC), The reaction mixture was then cooled to room temperature, further chilled with ice and then water, and made basic (pH of about 8) with solid sodium hydrogen carbonate. The reaction mixture was extracted with ethyl acetate, dried over sodium sulfate, filtered, and then concentrated to yield an oil (6 g) having the above-assigned structure as confirmed by thin-layer chromatography (TLC). The product was used directly in the next step without further separation.

D.  1-Methyl-3-ethyl-6-cyanomethyl-indazole

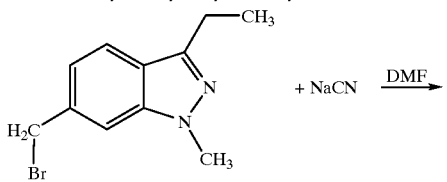

1-Methyl-3-ethy-6-bromomethyl-indazole (6 g, 24 mmol) prepared as above-described in Step C. was combined with sodium cyanate (2.7 g, 54 mmol) in 50 ml of dimethylformamide (DMF) and the reaction mixture was stirred at room temperature for 2 hours, at which time the reaction was complete, as indicated by thin-layer chromatography (TLC). The reaction mixture was diluted with water, extracted with ethyl acetate, dried overv sodium sulfate, and then filtered. The product was isolated by chromatography on a silica gel column eluted with a 1:2 mixture of ethyl acetate/hexane, to yield 4.5 g of pure product, the NMR spectra of which was consistent with the above-assigned structure.

E.  1-[1-Methyl-3-ethyl-indazole]-1-cyano-2-methyl-propane

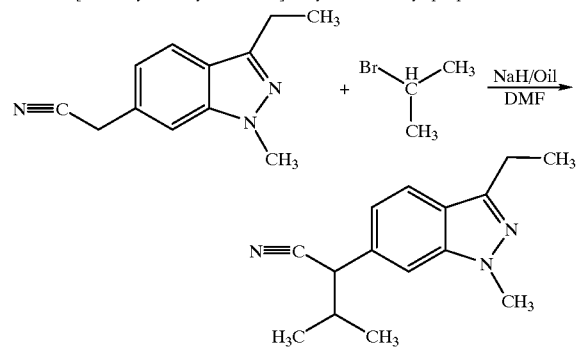

A solution of 1-methyl-3-ethyl-6-cyanomethyl-indazole (3 g, 15 mmol) prepared as above-described in Step D. in 5 ml of dimethylformamide (DMF) was added to a suspension of sodium hydride (NaH/60% mineral oil, 0.6 g, 15 mmol) in 15 ml of dry dimethylformamide (DMF) at room temperature and the reaction mixture was stirred for 5 hours. Iso-propylbromide (1.6 ml, 16.5 mmol) was then added to the reaction mixture, which was stirred at room temperature overnight. The reaction mixture was then worked up with 1N HCl, and extracted with ethyl acetate, dried over magnesium sulfate, and then concentrated on a roto-evaporator. The product was isolated by chromatography on a silica gel column eluting with a 1:2 mixture of ethyl acetate/hexane, to yield 3.6 g of a viscous oil, the NMR spectra of which was consistent with the above-assigned structure.

F.  1-[1-Methyl-3-ethyl-indazole]-1-cyano-1-iso-propyl-N-methylbutylamine

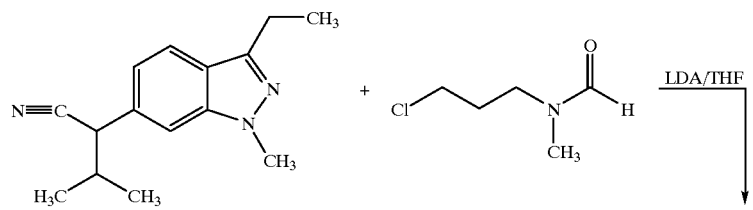

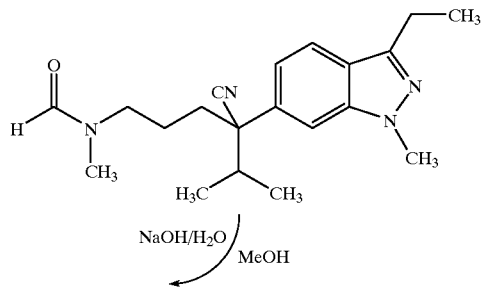

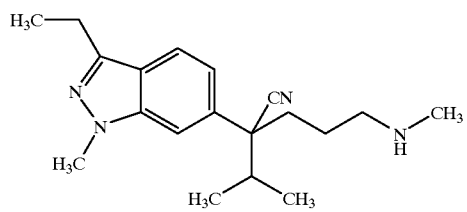

To a solution of 1-[1-methyl-3-ethyl-indazole]-1-cyano-2-methyl-propane (3.6 g, 15 mmol) prepared as above-described in Step E., in 40 ml of dry tetrahydrofuran (THF) there was added dropwise lithium di-iso-propyl amide (LDA, 2.0M, 9 ml, 18 mmol) dissolved in 10 ml of THF, while the temperature of the reaction mixture was held at 0° C. The reaction mixture was stirred for 2 hours at 0° C., after which the aldehyde (2.8 g, 21 mmol) was added while maintaining the temperature of the reaction mixture at 0° C. The reaction mixture was stirred overnight at room temperature, after which the reaction was determined to be complete by thin-layer chromatography (TLC) sampling. The reaction mixture was worked up by quenching with saturated aqueous ammonium chloride, and then extracted with ethyl acetate. The organic layer was separated, dried over sodium sulfate, and then filtered. After being concentrated on a roto-evaporator, the product was isolated by silica gel column chromatography eluting with a 1:2 mixture of ethyl acetate/hexane, to yield 1.5 g of a viscous oil product, the NMR spectra of which was consistent with the above-assigned structure. A solution of the protected amine was made up by placing 1.3 g (3.8 mmol) of the amine in 38 ml of methanol and then adding thereto a solution of 1.52 g (38 mmol) of sodium hydroxide in 8 ml of water. The reaction mixture was stirred at reflux for 10 hours, after which the reaction was determined to be complete by thin-layer chromatography (TLC) eluting with a 1:5 mixture of methanol/ethyl acetate. The methanol was removed on a roto-evaporator and the residue was extracted with dichloromethane, dried over sodium sulfate, filtered, concentrated, and then vacuum dried to yield the product having the above-assigned structure.

G. 3, 4-Dimethoxyphenethylbromide

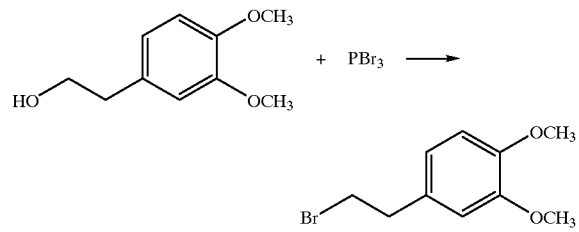

3,4-Dimethoxyphenethyl alcohol (2.7 g, 15 mmol) was mixed together with phosphorus tribromide (PBr₃, 4 ml) and the reaction mixture was stirred at 70° C. to 80° C. for 15 minutes and then cooled, after which it was treated with saturated sodium carbonate. The reaction mixture was then extracted with ethyl acetate, dried over sodium sulfate, and then filtered. The product was isolated by silica gel column chromatography eluting with a 1:4 mixture of ethyl acetate/hexane, to yield 2.0 g of an oil, the NMR spectra of which was consistent with the above-assigned structure.

H. 1-(1-Methyl-3-ethyl-indazole)-1-cyano-1-iso-propyl-N-[ethyl-(3, 4-dimethoxyphenyl)-N-methyl butylamine

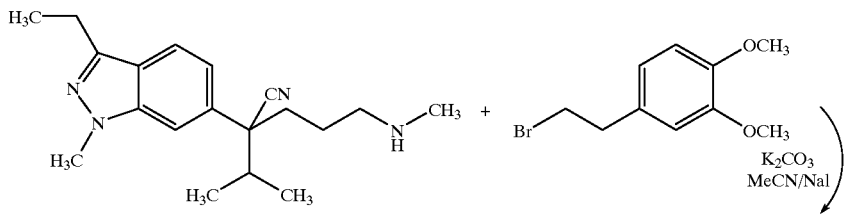

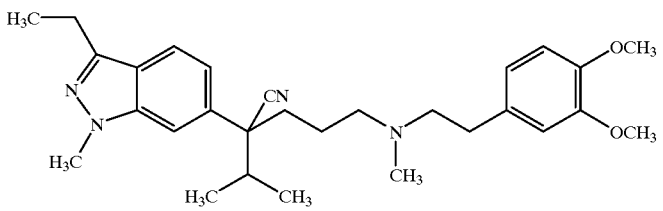

The 1-[1-Methyl-3-ethyl-indazole]-1-cyano-1-iso-propyl-N-methylbutylamine (930 mg, 3 mmol) and 3,4-Dimethoxyphenethylbromide (810 mg, 3.3 mmol) prepared in above-described Steps F. and G., respectively, were combined and stirred at room temperature for 24 hours, after which the reaction mixture was refluxed for 2 hours. The product was worked up and purified by silica gel column chromatography eluting with ethyl acetate to yield 1.0 g of an oil, the NMR spectra of which was consistent with the above-assigned structure.

EXAMPLE 4

1, N-[Bis-(1-methyl-3-ethyl-indazole]-1-cyano-1-iso-propyl-N-methylbutylamine

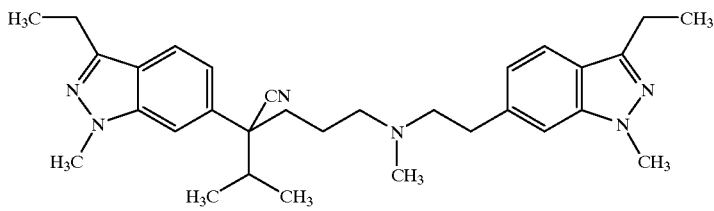

A. 1-Methyl-3-ethyl-6-hydroxyethyl-indazole

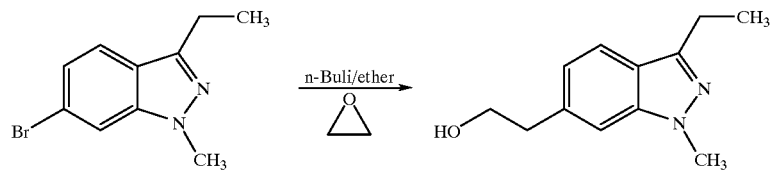

To a solution of 1-methyl-3-ethyl-6-bromo-indazole (8.35 g, 34.9 mmol) in 350 ml of diethylether was added dropwise n-butyl-lithium (17.4 ml, 43.6 mmol) at −78° C. under nitrogen. The reaction mixture was stirred at −78° C. for 1 hour and then allowed to warm to 0° C. to −20° C., after which it was recooled to −78° C. after which ethylene oxide (9 g) was added. The reaction mixture was stirred at −78° C. for 1 hour and then allowed to warm to room temperature and stirred at room temperature overnight. The reaction mixture was quenched with water and extracted with ethyl acetate, dried over sodium sulfate, and then filtered. The product was isolated by silica gel column chromatography eluting with a 6:4 mixture of etheyl acetate/petroleum ether to obtain 5.3 g of an oil, the NMR spectra of which was consistent with the above-assigned structure.

B. 1-Methyl-3-ethyl-6-bromoethyl-indazole

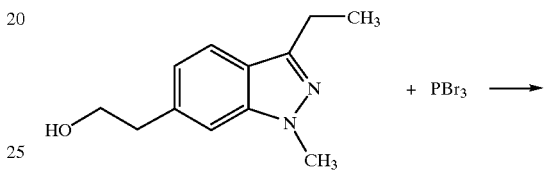

-continued

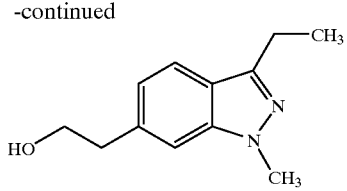

1-Methyl-3-ethyl-6-hydroxyethyl-indazole (4 g, 20 mmol) was mixed together with phosphorus tribromide (5.3 ml, 56 mmol) and the reaction mixture was then stirred at 70° C. to 80° C. for 15 minutes, after which it was cooled and treated with saturated sodium carbonate. The reaction mixture was extracted with ethyl acetate three times using 100 ml aliquot portions, and the organic layers were then combined, washed with brine, dried over sodium sulfate, filtered, and concentrated on a roto-evaporator. The product yield was 4.5 g of an oil, the NMR spectra of which was consistent with the above-assigned structure.

C. 1-[3, 4-Dimethoxyphenyl]-1-cyano-2-methylpropane

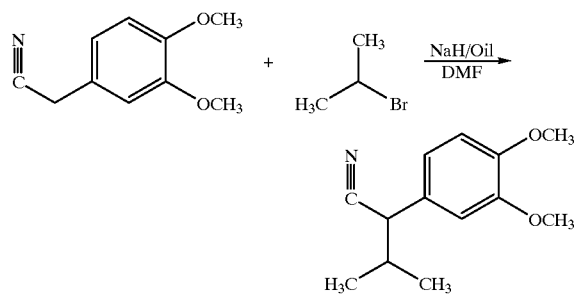

To a solution of 3,4-dimethoxybenzonitrile (35 g, 198 mmol) in 100 ml of dimethylformamide (DMF) was added a sodium hydride suspension in 60% mineral oil (10 ml, 250 mmol) and the reaction mixture was stirred for 5 hours at room temperature. Iso-propylbromide (21 ml, 227 mmol) was then added dropwise to the reaction mixture with stirring and the reaction mixture was then allowed to stand overnight at room temperature. The reaction mixture was then hydrolyzed with 5% hydrochloric acid and extracted with three times with 150 ml aliquots of ethyl acetate. The organic layers were combined, washed with brine, dried over sodium sulfate, filtered, and concentrated on a roto-evaporator. The product was obtained in 38.2 g yield as an oil, the NMR spectra of which was consistent with the above-assigned structure.

To a solution of 1-[3,4-Dimethoxyphenyl]-1-cyano-2-methylpropane (4.38 g, 20 mmol) in 150 ml of dry tetrahydrofuran (THF) there was added dropwise lithium di-iso-propyl amide (LDA, 2.0M, 11 ml, 22 mmol) while the temperature of the reaction mixture was held at 0° C. The reaction mixture was stirred for 2 hours at 0° C., after which the chloride (3.27 g, 20 mmol) was added while maintaining the temperature of the reaction mixture at 0° C. The reaction mixture was stirred overnight at room temperature, after which the reaction was complete, as indicated by thin-layer chromatography (TLC) sampling. The reaction mixture was worked up by quenching with saturated aqueous ammonium chloride and extracting with ethyl acetate. The organic layer was separated and dried over sodium sulfate, then filtered. After being concentrated on a roto-evaporator, the product was isolated by silica gel column chromatography eluting with a 1:2 mixture of ethyl acetate/hexane to give 2.9 g of product as a viscous oil, the NMR spectra of which was consistent with the above-assigned structure. In the next step, a solution of the protected amine was prepared by adding it to 50 ml of methanol and thereafter adding a solution of 5.5 g (130 mmol) of sodium hydroxide in 25 ml of water. The reaction mixture was stirred at reflux for 10 hours, whereupon it was found to be complete by thin-layer chromatography (TLC) sampling, eluting with a 1:5 mixture of methanol/ethyl acetate. The methanol was then removed on a rotoevaporator and the residue was extracted four times with 40 ml aliquots of dichloromethane. The organic layers were combined, washed with brine, washed with water, dried over sodium sulfate, filtered, and concentrated to yield 2.6 g of product as an oil, the NMR spectra of which was consistent with the above-assigned structure.

D. 1-[3, 4-Dimethoxyphenyl]-1-cyano-1-iso-propyl-N-methylbutylamine

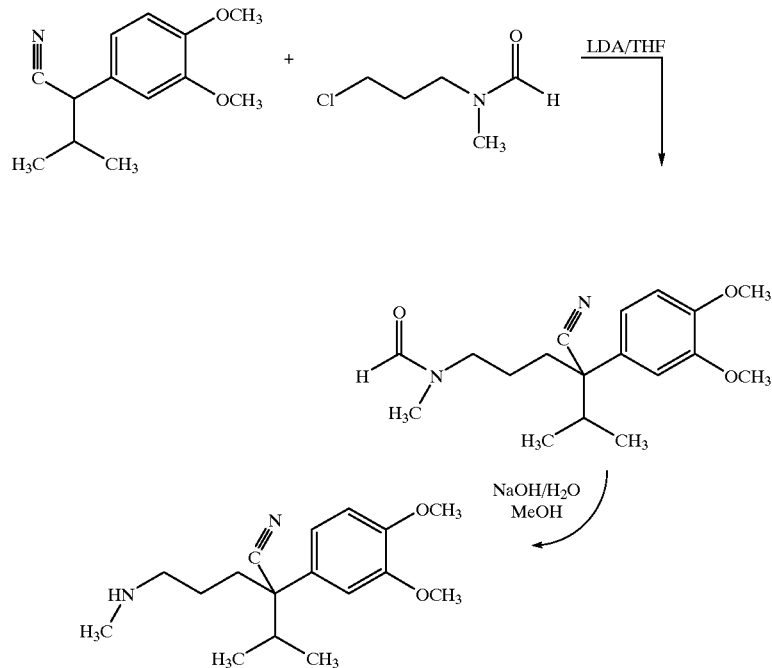

E. 1-[(3, 4-Dimethoxyphenyl)-1-cyano-1-iso-propyl]-N-[ethyl-indazole)]-N-methyl-butylamine

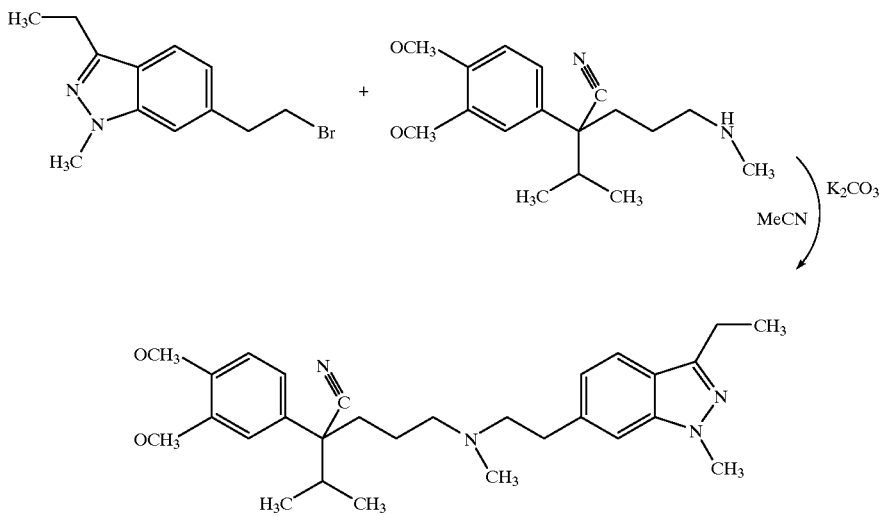

In a first preparation, 1-methyl-3-ethyl-6-bromoethyl-indazole (1 g, 3.9 mmol) prepared in accordance with above described Step B. was combined with 1-[3,4-dimethoxyphenyl]-1-cyano-1iso-propyl-N-methylbutylamine (1 g, 3.8 mmol) prepared in accordance with above-described Step D., potassium carbonate (1.6 g, 11.6 mmol), and acetonitrile (25 ml), and the reaction mixture was stirred at room temperature for 24 hours and then refluxed for 2 hours. In a second preparation, 1-methyl-3-ethyl-6-bromoethyl-indazole (0.6 g) was combined with 1-[3,4-dimethoxyphenyl]-1-cyano-1-iso-propyl-N-methylbutylamine (0.6 g), potassium carbonate (0.96 g), and acetonitrile (25 ml), and the reaction mixture was treated in the same manner as described above for the first preparation. The products from each preparation were worked up individually and purified by silica gel column chromatography, eluting with ethyl acetate, to yield 900 mg of product for the first preparation and 500 mg of product for the second preparation, both of which were an oil, the NMR spectra of which was consistent with the above-assigned structure.

F. 1, N-[bis-(1-methyl-3-ethyl-indazole)]-1-cyano-1-iso-propyl-N-methyl-butylamine

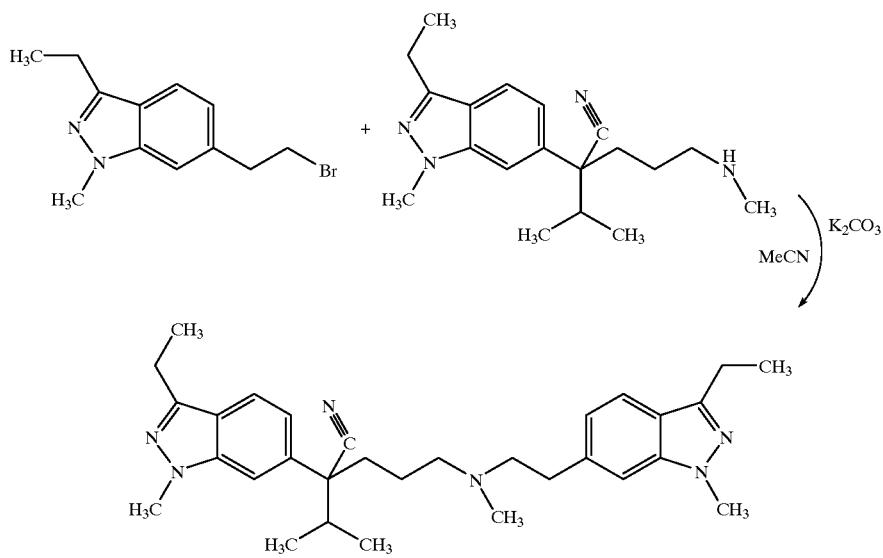

In a first preparation, 1-methyl-3-ethyl-6-bromoethyl-indazole (0.83 g, 3.1 mmol) prepared in accordance with above-described Step B.; 1-[1-methyl-3-ethyl-indazole]-1-cyano-1-iso-propyl-N-methyl-butylamine (0.88 g, 2.8 mmol) prepared in accordance with above-described Example 3, Step F; potassium carbonate (1.2 g, 8.4 mmol); and acetonitnile (25 ml) were combined and the reaction mixture was stirred at room temperature for 24 hours, then refluxed for 2 hours. The product was worked up and purified by silica gel column chromatography, eluting with ethyl acetate, to yield 700 mg of product as an oil, the NMR spectra of which was consistent with the above-assigned structure.

EXAMPLE 5

A. 3-Nitro-4-propyl-benzoic acid 9.44 g (57.5 mmol, 1.0 equiv.) of 4-propylbenzoic acid were partially dissolved in 50 mL conc. $H_2SO_4$ and chilled in an ice bath. A solution of 4.7 mL (74.7 mmol, 1.3 equiv) conc. $HNO_3$ in 10 mL conc. $H_2SO_4$ was added dropwise over 1–2 min. After stirring 1 hour at 0° C., the reaction mixture was poured into a 1 L beaker half full with ice. After stirring 10 minutes, the white solid which formed was filtered, washed 1×$H_2O$, and dried to give 12.01 g (100%) of the title compound: mp 106–109° C.; IR (KBr) 3200–3400, 2966, 2875, 2667, 2554, 1706, 1618, 1537, 1299, 921 cm$^{-1}$; $^1$H NMR (300 MHz, DMSO-$d_6$) d 0.90 (t, 3H, J=7.4 Hz), 1.59 (m, 2H), 2.82 (m, 2H), 7.63 (d, 1H, J=8.0 Hz), 8.12 (dd, 1H, J=1.7, 8.0 Hz), 8.33 (d, 1H, J=1.7 Hz); $^{13}$C NMR (75.5 MHz, DMSO-$d_6$) d 14.2, 23.7, 34.2, 125.4, 130.5, 132.9, 133.6, 141.4, 149.5, 165.9; Anal. calcd for $C_{10}H_{11}NO_4 \cdot 1/4H_2O$: C, 56.20; H, 5.42; N, 6.55. Found: C, 56.12; H, 5.31; N, 6.81.

B. 3-Amino-4-propyl-benzoic acid

A mixture of 11.96 g (57.2 mmol) 3-nitro-4-propyl-benzoic acid and 1.5 g 10% Pd/C, 50% water wet, in 250 mL $CH_3OH$ was placed on a Parr hydrogenation apparatus and shaken under 25 psi $H_2$ at ambient temperature. After 1 hour, the reaction mixture was filtered through celite, and the filtrate concentrated and dried to give 9.80 g (96%) of a pale yellow crystalline solid: mp 139.5–142.5° C.; IR (Kbr) 3200–2400, 3369, 3298, 2969, 2874, 2588, 1690, 1426, 916, 864 cm$^{-1}$; $^1$H NMR (300 Mhz, DMSO-$d_6$) d 0.90 (t, 3H, J=7.2 Hz), 1.52 (m, 2H), 2.42 (m, 2H), 5.08 (br s, 2H), 6.96 (d, 1H, J=7.8 Hz), 7.05 (dd, 1H, J=1.7, 7.8 Hz), 7.20 (d, 1H, J=1.7 Hz); MS (Cl, $NH_3$) m/z 180 (M+H$^+$, base); Anal. calcd for $C_{10}H_{13}NO_2 \cdot 1/3H_2O$: C, 64:85; N, 7.89; N, 7.56. Found: C, 64.69; H, 7.49; N, 7.86.

C. 3-Carboxy-6-propyl-benzenediazo t-butyl sulfide

A mixture of 8.80 g (49.1 mmol, 1.0 equiv) 3-amino-4-propyl-benzoic acid and 2.34 g (22.1 mmol, 0.45 equiv) sodium carbonate in 55 mL $H_2O$ was heated gently with a heat gun until mostly dissolved. The reaction mixture was chilled in an ice bath, and a solution of 3.73 g (54.0 mmol, 1.0 equiv.) sodium nitrite in 27 mL $H_2O$ was added dropwise. After 15 min., the reaction mixture was transferred to a dropping funnel and added over 10 minutes to a beaker containing 55 g of crushed ice and 10.6 mL concentrated HCl. After stirring 10 min., the contents of the beaker were transferred to a dropping funnel and added over 5 minutes to a room temperature solution of 5.31 mL (47.1 mmol, 0.96 equiv) t-butyl thiol in 130 mL ethanol. The pH was adjusted to 4–5 by addition of saturated aqueous $Na_2CO_3$ solution, and the reaction mixture was allowed to stir 1 hour at ambient temperature. 200 mL brine were added, and the mixture was filtered. The solid was washed 1×$H_2O$ and dried overnight to give 12.25 g (89%) of a brown/rust colored powder (caution-stench): mp 102° C. (dec); IR (KBr) 3200–2400, 2962, 2872. 2550, 1678, 1484, 1428, 1298, 1171 cm$^{-1}$; $^1$H NMR (300 MHz, DMSO-$d_6$) d 0.84 (t, 3H, J=7.3 Hz), 1.48 (m, 2H), 1.55 (s, 9H), 2.42 (m, 2H), 7.29 (d, 1H, J=1.6 Hz), 7.50 (d, 1H, J=8.0 Hz), 7.86 (dd, 1H, J=1.7, 7.9 Hz), 13.18 (br s, 1H); MS (thermospray, $NH_4OAc$) m/z 281 (M+H+, base); Anal. calcd for $C_{14}H_{20}N_2O_2S$: C, 59.96; H, 7.19; N, 9.99. Found: C, 59.71; H, 7.32; N, 10.02.

D. 3-Ethyl-1H-indazole-6-carboxylic acid

A solution of 12.0 g (42.8 mmol, 1.0 equiv) 3-carboxy-6-propyl-benzenediazo t-butyl sulfide in 150 mL DMSO was added dropwise over 15 min. to a room temperature solution of 44.6 g (398 mmol, 9.3 equiv) potassium t-butoxide in 200 mL DMSO. After stirring 2 hours at ambient temperature, the reaction mixture was poured into 1.5 L of 0° C. 1N HCl, stirred 5 min., then extracted 2×350 mL ethyl acetate. The ethyl acetate extracts (caution-stench) were combined, washed 2×250 mL $H_2O$, and dried over $MgSO_4$. Filtration, concentration of filtrate and drying gave a tan solid, which was triturated with 1 L of 1:3 $Et_2O$/Hexanes and dried to give 7.08 g (87%) of a tan crystalline powder: mp 248–251° C.; IR (KBr) 3301, 3300–2400, 2973, 2504, 1702, 1455, 1401, 1219 cm$^{-1}$; $^1$H NMR (300 MHz, DMSO-$d_6$) d 1.31 (t, 3H, J=7.6 Hz), 2.94 (q, 2H, J=7.6 Hz), 7.63 (dd, 1H, J=1.1, 8.4 Hz), 7.81 (d, 1H, J=8.4 Hz), 8.06 (d, 1H, J=1.1 Hz) 12.95 (br s, 1H); MS (Cl, $NH_3$) m/z 191 (M+H+, base); Anal. calcd for $C_{10}H_{10}N_2O_2$: C, 63.14; H, 5.30; N, 14.73. Found: C, 62.66; H, 5.42; N, 14.80.

E. 3-Ethyl-1H-indazole-6-carboxylic acid methyl ester 8.78 g (45.8 mmol, 1.1 equiv) 1-(3-dimethylaminopropyl)-3-ethylcarbodiimide hydrochloride were added in one portion to a room temperature solution of 7.92 g (41.6 mmol, 1.0 equiv) 3-ethyl-1H-indazole-6-carboxylic acid, 16.9 mL (416 mmol, 10 equiv) methanol and 5.59 g (45.8 mmol, 1.1 equiv) DMAP in 250 mL $CH_2Cl_2$. After 18 hours at room temperature, the reaction mixture was concentrated to 150 mL, diluted with 500 mL ethyl acetate, washed 2×100 mL 1N HCl, 1×100 mL $H_2O$, 1×100 mL brine, and dried over $Na_2SO_4$. Filtration, concentration of filtrate and drying gave 7.8 g of a brown solid, which was purified on a silica gel column (30% to 50% ethyl acetate/hexanes gradient) to give 6.41 g (75%) of a tan solid: mp 107–108° C.; IR (KBr) 3100–2950, 1723, 1222 cm$^{-1}$; $^1$H NMR (300 MHz, CDCl$_3$) d 8.19 (m, 1H), 7.7–7.8 (m, 2H), 3.96 (s, 3H), 3.05 (q, 2H, J=7.7 Hz), 1.43 (t, 3H, 7.7 Hz); MS (Cl, $NH_3$) m/z 205 (M+H$^+$, base); Anal. calcd for $C_{11}H_{12}N_2O_2$: C, 64.70; H, 5.92, N, 13.72. Found: C, 64.88; H, 6.01; N, 13.96.

F. 1-Cyclopentyl-3-ethyl-1H-indazol-6-carboxylic acid methyl ester 1.17 g (29.4 mmol, 1.05 equiv) sodium hydride, 60% oil dispersion, was added in one portion to a room temperature solution of 5.7 g (27.9 mmol, 1.0 equiv) 3-ethyl-1H-indazole-6-carboxylic acid methyl ester in 125 mL anhydrous DMF. After 20 minutes, 3.89 mL (36.6 mmol, 1.3 equiv) cyclopentyl bromide were added dropwise, and the reaction was mixture allowed to stir overnight at room temperature. The mixture was then poured into 1 L $H_2O$ and extracted 3×450 mL ethyl acetate. The organic extracts were combined, washed 3×400 mL $H_2O$, 1×200 mL brine, and dried over $Na_2SO_4$. Filtration, concentration of filtrate and drying gave an amber oil, which was purified on a silica gel column (10% ethyl acetate/hexanes, gravity) to give 5.48 g (72%) of a clear oil: $^1$H NMR (300 MHz, CDCl$_3$) d 8.16 (d, 1H, J=1.0 Hz), 7.7 (m, 2H), 5.00 (quintet, 1H, J=7.5 Hz), 3.97 (s, 3H), 3.01 (q, 2H, J=7.6 Hz), 2.2 (m, 4H), 2.0 (m, 2H), 1.8 (m, 2H), 1.39 (t, 3H, J=7.6 Hz); HRMS calcd for $C_{16}H_{20}N_2O_2$; 272.1526. Found: 272.15078.

G. (1-Cyclopentyl-3-ethyl-1H-indazol-6-yl)-methanol 7 mL (7.0 mmol, 1.0 equiv) lithium aluminum hydride, 1.0 M solution in THF, were added to a 0° C. solution of 1.02 g (7.05 mmol, 1.0 equiv) 1-cyclopentyl-3-ethyl-1H-indazole-6-carboxylic acid methyl ester in 50 mL anhydrous THF. After 20 minutes, 1 mL methanol was added cautiously, then the reaction mixture was poured into 500 mL of 5% $H_2SO_4$ and extracted 3×50 mL ethyl acetate. The organic extracts were combined, washed 2×40 mL $H_2O$, 1×40 mL brine, and dried over $Na_2SO_4$. Filtration, concentration of filtrate, and drying gave 1.58 g of a clear oil, which was purified on a silica gel column to give 1.53 g (89%) clear oil: IR ($CHCl_3$) 3606,3411, 3009, 2972, 2875, 1621, 1490 $cm^{-1}$; $^1$H NMR (300 Mhz, $CDCl_3$) d 7.65 (d, 1H, J=8.0 Hz), 7.42 (s, 1H), 7.06 (dd, 1H, J=1.0, 8.2 Hz), 4.92 (quintet, 1H, J=7.7 Hz), 4.84 (s, 2H), 2.98 (q, 2H, J=7.6 Hz), 2.2 (m, 4H), 2.0 (m, 2H), 1.7 (m, 3H), 1.38 (t, 3H, J=7.6 Hz); MS (thermospray, $NH_4OAc$) m/z 245 (M+H$^+$, base); HRMS calcd for $C_{15}H_{20}N_2O$+H: 245.1654. Found: 245.1675.

H. 1-Cyclopentyl-3-ethyl-1H-indazole-6-carbaldehyde 06 mg (0.301 mmol, 0.05 equiv) tetrapropylammonium perruthenate (VII) were added to a room temperature suspension of 1.47 g (6.02 mmol, 1.0 equiv) (1-cyclopentyl-3-ethyl-1H-indazol-6-yl)-methanol, 1.06 g (9.03 mmol, 1.5 equiv) N-methylmorpholine N-oxide and 3.01 g 4A molecular sieves in 12 mL anhydrous $CH_2Cl_2$. After 30 minutes, the reaction mixture was filtered through a short column of silica gel (eluted with $CH_2Cl_2$). Fractions containing product were concentrated, and the residue chromatographed on a silica gel column (15% ethyl acetate/hexanes, flash) to give 924 mg (63%) of a pale yellow solid: mp 41° C.; IR (KBr) 3053, 2966, 2872, 2819, 1695 $cm^{-1}$; $^1$H NMR (300 MHz, $CDCl_3$) d 10.13 (s, 1H), 7.93 (d, 1H, J=0.9 Hz), 7.77 (d, 1H, J=8.4 Hz), 7.60 (dd, 1H, J=1.2, 8.4 Hz), 5.00 (quintet, 1H, J=7.5 Hz), 3.01 (q, 2H, J=7.6 Hz), 2.2 (m, 4H), 2.0 (m, 2H), 1.7 (m, 2H), 1.39 (t, 3H, J=7.5 Hz); MS (Cl, $NH_3$) m/z 243 (M+H$^+$, base); Anal. calcd for $C_{15}H_{18}N_2O$: C, 74.35; H, 7.49; N, 11.56. Found: C, 74.17; H, 7.58; N, 11.79.

EXAMPLE 6

A. 4-Bromo-2-nitro-1-propyl-benzene 125 g (628 mmol, 1.0 equiv) 1-bromo-4-propyl-benzene were added in one portion to a 10° C. solution of 600 mL concentrated $H_2SO_4$ and 200 mL $H_2O$. With vigorous mechanical stirring, a room temperature mixture of 43.2 mL (691 mmol, 1.1 equiv) conc. $HNO_3$ (69–71%, 16M) in 150 mL conc. $H_2SO_4$ and 50 mL $H_2O$ was added dropwise over 30 minutes. The ice bath was allowed to warm to room temperature, and the reaction stirred at room temperature for 68 hours. The reaction mixture was poured into a 4 L beaker, loosely packed full with crushed ice. After stirring 1 hour, the mixture was transferred to a 4 L separatory funnel and extracted 4×800 mL isopropyl ether. The organic extracts were combined, washed 3×800 mL $H_2O$, 1×500 mL brine, and dried over $Na_2SO_4$. Filtration, concentration of filtrate and drying gave 150 mL of a yellow liquid, which was purified by silica gel chromatography (2 columns, 3 kg silica gel each, 2% ethyl acetate/hexanes) to afford 63.9 g (42%) of a yellow liquid. The desired regioisomer is the less polar of the two, which are formed in a 1:1 ratio. bp 108° C., 2.0 mm; IR ($CHCl_3$) 3031, 2966, 2935, 2875, 1531, 1352 $cm^{-1}$; $^1$H NMR (300 MHZ, $CDCl_3$) d 8.01 (d, 1H, J=2.1 Hz), 7.62 (dd, 1H, J=2.1, 8.3 Hz), 7.23 (d, 1H, J=8.3 Hz), 2.81 (m, 2H), 1.67 (m, 2H), 0.98 (t, 3H, J=7.4 Hz); $^{13}$C NMR (75.5 MHz, $CDCl_3$) d 13.94, 23.74, 34.43, 119.6, 127.4, 133.3, 135.7, 136.4, 149.8; GCMS (El) m/z 245/243 (M$^+$.), 147 (base); HRMS calcd for $C_9H_{10}NO_2BR$+H: 243.9973. Found: 243.9954.

B. 5-Bromo-2-propyl-phenylamine 121 g (639 mmol, 3.0 equiv) of stannous chloride (anhydrous) were added in one portion to a room temperature solution of 51.9 g (213 mmol, 1.0 equiv) 4-bromo-2-nitro-1-propyl-benzene in 1200 mL absolute ethanol and 12 mL (6 equiv) $H_2O$. After 24 hours at room temperature, most of the ethanol was removed on a rotary evaporator. The residue was poured into a 4 L beaker, three-quarters full with crushed ice and $H_2O$. 150 g of NaOH pellets were added portionwise, with stirring, until the pH=10 and most of the tin hydroxide has dissolved. The mixture was divided in half, and each half extracted 2×750 mL ethyl acetate. All four ethyl acetate extracts were combined, washed 1×500 mL each 1N NaOH, $H_2O$, and brine, then dried over $Na_2SO_4$. Filtration, concentration of filtrate and drying gave a yellow liquid, which was purified on a 1.2 kg silica gel column (1:12 ethyl acetate/hexanes) to give 41.83 g (92%) of a pale yellow liquid: IR ($CHCl_3$) 3490, 3404, 3008, 2962, 2933, 2873, 1620, 1491 $cm^{-1}$; $^1$H NMR (300 MHz, $CDCl_3$) d 6.8–6.9 (m, 3H), 3.90 br s, 2H), 2.42 (m, 2H0, 1.62 (m, 2H), 0.99 (t, 3H, J=7.3 Hz); GCMS (El) m/z 215/213 (M$^+$.), 186/184 (base); Anal. calcd for $C_9H_{12}NBr$: C, 50.49; H, 5.65; N, 6.54. Found: C, 50.77; H, 5.70; N, 6.50.

C. 6-Bromo-3-ethyl-1H-indazole 49.22 g (230 mmol, 1.0 equiv) 5-bromo-2-propyl-phenylamine were placed in a 3 L flask and chilled in an ice bath. A 0° C. solution of 57.5 mL (690 mmol, 3.0 equiv) conc. HCl in 165 mL $H_2O$ was added, and the resulting solid mass which formed was ground up until a fine white suspension resulted. 100 mL more H2O were added, then a solution of 15.9 g (230 mmol, 1.0 equiv) sodium nitrite in 75 mL $H_2O$ was added dropwise over 10 min. The ice bath was removed, and the reaction allowed to stir at room temperature for 30 minutes. The reaction mixture was then filtered through a sintered glass funnel, precooled to 0° C. The filtrate was chilled in an ice bath, and with mechanical stirring, a 0° C. solution/suspension of 32.8 g (313 mmol, 1.36 equiv) ammonium tetrafluoroborate in 110 mL $H_2O$ was added dropwise over 10 min. The thick white suspension which formed (aryl diazonium tetrafluoroborate salt) was allowed to stir 1.5 hours at 0° C. The mixture was then filtered, and the solid washed 1×200 mL 5% aq. $NH_4BF_4$ (cooled to 0° C.), 1×150 mL $CH_3OH$ (cooled to 0° C.), then 1×200 mL high vacuum, room temperature for 1 hour gave 54.47 g (76%) of the diazonium salt, an off-white solid.

1500 mL of ethanol free chloroform was placed in a 3 L flask, then 34.16 g (348 mmol, 2.0 equiv) potassium acetate (powdered and dried) and 2.3 g (8.7 mmol, 0.05 equiv) 18-crown-6 were added. After 10 minutes the diazonium salt was added in one portion, and the reaction mixture allowed to stir at room temperature under nitrogen atmosphere for 18 hours. The mixture was then filtered, the solid washed 2× with $CHCl_3$, and the filtrate concentrated to give 47 g of crude product (brown crystals). Silica gel chromatography (1.23 kg silica gel, ethyl acetate/hexanes gradient 15%, 20%, 40%) gave 21.6 g (55% for second step, 42% overall) of tan crystals: mp 112–114° C.; IR (KBr) 3205, 3008, 2969, 2925, 1616,1340, 1037 $cm^{-1}$; $^1$H NMR (300 MHz, $CDCl_3$) d 9.86

(br s, 1H), 7.61 (d, 1H, J=1.3 Hz), 7.57 (d, 1H, J=8.4 Hz), 7.24 (dd, 1H, J=1.5, 8.6 Hz), 2.99 (q, 2H, J=7.6 Hz), 1.41 (t 3H, J=7.6 Hz); MS (CI, NH$_3$) m/z 227/225 (M+H$^+$, base); Anal. calcd for C$_9$H$_9$N$_2$Br: C, 48.02; H, 4.03; N, 12.45. Found: C, 48.08; H, 3.87; N, 12.45.

D. 6-Bromo-1-cyclopentyl-3-ethyl-1H-indazole 2.46 g (61.4 mmol, 1.05 equiv) sodium hydride, 60% oil dispersion, was added in 0.5 g portions to a 10° C. solution of 13.17 g (58.5 mmol, 1.0 equiv) 6-bromo-3-ethyl-1H-indazole in 500 mL anhydrous DMF. The mixture was stirred at room temperature for 20 minutes, then a solution of 8.8 mL (81.9 mmol, 1.4 equiv) cyclopentyl bromide in 10 mL anhydrous DMF was added dropwise. After 18 hours, the reaction mixture was poured into 2 L H$_2$O and extracted 2×1 L ethyl acetate. The organic extracts were combined, washed 2×750 mL H$_2$O, 1×500 mL brine, and dried over Na$_2$SO$_4$. Filtration, concentration of filtrate and drying gave 20.7 g of crude product, which was purified on a silica gel column (1.1 kg silica gel, 3% ethyl acetate/hexanes) to give 10.6 g (62%) of an amber liquid: IR (CHCl$_3$)2972, 2875, 1606, 1501, 1048 cm$^{-1}$ ; $^1$H NMR (300 MHz, CDCl$_3$) d 7.56 (d, 1H, J=1.3 Hz), 7.52 (d, 1H, J=8.7 Hz), 7.17 (dd, 1H, J=1.5, 8.5 Hz), 4.83 (quintet, 1H, J=7.6 Hz), 2.96 (q, 2H, J=7.6 Hz), 2.15 (m, 4H), 2.0 (m, 2H), 1.65 (m, 2H), 1.36 (t, 3H, J=7.7 Hz); MS (thermospray, NH$_4$OAc) m/z 295/293 (M+H$^+$, base); Anal. calcd for C$_{14}$H$_{17}$N$_2$Br: C, 57:35; H, 5.84; N, 9.55. Found: C, 57.48; H, 5.83; N, 9.90.

E. (1-Cyclopentyl-3-ethyl-1H-indazole)-6-carbaldehyde 11.6 mL (28.4 mmol, 1.0 equiv) n-BuLi, 2.45 M in hexanes, were added to a −78° C. solution of 8.32 g (28.4 mmol, 1.0 equiv) 6-bromo-1-cyclopentyl-3-ethyl-1H-indazole in 200 mL anhydrous THF. After 30 min. at −78° C., 8.8 mL (114 mmol, 4.0 equiv) anhydrous DMF was added dropwise, and the reaction mixture was allowed to stir an additional 30 min. at −78° C. The mixture was warmed to room temperature over 1 hour, then 125 mL 1N HCl was added. After stirring for 10 minutes, most of the THF was removed on a rotary evaporator. The residue was diluted with 500 mL H$_2$O, and extracted 2×250 mL ethyl acetate. The organic extracts were combined, washed 1×100 mL H$_2$O, 1×100 mL brine, and dried over Na$_2$SO$_4$. Filtration, concentration of filtrate and drying gave a yellow oil, which was purified on a silica gel column (15% ethyl acetate/hexanes, gravity) to give 4.70 g (68%) of a yellow crystalline solid: $^1$H NMR (300 MHz, CDCl$_3$) identical to the spectrum of the compound from example 8.

F. (1-Cyclopentyl-3-ethyl-1H-indazol-6yl)-acetonitrile 4.44 mL (35.0 mmol, 1.5 equiv) trimethylsilyl chloride were added dropwise to a room temperature suspension of 5.65 g (23.3 mmol, 1.0 equiv) 1-cyclopentyl-3-ethyl-1H-indazole-6-carbaldehyde and 3.84 g (44.3 mmol, 1.9 equiv) lithium bromide in 115 mL anhydrous acetonitrile. After 15 minutes, the reaction mixture was cooled in an ice bath, and 6.84 mL (38.7 mmol, 1.66 equiv) 1,1,3,3-tetramethyldisiloxane were added dropwise, and the reaction was allowed to warm to room temperature over 2 hours. The reaction mixture was heated to reflux for 6 hours, then cooled to room temperature, diluted with 300 mL CH$_2$Cl$_2$, and filtered through Celite®. The filtrate was concentrated and dried at high vacuum, room temperature to give 13.08 g of a tan oily solid.

This solid was dissolved in 200 mL anhydrous DMF, 259 g (52.9 mmol, 2.27 equiv) sodium cyanide were added, and the mixture stirred at room temperature for 2 hours. The reaction mixture was then poured into 500 mL H$_2$O and extracted 3×200 mL ethyl acetate. The organic extracts were combined, washed 3×200 mL H$_2$O, 1×200 mL brine, and dried over Na$_2$SO$_4$. Filtration, concentration of filtrate and drying gave a brown oil, which was purified on a silica gel column (10%–20% ethyl acetate/hexanes gradient) to give 2.98 g of impure product and 2.05 g of recovered (impure) starting material.

The recovered starting material was resubjected to the reaction conditions described above, using 50 mL 1,1,3,3-tetramethyldisiloxane, followed by 50 mL DMF and 940 mg sodium cyanide. Silica gel chromatography gave 0.62 g of impure product, which was then combined with the 2.98 g lot of impure product and rechromatographed (10% ethyl acetate/hexanes) to give 3.27 g (55%) of a yellow oil: IR (CHCl$_3$) 3062, 2972, 2874, 2255, 1623 cm-$^1$; $^1$H NMR (300 MHz, CDCl$_3$) d 7.66 (d, 1H, J=8.3 Hz), 7.39 (s, 1H), 6.97 (dd, 1H, J=1.1, 8.4 Hz), 4.90 (quintet, 1H, J=7.6 Hz), 3.89 (s, 2H), 2.98 (q, 2H, J=7.6 Hz), 2.2 (m, 4H), 2.0 (m, 2H), 1.37 9t, 3H, J=7.4 Hz); MS (CI, NH$_3$) m/z 254 (M+H$^+$, base); Anal. calcd. for C$_{16}$H$_{19}$N$_3$: C, 75.86; H, 7.56; N, 16.59. Found: C, 75.84; H, 7.94; N, 16.60.

G. 4-Cyano-4-(1-cyclopentyl-3-ethyl-1H-indazol-6-yl)-heptanedioic acid dimethyl ester 530 mL (1.26 mmol, 0.1 equiv) triton B, 40% in methanol, was added to a room temperature solution of 3.19 g (12.6 mmol, 1.0 equiv) (1-cyclopentyl-3-ethyl-1H-indazol-6-yl)-acetonitrile in 100 mL anhydrous acetonitrile. The reaction mixture was heated to reflux, and 11.3 mL (126 mmol, 10.0 equiv) methyl acrylate was added dropwise. After 15 minutes, the reaction mixture was cooled to room temperature, and concentrated on a rotary evaporator. The residue was diluted with 300 mL ether, washed 1×50 mL 1N HCl, 1×50 mL brine, and dried over Na$_2$SO$_4$. Filtration, concentration of filtrate and drying gave a brown oil, which was purified on a silica gel column (20% ethyl acetate/hexanes, flash) to give 4.00 g (75%) of a yellow oil: IR (CHCl$_3$) 3031, 2972, 2955, 2874, 2250, 1735 cm$^{-1}$; $^1$H NMR (300 MHz, CDCl$_3$) d 7.68 (d, 1H, J=8.5 Hz), 7.49 (s, 1H), 6.97 (d, 1H, J=8.5 Hz); 4.93 (quintet, 1H, J=7.6 Hz), 3.58 (s, 6H), 2.97 (q, 2H), J=7.7 Hz), 2.45 (m, 6H), 2.2 (m, 6H), 2.0 (m, 2H), 1.8 m, 2H), 1.37 (t, 3H, J=7.7 Hz); MS (CI, NH$_3$) m/z 426 (M+H$^+$, base); Anal. calcd for C$_{24}$H$_{31}$N$_3$O$_4$: C, 67.74; H, 7.34; N, 9.88. Found: C, 67.76; H, 7.40; N, 10.08.

H. (±)-5-Cyano-5-(1-cyclopentyl-3-ethyl-1H-indazol-6-yl)-2-oxo-cyclahexane-carboxylic acid methyl ester 924 mg (23.1 mmol, 2.5 equiv) sodium hydride, 60% oil dispersion, was added in one portion to a room temperature solution of 3.93 g (9.24 mmol, 1.0 equiv) 4-cyano-4-(1-cyclopentyl-3-ethyl-1H-indazol-6-yl)-heptanedioic acid dimethyl ester in 100 mL anhydrous 1,2-dimethoxyethane. The reaction mixture was heated to reflux under nitrogen atmosphere for 1.5 hours, then cooled to room temperature. After 18 hours, the reaction mixture was quenched with 50 mL H$_2$O, poured into 200 mL ethyl acetate, and washed 1×100 mL 1N HCl. The aqueous layer was extracted 1×50 mL ethyl acetate. The organic extracts were combined, washed 1×50 mL brine, and dried over Na$_2$SO$_4$. Filtration, concentration of filtrate and drying gave a yellow oil, which was purified on a silica gel column (10% ethyl acetate/hexanes) to give 2.78 g (76%) of a white amorphous solid: IR (KRr) 2954, 2871, 2240, 1663, 1619 cm$^{-1}$; $^1$H NMR (300 MHz, CDCl$_3$) d 12.27 (s, 1H), 7.70 (d, 1H, J=8.5 Hz), 7.57 (s, 1H), 7.15 (dd, 1H, J=1.6, 8.5 Hz), 4.93 (quintet, 1H, J=7.6 Hz), 3.78 (s, 3H), 3.05 (m, 1H), 2.98 (q, 2H, J=7.6 Hz), 2.9 (m, 1H), 2.75 (m, 1H), 2.6 (m, 1H), 2.35 (m, 2H), 2.2 (m, 4H), 2.0 (m, 2H), 1.75 (m, 2H), 1.38 (t, 3H, J=7.6 Hz); MS (Cl, NH$_3$) m/z 394 (M+H$^+$, base); Anal. calcd for C$_{23}$H$_{27}$N$_3$O$_3$: C, 70.22; H, 6.92; N, 10.68. Found: C, 70.07; H, 7.01; N, 10.70.

I. 1-(1-Cyclopentyl-3-ethyl-1H-indazol-6-yl)-4-oxo-cyclohexanecarbonitrile

A mixture of 2.72 g (6.91 mmol, 1.0 equiv) (±)-5-cyano-5-(1-cyclopentyl-3-ethyl-1H-indazol-6-yl)-2-oxo-cyclohexanecarboxylic acid methyl ester and 2.58 g (44.2 mmol, 6.4 eqiv) sodium chloride in 50 mL dimethyl sulfoxide and 4 mL H$_2$O was heated in 140° C. oil bath under nitrogen atmosphere. After 3 hours, the reaction mixture was cooled to room temperature and allowed to stir for 72 hours. The reaction mixture was poured into 250 mL H$_2$O and extracted 2×150 mL ethyl acetate. The organic extracts were combined, washed 2×100 mL H$_2$O, 1×100 mL brine, and dried over Na$_2$SO$_4$. The crude product was purified on a silica gel column (20% ethyl acetate/hexanes) to give 1.82 g (78%) of a white crystalline solid: mp 81–89° C.; IR (KBr) 2969, 2951, 2872, 2236, 1716 cm$^{-1}$; $^1$H NMR (300 MHz, CDCl$_3$) d 7.71 (d, 1H, J=8.5 Hz), 7.58 (s, 1H), 7.16 (dd, 1H, J=1.5, 8.5 Hz), 4.93 (quintet, 1H, J=7.6 Hz), 3.0 (m, 4H), 2.7 (m, 4H), 2.45 (m, 2H), NH$_4$OAc) m/z 336 (M+H$^+$, base); Anal. calcd for C$_{21}$H$_{25}$N$_3$O: C, 75.20; H, 7.51; N, 12.53. Found: C, 74.06; H, 7.59; N, 12.41; HRMS calcd for C$_{21}$H$_{25}$N$_3$O+H: 336.20778. Found 336.2088.

EXAMPLE 7

A. 1-(1-Cyclopentyl-3-ethyl-1H-indazol-6-yl)-4-[1,3]dithian-2-ylidene-cyclohexane-carbonitrile 3.94 mL (9.84 mmol, 2.09 equiv) n-BuLi, 2.5 M in hexanes, was added dropwise to a 0° C. solution of 1.88 mL (9.89 mmol, 2.1 equiv) 2-trimethylsilyl-1,3-dithiane in 80 mL anhydrous THF. After 25 minutes at 0° C., the reaction mixture was cooled to –78° C. and a solution of 1.58 g (4.71 mmol, 1.0 equiv) 1-(1-cyclopentyl-3-ethyl-1H-indazol-6-yl)-4-oxo-cyclohexanecarbonitrile in 40 mL anhydrous THF was added. After 1 hours at –78° C., the reaction mixture was quenched by addition of 50 mL brine, then warmed to room temperature, diluted with 100 mL H$_2$O, and extracted 1×100 mL CH$_2$Cl$_2$ and 1×50 mL brine, and dried over Na$_2$SO$_4$. Filtration, concentration of filtrate and drying gave a clear oil, which was purified on a silica gel column (10% ethyl acetate/hexanes) to give 1.51 g (73%) of a white amorphous solid: IR (KBr) 2962, 2870, 2232, 1620, 1569, 1508, 1434, 1217 cm$^{-1}$; $^1$H NMR (300 MHz, CDCl$_3$) d 7.67 (d, 1H, J=8.5 Hz), 7.53 (s, 1H), 7.15 (dd, 1H, J=1.5, 8.6 Hz), 4.92 (quintet, 1H, J=7.6 Hz), 3.36 (m, 2H), 3.0 (m, 6H), 2.42 (m, 2H), 2.34 (m, 2H), 2.2 (m, 6H), 2.0 (m, 4H), 1.8 (m, 2H), 1.37 (t, 3H, J=7.5 Hz); MS (Cl, NH$_3$) m/z 438 (M+H$^+$, base); Anal. calcd for C$_{25}$H$_{31}$N$_3$S$_2$: C, 68.60; H, 7.14; N, 9.60. Found: C, 68.26; H, 7.29; N, 9.58.

B. Trans-4-cyano-4-(1-cyclopentyl-3-ethyl-1H-indazol-6-yl)cyclohexanecarboxylic acid methyl ester and cis-4-cyano-4-(1-cyclopentyl-3-ethyl-1H-indazol-6-yl)cyclohexanecarboxylic acid methyl ester A mixture of 1.45 g (3.31 mmol, 1.0 equiv) 1-(1-cyclopentyl-3-ethyl-1H-indazol-6-yl)-4-[1,3]dithian-2-ylidene-cyclohexane-carbonitrile, 3.59 g (13.2 mmol, 4.0 equiv) mercury (II) chloride and 1.48 mL (16.9 mmol, 5.1 equiv) 70% perchloric acid in 60 mL methanol was heated to reflux under nitrogen atmosphere. After 2 hours, the reaction mixture was cooled to room temperature, diluted with 250 mL CH$_2$Cl$_2$ and filtered through Celite®. The filtrate was washed 1×100 mL saturated aqueous NaHCO$_3$, 1×75 mL 10% aqueous sodium sulfite, 1×100 mL H$_2$O, and dried over Na$_2$SO$_4$. Filtration, concentration of filtrate and drying gave a clear oil, which was purified on a silica gel column (15% ethyl acetate/hexanes) to give 340 mg (27%) of trans isomer (less polar) as a white solid, and 794 mg (63%) of cis isomer (more polar) as a white solid:

data for trans isomer: mp 79–82° C.; IR (KBr) 2973, 2949, 2890, 2871, 2235, 1721, 1618, 1484, 1453, 1217, 1170 cm$^{-1}$; $^1$H NMR (300 MHz, CDCl$_3$) d 7.67 (d, 1H, J=8.4 Hz), 7.52 (s, 1Y), 7.14 (dd, 1H, J=1.4, 8.5 Hz), 4.93 (quintet, 1H, J=7.6 Hz), 3.74 (s, 3H), 2.97 (q, 2H, J=7.6 Hz), 2.85 (m 1H0, 2.3 (m, 2H), 2.2 (m, 10H), 2.0 (m, 2H), 1.75 (m, 2H), 1.37 (t, 3H, J=7.6 Hz); MS (Cl, NH$_3$) m/z 380 (M+H$^+$, base); Anal. calcd for C$_{23}$H$_{29}$N$_3$O$_2$: C, 72.79; H, 7.70; N, 11.07. Found: C, 73.05; H, 7.80; N, 11.03.

data for cis isomer: mp 112–114° C.; IR (KBr) 3065, 2952, 2866, 2234, 1731, 1622, 1487, 1445, 1220, 1204 cm$^{-1}$; $^1$H NMR (300 MHz, CDCl$_3$) d 7.68 (d, 1H, J=8.5 Hz), 7.55 (s, 1H), 7.14 (dd, 1H, J=1.3, 8.4 Hz), 4.93 (quintet, 1H, J=7.6 Hz), 3.73 (s, 3H), 2.98 (q, 2H, J=7.6 Hz), 2.42 (m, 1H), 2.36 (m, 1H), 1.9–2.3 (m, 13H), 1.8 (m, 2H), 1.37 (t, 3H, J=7.5 Hz); MS (Cl, NH$_3$) m/z 380 (M+H$^+$, base); Anal. calcd for C$_{23}$H$_{29}$N$_3$O$_2$: C, 72.79; H, 7.70; N, 11.07. Found: C, 72.93; H, 7.56; N, 10.92.

EXAMPLE 8

Trans-4-cyano-4-(1-cyclopentyl-3-ethyl-1H-indazol-6-yl)-cyclohexanecarboxylic acid A mixture of 337 mg (0.888 mmol, 1.0 equiv) trans-4-cyano-4-(1-cyclopentyl-3-ethyl-1H-indazol-6-yl)-cyclohexanecarboxylic acid methyl ester in 10 mL methanol, 2 mL THF and 2.7 mL (2.66 mmol, 3.0 equiv) 1N NaOH was allowed to stir at room temperature. After 3 hours, the reaction mixture was concentrated on a rotary evaporator, diluted with 100 mL H$_2$O, acidified to pH 1, and extracted 2×70 mL ethyl acetate. The organic extracts were combined, washed 1×50 mL H$_2$O, 1×50 mL brine, and dried over Na$_2$SO$_4$. Filteration, concentration and drying gave a white solid, which was purified on a silica gel column (5% CH$_3$OH/CH$_2$Cl$_2$) to give 197 mg (61%) of a white amorphous solid: IR (KBr) 3200–2500, 3060, 2963, 2871, 2245, 1729, 1702, 1621, 1453, 1219 cm$^{-1}$; $^1$H NMR (300 MHz, DMSO-d$_6$) d 12.4 (br s, 1H), 7.77 (d, 1H, J=8.5 Hz), 7.69 (s, 1H), 7.20 (dd, 1H, J=1.3, 8.5 Hz); 5.17 (quintet, 1H, J=7.6 Hz), 2.90 (q, 2H, J=7.6 Hz), 2.75 (m, 1H), 1.9–2.3 (m, 16H), 1.7 (m, 2H), 1.28 (t, 3H, J=7.6 Hz); MS (Cl, NH$_3$) m/z 366 (M+H$^+$, base); Anal. calcd for C$_{22}$H$_{27}$N$_3$O$_2$: C, 72.29; H, 7.45; N, 11.50. Found: C, 71.98; H, 7.75; N, 11.21.

EXAMPLE 9

Cis-4-cyano-4-(1-cyclopentyl-3-ethyl-1H-indazol-6-yl)-cyclohexanecarboxylic acid A mixture of 831 mg (2.19 mmol, 1.0 equiv) cis-4-cyano-4-(1-cyclopentyl-3-ethyl-1H-indazol-6-yl)-cyclohexanecarboxylic acid methyl ester in 20 mL methanol, 4 mL THF and 6.6 mL (6.57 mmol, 3.0 equiv) 1N NaOH was allowed to stir at room temperature. After 1.5 hours, the reaction mixture was concentrated on a rotary evaporator, diluted with 100 mL $H_2O$, acidified to pH 1, and extracted 2×70 mL ethyl acetate. The organic extracts were combined, washed 1×50 mL $H_2O$, 1×50 mL brine, and dried over $Na_2SO_4$. Filtration, concentration and drying gave 0.80 g of a white solid, which was purified on a silica gel column (5% $CH_3OH/CH_2Cl_2$) to give 730 mg (91%) of a white crystalline solid. Recrystallization from ethyl acetate/hexanes gave 538 mg of white crystals: mp 197–199° C.; IR (KBr) 3200–2600, 3061, 2961, 2948, 2939, 2871, 2245, 1732, 1625, 1451, 1255, 1185, 1169 cm$^{-1}$; $^1$H NMR (300 MHz, DMSO-d$_6$) d 12.35 (brs, 1H), 7.77 (d, 1H, J=8.6 Hz), 7.73 (s, 1H0, 7.27 (dd, 1H, J=1.5, 8.5 Hz), 5.13 (quintet, 1H, J=7.5 Hz), 2.90 (q, 2H, J=7.6 Hz), 2.42 (m, 1H), 2.30 (m, 2H), 1.7–2.1 (m, 14H), 1.29 (t, 3H, J=7.5 Hz); MS (Cl, NH$_3$) m/z 366 (M+H$^+$, base); Anal. calcd for $C_{22}H_{27}N_3O_2$: C, 72.29; H, 7.45; N, 11.50. Found: C, 72.01; H, 7.60; N, 11.29.

EXAMPLE 10

A. 6-Bromo-1-cyclohex-2-enyl-3-ethyl-1H-indazole 2.12 g (52.9 mmol, 1.05 equiv) sodium hydride, 60% oil dispersion, was added in four portions over 10 min. to a room temperature solution of 11.35 g (50.4 mmol, 1.0 equiv) 6-bromo-ethyl-1H-indazole in 300 mL anhydrous DMF. After stirring 20 min., 9.0 mL (70.6 mmol, 1.4 equiv) 3-bromo-cyclohexene were added dropwise, and the reaction concentrated and dried at high vacuum, room temperature to give 7.52 g of an orange/yellow solid.

This solid was dissolved in anhydrous DMF, 1.56 g (31.8 mmol, 2.27 equiv) sodium cyanide were added, and the mixture stirred at room temperature for 2.5 h. The reaction mixture was then poured into 400 mL $H_2O$ and extracted 3×200 mL ethyl acetate. The organic extracts were combined, washed 3×150 mL $H_2O$, 1×150 mL brine, and dried over $Na_2SO_4$. Filtration, concentration of filtrate and drying gave a yellow oil, which was purified on a silica gel column (5%–10% ethyl acetate/hexanes gradient) to give 1.40 g (38%) of a yellow/green oil; MS (Cl, NH$_3$) 268 (M+H$^+$, base); Anal. calcd for $C_{17}H_{21}N_3$: C, 76.38; H, 7.92; N, 15.72. Found C, 76.43; H, 7.53; N, 15.39.

B. 6-Bromo-1-cyclohexyl-3-ethyl-1H-indazole

A mixture of 10.22 g (33.5 mmol, 1.0 equiv) 6-bromo-1-cyclohex-2-enyl-3-ethyl-1H-indazole and 1.5 g 10% Pt/C in 1 L cyclohexane was placed on a Parr® hydrogenation apparatus and shaken under 2–5 psi $H_2$ at room temperature. After 1 h, the reaction mixture was filtered through celite®, and the filtrate concentrated on a rotary evaporator and chromatographed (5% ethyl acetate/hexanes, flash) to give 9.70 g (94%) of a pale yellow oil: MS (Cl, NH$_3$) m/z 309/307 (M+H$^+$, base); Anal. calcd for $C_{15}H_{19}N_2Br$: C, 58.64; H, 6.23; N, 9.12. Found: C, 58.56; H, 6.29; N, 8.77.

C. 1-Cyclohexyl-3-ethyl-1H-indazole-6-carbaldehyde

This compound was prepared according to the method of example 2.E., using 5.02 g (16.3 mmol, 1.0 equiv) 6-bromo-1-cyclohexyl-3-ethyl-1H-indazole as starting material to give 3.65 g (87%) of a pale yellow oil. MS (Cl, NH$_3$) m/z 257 (M+H$^+$, base); Anal. calcd for $C_{16}H_{20}N_2O$: C, 74.97; H, 7.87; N, 10.93. Found: C, 75.00; H, 7.70; N, 10.74.

D. (1-(Cyclohexyl-3-ethyl-1H-indazol-6-yl)-acetonitrile 2.7 mL (21.0 mmol, 1.5 equiv) trimethylsilyl chloride were added dropwise to a room temperature suspension of 3.58 g (14.0 mmol, 1.0 equiv) 1-cyclohexyl-3-ethyl-1H-indazole-6-carbaldehyde and 2.31 g (26.6 mmol, 1.9 equiv) lithium bromide in 100 mL anhydrous acetonitrile. After 15 min., the reaction mixture was cooled in an ice bath, and 4.1 mL (23.2 mmol, 1.66 equiv) 1,1,3,3-tetramethyldisiloxane were added dropwise, and the reaction was allowed to warm to room temperature over 30 min. The reaction mixture was heated to reflux for 3 h, then cooled to room temperature, diluted with 300 mL $CH_2Cl_2$, and filtered through Celite®. The filtrate was concentrated and dried at high vacuum, room temperature to give 7.52 g of an orange/yellow solid.

This solid was dissolved in 100 mL anhydrous DMF, 1.56 g (31.8 mmol, 2.27 equiv) sodium cyanide were added, and the mixture stirred at room temperature for 2.5 h. The reaction mixture was then poured into 400 mL $H_2O$ and extracted 3×200 mL ethyl acetate. The organic extracts were combined, washed 3×150 mL $H_2O$, 1×150 mL brine, and dried over $Na_2SO_4$. Filtration, concentration of filtrate and drying gave a yellow oil, which was purified on a silica gel column (5%–10% ethyl acetate/hexanes gradient) to give 1.40 g (38%) of a yellow/green oil: MS (Cl, NH$_3$) 268 (M+H$^+$, base); Anal. calcd for $C_{17}H_{21}N_3$: C, 76.38; H, 7.92; N, 15.72. Found: C, 76.43; H, 7.53; N, 15.39.

E. 4-Cyano-4-(1-cyclohexyl-3-ethyl-1H-indazol-6-yl)-heptanedioic acid dimethyl ester This compound was prepared according to the method of example 2.G., using 1.33 g (4.98 mmol, 1.0 equiv) of (1-cyclohexyl-3-ethyl-1H-indazol-6-yl)-acetonitrile as starting material, to give 1.38 g (63%) of a yellow oil; MS (Cl, NH$_3$) m/z 440 (M+H$^+$, base); Anal. calcd for $C_{25}H_{33}N_3O_4$: C, 68.32; H, 7.57; N, 9.56. Found: C, 68.18; H, 7.52; N, 9.28.

F. 5-Cyano-5-(1-cyclohexyl-3-ethyl-1H-indazol-t-yl)-2-oxo-cyclohexanecarboxylic acid methyl ester This compound was prepared according to the method of example 2.H., using 1.33 g (3.03 mmol, 1.0 equiv) 4-cyano-(1-cyclohexyl-3-ethyl-1H-indazol-6-yl)-heptanedioic acid dimethyl ester as starting material, to give 983 mg (80%) of a white amorphous solid: MS (Cl, NH$_3$) m/z 408 (M+H$^+$, base); Anal. calcd for $C_{24}H_{29}N_3O_3$: C, 70.75; H, 7.18; N, 10.31. Found: C, 70.75; H, 7.33; N, 10.19.

G. 1-(1-Cyclohexyl-3-ethyl-1H-indazol-6-yl)-4-oxo-cyclohexanecarbonitrile

This compound was prepared according to the method of example 2.I., using 933 mg (2.29 mmol, 1.0 equiv) 5-cyano-5-(1-cyclohexyl-3-ethyl-1H-indazol-6-yl)-2-oxocyclohexane-carboxylic acid methyl ester as starting material, to give 588 mg (74%) of a white amorphous solid: MS (Cl, NH$_3$) m/z 350 (M+H$^+$, base); Anal. calcd for $C_{22}H_{27}N_3O$: C, 75.62; H, 7.79; N, 12.03. Found: C, 75.57; H, 7.90; N, 12.15.

EXAMPLE 11

Cis-4-cyano-4-(1-cyclohexyl-3-ethyl-1H-indazol-6-yl)-cyclohexanecarboxylic acid methyl ester and trans-4-cyano-4-(1-cyclohexyl-3-ethyl-1H-indazol-6-yl)-cyclohexanecarboxylic acid methyl ester These compounds were prepared according to the method of example 3.B.,using 540 mg (1.20 mmol, 1.0 equiv) 1-(1-cyclohexyl-3-ethyl-1H-indazol-6-yl)-4-[1,3]dithian-2-ylidene-cyclohexane-carbonitrile as starting material, to give 117 mg (25%) of trans isomer as a white oily solid, and 233 mg (50%) of cis isomer as a white crystalline solid:

Data for trans isomer: $^1$H NMR (300 MHz, CDCl$_3$) d 7.68 (d, 1H, J=8.4 Hz), 7.50 (d, 1H, J=0.8 Hz), 7.13 (dd, 1H, J=1.6, 8.5 Hz), 4.34 (m, 1H), 3.74 (s, 3H), 2.98 (q, 2H, J+7.6 Hz), 2.85 (m, 1H), 2.35 (m, 2H), 1.9–2.2 (m, 12H), 1.8 (m, 2H), 1.55 (m, 2H), 1.37 (t, 3H, J=7.6 Hz); MS (CI, NH$_3$) m/z 394 (M+H$^+$, base); Anal. calcd for C$_{24}$H$_{31}$N$_3$O$_2$: C, 73.25; H, 7.95; N, 10.68. Fund: C, 73.07; H, 8.12; N, 10.89.

Data for cis isomer: 1H NMR (300 MHz, CDCl$_3$) d 7.68 (d, 1H, J=8.4 Hz), 7.53 (d, 1H, J=0.9 Hz), 7.14 (dd, 1H, J=1.6, 8.5 Hz), 4.34 (m, 1H), 3.74 (s, 3H), 2.98 (, 2H, J=7.6 Hz), 2.43 (m, 1H), 1.9–2.3 (m, 15H), 1.8 (m, 1H), 1.5 (m, 2H), 1.37 (t, 3H, JJ=7.6 Hz); MX (CI, NH$_3$) m/z 394 (M+$^+$, base); Ana. calcd for C$_{24}$H$_{31}$N$_3$O$_2$: C, 73.25; H, 7.95; N, 10.68. Found: C, 73.17; H, 7.89; N, 10.43.

EXAMPLE 12

Cis-4-cyano-4-(1-cyclohexyl-3-ethyl-1H-indazol-6-yl)-cyclohexanecarboxylic acid

This compound was prepared according to the method of example 5, using 201 mg (0.511 mmol, 1.0 equiv) cis-4-cyano-4-(1-cyclohexyl-3-ethyl-1H-indazol-6-yl)-cyclohexane-carboxylic acid methyl ester as starting material, to give 178 mg (92%) of a white crystalline solid, which was recrystallized from ethyl acetate hexanes to give 153 mg of a white crystalline powder; mp 192–194° C.; Anal. calculated for C$_{23}$H$_{29}$N$_3$O$_2$: C, 72.79; H, 7.70; N, 11.07. Found: C, 72.25; H, 7.99; N, 10.97.

EXAMPLE 13

Cis-1-(1-cyclohexyl-3-ethyl-1H-indazole-6-yl)-4-hydroxylmethylcyclohexane carbonitrile To a stirred solution of the product from Example 8 (220 mg, 0.58 mmol.) in dry tetrahydrofuran (5 mL) at 0° C. was added dropwise a solution of borane in tetrahydrofuran (1M, 1.3 mL, 1.3 mmol). The mixture was stirred at 0° C. for one hour then quenched by the slow addition of methanol (1 mL). The mixture was poured into water (100 mL) and extracted with ethyl acetate (2×100 mL). The organic extracts were combined, washed with water (1×20 mL), brine (1×20 mL) dried over magnesium sulfate and concentrated to give an oil. A separate identical experiment was carried out using the product from Example 8 (100 mg, 0.26 mmol.) and borane in tetrahydrofuran (1M, 0.6 mL, 0.58 mmol.). The crude product from both experiments were combined and chromatographed on Silica Gel eluting with 2.5% methanol in methylene chloride (v/v) to give an oil. Recrystallization from ethyl acetate/hexanes yielded 214 mg white solid (67%) mp 117–9° C. mass spectrum (m/e) 367 (M+1, 20), 366 (M+, 100).

EXAMPLE 14

Cis-4-Cyano-4-(1-cyclohexyl-3-ethyl-1H-indazol-6-yl)-cyclohexanecarboxylic acid amide A mixture of the product from Example 8 (150 mg, 0.4 mmol.) thionyl chloride (36 uL, 0.49 mmol) and dimethylformamide (5 mL) in dry methylene chloride (3 mL) was refluxed for four hours. The mixture was cooled to 0° C. and dry ammonia gas was bubbled with chloroform (200 mL), washed with water (1×40 mL) dried over magnesium sulfate and concentrated to give a solid. Recrystallization from ethyl acetate/hexane yielded 125 mg white solid (83%) mp 180–2° C. mass spectrum (m/e) (M+1, 20), 379 (M+, 100).

EXAMPLE 15

Trans-4-Cyano-4-(1-cyclohexyl-3-ethyl-1H-indazol-6-yl)-cyclohexanecarboxylic acid amide The title compound was prepared in a manner analogous to the synthesis provided in Example 4. The melting point of the isolated product was 140–143° C.

EXAMPLE 16

Cis-1-(1-cyclohexyl-3-ethyl-1H-indazol-6-yl)-4-(1-hydroxy-1-methyl-ethyl)cyclohexanecarbonitrile To a stirred solution of cis cyano-4-(1-cyclohexyl-3-ethyl-1H-indazolol-6-yl)-cyclohexanecarboxylic acid methyl ester (360 mg, 0.90 mmol) in 10 mL of dry tetrahydrofuran at −40° C. under nitrogen atmosphere was added 0.7 mL (2.1 mmol) of 3.0 M methyl magnesium bromide. Reaction mixture was allowed to warm up to room temperature over a period of one hour and stirred at room temperature for 3 hours. After this time, reaction mixture was quenched with excess of methanol (5.0 mL) and worked up by pouring into 100 mL of water and acidification with oxalic acid. Extraction with ethyl acetate followed by washing of ethyl acetate extract with water, brine and drying over magnesium sulfate (MgSO$_4$). Removal of ethyl acetate in vacuo gave crude final product which was homogenous by TLC analysis. Recrystallization from ethyl acetateihexane gave 180 mg of pure final product or a white solid, mp=58–60° C. MS m/z 394 (M+H$^+$, base).

EXAMPLE 17

Cis-1-(1-cyclopentyl-3-ethyl-1H-indazol-6-yl)-4-hydroxycyclohexanecarbonitrile

To a stirred solution of 2.9 g (8.6 mmol) 1-(1-cyclopentyl-3-ethyl-1H-indazol-6-yl)-4-oxo-cyclohexanecarbonitrile (compound 2G page 35 of PC) in 100 mL absolute methanol at 0° C. was added sodium borohydride 382 mg (10.8 mmol) portionwise. The mixture was stirred at 0° C. for 30 min, then quenched with 2 mL saturated ammonium chloride solution. The mixture was concentrated to a volume of 20 mL, poured into a mixture of 100 mL water and 100 mL saturated ammonium chloride solution and extracted with ethyl acetate (2×200 mL). The organic extract was combined, washed with water (1×100 mL), brine (1×100 mL), dried (MgSO$_4$) and concentrated to give an oil. Chromatography on silica gel eluting with ethyl acetate/hexanes (1:1) afforded an oil. Recrystallization from ethyl acetate/hexanes yielded 1.9 g (66%) cis-1-(1-cyclopentyl-3-ethyl-1H-indazole-6-yl)-4-hydroxycyclohexane-carbonitrile as a white solid. mp 107–109° C.

Anal. Calc'd. for C$_{21}$H$_{27}$N$_3$O: C, 74.74; H, 8.06; N, 12.45. Found: C, 74.81; H, 8.04; N, 12.43.

EXAMPLE 18

Cis-1-[3-ethyl-1(4-fluorophenyl)-1H-indazol-6-yl]-4-hydroxy-cyclohexanecarbonitrile The title compound was prepared in an analogous manner to that described in the immediately preceding example for preparation of cis-1-(1-cyclopentyl-3-ethyl-1H-indazol-6-yl)-4-hydroxy-cyclohexanecarbonitrile, starting with 0.415 g (1.148 mmol) of 1-(4-fluorophenyl-3-ethyl-1H-indazol-6-yl)-4-oxo-cyclohexanecarbonitrile to give 0.28 g (76%) of white crystalline solid. mp=132–134° C.

Anal. Calc'd. for C$_{22}$H$_{22}$N$_3$OF: C, 72.71; H, 6.10; N, 11.56. Found: C, 72.55; H, 6.22; N, 11.40.

The 1-(4-fluorophenyl-3-ethyl-1H-indazol-6-yl)-4-oxo-cyclohexanecarbonitrile starting material was prepared from 6-bromo-3-ethyl-1-(4-fluorophenyl)-1H-indazole following the chemical synthesis sequence outlined in Scheme 3 (intermediate X→XIX) and described above in more detail.

EXAMPLE 19

Cis-1-(1-cyclohexyl-3-ethyl-1H-indazol-6-yl)-4-hydroxy-cyclohexanecarbonitrile

The title compound was prepared in an analogous manner to that described in a preceding example for preparation of cis-(1-cyclopentyl-3-ethyl-1H-indazol-6-yl)-4-hydroxy-cyclohexanecarbonitrile, starting with 1-(1-cyclohexyl-3-ethyl-1H-indazol-6-yl)-4-oxo-cyclohexanecarbonitrile. mp=124–126° C.; MS m/z 352 (M+H$^+$, base).

EXAMPLE 20

Trans-1-(1-Cyclobutyl-3-ethyl-1H-indazol-6-yl)-4-hydroxycyclohexanecarbonitrile

The title compound was prepared in an analogous manner to that described in a preceding example for preparation of cis-(1-cyclopentyl-3-ethyl-1H-indazol-6-yl)-4-hydroxy-cyclohexanecarbonitrile, starting from 1-(1-cyclobutyl-3-ethyl-1H-indazol-6-yl)-4-oxo-cyclohexanecarbonitrile. mp=60–65° C.; MS m/z 324 (M+H$^+$, base).

EXAMPLE 21

Cis-1-(1-cyclopentyl-3-ethyl-1H-indazol-6-yl-)-4-hydroxy-4-methyl-cyclohexane-carbonitrile and trans-1-(1-cyclopentyl-3-ethyl-1H-indazol-6-yl)-4-hydroxy-4-methyl-cyclohexanecarbonitrile To a stirred suspension of 0.275 grams (1.115 mmol) of anhydrous CeCl$_3$ in 10 mL of dry tetra-hydrofuran under N2 atmosphere at 0° C. was added dropwise 0.4 mL (1.115 mmol) of 3.0 N CH$_3$MgCl. The reaction mixture was stirred at 0° C. for one hour. After this time, 0.3 g (0.891 mmol) of 1-(1-cyclopentyl-3-ethyl-1H-indazole-6-yl)-4-oxo-cyclohexanecarbonitrile dissolved in 10 mL of anhydrous tetrahydrofuran was added dropwise and the reaction mixture stirred at 0° C. for 1 hour. The mixture was quenched with 5 mL of 2N HOAc. The mixture was poured onto 100 mL of H$_2$O and extracted with ethyl acetate (2×100 mL). The organic extracts were combined, washed with H$_2$O (1×100 mL), brine (1×200 mL) and dried over MgSO$_4$. Filtration, concentration and purification on a silica gel column (2% EtOAc/hexane) gave 0.15 grams of less polar product (trans isomer) as amorphous solid. MS (Cl, NH$_3$) m/z 353 (M+H$^+$, base) and 0.045 grams of more polar product (cis isomer) as a white crystalline product. mp=156–158° C. MS (Cl, NH$_2$) m/z 352 (M+H$^+$, base).

EXAMPLE 22

Cis-4-cyano-4-(1-cyclobutyl-3-ethyl-1H-indazol-6-yl-)-cyclohexanecarboxylic acid This compound was prepared according to the method of Example 5 using 0.28 g (0.767 mmol) of cis-4-cyano-4-(1-cyclobutyl-3-ethyl-1H-indazol-6-yl)-cyclohexanecarboxylic acid methyl ester as a starting material to give 0.24 grams (89%) of white solid, which was recrystallized from ethyl acetate/hexane to give 0.15 grams of white crystalline product. mp=201–203° C.; MS (m/z) 352 (M+H$^+$, base).

EXAMPLE 23

Trans-4-cyano-4-(1-cyclobutyl-3-ethyl-1H-indazol-6-yl-)-cyclohexanecarboxylic acid This compound was prepared according to the method of Example 4 using 0.13 g (0.356 mmol) of trans-4-cyano-4-(1-cyclobutyl-3-ethyl-1H-indazol-6-yl)-cyclohexanecarboxylic acid methyl ester as a starting material to give white solid. Purification on silica gel column using 5% methanol/95% methylene chloride gave pure product (80 mg) which was recrystallized from ethyl acetate/hexane to give 43 mg of white crystalline solid; mp=157–159° C., MS (m/z) 312, (M+H$^+$, base).

EXAMPLE 24

6-Bromo-3-ethyl-1-(4-fluorophenyl)-1H-indazole

Methanesulfonic acid 5-bromo-2-propionyl-phenyl ester, prepared as described in U.S. Ser. No. 08/046,858, filed May 8, 1997 as Attorney Docket No. PC9798, 30 grams (97.66 mmol) was combined with 4-fluorophenyl hydrazine hydrochloride (31.76 g, 175.33 mmol) and sodium acetate (30 g, 364 mmol) in mesitylene (400 mL). The reaction mixture was heated to reflux in a Dean-Stark apparatus for 96 hours. The reaction mixture was cooled to room temperature and concentrated under reduced pressure. The crude product was diluted with 500 mL of diethyl ether and 600 mL of water. Organic layer was separated and aqueous layer extracted with 500 mL of ethyl acetate. Combined organic extracts were washed with water (2×600 mL), brine (1×200 mL), dried over MgSO$_4$ and concentrated which gave a brown-red oil. Hexane (600 mL) was added to crude reaction product and the mixture boiled in a steam bath for a few minutes. This was followed by cooling still the heterogeneous mixture to room temperature and allowing to stand at room temperature for 12–14 hours. The reaction mixture was filtered, undissolved solid washed with additional hexane and filtrate which contained approximately 80% pure desired product concentrated in vacuo to give brown-yellow solid. Purification of this product on silica gel column and eluting with 15% ethyl acetate/85% hexane gave 14.1 grams of light brown-tan solid. Recrystallization from hexane gave light tan needles. mp=72–73° C.; MS (APCl) m/z 319 (base).

EXAMPLE 25

4-[3-Ethyl-1-(4-fluorophenyl)-1H-indazole-6-yl]-4-hydroxy-cyclohexanecarboxylic acid ethyl ester This compound was prepared according to the method described in Example 6 of U.S. Ser. No. 08/046,858, filed May 8, 1997 as Attorney Docket No. PC9798, starting with 3.0 grams (9.4 mmol) of 6-bromo-3-ethyl-1-(4-fluorophenyl)-1H-indazole and 2.0 grams (11.7 mmol) of 4-oxo-cyclohexanecarboxylic acid ethyl ester to give after silica gel flash column chromatography (using 20% ethyl acetate 80% hexane as elutant) 2.17 grams of light yellow semi-solid which was a mixture of diastereoisomers. $^1$H NMR (400 MHz, CDCl$_3$) δ1.25–1.3 (t, 3H); 1.4–1.5 (t, 3H); 1.6–1.78 (m, 2H); 1.8–2.5 (m, 7H); 2.70 (m, 1H); 3.04 (m, 2H); 4.16 (m, 2H); 7.17–7.28 (m, 3H); 7.61–7.79 (m, 4H); MS, m/z 324.4 (M+H$^+$, base).

EXAMPLE 26

4-Cyano-4-[3-ethyl-1-(4-fluorophenyl)-1H-indazole-6-yl]cyclohexanecarboxylic acid ethyl ester and 4-[3-ethyl-1-(4-fluoro-phenyl)-1H-indazol-6-yl]cyclohex-3-enecarboxylic acid ethyl ester This compound was prepared according to the method described in Example 7 of U.S. Ser. No. 08/046,858, filed May 8, 1997 as Attorney Docket No. PC9798, starting with 2.1 grams (5.12 mmol) of 4-[3-ethyl-1-(4-fluorophenyl)-1H-indazole-6-yl]-4-hydroxy-cyclohexanecarboxylic acid ethyl ester to give after silica gel Flash 40 Biotage column chromatography (10% EtOAc/90% hexane) 0.714 grams of product which existed as a mixture of diastereoisorners, MS, m/z 420 (M+H$^+$, base); $^1$H NMR (400 MHz, CDCl$_3$) δ1.27 (t, J=7.26, 3H), 1.43 (t, J=7.68, 3H), 1.57 (S, 2H), 1.85–1.98 (m, 2H); 2.02–2.19 (m, 2H); 2.18–2.40 (m, 3H); 3.04 (q, J=7.67, 2H); 4.15 (q, J=7.26, 2H); 7.2–7.3 (m, 3H); 7.61 (m, 2H); 7.71 (s, 1H); 7.71 (d, J=8.5, 1H). In addition to the desired product 4-cyano-4-[3-ethyl-1-(4-fluorophenyl)-1H-indazol-6-yl]cyclohexanecarboxylic acid ethyl ester, a major byproduct, namely 4-[3-ethyl-1-(4-fluoro-phenyl)-1H-indazol-6-yl]cyclohex-3-enecarboxylic acid ethyl ester (1.16 grams) was obtained. MS m/z 393 (M+H$^+$, base). $^1$H NMR (400 MHz, CDCl$_3$) δ1.24 (m, 3H); 1.43 (m, 3H); 1.6–2.7 (m, 7H); 3.02 (m, 2H); 4.13 (m, 2H); 6.17 (br, s 1H); 7.15–7.25 (m, 4H); 7.50 (s, 1H); 7.61–7.67 (m, 2H).

EXAMPLE 27

Cis-4-cyano-4-[3-ethyl-1-(4-fluorophenyl)-1H-indazol-6-yl]-cyclohexanecarboxylic acid This compound was prepared in analogous manner as cis-4-cyano-4-(1-cyclohexyl-3-ethyl-1H-indazol-6-yl)-cyclohexanecarboxylic acid, synthesis of which is described in detail in Schemes I and II of U.S. Ser. No. 60/046,858, filed May 8, 1997 as starting with 0.71 grams (1.694 mmol) of 4-cyano-4-[3-ethyl-1-(4-fluorophenyl)-1H-indazol-6-yl]-cyclohexanecarboxylic acid ethyl ester.

mp=173–175° C.; MS m/z 392 (M+H$^+$, base). Anal. Calc'd for C$_{23}$H$_{23}$O$_2$N$_2$F: C, 70.57; H, 5.66; N, 10.73. Found: C, 70.39; H, 5.61; N 10.82. $^1$H NMR (400 MHz, CDCl$_3$) δ1.42–1.45 (t, J=7.57, 3H); 1.91 (t, J=13.28, 2H); 2.09 (m, 2H); 2.23–2.35 (m, 4H); 2.40–2.48 (m, 1H); 3.06 (q, J=7.67, 2H); 7.2–7.26 (m, 2H); 7.29 (d, J=7.47, 1H); 7.60 (m, 2H); 7.71 (s, 1H); 7.78 (d, J=8.5, 7H).

Alternatively, cis-4-cyano-4-[3-ethyl-1-(4-fluorophenyl)-1H-indazole-6-yl]cyclohexane-carboxylic acid can be prepared in analogous manner as cis-4-cyano-4-(1-cyclohexyl-3-ethyl-1H-indazol-6-yl)cyclohexanecarboxylic acid starting with 6-bromo-3-ethyl-1-(4-fluorophenyl)-1H-indazole following the synthetic steps outlined in Scheme 2, step 5, and Scheme 3, steps 1–7 described further above in more detail.

EXAMPLE 28

4-(3-ethyl-1-(4-fluorophenyl)-1H-indazol-6-yl)-cyclohex-3-ene-carboxylic acid

To a stirred solution of 1.13 g (2.87 mmol) of 4-(3-ethyl-1-(4-fluorophenyl)-1H-indazol-6-yl)-cyclohex-3-ene-carboxylic acid ethyl ester dissolved in 50 mL of methanol and 15 mL of tetrahydrofuran was added 8.62 mL (8.61 mmol) of 1N sodium hydroxide and reaction mixture heated to reflux for 3 hr. After 3 hr, the reaction mixture was concentrated on a rotary evaporator, diluted with 200 mL of H$_2$O, acidified to pH 1 with 1N HCl and extracted 2×200 mL ethyl acetate. The organic extracts were combined, washed with water, brine and dried over Na$_2$SO$_4$. Filtration, concentration and drying gave crude product. Recrystallization from ethyl acetate/hexane gave 0.31 grams of white crystalline product mp=214–216° C.; MS, m/z 365 (M+H$^+$, base).

EXAMPLE 29

1-Cyclohexyl-3-ethyl-6-fluoro-1H-indazole

To a solution of 1-(2,4-difluoro-phenyl)-propan-1-one (21.29 g, 125.1 mmol) in toluene (120 mL) was added sodium acetate (26.75 g, 326.1 mmol) and cyclohexylhydrazine mesylate (34.0 g, 163 mmol). The reaction mixture was heated to reflux in a Dean-Stark apparatus for 12 hours. The reaction was cooled to room temperature and poured into 1 N hydrochloric acid (100 mL). The toluene layer was separated and washed with water (75 mL) and brine (75 mL). The organic layer was dried over magnesium sulfate, filtered, and concentrated to yield 30.07 g of 1-cyclohexyl-3-ethyl-6-fluoro-1H-indazole (98% yield). $^1$H NMR (400 MHz, CDCl$_3$) d 1.33 (t, 3, J=7.7), 1.35–1.44 (m, 2), 1.47–1.96 (m, 8), 2.93 (q, 2, J=7.7), 4.14–4.22 (m1), 6.81 (dt, 1, J=8.9, 2.1), 6.99 (dd, 1, J=9.8, 2.1), 7.40 (ddd, 1, J=8.7, 5.2, 0.4). $^{13}$C NMR (100 MHz, CDCl$_3$) d 13.97, 20.53, 25.37, 25.84, 32.32, 58.18, 94.77 (d, J=27.4), 109.11 (d, J=26.0), 119.38, 121.75 (d, J=11.5), 139.89 (d, J=13.0), 146.61, 161.95 (d, J=242). IR 2968, 2934, 2856, 1624, 1507, 1174, 1125, 825 cm$^{-1}$. Analysis calculated for C$_{15}$H$_{19}$FN$_2$: C, 73.14; H, 7.77; N, 11.37. Found: C, 73.33; H, 7.90; N, 11.46.

EXAMPLE 30

1-(1-Cyclohexyl-3ethyl-1H-indazol-6-yl) cyclohexane-1,4-dicarbonitrile

To a solution of 1-cyclohexyl-3-ethyl-6-fluoro-1H-indazole (1.50 g, 6.09 mmol) and cylohexane-1,4-dicarbonitrile (3.27 g, 24.4 mmol) in toluene (15 mL) was added potassium bis(trimethylsilyl) amide (1.82 g, 9.12 mmol). The reaction mixture was heated to 100° C. and stirred for 5 hours. The reaction mixture was cooled to room temperature and poured into 1N HCl (15 mL). The layers were separated and the organic extracts were concentrated. The crude product was stirred in 20% EtOAc/Hexanes (15 mL) for 20 minutes and the solids were filtered (1.1 g of cylohexane-1,4-dicarbonitrile recovered). The filtrate was concentrated to a crude oil. For characterization purposes, the diastereoisomers were obtained by purification by chromatography on silica gel (125 g) eluting with 2:1 hexanes/ethylacetate (1.69 g product isolated, 77% yield). Higher Rf diastereoisomer: $^1$H NMR (400 MHz, CDCl$_3$) d 1.37 (t, 3, J=7.7), 1.24–1.78 (m, 4), 1.92–2.10 (m, 6), 2.19–2.35 (m, 8), 2.98 (q, 2, J=7.7), 3.15–3.17 (m, 1), 4.30–4.39 (m, 1), 7.19 (dd, 1, J=8.5, 1.7), 7.51 (d, 1, J=0.8), 7.71 (d, 1, J=8.5). $^{13}$C NMR (100 MHz, CDCl$_3$) d 14.07, 20.60, 25.34, 25.79, 25.92, 32.61, 33.36, 44.30, 57.66, 105.92, 117.04, 121.00, 121.52, 121.79, 122.09.137.33, 139.54, 146.41. IR 2934, 2239, 1620, 1448, 1435, 1238, 1049, 803 cm$^{-1}$. Analysis calculated for C$_{25}$H$_{28}$N$_4$: C, 76.63; H, 7.83; N, 15.54. Found: C, 76.69; H, 7.87; N, 15.65. Lower Rf diastereoisomer: $^1$H NMR (400 MHz, CDCl$_3$) d 1.36 (t, 3, J=7.7), 1.42–1.53 (m, 2), 1.74–1.82 (m, 2), 1.89–2.08 (m, 8), 2.17–2.34 (m, 6), 2.58 (tt, 1, J=12.2, 3.5), 2.97 (q, 2, J=7.7), 4.28–4.36 (m, 1), 7.09 (dd, 1, J=8.5, 1.7), 7.49 (d, 1, J=1.0), 7.69 (d, 1, J=8.5). $^{13}$C NMR (100 MHz, CDCl$_3$) d 14.02, 20.57, 25.32, 25.81, 27.07 27.27, 32.57, 36.04, 43.63, 57.75, 106.05, 116.65, 121.17, 121.50, 122.13, 137.17, 139.54, 146.38. IR 2935, 2231, 1620, 1447, 1211, 1061, 807 cm$^{-1}$. Analysis calculated for C$_{25}$H$_{28}$N$_4$: C, 76.63; H, 7.83; N, 15.54. Found: C, 76.52; H, 7.95; N, 15.37.

EXAMPLE 31

4-Cyano-4-(1-cyclohexyl-3-ethyl-1H-indazol-6-yl) cyclohexanecarboxylic acid ethyl ester To a solution of 1-(1-cyclohexyl-3-ethyl-1H-indazol-6-yl)-cyclohexane-1,4-dicarbonitrile (2.58 g, 7.16 mmol) in ethanol (35 mL) was bubbled hydrochloric acid gas for 20 minutes. The reaction mixture was stirred 20 minutes after which the solvent was concentrated. To the crude product was added toluene (20 mL) and water (20 mL) and the mixture was stirred for 8 hours. The layers were separated and the toluene layer was concentrated to a crude foam. For characterization purposes, the diastereoisomers were obtained by purification by chromatography on silica gel eluting with 4:1 hexanes/ethylacetate (2.37 g product isolated, 81% yield).

What is claimed is:

1. A compound useful for treating a disease or condition mediated by or associated with adrenergic $\alpha_1$-antagonist or $\beta_1$-agonist activity consisting of Formula ($I^1$) or ($I^2$):

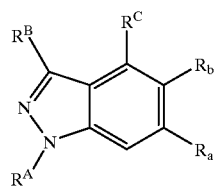

(I¹)

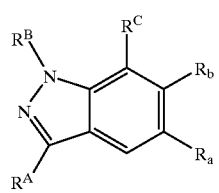

(I²)

or a pharmaceutically acceptable salt, prodrug, or metabolite thereof, wherein:

$R^C$ is a member independently selected from the group consisting of hydrogen; hydroxy; —O—($C_1$–$C_4$)alkyl; and phenyl substituted by 0 to 2 substituents $R^s$ where $R^s$ is a member independently selected from the group consisting of Br, Cl, or F; ($C_1$–$C_4$) alkoxy; and $CF_3$ $R^A$ is a member independently selected from the group consisting of hydrogen; ($C_1$–$C_9$) alkyl; —$(CH_2)_n$ ($C_3$–$C_{10}$) cycloalkyl wherein n is 0 to 2; —($C_1$–$C_6$) alkyl($C_1$–$C_6$) alkoxy; ($C_2$–$C_6$) alkenyl; —$(CH_2)_n$ ($C_3$–$C_9$) heterocyclyl wherein n is 0 to 2; and —$(Z')_b$ $(Z'')_c(C_6$–$C_{10}$) aryl wherein b and c are each independently 0 or 1, Z' is ($C_1$–$C_6$) alkylene or ($C_2$–$C_6$) alkenylene, and Z" is —O—, —S—, —$SO_2$—, or —N($R^9$)—, and wherein said alkyl, alkenyl, alkoxyalkyl, heterocyclyl, and aryl moieties of said $R^A$ (groups are substituted by 0 to 3 substituents independently selected from halo; hydroxy; ($C_1$–$C_5$) alkyl; ($C_2$–$C_5$) alkenyl; ($C_1$–$C_5$) alkoxy; ($C_3$–$C_6$) cycloalkoxy; trifluoromethyl; nitro; —C(=O)$OR^9$; —C(=O)$NR^9R^{10}$, —$NR^9R^{10}$, and —S(=O)$_2NR^9R^{10}$;

where said aryl moiety consists of a member selected from the group consisting of phenyl; naphthyl; indenyl (from 2,3-dihydro-1H-indene); indanyl; and fluorenyl (from 9-H-fluorene);

where said heterocyclyl moiety consists of a member independently selected from the group consisting of acridinyl; benzimidazolyl; benzodioxolane; 1,3-benzodioxol-5-yl; benzo[b]furanyl; benzo[b]thiophenyl; benzoxazolyl; benzthiazolyl; carbazolyl; cinnolinyl; 2,3-dihydrobenzofuranyl; 1,3-dioxane; 1,3-dioxolane; 1,3-dithiane; 1,3-dithiolane; furanyl; imidazolidinyl; imidazolinyl imidazolyl; 1H-indazolyl; indolinyl; indolyl; 3H-indolyl; isoindolyl; isoquinolinyl; isothiazolyl; isoxazolyl; morpholinyl; 1,8-naphthyridinyl; oxadiazolyl; 1,3-oxathiolane; oxazolidinyl; oxazolyl; oxiranyl; parathiazinyl; phenazinyl; phenothiazinyl; phenoxazinyl; phthalazinyl; piperazinyl; piperidinyl; pteridinyl; pyranyl; pyrazinyl; pyrazolidinyl; pyrazolinyl; pyrazolo[1,5-c]triazinyl; pyrazolyl; pyridazinyl; pyridyl; pyrimidinyl; pyrimidyl; pyrrolyl; pyrrolidinyl; purinyl; quinazolinyl; quinolinyl; 4H-quinolizinyl; quinoxalinyl; tetrazolidinyl; tetrazolyl; thiadiazolyl; thiazolidinyl; thiazolyl; thienyl; thiomorpholinyl; triazinyl; and triazolyl; and $R^9$ and $R^{10}$ are independently selected from the group consisting of hydrogen and ($C_1$–$C_4$) alkyl substituted by 0 to 3 fluorine atoms;

$R^B$ is a member independently selected from the group consisting of hydrogen; ($C_1$–$C_9$) alkyl; ($C_2$–$C_3$) alkenyl; phenyl; ($C_3$–$C_7$) cycloalkyl; and —($C_1$–$C_2$) alkyl ($C_3$–$C_7$) cycloalkyl; wherein said alkyl, alkenyl and phenyl $R^B$ groups are substituted with 0 to 3 substituents independently selected from the group consisting of methyl;ethyl; trifluoromethyl; and halo; and $R_a$ and $R_b$ are each individually and independently a member selected from the group consisting of hydrogen and a substituent defined under (II) below, provided that both of $R_a$ and $R_b$ cannot be hydrogen at the same time;

(II) wherein said compound of Formula ($I^1$) or ($I^2$) having adrenergic $\alpha_1$-antagonist or $\beta_1$-agonist activity consists of a compound of Formulas (6.22) or (6.23):

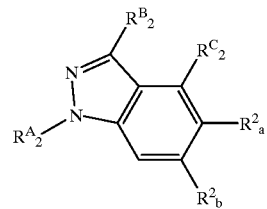

(6.22)

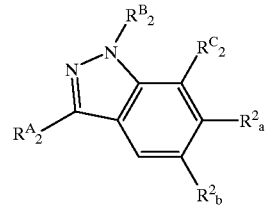

(6.23)

wherein $R^C_2$ and $R^A_2$ and $R^B_2$ have the same meaning as $R^A$, $R^B$, and $R^C$ recited above, to which they correspond, but are selected on an independent basis therefrom; and $R^2_a$ and $R^2_b$ are each individually and independently a member selected from the group consisting of hydrogen and the substituents defined by partial Formulas (6.24), (6.26), (6.41), (6.43), (6.48), and (6.50) below, provided that both of $R^2_a$ and $R^2_b$ cannot be hydrogen at the same time:

(II-A)

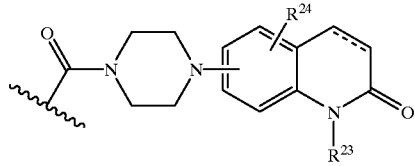
(6.24)

wherein the dashed line represents an optional double bond; $R^{23}$ is a member selected from the group consisting of hydrogen; $(C_1-C_4)$ alkyl, $(C_2-C_4)$ alkenyl, and phenyl$(C_1-C_4)$ alkyl-, where said alkyl, alkenyl, and phenyl or alkyl group attached thereto are substituted by 0 to 3 substituents $R^5$, where the substituent $R^5$ is as defined herein, but independently selected therefrom; and $R^{24}$ is a member selected from the group consisting of hydrogen and $(C_1-C_4)$ alkoxy;

(II-B) $R^2_a$ and $R^2_b$ are taken together to form the moiety of partial Formula (6.26):

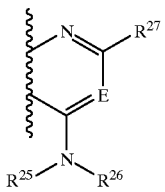
(6.26)

wherein E represents N, resulting in a pyrimidinyl moiety and overall a quinazoline series of compounds; or represents CH, resulting in a pyridyl moiety and overall a quinoline series of compounds; $R^{25}$ and $R^{26}$ are each a member independently selected from the group consisting of hydrogen; $(C_1-C_6)$ alkyl; $(C_2-C_6)$ alkenyl; $(C_3-C_8)$ cycloalkyl; hydroxy$(C_1-C_6)$ alkyl; phenyl; benzyl; phenylethyl; and 2-furfuryl; and $R^{27}$ is independently selected from the group consisting of:

| (a) | (b) |
|---|---|
| 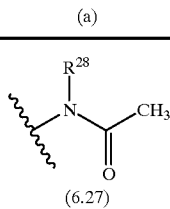<br>(6.27) | 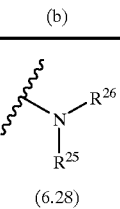<br>(6.28) |
| (c) | (d) |
| Morpholino;<br>1-Azacycloheptyl;<br>1-Azacyclooctyl;<br>Pyrrolidino;<br>Piperidino | 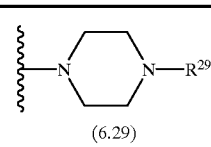<br>(6.29) |

-continued

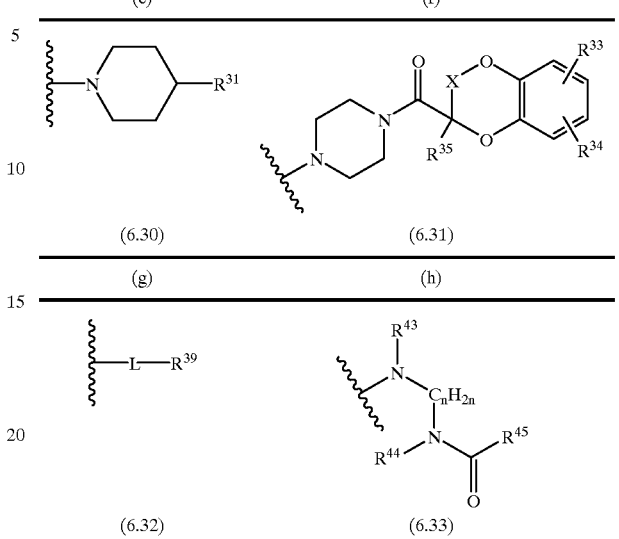

| (e) | (f) |
|---|---|
| (6.30) | (6.31) |
| (g) | (h) |
| (6.32) | (6.33) | wherein ◊ ◊ $R^{28}$ is a member selected from the group consisting of hydrogen; acetyl;; $(C_1-C_6)$ alkyl; and $(C_2-C_6)$ alkenyl; ◊ ◊ $R^{29}$ is a member selected from the group consisting of; hydrogen; $(C_1-C_6)$ alkyl; hydroxy$(C_1-C_6)$ alkyl; allyl; propargyl; 2-methylallyl; phenyl unsubstituted or substituted by bromo or chloro; benzyl unsubstituted or substituted by bromo or chloro; trifluoromethyl; methoxyphenyl; methylphenyl; carboxylic acid $(C_1-C_6)$ alkyl ester; carboxylic acid $(C_2-C_6)$ alkenyl ester; and —C(=O)—$R^{30}$, where ◊ ◊ $R^{30}$ is a member independently selected from the group consisting of $(C_1-C_6)$ alkyl; —O—$(C_1-C_6)$ alkyl; hydroxy$(C_1-C_6)$ alkyl-O—; —O—$(C_2-C_6)$ alkenyl; phenyl unsubstituted or substituted by bromo, chloro, methyl, 3,4,5-trimethoxy, or trifluoromethyl; naphthyl; furyl; benzofuryl; thienyl; pyridyl; tetrahydrofuryl; and tetrahydropyran; ◊ ◊ $R^{31}$ is a member independently selected from the group consisting of hydrogen; $(C_1-C_6)$ alkyl; $(C_1-C_4)$ alkoxy; hydroxy; hydroxy$(C_1-C_3)$ alkyl; phenyl; benzyl; and 4-phenyl-4-carboxylic acid $(C_1-C_6)$ alkyl ester; ◊ ◊ $R^{33}$ and $R^{34}$ are each independently a member selected from the group consisting of hydrogen; $(C_1-C_6)$ alkyl; $(C_1-C_6)$ alkoxy; bromo, chloro and fluoro; —C(=O)$(C_1-C_6)$ alkyl; —O(=O)—O—$(C_1-C_6)$ alkyl; and —C(=O) $NR^{36}R^{37}$ and —S(=O)$_2NR^{36}R^{37}$, where ◊ ◊ $R^{36}$ and $R^{37}$ are each independently hydrogen or $(C_1-C_6)$ alkyl; ◊ ◊ $R^{35}$ is independently hydrogen or $(C_1-C_6)$ alkyl; ◊ ◊ X is —CHR$^{35}$— or —CH$_2$CH$_2$— where $R^{35}$ is as defined above; ◊ ◊ L is absent or represents (i) a heterocyclic group of partial Formula (6.32.1):

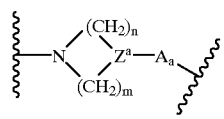
(6.32.1)

where N is attached to the 2-position of the quinoline or quinazoline ring; ◊ ◊ $A^a$ is absent or represents C(=O) or S(=O)$_2$; ◊ ◊ $Z^a$ represents CH or N; ◊ ◊ m is an integer selected from 1 and 2, as; well as from 0 when $Z^a$ represents CH; and ◊ ◊ n is an integer selected from 1, 2, and 3; provided that the sum of m and n is an integer selected from 2, 3, 4, and 5; or (ii) a moiety of partial Formula (6.32.2):

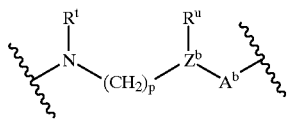
(6.32.2)

where N is attached to the 2-position of the quinoline or quinazoline ring; ◊ ◊ $A^b$ and $Z^b$ have the same definition as $A^a$ and $Z^a$ above; ◊ ◊ $R^t$ and $R^u$ are each a member independently selected from the group consisting of hydrogen and (C$_1$–C$_4$) alkyl; and ◊ ◊ p is an integer selected from 1, 2, and 3, provided that when $Z^b$ is CH, p may also be selected from 0; ◊ ◊ $R^{39}$ is a member independently selected from the group consisting of 4-, 5-, and 6-membered heterocyclic rings containing 1 or 2 heteroatoms selected from N, O, and S, said ring optionally being fused to a benzene ring or to a 5- or 6-membered heterocyclic ring containing 1 or 2 heteroatoms selected from N, O, and S, said ring system comprising $R^{39}$ being substituted by 0 to 2 members selected from the group consisting of OH; (C$_1$–C$_4$) alkyl; (C$_1$–C$_4$) alkoxy; Br, Cl, or F; S(=O)$_2$NR'R''; and NHS(=O)$_2$(C$_1$–C$_4$) alkyl; and when said ring heteroatom is S, it may be substituted by 0 to 2 oxygen atoms; and R' and R'' are as defined above, but independently selected therefrom; (C$_1$–C$_6$) alkyl; benzyl unsubstituted or substituted by fluoro, bromo, chloro, or methoxy; and where $A^a$ is absent, —C(=O)—$R^{40}$, where ◊ ◊ $R^{40}$ is a member independently selected from the group consisting of (C$_1$–C$_6$) alkyl; phenyl unsubstituted of substituted by fluoro, bromo, chloro, methoxy, or methanesulfonyl; styryl unsubstituted or ring substituted by fluoro, bromo, chloro, methoxy, or 3,4-methylenedioxy; 4-morpholino; and 2-furyl; including particularly wherein $R^{27}$ is a 1,4-diazepan of partial Formula (6.32.3):

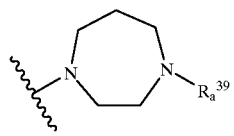
(6.32.3)

where ◊ ◊ $R_a^{39}$ has the same definition as $R^{39}$ but is independently selected therefrom; provided that —L—$R^{39}$ of partial Formula (6.32) may not be piperidine or piperazine; ◊ ◊ $R^{43}$ and $R^{44}$ are each a member independently selected from the group consisting of hydrogen; (C$_1$–C$_4$)alkyl; and benzyl; ◊ ◊ n is an integer selected from 2, 3, and 4; and ◊ ◊ $R^{45}$ is (C$_3$–C$_6$) cycloalkyl or a radical selected from the group consisting of:

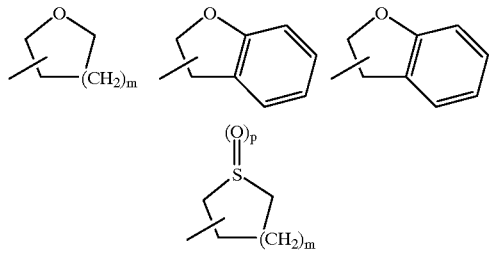

where ◊ ◊ m is an integer independently selected from 0, 1 and 2; and ◊ ◊ p is an integer independently selected from 0, 1 and 2;

(II-C)
(6.41)
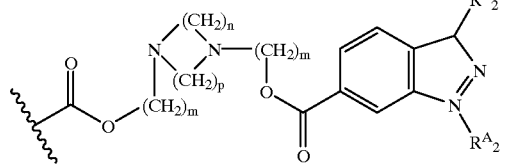

wherein m is an integer independently selected from 2 and 3 in each instance of its occurrence; n is an integer selected from 2, 3, and 4; p is an integer selected from 2 and 3; and n and p together represent a total which is an integer selected from 5, 6, and 7;

(II-D)
(6.43)
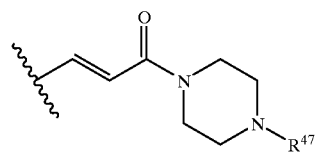

wherein $R^{47}$ is a member independently selected from the group consisting of:
(a) (C$_1$–C$_4$) alkyl unsubstituted or substituted by 1 or 2 hydroxyl groups; phenyl(C$_1$–C$_4$) alkyl- unsubstituted or substituted on the phenyl portion thereof by 1 or 2 hydroxyl groups; and cinnamyl;
(b) —CH$_2$C(=O)NHR$^{48}$ where $R^{48}$ is a member independently selected from the group consisting of (C$_1$–C$_4$) alkyl; and phenyl unsubstituted or substituted by (C$_1$–C$_4$) alkoxy, trifluoromethyl, fluoro, bromo, or chloro;
(c) —CH$_2$C(=O)NHR$^{49}$R$^{50}$ where $R^{49}$ and $R^{50}$ are each defined the same as $R^{48}$; but are selected on an independent basis therefrom;
(d) a radical of partial Formula (6.44):

(6.44)
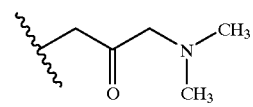

wherein the nitrogen atom forms part of a heterocyclic radical selected from the group consisting of morpholino; hexamethylene-imino; and pyrrolidino; and
(e) —CH$_2$C(=O)OR$^{51}$ where $R^{51}$ is hydrogen or (C$_1$–C$_4$) alkyl;

(II-E)

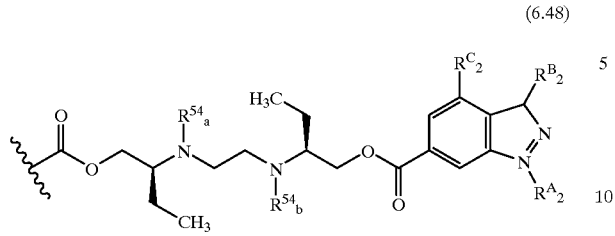

(6.48)

wherein $R^C_2$ is a member independently selected from the group consisting of hydrogen; hydroxy; and —O—$(C_1$–$C_4)$ alkyl, in accordance with whether an inclusionary or exclusionary bioisostere is intended; and $R^{54}_a$ and $R^{54}_b$ are independently selected from the group consisting of $C_nH_{2n+1}$ where n is an integer selected from 1, 2, 3, and 4; and (II-F)

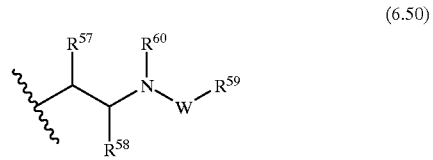

(6.50)

wherein $R^{57}$ is a member independently selected from the group consisting of hydrogen; $(C_1$–$C_2)$ alkyl; and hydroxy;

$R^{58}$ is a member independently selected from the group consisting of hydrogen; and $(C_1$–$C_2)$ alkyl;

W is —C($R^{64}$)($R^{65}$)—; —CH($R^{64}$)CH($R^{65}$)—; or —CH($R^{64}$)CH($R^{65}$)CH$_2$—; where $R^{64}$ is a member independently selected from the group consisting of hydrogen and methyl; and $R^{65}$ is a member independently selected from the group consisting of hydrogen, methyl, and hydroxy;

$R^{59}$ is a member selected independently from the group consisting of hydrogen; methyl; phenyl; and benzoyl; where said phenyl and benzoyl groups are unsubstituted or substituted by a member independently selected from the group consisting of m-hydroxy; p-hydroxy; m- and p-dihydroxy; m-$(C_1$–$C_2)$alkyl; $(C_1$–$C_3)$alkoxy; fluoro; chloro; cyano; hydroxymethyl; acetyl; and o-allyl; and $R^{60}$ is a member independently selected from the group consisting of hydrogen; and methyl.

2. A pharmaceutical composition consisting of a therapeutically effective amount of a compound according to claim 1 together with a pharmaceutically acceptable carrier therefor.

3. A method of treating or preventing a disease or condition consisting of administering to a patient in need of such treatment a therapeutically effective amount of an active ingredient possessing adrenergic $\alpha_1$-antagonist or $\beta_1$-agonist activity, where each said disease or condition is mediated by or associated with interaction between receptors and ligands characteristic of said disease or condition which are positively affected by said active ingredient, wherein said active ingredient is a compound according to claim 1.

\* \* \* \* \*